United States Patent
Clarke et al.

(10) Patent No.: US 10,251,904 B2
(45) Date of Patent: Apr. 9, 2019

(54) METHODS FOR TREATING ARENAVIRIDAE AND CORONAVIRIDAE VIRUS INFECTIONS

(71) Applicant: Gilead Sciences, Inc., Foster City, CA (US)

(72) Inventors: Michael O'Neil Hanrahan Clarke, Redwood City, CA (US); Joy Yang Feng, Hillsborough, CA (US); Robert Jordan, Foster City, CA (US); Richard L. Mackman, Millbrae, CA (US); Adrian S. Ray, Burlingame, CA (US); Dustin Siegel, Half Moon Bay, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 114 days.

(21) Appl. No.: 15/267,433

(22) Filed: Sep. 16, 2016

(65) Prior Publication Data

US 2017/0071964 A1     Mar. 16, 2017

Related U.S. Application Data

(60) Provisional application No. 62/239,696, filed on Oct. 9, 2015, provisional application No. 62/219,302, filed on Sep. 16, 2015.

(51) Int. Cl.
  *A61K 31/706*    (2006.01)
  *A61K 31/7056*    (2006.01)

(52) U.S. Cl.
  CPC ........ *A61K 31/706* (2013.01); *A61K 31/7056* (2013.01)

(58) Field of Classification Search
  None
  See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,105,493 B2 | 9/2006 | Sommadossi et al. | |
| 7,125,855 B2 | 10/2006 | Bhat et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,807,653 B2 | 10/2010 | Cook et al. | |
| 7,842,672 B2 | 11/2010 | Boojamra et al. | |
| 7,973,013 B2 | 7/2011 | Cho et al. | |
| 7,994,139 B2 | 8/2011 | Babu et al. | |
| 8,008,264 B2 * | 8/2011 | Butler .................. | C07H 19/23 514/23 |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 * | 11/2012 | Butler .................. | C07H 19/23 514/23 |
| 8,415,308 B2 | 4/2013 | Cho et al. | |
| 8,455,451 B2 | 6/2013 | Cho et al. | |
| 8,853,171 B2 * | 10/2014 | Butler .................. | C07H 19/23 514/23 |
| 8,871,737 B2 | 10/2014 | Smith et al. | |
| 8,980,865 B2 | 3/2015 | Wang | |
| 9,090,642 B2 | 7/2015 | Cho et al. | |
| 9,243,022 B2 | 1/2016 | Beigelman et al. | |
| 9,249,174 B2 | 2/2016 | Beigelman et al. | |
| 9,278,990 B2 | 3/2016 | Smith et al. | |
| 9,388,208 B2 | 7/2016 | Clarke et al. | |

(Continued)

FOREIGN PATENT DOCUMENTS

| | | |
|---|---|---|
| AU | 2010/295392 B2 | 4/2012 |
| CA | 2367921 C | 7/2009 |

(Continued)

OTHER PUBLICATIONS

Cho et al., Bioorganic and Medicinal Chemistry Letters, 2012, pp. 2705-2707.*

(Continued)

*Primary Examiner* — Traviss C McIntosh, III
(74) *Attorney, Agent, or Firm* — Mintz, Levin, Cohn, Ferris, Glovsky and Popeo, P.C.

(57) ABSTRACT

Provided are methods for treating Arenaviridae and Coronaviridae virus infections by administering nucleosides and prodrugs thereof, of Formula I:

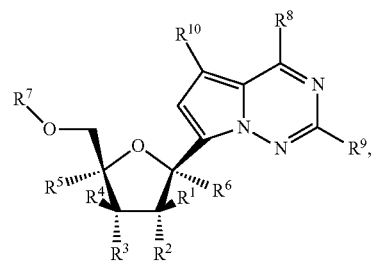

Figure 1:
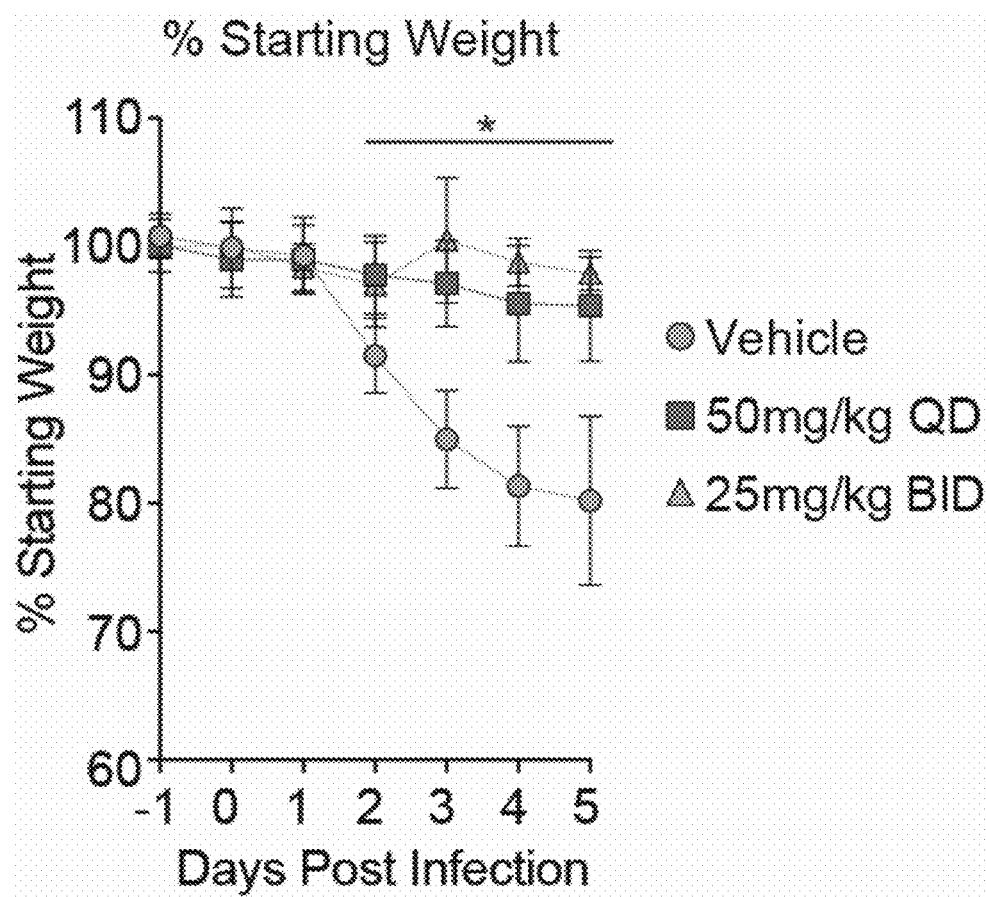

wherein the 1' position of the nucleoside sugar is substituted. The compounds, compositions, and methods provided are particularly useful for the treatment of Lassa virus and Junin virus infections.

43 Claims, 6 Drawing Sheets
Specification includes a Sequence Listing.

(56) References Cited

U.S. PATENT DOCUMENTS

| | | | |
|---|---|---|---|
| 9,481,703 B2 | 11/2016 | Kalayanov et al. | |
| 9,487,544 B2 | 11/2016 | Cho et al. | |
| 9,540,411 B2 | 1/2017 | Kalayanov et al. | |
| 9,605,018 B2 | 3/2017 | Wang et al. | |
| 9,701,682 B2 | 7/2017 | Clarke et al. | |
| 9,724,360 B2* | 8/2017 | Chun | C07D 487/04 |
| 9,949,994 B2* | 4/2018 | Chun | C07D 487/04 |
| 2003/0050229 A1 | 3/2003 | Sommadossi et al. | |
| 2004/0006002 A1 | 1/2004 | Sommadossi et al. | |
| 2004/0023901 A1 | 2/2004 | Cook et al. | |
| 2004/0063658 A1 | 4/2004 | Roberts et al. | |
| 2004/0067901 A1 | 4/2004 | Bhat et al. | |
| 2004/0138170 A1 | 7/2004 | Montgomery et al. | |
| 2005/0187180 A1 | 8/2005 | Loeb et al. | |
| 2005/0215513 A1 | 9/2005 | Boojamra et al. | |
| 2005/0250728 A1 | 11/2005 | Bantia et al. | |
| 2006/0058303 A1 | 3/2006 | Chambers et al. | |
| 2006/0241064 A1 | 10/2006 | Roberts et al. | |
| 2008/0107628 A1 | 5/2008 | Boojamra et al. | |
| 2008/0161324 A1 | 7/2008 | Johansen et al. | |
| 2008/0280842 A1 | 11/2008 | MacCoss et al. | |
| 2009/0004138 A1 | 1/2009 | Francom et al. | |
| 2009/0221524 A1 | 9/2009 | Kotra et al. | |
| 2009/0233879 A1 | 9/2009 | Reddy et al. | |
| 2009/0317361 A1 | 12/2009 | Cho et al. | |
| 2010/0015094 A1 | 1/2010 | Babu et al. | |
| 2010/0016251 A1 | 1/2010 | Sofia et al. | |
| 2010/0021425 A1 | 1/2010 | Butler et al. | |
| 2010/0035835 A1 | 2/2010 | Narjes et al. | |
| 2010/0035836 A1 | 2/2010 | Francom et al. | |
| 2010/0203015 A1 | 8/2010 | Butler et al. | |
| 2010/0234584 A1 | 9/2010 | Chang | |
| 2010/0291031 A2 | 11/2010 | Francom et al. | |
| 2010/0298257 A1 | 11/2010 | Ross et al. | |
| 2011/0070194 A1 | 3/2011 | Cho et al. | |
| 2011/0084230 A1 | 4/2011 | Knochel et al. | |
| 2011/0230654 A1 | 9/2011 | Butler et al. | |
| 2011/0257122 A1 | 10/2011 | Sofia et al. | |
| 2011/0293563 A1 | 12/2011 | Cho et al. | |
| 2012/0009147 A1 | 1/2012 | Cho et al. | |
| 2012/0020921 A1 | 1/2012 | Cho et al. | |
| 2012/0027752 A1 | 2/2012 | Mackman et al. | |
| 2012/0071434 A1 | 3/2012 | Smith et al. | |
| 2012/0107274 A1 | 5/2012 | Clarke et al. | |
| 2013/0034521 A1 | 2/2013 | Butler et al. | |
| 2013/0143835 A1 | 6/2013 | Eneroth et al. | |
| 2013/0281686 A1 | 10/2013 | Cho et al. | |
| 2013/0315868 A1 | 11/2013 | Mayes | |
| 2013/0344028 A2 | 12/2013 | Butler et al. | |
| 2015/0111839 A1 | 4/2015 | Mackman et al. | |
| 2015/0133395 A1 | 5/2015 | Clarke et al. | |
| 2015/0152116 A1 | 6/2015 | Mackman et al. | |

FOREIGN PATENT DOCUMENTS

| | | |
|---|---|---|
| CN | 1291994 A | 4/2001 |
| CN | 1443189 A | 9/2003 |
| CN | 1498221 A | 5/2004 |
| CN | 1852915 A | 10/2006 |
| CN | 101043893 A | 9/2007 |
| CN | 101611046 A | 12/2009 |
| CN | 102906102 A | 1/2013 |
| EA | 201071170 A1 | 8/2011 |
| EA | 201171417 A1 | 5/2012 |
| EA | 201200525 A1 | 9/2012 |
| EP | 2480559 B1 | 8/2012 |
| EP | 2396340 B1 | 12/2013 |
| JP | 41017629 | 10/1966 |
| JP | 2004520367 A | 7/2004 |
| JP | 2008502685 A | 1/2008 |
| JP | 2008518934 A | 6/2008 |
| TW | 1401084 B | 7/2013 |
| WO | WO-1991/019721 A1 | 12/1991 |
| WO | WO-2000/56734 A1 | 9/2000 |
| WO | WO-2001/32153 A2 | 5/2001 |
| WO | WO-2001/60315 A2 | 8/2001 |
| WO | WO-2001/90121 A2 | 11/2001 |
| WO | WO-2002/008241 | 1/2002 |
| WO | WO-2002/18404 A2 | 3/2002 |
| WO | WO-2002/32920 A2 | 4/2002 |
| WO | WO-2002/057287 A2 | 7/2002 |
| WO | WO-2002/057425 A2 | 7/2002 |
| WO | WO-2003/093272 A1 | 11/2003 |
| WO | WO 2003/093273 A1 | 11/2003 |
| WO | WO 2003/100009 A2 | 12/2003 |
| WO | WO-2004/046331 A2 | 6/2004 |
| WO | WO-2005/009418 A2 | 2/2005 |
| WO | WO-2005/123087 A2 | 12/2005 |
| WO | WO-2006/031725 A2 | 3/2006 |
| WO | WO-2006/050161 A2 | 5/2006 |
| WO | WO-2006/065335 A2 | 6/2006 |
| WO | WO-2006/121820 A1 | 11/2006 |
| WO | WO-2007/027248 A2 | 3/2007 |
| WO | WO-2007/056170 A2 | 5/2007 |
| WO | WO-2007/064883 A2 | 6/2007 |
| WO | WO-2007/064931 A2 | 6/2007 |
| WO | WO-2007/065289 A2 | 6/2007 |
| WO | WO-2007/097991 A2 | 8/2007 |
| WO | WO-2007/135134 A1 | 11/2007 |
| WO | WO-2008/005542 A2 | 1/2008 |
| WO | WO-2008/055870 | 5/2008 |
| WO | WO-2008/079206 A1 | 7/2008 |
| WO | WO-2008/082601 A2 | 7/2008 |
| WO | WO-2008/085508 A2 | 7/2008 |
| WO | WO-2008/089105 A2 | 7/2008 |
| WO | WO-2008/116064 A2 | 9/2008 |
| WO | WO-2008/121634 A2 | 10/2008 |
| WO | WO-2008/141079 A1 | 11/2008 |
| WO | WO-2009/009951 A1 | 1/2009 |
| WO | WO-2009/131926 A1 | 10/2009 |
| WO | WO-2009/132123 A1 | 10/2009 |
| WO | WO-2009/132135 A1 | 10/2009 |
| WO | 2010002877 A2 | 1/2010 |
| WO | WO-2010036407 A2 | 4/2010 |
| WO | WO-2010/093608 A1 | 8/2010 |
| WO | WO-2010/099458 A1 | 9/2010 |
| WO | WO-2010/135569 A1 | 11/2010 |
| WO | WO-2011/011303 | 1/2011 |
| WO | WO-2010/111381 A3 | 3/2011 |
| WO | WO-2011/035231 A1 | 3/2011 |
| WO | WO-2011/035250 A1 | 3/2011 |
| WO | WO-2011/123645 A2 | 10/2011 |
| WO | WO-2011/123672 A1 | 10/2011 |
| WO | WO-2011/150288 A1 | 12/2011 |
| WO | WO-2012/012465 A1 | 1/2012 |
| WO | WO-2012/012776 A1 | 1/2012 |
| WO | WO-2012/039787 A1 | 3/2012 |
| WO | WO-2012/039791 A1 | 3/2012 |
| WO | WO-2012/051570 A1 | 4/2012 |
| WO | WO-2013/084165 A1 | 6/2013 |
| WO | WO-2014/042433 A2 | 3/2014 |
| WO | 2014078778 A2 | 5/2014 |
| WO | 2014116755 A1 | 7/2014 |
| WO | WO-2015/069939 A1 | 5/2015 |
| WO | WO-2016/069825 A1 | 5/2016 |
| WO | WO-2016/069826 A1 | 5/2016 |
| WO | WO-2016/069827 A1 | 5/2016 |
| WO | WO-2017/049060 A1 | 3/2018 |

OTHER PUBLICATIONS

European Patent Office, International Search Report and Written Opinion for International Patent Application No. PCT/US2016/052092, dated Oct. 11, 2016, 11 pages.

Cho, et al., Synthesis and antiviral activity of a series of 1'-substituted 4-aza-7,9-dideazaadenosine C-nucleosides, Bioorganic & Medicinal Chemistry Letters, 2012, pp. 2705-2707.

Warren, et al., Therapeutic efficacy of the small molecules GS-5734 against Ebola virus in rhesus monkeys, Nature, Mar. 17, 2016, 19 pages.

Alessandrini, et al., Synthesis of Differently Protected 1-C-methyl-ribofuranoses Intermediates for the Preparation of Biologically

(56) References Cited

OTHER PUBLICATIONS

Active 1'-C-methyl-ribonucleosides, Journal of Carbohydrate Chemistry, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Arimilli, M.N., et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
ARIPO Patent Office, Form 21 and Substantive Examination Report (in English) for AP Application No. AP/P/2010/005439, dated Mar. 18, 2014.
ARIPO Patent Office, Form 21 for AP Patent Application No. AP/P/2011/005818, Sep. 19, 2013.
ARIPO Patent Office, Official Action (ARIPO Form No. 18) with Substantive Search and Examination Report for AP Application No. AP/P/2010/005414, dated Mar. 14, 2014.
ARIPO Patent Office, Search and Exam Report for AP Application No. AP/P/2012/006189, dated Jun. 26, 2014.
ARIPO Patent Office, Search Report for AP Patent Application No. AP/P/2011/005818, dated Sep. 19, 2013.
Asbun, et al., Synthesis of 5-substituted Pyrimidines. II, Journal of Organic Chemistry, 1968, pp. 140-142, vol. 31.
Australia Patent Office, First Examination Report for AU Patent Application No. 2009240630, dated Jun. 14, 2012.
Australia Patent Office, First Examination Report for AU Patent Application No. 2009240642, dated Aug. 2, 2012.
Australia Patent Office, Patent Examination Report No. 1 for AU Application No. 2011280910, dated Jun. 10, 2014.
Australia Patent Office, Patent Examination Report No. 1 for AU Application No. 2011306066, dated Nov. 21, 2013.
Australia Patent Office, Patent Examination Report No. 1 for AU Patent Application No. 2010213873, dated Jun. 4, 2014.
Australia Patent Office, Patent Examination Report No. 1 for AU Patent Application No. 2010295392, dated Sep. 16, 2014.
Australia Patent Office, Patent Examination Report No. 1 for AU Patent Application No. 2011282241, dated Jul. 9, 2014.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of feline (FIPV) and human (SARS) coronavirus by semisynthetic derivatives of glycopeptide antibiotics, Antiviral Research, Mar. 14, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Belokon, et al., Optimized catalysts for the asymmetric addition of trimethylsilyl cyanide to aldehydes and ketones, Tetrahedron, 2001, pp. 771-779, vol. 57.
Benksim, et al., A Novel Stereospecific Synthesis of Glycosyl Cyanides from 1,2-O-sulfinyl Derivatives, Organic Letters, 2004, pp. 3913-3915, vol. 6, No. 22.
Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.
Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, G. et al., Design and Synthesis of Inhibitors of Adenosine and AMP Deaminases, Organic Letters, 2001, pp. 839-842, vol. 3, No. 6.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Brown, Progress towards improving antiviral therapy for hepatitis C virus polymerase inhibitors. Part O: Nucleoside analogues, 2009, pp. 709-725, vol. 18.
Bullard-Feibelman, et al., The FDA-approved drug Sofosbuvir inhibits Zika Virus infection, Antiviral Res., Jan. 1, 2018, pp. 134-140, vol. 137.
Burns, A glimmer of hope for a fatal feline disease, American Veterinary Medical Association, Dec. 15, 2017, 5 pages.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.
Cabirol, et al., Robust and Efficient, yet Uncatalyzed, Synthesis of Triarylsilyl-protected Cyanohydrins from Ketones, 2008, pp. 2446-2449, vol. 73.
Caira, Crystalline Polymorphism of Organic Compounds, Topics in Current Chemistry, 1998, pp. 163-208, vol. 198.
Calès, et al., Treatment of liver fibrosis: clinical aspects, Gastroentérologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple -αβ-butenolides-II, Tetrahedron, 1982, pp. 2395-2402, vol. 38, No. 15.
Canadian Patent Office, Office Action for CA Patent Application No. 2,773,772, dated Aug. 12, 2014.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Chapman, et al., RSV604, a Novel Inhibitor of Respiratory Syncytial Virus Replication, Antimicrobial Agents and Chemotherapy, 2007, pp. 3346-3353, vol. 51, No. 9.
Chile Patent Office, First Office Action for CL Patent Application No. 1906-2011, dated May 7, 2013.
Chile Patent Office, Opposition filed Against CL Patent Application 00076-2013, dated Jun. 18, 2014.
Chile Patent Office, Opposition for CL Patent Application No. 727-2013, dated Oct. 15, 2013.
Chile Patent Office, Second Office Action for CL Patent Application No. 1906-2011, dated Oct. 16, 2013.
Chinese Patent Office, First Examination Report for CN Patent Application No. 200980120218.8, dated Nov. 13, 2012.
Chinese Patent Office, First Office Action for CN Patent Application No. 201080011960.0, dated Jun. 8, 2013.
Chinese Patent Office, Notification of Reexamination for CN Patent Application No. 200980120218.8, dated Sep. 1, 2014.
Chinese Patent Office, Notification of the First Office Action and Search Report for CN Patent Application No. 201080041902.X, dated Nov. 12, 2013.
Chinese Patent Office, Notification of the First Office Action for CN Patent Application No. 201180035776.1, dated Feb. 27, 2014.
Chinese Patent Office, Notification of the First Office Action, with Search Report, for CN Patent Application No. 201080041946.2, dated Dec. 18, 2013.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Office Action for CN Patent Application No. 200980114224.2, dated Aug. 19, 2013.
Chinese Patent Office, Office Action for CN Patent Application No. 200980114224.2, dated Nov. 30, 2012.
Chinese Patent Office, Office Action with Search Report for CN Patent Application No. 201180035281.9, dated Jun. 27, 2014.
Chinese Patent Office, Rejection Decision for CN Patent Application No. 200980120218.8, dated Feb. 7, 2014.

(56) References Cited

OTHER PUBLICATIONS

Chinese Patent Office, Second Examination Report for CN Patent Application No. 200980120218.8, dated Jun. 21, 2013.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of [beta]-d-2'-deoxy-2'-[alpha]-fluoro-4'[alpha]-cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Columbia Patent Office, First Examination Report (in English) for CO Patent Application No. 10-131479, dated Oct. 23, 2012.
Columbia Patent Office, First Examination Report for CO Patent Application No. 10-121513-5, dated Dec. 10, 2012.
Columbia Patent Office, Office Action for CO Application No. 13 004212, dated Dec. 4, 2013.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-131479, Sep. 27, 2013.
Columbia Patent Office, Resolution No. 72986 for CO Patent Application No. 10-121513-5, Dec. 23, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dudfield, P. et al., Synthesis of C- ribosyl imidazo[2,1-f][1,2,4]triazines as inhibitors of adenosine and AMP deaminases, J. Chem. Soc, Perkin Trans I, 1999, pp. 2929-2936.
Dymock, et al., Novel approaches to the treatment of hepatitis C virus infection, Antiviral Chemistry & Chemotherapy, 2000, pp. 79-96, vol. 11, No. 2.
Ecuador Patent Office, Opposition for EC Patent Application No. SP-13-12451, Apr. 23, 2014.
Ecuador Patent Office, Opposition for EC Patent Application No. SP-2012-11817, May 27, 2013.
Ecuador Patent Office, Statement of Opposition for EC Patent Application No. SP-10-10609, Mar. 31, 2011.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
El Salvador Patent Office, Official Action for SV National Phase Entry of International Application No. PCT/US2010/049471, dated Nov. 6, 2013.
Eurasian Patent Office, First Examination Report for EA Patent Application No. 201071128, dated Apr. 25, 2012.
Eurasian Patent Office, First Examination Report for EA Patent Application No. 201071170, dated Apr. 25, 2012.
Eurasian Patent Office, First Office Action for EA Patent Application No. 201190110/28, dated Apr. 26, 2012.
Eurasian Patent Office, First Office Action for EA Patent Application No. 201390141/28, with English translation, dated Aug. 14, 2014.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Examination Report for EA Patent Application No. 201071170, dated Oct. 25, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Examination Report for EA Patent Application No. 201071170, dated Oct. 10, 2013.
Eurasian Patent Office, Third Office Action for EA Application No. 201190110/28, dated Oct. 18, 2013.
European Patent Office, Communication pursuant to Article 94(3) EPC for EP Patent Application No. 10763083.2, dated May 2, 2014.
European Patent Office, Communication pursuant to Article 94(3) EPC for EP Patent Application No. 11715792.5, dated Feb. 14, 2014.
European Patent Office, Communication under 161/162 for EP Patent Application No. 10704068.5, dated Sep. 6, 2011.
European Patent Office, Communication under 161/162 for EP Patent Application No. 10763083.2, dated May 11, 2012.
European Patent Office, Communication under 161/162 for EP Patent Application No. 11715792.5, dated Apr. 26, 2013.
European Patent Office, Communication under 161/162 for EP Patent Application No. 11743400.1, dated Feb. 26, 2013.
European Patent Office, Communication under 161/162 for EP Patent Application No. 11743709.5, dated Mar. 1, 2013.
European Patent Office, Extended European Search Report for EP Application No. 13194605.5, dated Mar. 13, 2014.
European Patent Office, First Office Action for EP Patent Application No. 10704068.5, dated Jun. 18, 2012.
European Patent Office, International Preliminary Report on Patentability and Written Opinion for PCT International Application No. PCT/US2009/041432, dated Oct. 26, 2010, 7 pages.
European Patent Office, International Preliminary Report on Patentability and Written Opinion for PCT International Application No. PCT/US2010/049471, dated Mar. 27, 2012, 7 pages.

(56) References Cited

OTHER PUBLICATIONS

European Patent Office, International Preliminary Report on Patentability and Written Opinion for PCT International Application No. PCT/US2010/049508, dated Mar. 27, 2012, 6 pages.
European Patent Office, International Preliminary Report on Patentability and Written Opinion for PCT International Application No. PCT/US2011/038253, dated Dec. 4, 2012, 6 pages.
European Patent Office, International Preliminary Report on Patentability and Written Opinion for PCT International Application No. PCT/US2011/044581, dated Jan. 22, 2013, 7 pages.
European Patent Office, International Preliminary Report on Patentability for PCT International Application No. PCT/US2009/041447, dated Oct. 26, 2010, 7 pages.
European Patent Office, International Preliminary Report on Patentability for PCT International Application No. PCT/US2010/023586, dated Aug. 16, 2011, 6 pages.
European Patent Office, International Preliminary Report on Patentability for PCT International Application No. PCT/US2011/028897, dated Mar. 26, 2013, 7 pages.
European Patent Office, International Preliminary Report on Patentability for PCT International Application No. PCT/US2011/029441, dated Mar. 26, 2013, 7 pages.
European Patent Office, International Preliminary Report on Patentability for PCT International Application No. PCT/US2011/045102, dated Jan. 22, 2013, 5 pages.
European Patent Office, International Preliminary Report on Patentability for PCT International Application No. PCT/US2015/057932, dated May 2, 2017, 11 pages.
European Patent Office, International Preliminary Report on Patentability for PCT International Application No. PCT/US2015/057933, dated May 2, 2017, 7 pages.
European Patent Office, International Preliminary Report on Patentability for PCT International Application No. PCT/US2015/057934, dated May 2, 2017, 14 pages.
European Patent Office, International Search Report and Written Opinion for PCT International Application No. PCT/US2009/041447, dated Aug. 7, 2009, 5 pages.
European Patent Office, International Search Report and Written Opinion for PCT International Application No. PCT/US2010/023586, dated Aug. 4, 2010, 4 pages.
European Patent Office, International Search Report and Written Opinion for PCT International Application No. PCT/US2010/049471, dated Nov. 18, 2010, 5 pages.
European Patent Office, International Search Report and Written Opinion for PCT International Application No. PCT/US2010/049508, dated Nov. 5, 2010, 4 pages.
European Patent Office, International Search Report and Written Opinion for PCT International Application No. PCT/US2011/028897, dated Aug. 1, 2011, 6 pages.
European Patent Office, International Search Report and Written Opinion for PCT International Application No. PCT/US2011/029441, dated Aug. 1, 2011, 5 pages.
European Patent Office, International Search Report and Written Opinion for PCT International Application No. PCT/US2011/038253, dated Jul. 29, 2011, 4 pages.
European Patent Office, International Search Report and Written Opinion for PCT International Application No. PCT/US2011/044581, dated Nov. 7, 2011, 4 pages.
European Patent Office, International Search Report and Written Opinion for PCT International Application No. PCT/US2011/045102, dated Nov. 9, 2011, 4 pages.
European Patent Office, International Search Report and Written Opinion for PCT International Application No. PCT/US2015/057932, dated May 6, 2016, 7 pages.
European Patent Office, International Search Report and Written Opinion for PCT International Application No. PCT/US2015/057933, dated Jan. 21, 2016, 9 pages.
European Patent Office, International Search Report and Written Opinion for PCT International Application No. PCT/US2015/057934, dated Mar. 18, 2016, 20 pages.
European Patent Office, International Search Report and Written Opinion for PCT International Application No. PCT/US2017/028243, dated Aug. 29, 2017, 12 pages.
European Patent Office, International Search Report and Written Opinion for PCT International Application No. PCT/US2017/028251, dated Sep. 13, 2017, 22 pages.
European Patent Office, International Search Report and Written Opinion for PCT International Application No. PCT/US2018/022166, dated May 25, 2018, 13 pages.
European Patent Office, International Search Report and Written Opinion for PCT International Application No. PCT/US2018/029974, dated Sep. 18, 2018, 21 pages.
European Patent Office, International Search Report for PCT International Application No. PCT/US2009/041432, dated Aug. 11, 2009, 5 pages.
Farquhar, et al., Biologically Reversible Phosphate-Protective Groups, Journal of Pharmaceutical Sciences, 1983, pp. 324-325, vol. 72, No. 3.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, et al., Protective Groups in Organic Synthesis, 1991, pp. 118-142, John Wiley & Sons.
Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.
Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, K. et al., Stereoselective Synthesis of 1'-C-Branched Uracil Nucleosides From Uridine, Nucleosides & Nucleotides, 1995, pp. 417-420, vol. 14, No. 3-5.
Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.
Hayashi, M. et al., C-Nucleosides, A Synthesis of 2-Substituted 7-(b-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.
Hecker, et al., Liver Targeted Prodrugs of 2'-C-Methyladenosine for Therapy of Hepatitis C Virus Infection, J. Med. Chem., 2007, pp. 3891-3896, vol. 50, No. 16.
Hoffmann, et al., When, in the context of drug design, can a fluorine atom successfully substitute a hydroxyl group?, International Journal of Quantum Chemistry, 2002, pp. 419-427, vol. 89.

(56) References Cited

OTHER PUBLICATIONS

Indonesia Patent Office, First Examination Report for ID Patent Application No. W00 2010 03923, dated Apr. 5, 2013.
Indonesia Patent Office, First Examination Report for ID Patent Application No. W00 2010 03957, dated Apr. 25, 2013.
Indonesia Patent Office, Substantive Examination Report Stage 1 for ID Application No. W-00201103126, dated Jun. 10, 2014.
Israel Patent Office, First Examination Report for IL Patent Application No. 208515, dated Jan. 6, 2013.
Israel Patent Office, First Examination Report for IL Patent Application No. 208701, dated Jan. 13, 2013.
Israel Patent Office, First Office Action for IL Patent Application No. 214396, dated Jul. 8, 2013.
Israel Patent Office, Notification of Defects for IL Patent Application No. 208515, dated Aug. 25, 2014.
Israel Patent Office, Notification of Defects for IL Patent Application No. 214396, dated Nov. 11, 2013.
Israel Patent Office, Notification of Defects for IL Patent Application No. 218599, dated Aug. 25, 2014.
Israel Patent Office, Notification of Defects for IL Patent Applicaton No. 208701, dated Aug. 25, 2014.
Israel Patent Office, Notification Prior to Examination for IL Patent Application No. 218599, dated Nov. 13, 2012.
Israel Patent Office, Notification Prior to Examination for IL Patent Application No. 218752, dated Jan. 20, 2014.
Israel Patent Office, Supplement to First Examination Report for IL Patent Application No. 208515, dated Jan. 15, 2013.
Itoh, Y. et al., Divergent and Stereocontrolled Approach to the Synthesis of Uracil Nucleosides Branched at the Anomeric Position, J. Org. Chem., 1995, pp. 656-662, vol. 60.
Japanese Patent Office, First Examination Report for JP Patent Application No. 2011-506429, dated Aug. 22, 2013.
Japanese Patent Office, First Examination Report for JP Patent Application No. 2011-506435, dated Aug. 22, 2013.
Japanese Patent Office, Notification of Reasons for Rejection for JP Application No. 2011-549324, dated Jul. 28, 2014.
Japanese Patent Office, Notification of Reasons for Rejection for JP Application No. 2011-549324, dated Mar. 26, 2014.
Japanese Patent Office, Notification of Reasons for Rejection for JP Patent Application No. 2012-529958, dated Aug. 5, 2014.
Japanese Patent Office, Notification of Reasons for Rejection for JP Patent Application No. 2012-529963, dated Aug. 28, 2014.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.
Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.
Khamnei, et al., Neighboring Group Catalysis in the Design of Nucleotide Prodrugs, J. Med. Chem., 1996, pp. 4109-4115, vol. 39, No. 20.
Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistry, 2006, pp. 3793-3799, vol. 281, No. 7.
Knutsen, L. et al., Synthesis of Imidazo-fused Bridgehead-nitrogen C-Nucleosides : Coupling-Elimination Reactions of 2,5-Anhydro-3,4,6-tri-O-benzoyl-D- allonic Acid, J. Chem. Soc. Perkin Trans I, 1985, pp. 621-630.
Knutsen, L. et al., Synthesis of Imidazo-fused Bridgehead-nitrogen C-Nucleosides via Dehydrative Coupling Reactions of 2,5-Anhydro-3,4,6-tri-O-benzoyl-D- allonic Acid, J. Chem. Soc. Perkin Trans I, 1984, pp. 229-238.
Kobe, et al., Use of Distance Geometry Approach for the in Vitro Antiviral Activity Evaluation of N-bridgehead C-nucleosides, European J. Med. Chem., 1992, pp. 259-266, vol. 27, No. 3.

Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.
Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.
Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.
Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.
Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.
Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.
Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.
McGuigan, et al., Intracellular Delivery of Bioactive AZT Nucleotides by Aryl Phosphate Derivatives of Azt, J. Med. Chem., 1993, pp. 1048-1052, vol. 36, No. 8.
Meppen, et al., Cyclic phosphoramidates as prodrugs of 2'-C-methylcytidine, European Journal of Medicinal Chemistry, 2009, pp. 3765-3770, vol. 49, No. 9.
Meppen, et al., Medi-404—A Prodrug Approach for the Treatment of HCV Infection, Abstracts of papers, 236th ACS National Meeting, Philadelphia, PA, United States, Aug. 17-21, 2008.
Metobo, et al., Practical synthesis of 10-substituted Tubercidin C-nucleoside analogs, Tetrahedron Letters, 2011, pp. 484-486, vol. 53.
Mexico Patent Office, English translation of Office Action for MX Application No. MX/a/2013/003179, dated Feb. 25, 2014.
Mexico Patent Office, First Examination Report (in English) for MX Patent Application No. MX/a/2010/011661, dated Oct. 26, 2011.
Mexico Patent Office, Office Action for MX Application No. MX/a/2011/008409, dated Mar. 25, 2014.
Mexico Patent Office, Office Action for MX Application No. MX/a/2013/000656, dated Apr. 22, 2014.
Mexico Patent Office, Office Action for MX Application No. MX/a/2013/000656, dated Aug. 4, 2014.
Mexico Patent Office, Office Action for MX Application No. MX/a/2013/000744, dated Apr. 22, 2014.
Migliaccio, et al., Characterization of Resistance to Non-obligate Chain-terminating Ribonucleoside Analogs That Inhibit Hepatitis C Virus Replication in vitro, The Journal of Biological Chemistry, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.

(56) References Cited

OTHER PUBLICATIONS

Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.

Murphy, et al., The nucleoside analog GS-441524 strongly inhibits feline infections peritonitis (FIP) virus in tissue culture and experimental cat infection studies, Veterinary Microbiology, ND, pp. 226-233, vol. 219.

Neumann, et al., Hepatitis C Viral Dynamics in Vivo and the Antiviral Efficacy of Interferon-α Therapy, Science, 1998, pp. 103-107, vol. 282.

New Zealand Patent Office, First Examination Report for NZ Patent Application No. 588400, dated Apr. 11, 2011.

New Zealand Patent Office, First Examination Report for NZ Patent Application No. 588670, dated Apr. 8, 2011.

New Zealand Patent Office, First Examination Report for NZ Patent Application No. 608070, dated Nov. 7, 2013.

New Zealand Patent Office, Further Examination Report for NZ Application No. 594370, dated Oct. 8, 2013.

New Zealand Patent Office, Second Examination Report and Notice of Acceptance for NZ Patent Application No. 588400, dated Jul. 27, 2012.

Nishimura, et al., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.

Ogura, et al., Reaction of Ethynyl Compounds with Lactones, Journal of Organic Chemistry, 1972, pp. 72-75, vol. 37, No. 1.

Otter, B. et al., Conformational Properties of Purine-Like C-Nucleosides, Nucleosides & Nucleotides, 1996, pp. 793-807, vol. 15, No. 1-3.

Pankiewicz, et al., C-Nucleoside Analogues of Nicotinamide Mononucleotide (NMN), Nucleosides and Nucleotides, 1988, pp. 589-593, vol. 7, No. 5&6.

Pankiewicz, et al., Efficient Synthesis of 5-(β-D-Ribofuranosyl)nicotinamide and its α-Isomer, Journal of Organic Chemistry, 1988, pp. 3473-3479, vol. 53.

Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.

Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.

Patil, et al., Synthesis of some new thieno[3,4-d]pyrimidines and their C-nucleosides, Journal of Heterocyclic Chemistry, 1993, pp. 509-515, vol. 30, No. 2.

Patil, S. et al., 4-Aza-7,9-Dideazaadenosine, a New Cytotoxic Synthetic C-Nucleoside Analogue of Adenosine, Tetrahedron Letters, 1994, pp. 5339-5342, vol. 35, No. 30.

Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.

Peru Patent Office, Office Action in PE Application No. 1464, dated Sep. 12, 2013.

Piccirilli, et al., A Direct Route to 3-(D-Ribofuranosyl)pyridine Nucleosides, Helvetica Chimica Acta, 1991, pp. 397-406, vol. 74.

Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.

Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.

Puech, et al., Intracellular Delivery of Nucleoside Monophosphates through a Reductase-mediated Activation Process, Antiviral Research, 1993, pp. 155-174, vol. 22, No. 4.

Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.

Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.

Reddy, et al., Stereoselective Synthesis of Nucleoside Monophosphate HepDirectTM Prodrugs, Tet. Lett., 2005, pp. 4321-4324, vol. 46.

Sacramento, et al., The clinically approved antiviral drug Sofosbuvir inhibits Zika Virus replication, Nature, Jan. 18, 2017.

Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.

Schultz, Prodrugs of Biologically Active Phosphate Esters, Bioorganic & Medicinal Chemistry, 2003, pp. 885-898, vol. 11.

Scott, et al., Interferon-a-2b Plus Ribavirin: A Review of its Use in the Management of Chronic Hepatitis C, Drugs, 2002, pp. 507-556, vol. 62, No. 3.

Shekunov, et al., Crystallization processes in pharmaceutical technology and drug delivery design, Journal of Crystal Growth, 2000, pp. 122-136, vol. 211.

Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Jan. 26, 2017, 51 pages.

Silverman et al., The Organic Chemistry of Drug Design and Drug Action, 1992, pp. 19-23.

Silverman, The Organic Chemistry of Drug Design and Drug Action, 2nd Ed., 2004, pp. 29-34.

Srivastav, et al., Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.

Taiwan Patent Office, First Examination Report for TW Patent Application No. 098113324, dated Oct. 30, 2012.

Taiwan Patent Office, Office Action with Search Report for TW Patent Application No. 099131868, dated May 22, 2014.

Taiwan Patent Office, Office Action with Search Report for TW Patent Application No. 102115415, dated May 15, 2014.

Tapia, et al., Combination of a Mutagenic Agent with a Reverse Transcriptase Inhibitor Results n Systematic Inhibition of HIV-1 Infection, Virology, 2005, pp. 1-8, vol. 338.

Uchiyama, et al., O-selective Phosphorylation of Nucleosides without N-protection, J. Org. Chem., Jan. 1, 1993, vol. 58, No. 2.

Ukraine Patent Office, First Examination Report for UA Patent Application No. 2010 13030, dated Mar. 2, 2013.

Ukraine Patent Office, First Office Action for UA Application No. a 2011 10568, dated Apr. 7, 2014.

Ukraine Patent Office, Second Office Action for UA Patent Application No. 2011 10568, dated Aug. 11, 2014.

United States Patent and Trademark Office, Final Rejection for U.S. Appl. No. 12/886,248, dated Aug. 21, 2014.

United States Patent and Trademark Office, Notice of Allowance for U.S. Appl. No. 13/649,511, dated Feb. 13, 2014.

United States Patent and Trademark Office, Notice of Allowance for U.S. Appl. No. 13/649,511, dated Jun. 3, 2014.

United States Patent and Trademark Office, Notice of Allowance for U.S. Appl. No. 12/428,176, dated Apr. 12, 2011.

United States Patent and Trademark Office, Notice of Allowance for U.S. Appl. No. 12/428,176, dated Jan. 6, 2011.

United States Patent and Trademark Office, Notice of Allowance for U.S. Appl. No. 12/428,234, dated Apr. 7, 2011.

United States Patent and Trademark Office, Notice of Allowance for U.S. Appl. No. 12/702,957, dated Apr. 26, 2011.

United States Patent and Trademark Office, Notice of Allowance for U.S. Appl. No. 12/885,917, dated Feb. 17, 2011.

United States Patent and Trademark Office, Notice of Allowance for U.S. Appl. No. 13/050,820, dated Jan. 31, 2013.

(56) References Cited

OTHER PUBLICATIONS

United States Patent and Trademark Office, Notice of Allowance for U.S. Appl. No. 13/117,060, dated Aug. 10, 2012.
United States Patent and Trademark Office, Notice of Allowance for U.S. Appl. No. 13/117,060, dated Nov. 28, 2012.
United States Patent and Trademark Office, Notice of Allowance for U.S. Appl. No. 13/196,117, dated Jul. 16, 2012.
United States Patent and Trademark Office, Notice of Allowance for U.S. Appl. No. 13/196,117, dated Mar. 27, 2012.
United States Patent and Trademark Office, Office Action (Restriction Requirement) for U.S. Appl. No. 12/886,248, dated Sep. 14, 2012.
United States Patent and Trademark Office, Office Action for U.S. Appl. No. 14/613,719, dated Jul. 21, 2016.
United States Patent and Trademark Office, Office Action for U.S. Appl. No. 14/613,719, dated Nov. 4, 2016.
United States Patent and Trademark Office, Office Action for U.S. Appl. No. 12/428,234, dated Dec. 23, 2010.
United States Patent and Trademark Office, Office Action for U.S. Appl. No. 12/702,957, dated Dec. 23, 2010.
United States Patent and Trademark Office, Office Action for U.S. Appl. No. 12/886,248, dated Mar. 4, 2013.
United States Patent and Trademark Office, Office Action for U.S. Appl. No. 12/886,248, dated Nov. 6, 2012.
United States Patent and Trademark Office, Office Action for U.S. Appl. No. 13/050,820, dated Mar. 27, 2012.
United States Patent and Trademark Office, Office Action for U.S. Appl. No. 13/050,820, dated Oct. 16, 2012.
United States Patent and Trademark Office, Office Action for U.S. Appl. No. 13/196,117 dated Sep. 23, 2011.
United States Patent and Trademark Office, Office Action for U.S. Appl. No. 13/649,511, dated Aug. 15, 2013.
United States Patent and Trademark Office, Office Action for U.S. Appl. No. 13/649,511, dated Jan. 22, 2013.
United States Patent and Trademark Office, Office Action for U.S. Appl. No. 13/813,886, dated Sep. 24, 2014.
United States Patent and Trademark Office, Pre-Appeal Brief for U.S. Appl. No. 14/613,719, dated Feb. 6, 2017.
United States Patent and Trademark Office, Pre-Appeal Decision for U.S. Appl. No. 14/613,719, dated Mar. 14, 2017.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Vietnam Patent Office, First Examination Report for VN Patent Application No. 1-2010-02653, dated Apr. 26, 2012.
Vietnam Patent Office, First Examination Report for VN Patent Application No. 1-2010-02939, dated Apr. 19, 2012.
Vietnam Patent Office, First Office Action for VN Patent Application No. 1-2012-03895, dated Feb. 8, 2013.
Vietnam Patent Office, Second Examination Report for VN Patent Application No. 1-2010-02939, dated Jul. 26, 2012.
Wu, et al., Synthetic Methodologies for C-Nucleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.
Yoshimura, Y. et al., Synthesis and Biological Evaluation of 1'-C-Cyano-Pyrimidine Nucleosides, Nucleosides & Nucleotides, 1996, pp. 305-324, vol. 15, No. 1-3.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.
Barl, et al., The halogen/magnesium-exchange using iPrMgCl—LiCl and related exchange reagents, Heterocycles, Jan. 2014, pp. 827-844, vol. 88, No. 2.
Cho, et al., Practical synthesis of 1'-substituted Tubercidin C-nucleoside analogs, Tetrahedron Letters, Feb. 2012, pp. 484-486, vol. 53, No. 5.

\* cited by examiner

FIG. 3A
FIG. 3B
FIG. 3C
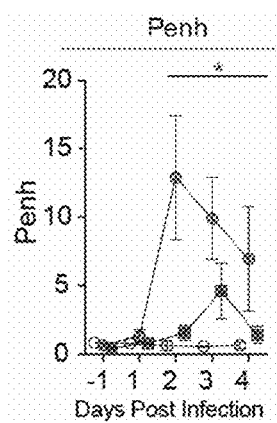
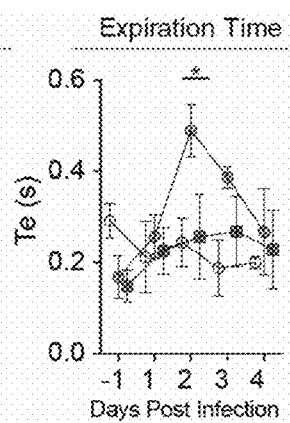
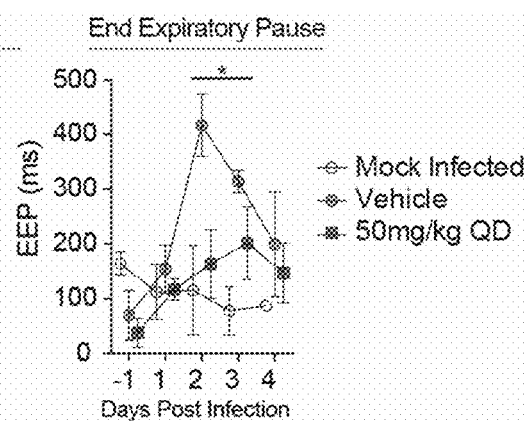
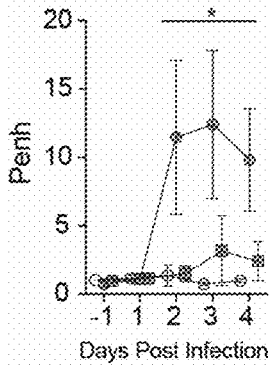
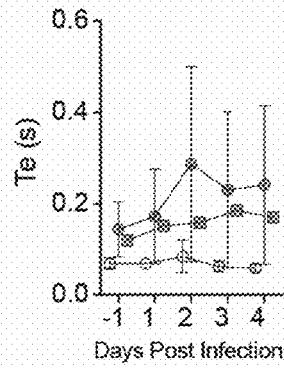
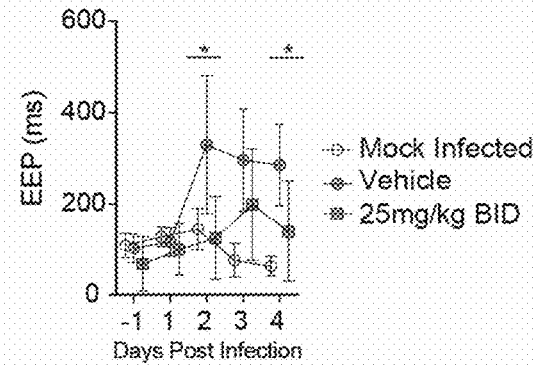
FIG. 3D
FIG. 3E
FIG. 3F

METHODS FOR TREATING ARENAVIRIDAE AND CORONAVIRIDAE VIRUS INFECTIONS

CROSS-REFERENCES TO RELATED APPLICATIONS

This patent application claims the benefit under 35 U.S.C. § 119(e) of U.S. Provisional Patent Application No. 62/219,302, filed Sep. 16, 2015 and U.S. Provisional Application No. 62/239,696, filed Oct. 9, 2015. The foregoing applications are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 1137P2C_2016-11-28_Sequence_Listing.txt, date recorded: Nov. 29, 2016, size: 1 KB).

FIELD OF THE INVENTION

The invention relates generally to methods and compounds for treating Arenaviridae virus infections, particularly methods and nucleosides and prodrugs thereof for treating Lassa virus and Junin virus. The invention relates generally to methods and compounds for treating Coronaviridae virus infections, particularly methods and nucleosides and prodrugs thereof for treating SARS virus and MERS virus.

BACKGROUND OF THE INVENTION

Lassa virus is a segmented negative-sense RNA virus that belongs to the family Arenaviridae. Arenaviruses are further sub-divided into the Old World and New World virus complexes based on serological cross-reactivity, phylogenetic relations, and geographical distribution, (Wulff, 1978; Bowen, 1997). The New World arenavirus complex comprises viruses that circulate in North America (i.e., Whitewater Arroyo (WWAV), Tamiami (TAMV), and Bear Canyon (BCNV) viruses) and South America (i.e., Tacaribe (TACV), Junin (JUNV), Machupo (MACV), Guanarito (GTOV), and Sabia (SABV) viruses). The Old World complex includes arenaviruses that circulate in Africa, Europe, and Asia (i.e., lymphocytic choreomeningitis (LCMV) and Lassa (LASV) viruses). The range of reservoir rodent species restricts the geographic occurrence of arenaviruses, with the exception of LCMV that is distributed worldwide due to its association with *Mus domesticus* and *M. musculus*, which have migrated globally (Salazar-Bravo, 2002). The reservoir hosts of LASV are rodents of the genus *Mastomys* that are enzootic in sub-Saharan Africa (Salazar-Bravo, 2002). At least seven arenaviruses are known to cause severe hemorrhagic fever in humans, among which are LASV, JUNV, MACV, GTOV, and SABV that are endemic in West Africa, Argentina, Bolivia, Venezuela, and Brazil, respectively, and recently discovered Lujo (LUJV) and Chapare (CHAPV) viruses that originated in Zambia and Bolivia, respectively (Breise, 2009; Delgado, 2008).

Lassa virus (LASV) is endemic to West Africa with an estimated 300,000-500,000 people infected annually (McCormick, 1987). Transmission occurs through contact with infected rodents (*Mastomys natalensis*) or virus-contaminated rodent excreta, and person-to-person transmission, especially in hospital settings, has been documented (McCormick, 1987). Disease caused by LASV ranges from subclinical infection to mild to severe hemorrhagic fever that is associated with multi-organ failure. Mortality rates associated with LASV infection vary and range from approximately 2% to 15% for hospitalized cases and can exceed 50% in certain outbreak scenarios (McCormick, 1987; Fisher-Hoch, 1995). Despite the high incidence and associated morbidity and mortality, there is no approved therapy to treat LASV infection in humans. Supportive care and early administration of ribavirin are current standard of care.

LASV initially infects monocytes, macrophages, and dendritic cells and spreads systemically to produce a primary viremia that leads to infection of internal organs. Virus replication leads to a rise in inflammatory cytokine levels and development of coagulopathies resulting in vascular leakage, hypovolemic shock and multi-organ failure (Hensley, 2011).

Replication of arenaviruses is catalyzed by the L polymerase protein that utilizes viral RNA templates that consist of genomic RNA encapsidated by the viral nucleocapsid protein NP and comprises viral ribonucloprotein (RNP) (Buchmeier, 2007). Replication is initiated upon viral entry into the host cell where the L polymerase, associated with the viral RNP, initiates transcription from the genome promoter located at the 3'-end of each genomic RNA segment, L and S. The primary transcription event results in the synthesis of NP and L polymerase mRNA encoded in antigenomic orientationfrom the S and L segments, respectively. Transcription terminates at the distal side of the stem-loop (SL) structure within the intergenomic region (IGR). Arenaviruses utilize a cap snatching strategy to acquire the cap structures of cellular mRNAs to facilitate translation. Cap snatching is mediated by the endonuclease activity of the L polymerase that is co-factored by the cap binding activity of NP to produce capped non-polyadenylated mRNAs. Subsequently, the L polymerase adopts a replicase mode and moves across the IGR to generate a full-length complementary antigenomic RNA (agRNA). This agRNA serves as a template for the synthesis of GPC and Z mRNAs encoded in genomic orientationfrom the S and L segments, respectively, and for the synthesis of full-length genomic RNA (gRNA) (Buchmeier, 2007; Franze-Fernandez, 1987; Meyer, 1993; Qi, 2010; Lelke, 2010; Morin, 2010).

Human coronaviruses, first identified in the mid-1960s, are common viruses that infect most people at some time in their life, generally causing mild to moderate upper respiratory and gastrointestinal tract illnesses. The novel coronavirus referred to as "Middle East Respiratory Syndrome Coronavirus" (MERS-CoV or MERS) was first reported in Saudi Arabia in 2012 and has spread to several other countries. SARS-CoV, the coronavirus responsible for Severe Acute Respiratory Syndrome (SARS) was first recognized in China in 2002 and led to a worldwide outbreak in 2002 and 2003.

SUMMARY OF THE INVENTION

Provided are methods and compounds for the treatment of infections caused by the Arenaviridae virus family.

Provided is a method for treating an Arenaviridae infection in a human in need thereof comprising administering a therapeutically effective amount of a compound of Formula I:

Formula I

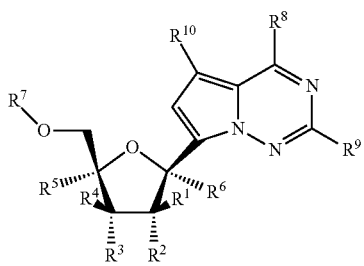

or a pharmaceutically acceptable salt or ester, thereof; wherein:
each $R^1$ is H or halogen;
each $R^2$, $R^3$, $R^4$ or $R^5$ is independently H, $OR^a$, $N(R^a)_2$, $N_3$, CN, $NO_2$, $S(O)_nR^a$, halogen, $(C_1\text{-}C_8)$alkyl, $(C_4\text{-}C_8)$carbocyclylalkyl, $(C_1\text{-}C_8)$substituted alkyl, $(C_2\text{-}C_8)$alkenyl, $(C_2\text{-}C_8)$substituted alkenyl, $(C_2\text{-}C_8)$alkynyl or $(C_2\text{-}C_8)$substituted alkynyl;
or any two $R^2$, $R^3$, $R^4$ or $R^5$ on adjacent carbon atoms when taken together are —O(CO)O— or when taken together with the ring carbon atoms to which they are attached form a double bond;
$R^6$ is $OR^a$, $N(R^a)_2$, $N_3$, CN, $NO_2$, $S(O)_nR^a$, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, halogen, $(C_1\text{-}C_8)$alkyl, $(C_4\text{-}C_8)$carbocyclylalkyl, $(C_1\text{-}C_8)$substituted alkyl, $(C_2\text{-}C_8)$alkenyl, $(C_2\text{-}C_8)$substituted alkenyl, $(C_2\text{-}C_8)$alkynyl, $(C_2\text{-}C_8)$substituted alkynyl, or $(C_6\text{-}C_{20})$aryl$(C_1\text{-}C_8)$alkyl;
$R^7$ is selected from a group consisting of
a) H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), or —SO$_2$N$R^{11}R^{12}$, wherein each $(C_1\text{-}C_8)$alkyl, $(C_2\text{-}C_8)$alkenyl, $(C_2\text{-}C_8)$alkynyl or $(C_6\text{-}C_{20})$aryl$(C_1\text{-}C_8)$alkyl of each $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1\text{-}C_8)$alkyl may be optionally replaced with —O—, —S— or —$NR^a$—, b)
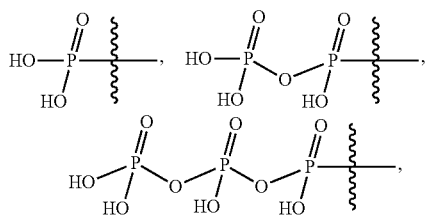

c)
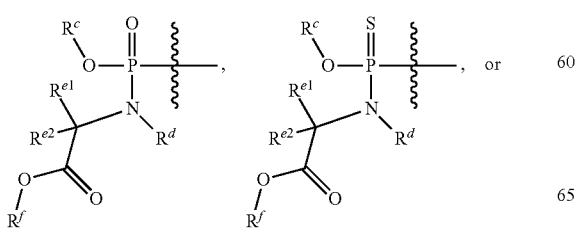

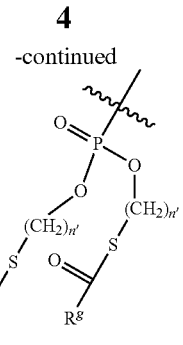

wherein:
$R^c$ is selected from phenyl, 1-naphthyl, 2-naphthyl,

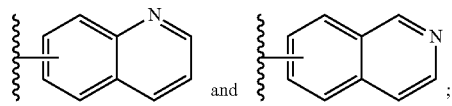

$R^d$ is H or $CH_3$;
$R^{e1}$ and $R^{e2}$ are each independently H, $(C_1\text{-}C_6)$alkyl or benzyl;
$R^f$ is selected from H, $(C_1\text{-}C_8)$alkyl, benzyl, $(C_3\text{-}C_6)$cycloalkyl, and —$CH_2$—$(C_3\text{-}C_6)$cycloalkyl;
$R^g$ is selected from $(C_1\text{-}C_8)$alkyl, —O—$(C_1\text{-}C_8)$alkyl, benzyl,
—O-benzyl, —$CH_2$—$(C_3\text{-}C_6)$cycloalkyl,
—O—$CH_2$—$(C_3\text{-}C_6)$cycloalkyl, and $CF_3$; and
n' is selected from 1, 2, 3, and 4; and
d) a group of the formula:

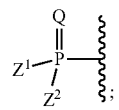

wherein:
Q is O, S, NR, $^+$N(O)(R), N(OR), $^+$N(O)(OR), or N—$NR_2$;
$Z^1$ and $Z^2$, when taken together, are -$Q^1$(C($R^y$)$_2$)$_3Q^1$-;
wherein
each $Q^1$ is independently O, S, or NR; and
each $R^y$ is independently H, F, Cl, Br, I, OH, R, —C(=$Q^2$)R, —C(=$Q^2$)OR, —C(=$Q^2$)N(R)$_2$, —N(R)$_2$, —$^+$N(R)$_3$, —SR, —S(O)R, —S(O)$_2$R, —S(O)(OR), —S(O)$_2$(OR), —OC(=$Q^1$)R, —OC(=$Q^2$)OR, —OC(=$Q^2$)(N(R)$_2$), —SC(=$Q^2$)R, —SC(=$Q^2$)OR, —SC(=$Q^2$)(N(R)$_2$), —N(R)C(=$Q^2$)R, —N(R)C(=$Q^2$)OR, —N(R)C(=$Q^2$)N(R)$_2$, —SO$_2$NR$_2$, —CN, —$N_3$, —$NO_2$, —OR, or $Z^3$; or when taken together, two $R^y$ on the same carbon atom form a carbocyclic ring of 3 to 7 carbon atoms;
each $Q^2$ is independently, O, S, NR, $^+$N(O)(R), N(OR), $^+$N(O)(OR), or N—$NR_2$; or
$Z^1$ and $Z^2$ are each, independently, a group of the Formula Ia:

Formula Ia $$\left[ R^x \!-\!\!\left(\!\!Q^3\!-\!\!\underset{\underset{R^x}{\overset{\overset{Q^2}{\|}}{\underset{Q^3}{|}}}}{P}\!-\!\!Q^3\!\right)\!\!\right]_{M2}$$

wherein:
each $Q^3$ is independently a bond, O, $CR_2$, NR, $^+N(O)(R)$, $N(OR)$, $^+N(O)(OR)$, $N\!-\!NR_2$, S, S—S, S(O), or $S(O)_2$;
M2 is 0, 1 or 2;
each $R^x$ is independently $R^y$ or the formula:

$$\left\{\!\!\left[\!\underset{\underset{M1a}{}}{\overset{\overset{Q^2}{\|}}{\underset{Q^3}{|}}}\!\right]\!\!\left[\underset{\underset{M12c}{}}{\overset{R^y\;\;R^y}{\bigvee}}\right]\!\!\left(\!Q^3\!\right)_{\!\!M1c}\!\!\left[\underset{\underset{M1d}{}}{\overset{\overset{Q^2}{\|}}{\underset{Q^3}{|}}}\!\right]\!\!R^y\right.$$

wherein:
each M1a, M1c, and M1d is independently 0 or 1;
M12c is 0, 1, 2, 3, 4, 5, 6, 7, 8, 9, 10, 11 or 12;
$Z^3$ is $Z^4$ or $Z^5$;
$Z^4$ is R, $-C(Q^2)R^y$, $-C(Q^2)Z^5$, $-SO_2R^y$, or $-SO_2Z^5$; and
$Z^5$ is a carbocycle or a heterocycle wherein $Z^5$ is independently substituted with 0 to 3 $R^y$ groups;
$R^8$ is halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1\text{-}C_8)$alkyl, $(C_2\text{-}C_8)$alkenyl, $(C_2\text{-}C_8)$alkynyl, $(C_4\text{-}C_8)$carbocyclylalkyl, $(C_6\text{-}C_{20})$optionally substituted aryl, optionally substituted heteroaryl, $-C(=O)(C_1\text{-}C_8)$alkyl, $-S(O)_n(C_1\text{-}C_8)$alkyl, $(C_6\text{-}C_{20})$aryl$(C_1\text{-}C_8)$alkyl, $OR^{11}$ or $SR^{11}$;
each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $R^{11}$, $OR^{11}$ or $SR^{11}$;
each $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$carbocyclylalkyl, $(C_6\text{-}C_{20})$optionally substituted aryl, optionally substituted heteroaryl, $-C(=O)(C_1\text{-}C_8)$alkyl, $-S(O)_n(C_1\text{-}C_8)$alkyl or $(C_6\text{-}C_{20})$aryl$(C_1\text{-}C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or $-NR^a-$;
each $R^a$ is independently H, $(C_1\text{-}C_8)$alkyl, $(C_2\text{-}C_8)$alkenyl, $(C_2\text{-}C_8)$alkynyl, $(C_6\text{-}C_{20})$aryl$(C_1\text{-}C_8)$alkyl, $(C_4\text{-}C_8)$carbocyclylalkyl, $-C(=O)R$, $-C(=O)OR$, $-C(=O)NR_2$, $-C(=O)SR$, $-S(O)R$, $-S(O)_2R$, $-S(O)(OR)$, $-S(O)_2(OR)$, or $-SO_2NR_2$;
each R is independently H, $(C_1\text{-}C_8)$ alkyl, $(C_1\text{-}C_8)$ substituted alkyl, $(C_2\text{-}C_8)$alkenyl, $(C_2\text{-}C_8)$ substituted alkenyl, $(C_2\text{-}C_8)$ alkynyl, $(C_2\text{-}C_8)$ substituted alkynyl, $(C_6\text{-}C_{20})$aryl, $(C_6\text{-}C_{20})$substituted aryl, $(C_2\text{-}C_{20})$heterocyclyl, $(C_2\text{-}C_{20})$substituted heterocyclyl, $(C_6\text{-}C_{20})$aryl$(C_1\text{-}C_8)$alkyl or substituted $(C_6\text{-}C_{20})$aryl$(C_1\text{-}C_8)$alkyl;
each n is independently 0, 1, or 2; and
wherein each $(C_1\text{-}C_8)$alkyl, $(C_2\text{-}C_8)$alkenyl, $(C_2\text{-}C_8)$alkynyl or $(C_6\text{-}C_{20})$aryl$(C_1\text{-}C_8)$alkyl of each $R^2$, $R^3$, $R^5$, $R^6$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1\text{-}C_8)$alkyl may be optionally replaced with —O—, —S— or $-NR^a-$.

In another embodiment, the method comprises administering a therapeutically effective amount of a racemate, enantiomer, diastereomer, tautomer, polymorph, pseudopolymorph, amorphous form, hydrate or solvate of a compound of Formula I or a pharmaceutically acceptable salt or ester thereof to a mammal in need thereof.

In another embodiment, the method comprises treating an Arenaviridae infection in a human in need thereof by administering a therapeutically effective amount of a compound of Formula I or a pharmaceutically acceptable salt or ester thereof.

In another embodiment, the method comprises treating a Lassa virus infection in a human in need thereof by administering a therapeutically effective amount of a compound of Formula I or a pharmaceutically acceptable salt or ester thereof.

In another embodiment, the method comprises treating a Junin virus infection in a human in need thereof by administering a therapeutically effective amount of a compound of Formula I or a pharmaceutically acceptable salt or ester thereof.

In another embodiment, the method of treating an Arenaviridae infection in a human in need thereof comprises administering a therapeutically effective amount of a pharmaceutical composition comprising an effective amount of a Formula I compound, or a pharmaceutically acceptable salt or ester thereof, in combination with a pharmaceutically acceptable diluent or carrier.

In another embodiment, the method of treating an Arenaviridae infection in a human in need thereof comprises administering a therapeutically effective amount of a pharmaceutical composition comprising an effective amount of a Formula I compound, or a pharmaceutically acceptable salt or ester thereof, in combination with at least one additional therapeutic agent.

In another embodiment, the method comprises administering a therapeutically effective amount of a combination pharmaceutical agent comprising:
a) a first pharmaceutical composition comprising a compound of Formula I; or a pharmaceutically acceptable salt, solvate, or ester thereof; and
b) a second pharmaceutical composition comprising at least one additional therapeutic agent active against infectious Arenaviridae viruses.

In another embodiment, the present application provides for a method of inhibiting an Arenaviridae RNA-dependent RNA polymerase, comprising contacting a cell infected with an Arenaviridae virus with an effective amount of a compound of Formula I; or a pharmaceutically acceptable salts, solvate, and/or ester thereof.

In another embodiment, provided is the use of a compound of Formula I or a pharmaceutically acceptable salt, solvate, and/or ester thereof to treat a viral infection caused by an Arenaviridae virus.

Provided is a method for treating a Coronaviridae infection in a human in need thereof comprising administering a therapeutically effective amount of a compound of Formula I:

Formula I or a pharmaceutically acceptable salt or ester, thereof;
wherein:
  each $R^1$ is H or halogen;
  each $R^2$, $R^3$, $R^4$ or $R^5$ is independently H, $OR^a$, $N(R^a)_2$, $N_3$, CN, $NO_2$, $S(O)_nR^a$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl or $(C_2-C_8)$substituted alkynyl;
    or any two $R^2$, $R^3$, $R^4$ or $R^5$ on adjacent carbon atoms when taken together are —O(CO)O— or when taken together with the ring carbon atoms to which they are attached form a double bond;
  $R^6$ is $OR^a$, $N(R^a)_2$, $N_3$, CN, $NO_2$, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or $(C_6-C_{20})$aryl$(C_1-C_8)$alkyl;
  $R^7$ is selected from a group consisting of
    a) H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)$_2$($OR^{11}$), or —SO$_2NR^{11}R^{12}$,
      wherein each $(C_1-C_8)$alkyl, $(C_2-C_8)$alkenyl, $(C_2-C_8)$alkynyl or $(C_6-C_{20})$aryl$(C_1-C_8)$alkyl of each $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$alkyl may be optionally replaced with —O—, —S— or —$NR^a$—,
    b)

c)

wherein:
  $R^c$ is selected from phenyl, 1-naphthyl, 2-naphthyl, and $R^d$ is H or CH$_3$;
  $R^{e1}$ and $R^{e2}$ are each independently H, $(C_1-C_6)$alkyl or benzyl;
  $R^f$ is selected from H, $(C_1-C_8)$alkyl, benzyl, $(C_3-C_6)$cycloalkyl, and —CH$_2$—$(C_3-C_6)$cycloalkyl;
  $R^g$ is selected from $(C_1-C_8)$alkyl, —O—$(C_1-C_8)$alkyl, benzyl, —O-benzyl, —CH$_2$—$(C_3-C_6)$cycloalkyl, —O—CH$_2$—$(C_3-C_6)$cycloalkyl, and CF$_3$; and
  n' is selected from 1, 2, 3, and 4; and
  d) a group of the formula:

wherein:
  Q is O, S, NR, $^+$N(O)(R), N(OR), $^+$N(O)(OR), or N—NR$_2$;
  $Z^1$ and $Z^2$, when taken together, are -$Q^1$(C($R^y$)$_2$)$_3Q^1$-;
  wherein
    each $Q^1$ is independently O, S, or NR; and
    each $R^y$ is independently H, F, Cl, Br, I, OH, R, —C(=$Q^2$)R, —C(=$Q^2$)OR, —C(=$Q^2$)N(R)$_2$, —N(R)$_2$, —$^+$N(R)$_3$, —SR, —S(O)R, —S(O)$_2$R, —S(O)(OR), —S(O)$_2$(OR), —OC(=$Q^1$)R, —OC(=$Q^2$)R, —OC(=$Q^2$)OR, —OC(=$Q^2$)(N(R)$_2$), —SC(=$Q^2$)R, —SC(=$Q^2$)OR, —SC(=$Q^2$)(N(R)$_2$), —N(R)C(=$Q^2$)R, —N(R)C(=$Q^2$)OR, —N(R)C(=$Q^2$)N(R)$_2$, —SO$_2$NR$_2$, —CN, —$N_3$, —$NO_2$, —OR, or $Z^3$; or when taken together, two $R^y$ on the same carbon atom form a carbocyclic ring of 3 to 7 carbon atoms;

each $Q^2$ is independently, O, S, NR, $^+$N(O)(R), N(OR), $^+$N(O)(OR), or N—$NR_2$; or $Z^1$ and $Z^2$ are each, independently, a group of the Formula Ia:

$$\left[R^x-\left(Q^3-\overset{\overset{Q^2}{\|}}{\underset{\underset{R^x}{|}}{\underset{|}{P}}}-Q^3-\right)\right]_{M2}$$  Formula Ia wherein:

each $Q^3$ is independently a bond, O, $CR_2$, NR, $^+$N(O)(R), N(OR), $^+$N(O)(OR), N—$NR_2$, S, S—S, S(O), or $S(O)_2$;

M2 is 0, 1 or 2;

each $R^x$ is independently $R^y$ or the formula:

wherein:

each M1a, M1c, and M1d is independently 0 or 1;

M12c is 0, 1, 2, 3, 4, 5, 6, 7, 8, 9, 10, 11 or 12;

$Z^3$ is $Z^4$ or $Z^5$;

$Z^4$ is R, —$C(Q^2)R^y$, —$C(Q^2)Z^5$, —$SO_2R^y$, or —$SO_2Z^5$; and $Z^5$ is a carbocycle or a heterocycle wherein $Z^5$ is independently substituted with 0 to 3 $R^y$ groups;

$R^8$ is halogen, $NR^{11}R^{12}$, $N(R^{11})OR^{11}$, $NR^{12}$, $N_3$, NO, $NO_2$, CHO, CN, —CH(=$NR^{11}$), —CH=$NNHR^{11}$, —CH=N(O$R^{11}$), —CH(O$R^{11}$)$_2$, —C(=O)$NR^{11}R^{12}$, —C(=S)$NR^{11}R^{12}$, —C(=O)O$R^{11}$, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)optionally substituted aryl, optionally substituted heteroaryl, —C(=O)($C_1$-$C_8$)alkyl, —S(O)$_n$($C_1$-$C_8$)alkyl, ($C_6$-$C_{20}$)aryl($C_1$-$C_8$)alkyl, O$R^{11}$ or S$R^{11}$;

each $R^9$ or $R^{10}$ is independently H, halogen, $NR^{11}R^{12}$, $N(R^{11})OR^{11}$, $NR^{11}R^{12}$, $N_3$, NO, $NO_2$, CHO, CN, —CH(=$NR^{11}$), —CH=$NHNR^{11}$, —CH=N(O$R^{11}$), —CH(O$R^{11}$)$_2$, —C(=O)$NR^{11}R^{12}$, —C(=S)$NR^{11}R^{12}$, —C(=O)O$R^{11}$, $R^{11}$, O$R^{11}$ or S$R^{11}$;

each $R^{11}$ or $R^{12}$ is independently H, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)optionally substituted aryl, optionally substituted heteroaryl, —C(=O)($C_1$-$C_8$)alkyl, —S(O)$_n$($C_1$-$C_8$)alkyl or ($C_6$-$C_{20}$)aryl($C_1$-$C_8$)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —$NR^a$—;

each $R^a$ is independently H, ($C_1$-$C_8$)alkyl, ($C_2$-$C_8$)alkenyl, ($C_2$-$C_8$)alkynyl, ($C_6$-$C_{20}$)aryl($C_1$-$C_8$)alkyl, ($C_4$-$C_8$)carbocyclylalkyl, —C(=O)R, —C(=O)OR, —C(=O)$NR_2$, —C(=O)SR, —S(O)R, —S(O)$_2$R, —S(O)(OR), —S(O)$_2$(OR), or —$SO_2NR_2$; wherein each R is independently H, ($C_1$-$C_8$) alkyl, ($C_1$-$C_8$) substituted alkyl, ($C_2$-$C_8$)alkenyl, ($C_2$-$C_8$) substituted alkenyl, ($C_2$-$C_8$) alkynyl, ($C_2$-$C_8$) substituted alkynyl, ($C_6$-$C_{20}$)aryl, ($C_6$-$C_{20}$)substituted aryl, ($C_2$-$C_{20}$)heterocyclyl, ($C_2$-$C_{20}$)substituted heterocyclyl, ($C_6$-$C_{20}$)aryl($C_1$-$C_8$)alkyl or substituted ($C_6$-$C_{20}$)aryl($C_1$-$C_8$)alkyl;

each n is independently 0, 1, or 2; and wherein each ($C_1$-$C_8$)alkyl, ($C_2$-$C_8$)alkenyl, ($C_2$-$C_8$)alkynyl or ($C_6$-$C_{20}$)aryl($C_1$-$C_8$)alkyl of each $R^2$, $R^3$, $R^5$, $R^6$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said ($C_1$-$C_8$)alkyl may be optionally replaced with —O—, —S— or —$NR^a$—.

In another embodiment, the method comprises administering a therapeutically effective amount of a racemate, enantiomer, diastereomer, tautomer, polymorph, pseudopolymorph, amorphous form, hydrate or solvate of a compound of Formula I or a pharmaceutically acceptable salt or ester thereof to a mammal in need thereof.

In another embodiment, the method comprises treating a Coronaviridae infection in a human in need thereof by administering a therapeutically effective amount of a compound of Formula I or a pharmaceutically acceptable salt or ester thereof.

In another embodiment, the method comprises treating a MERS virus infection in a human in need thereof by administering a therapeutically effective amount of a compound of Formula I or a pharmaceutically acceptable salt or ester thereof.

In another embodiment, the method comprises treating a SARS virus infection in a human in need thereof by administering a therapeutically effective amount of a compound of Formula I or a pharmaceutically acceptable salt or ester thereof.

In another embodiment, the method of treating a Coronaviridae infection in a human in need thereof comprises administering a therapeutically effective amount of a pharmaceutical composition comprising an effective amount of a Formula I compound, or a pharmaceutically acceptable salt or ester thereof, in combination with a pharmaceutically acceptable diluent or carrier.

In another embodiment, the method of treating a Coronaviridae infection in a human in need thereof comprises administering a therapeutically effective amount of a pharmaceutical composition comprising an effective amount of a Formula I compound, or a pharmaceutically acceptable salt or ester thereof, in combination with at least one additional therapeutic agent.

In another embodiment, the method comprises administering a therapeutically effective amount of a combination pharmaceutical agent comprising:

a) a first pharmaceutical composition comprising a compound of Formula I; or a pharmaceutically acceptable salt, solvate, or ester thereof; and b) a second pharmaceutical composition comprising at least one additional therapeutic agent active against infectious Coronaviridae viruses.

In another embodiment, the present application provides for a method of inhibiting a Coronaviridae RNA-dependent RNA polymerase, comprising contacting a cell infected with a Coronaviridae virus with an effective amount of a compound of Formula I; or a pharmaceutically acceptable salts, solvate, and/or ester thereof.

In another embodiment, provided is the use of a compound of Formula I or a pharmaceutically acceptable salt, solvate, and/or ester thereof to treat a viral infection caused by a Coronaviridae virus.

DESCRIPTION OF THE FIGURES

FIG. 1: Changes in body weight post infection in vehicle and Compound 32-treated mice FIG. 2A and FIG. 2B: Viral load in lung tissue at Day 2 and 5 post infection in vehicle and Compound 32-treated mice FIG. 3A-F: Whole Body Plethysmography of Mice Infected with SARS-CoV FIG. 4A. Changes in body weight post infection in vehicle and Compound 32-treated monkey FIG. 4B. Changes in body temperature post infection in vehicle and Compound 32-treated monkey FIG. 4C. Changes in respiratory rate post infection in vehicle and Compound 32-treated monkey FIG. 5. Tissue viral RNA concentrations by treatment group. Viral load was measured qRT-PCR.

DETAILED DESCRIPTION OF THE INVENTION

I. Definitions

Unless stated otherwise, the following terms and phrases as used herein are intended to have the following meanings:

When trade names are used herein, applicants intend to independently include the trade name product and the active pharmaceutical ingredient(s) of the trade name product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, and octyl ($—(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy ($—O—CH_3$ or —OMe), ethoxy ($—OCH_2CH_3$ or -OEt), t-butoxy ($—O—C(CH_3)_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, $—CF_3$, $—CHF_2$, $—CFH_2$, $—CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl ($—CH{=}CH_2$), allyl ($—CH_2CH{=}CH_2$), cyclopentenyl ($—C_5H_7$), and 5-hexenyl ($—CH_2CH_2CH_2CH_2CH{=}CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic ($—C{\equiv}CH$), propargyl ($—CH_2C{\equiv}CH$), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene ($—CH_2—$), 1,1-ethyl ($—CH(CH_3)—$), 1,2-ethyl ($—CH_2CH_2—$), 1,1-propyl ($—CH(CH_2CH_3)—$), 1,2-propyl ($—CH_2CH(CH_3)—$), 1,3-propyl ($—CH_2CH_2CH_2—$), 1,4-butyl ($—CH_2CH_2CH_2CH_2—$), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene ($—CH{=}CH—$).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene ($—C{\equiv}C—$), propargyl ($—CH_2C{\equiv}C—$), and 4-pentynyl ($—CH_2CH_2CH_2C{\equiv}C—$).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^3$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH (aryl), —N(alkyl)(aryl), —N(alkyl)(heterocyclyl), —N(carbocyclyl)(heterocyclyl), —N(aryl)(heteroaryl), —N(alkyl) (heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b{}_2$, —N+R$^b{}_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b{}_2$, —S(=O)$_2$—, —S(=O)$_2$OH, —S(=O)$_2$R$^b$, —OS(=O)$_2$OR$^b$, —S(=O)$_2$NR$^b{}_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O) (OR$^b$)(O$^-$), —C(=O)R$^b$, —C(=O)X, —C(S)R$^b$, —C(O) OR$^b$, —C(O)O$^-$, —C(S)OR$^b$, —C(O)SR$^b$, —C(S)SR$^b$, —C(O)NR$^b{}_2$, —C(S)NR$^b{}_2$, —C(=NR$^b$)NR$^b{}_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

A "prodrug" is defined in the pharmaceutical field as a biologically inactive derivative of a drug that upon administration to the human body is converted to the biologically active parent drug according to some chemical or enzymatic pathway.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocylyls include, for example, heterocyclic rings substituted with any of the substituents disclosed herein including carbonyl groups. A non-limiting example of a carbonyl substituted heterocyclyl is:

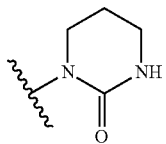

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

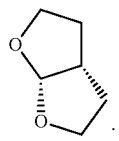

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^a$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to an acyclic akyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I-IV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-IV (e.g., the carbon atoms of said ($C_1$-$C_8$)alkyl may be optionally replaced by —O—, —S—, or —$NR^a$—) means that one or more of the methylene groups of the ($C_1$-$C_8$)alkyl may be replaced by 0, 1, 2, or more of the groups specified (e.g., —O—, —S—, or —$NR^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —$CH_2(C^*)H_2(C^*)H_2CH_3$ or alkylene moiety —$CH_2(C^*)H_2(C^*)H_2CH_2$— the $C^*$ atoms would be considered to be the non-terminal carbon atoms.

Certain Q and $Q^1$ alternatives are nitrogen oxides such as $^+N(O)(R)$ or $^+N(O)(OR)$. These nitrogen oxides, as shown here attached to a carbon atom, can also be represented by charge separated groups such as

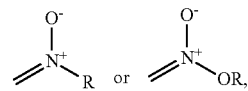

respectively, and are intended to be equivalent to the aforementioned representations for the purposes of describing this invention.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

In some embodiments of the compounds of Formula I-IV, one or more of $Z^1$ or $Z^2$ are independently a radical of a nitrogen-linked naturally occurring α-amino acid ester. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substituent R, particularly those in which R is optionally substituted ($C_1$-$C_8$)alkyl.

The term "purine" or "pyrimidine" base comprises, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-5-iodopyrimidine, $C^6$-iodo-pyrimidine, $C^5$—Br-vinyl pyrimidine, $C^6$—Br-vinyl pyriniidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. The purine and pyrimidine bases of Formula I-III are linked to the ribose sugar, or analog thereof, through a nitrogen atom of the base. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

Unless otherwise specified, the carbon atoms of the compounds of Formula I-IV are intended to have a valence of four. In some chemical structure representations where carbon atoms do not have a sufficient number of variables attached to produce a valence of four, the remaining carbon substituents needed to provide a valence of four should be assumed to be hydrogen. For example,

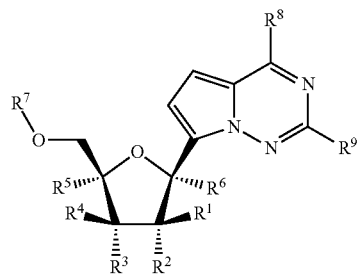

has the same meaning as

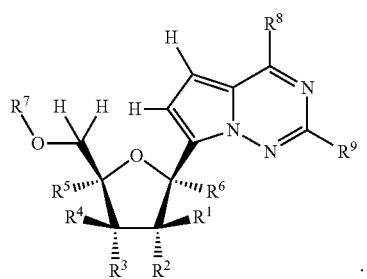

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive. "Hydroxy protecting groups" refers to those protecting groups useful for protecting hydroxy groups (—OH).

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-IV may have a chiral phosphorus atom when $R^7$ is

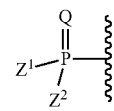

and $Z^1$ and $Z^2$ are different. When at least one of either $Z^1$ or $Z^2$ also has a chiral center, for example with $Z^1$ or $Z^2$ is a nitrogen-linked, chiral, naturally occurring α-amino acid ester, then the compound of Formula I-IV will exists as diastereomers because there are two centers of chirality in the molecule. All such diastereomers and their uses described herein are encompassed by the instant invention. Mixtures of diastereomers may be separate under high resolution analytical procedures such as electrophoresis, crystallization and/or chromatography. Diastereomers may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I-IV present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I-IV, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Coupling agent" refers to an agent capable of coupling two disparate compounds. Coupling agents can be catalytic or stoichiometric. For example, the coupling agents can be a lithium based coupling agent or a magnesium based coupling agent such as a Grignard reagent. Exemplary coupling agents include, but are not limited to, n-BuLi, $MgCl_2$, iPrMgCl, tBuMgCl, PhMgCl or combinations thereof.

"Silane" refers to a silicon containing group having the formula $SiR_4$, where each R group can be alkyl, alkenyl, cycloalkyl, phenyl, or other silicon containing groups. When the silane is linked to another compound, the silane is referred to as a "silyl" and has the formula —$SiR_3$.

"Halo-silane" refers to a silane having at least one halogen group linked to the silicon atom. Representative halo-silanes have the formula Halo-$SiR_3$, where each R group can be alkyl, alkenyl, cycloalkyl, phenyl, or other silicon containing groups. Specific halo-silanes include Cl—$Si(CH_3)_3$, and Cl—$Si(CH_3)_2CH_2CH_2Si(CH_3)_2$—Cl.

"Non-nucleophilic base" refers to an electron donor, a Lewis base, such as nitrogen bases including triethylamine, diisopropylethyl amine, N,N-diethylaniline, pyridine, 2,6-lutidine, 2,4,6-collidine, 4-dimethylaminopyridine, and quinuclidine.

"Leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, mesylate, tosylate, triflate, 4-nitrobenzenesulfonate, 4-chlorobenzenesulfonate, 4-nitrophenoxy, pentafluorophenoxy, etc. One of skill in the art will recognize other leaving groups useful in the present invention.

"Deprotection agent" refers to any agent capable of removing a protecting group. The deprotection agent will depend on the type of protecting group used. Representative deprotection agents are known in the art and can be found in *Protective Groups in Organic Chemistry*, Peter G. M. Wuts and Theodora W. Greene, 4th Ed., 2006.

II. Compounds of the Present Invention

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

Provided is a method for treating an Arenaviridae infection in a human in need thereof comprising administering a therapeutically effective amount of a compound of Formula I:

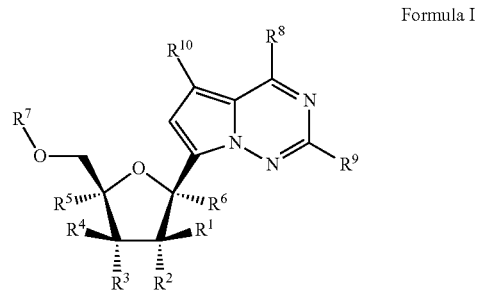

Formula I or a pharmaceutically acceptable salt or ester, thereof;
wherein:
each $R^1$ is H or halogen;
each $R^2$, $R^3$, $R^4$ or $R^5$ is independently H, $OR^a$, $N(R^a)_2$, $N_3$, CN, $NO_2$, $S(O)_nR^a$, halogen, ($C_1$-$C_8$)alkyl, ($C_4$-$C_8$)carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl or ($C_2$-$C_8$)substituted alkynyl;
or any two $R^2$, $R^3$, $R^4$ or $R^5$ on adjacent carbon atoms when taken together are —O(CO)O— or when taken together with the ring carbon atoms to which they are attached form a double bond;
$R^6$ is $OR^a$, $N(R^a)_2$, $N_3$, CN, $NO_2$, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, halogen, ($C_1$-$C_8$)alkyl, ($C_4$-$C_8$)carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl, ($C_2$-$C_8$)substituted alkynyl, or ($C_6$-$C_{20}$)aryl($C_1$-$C_8$)alkyl;
$R^7$ is selected from a group consisting of
a) H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), or —SO$_2NR^{11}R^{12}$, wherein each $(C_1-C_8)$alkyl, $(C_2-C_8)$alkenyl, $(C_2-C_8)$alkynyl or $(C_6-C_{20})$aryl$(C_1-C_8)$alkyl of each $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$alkyl may be optionally replaced with —O—, —S— or —NR$^a$—, b)

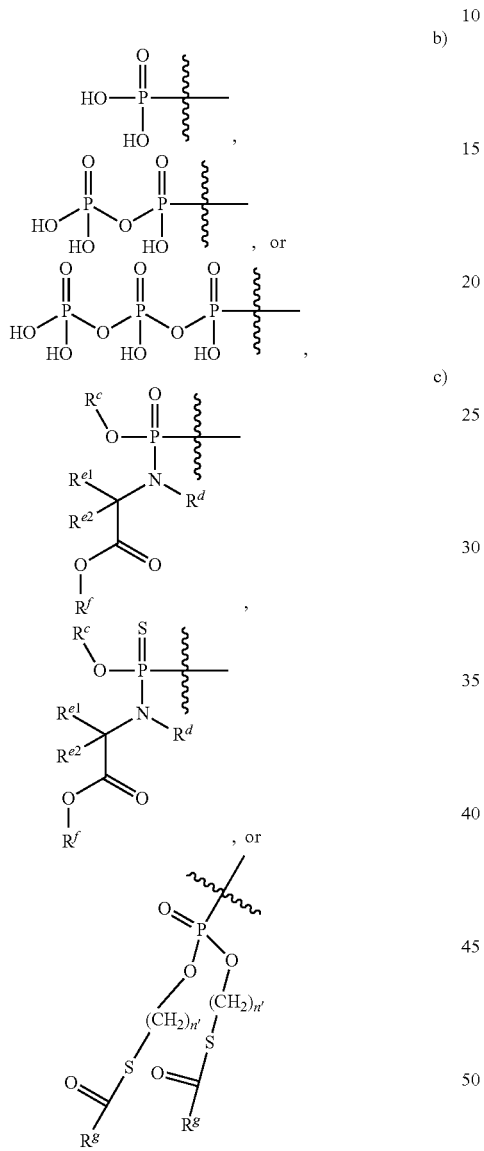

wherein:
$R^c$ is selected from phenyl, 1-naphthyl, 2-naphthyl,

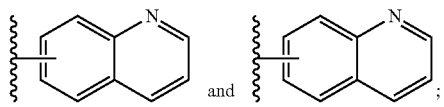

$R^d$ is H or $CH_3$;
$R^{e1}$ and $R^{e2}$ are each independently H, $(C_1-C_6)$alkyl or benzyl;

$R^f$ is selected from H, $(C_1-C_8)$alkyl, benzyl, $(C_3-C_6)$cycloalkyl, and —$CH_2$—$(C_3-C_6)$cycloalkyl;
$R^g$ is selected from $(C_1-C_8)$alkyl, —O—$(C_1-C_8)$alkyl, benzyl, —O-benzyl, —$CH_2$—$(C_3-C_6)$cycloalkyl, —O—$CH_2$—$(C_3-C_6)$cycloalkyl, and $CF_3$; and
n' is selected from 1, 2, 3, and 4; and
d) a group of the formula:

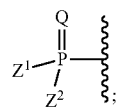

wherein:
Q is O, S, NR, $^+$N(O)(R), N(OR), $^+$N(O)(OR), or N—$NR_2$;
$Z^1$ and $Z^2$, when taken together, are -$Q^1(C(R^y)_2)_3Q^1$-;
wherein
each $Q^1$ is independently O, S, or NR; and
each $R^y$ is independently H, F, Cl, Br, I, OH, R, —C(=$Q^2$)R, —C(=$Q^2$)OR, —C(=$Q^2$)N(R)$_2$, —N(R)$_2$, —$^+$N(R)$_3$, —SR, —S(O)R, —S(O)$_2$R, —S(O)(OR), —S(O)$_2$(OR), —OC(=$Q^1$)R, —OC(=$Q^2$)OR, —OC(=$Q^2$)(N(R)$_2$), —SC(=$Q^2$)R, —SC(=$Q^2$)OR, —SC(=$Q^2$)(N(R)$_2$), —N(R)C(=$Q^2$)R, —N(R)C(=$Q^2$)OR, —N(R)C(=$Q^2$)N(R)$_2$, —SO$_2$NR$_2$, —CN, —N$_3$, —NO$_2$, —OR, or $Z^3$; or when taken together, two $R^y$ on the same carbon atom form a carbocyclic ring of 3 to 7 carbon atoms;
each $Q^2$ is independently, O, S, NR, $^+$N(O)(R), N(OR), $^+$N(O)(OR), or N—$NR_2$; or
$Z^1$ and $Z^2$ are each, independently, a group of the Formula Ia:

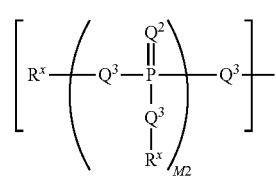

Formula Ia wherein:
each $Q^3$ is independently a bond, O, CR$_2$, NR, $^+$N(O)(R), N(OR), $^+$N(O)(OR), N—$NR_2$, S, S—S, S(O), or S(O)$_2$;
M2 is 0, 1 or 2;
each $R^x$ is independently $R^y$ or the formula:

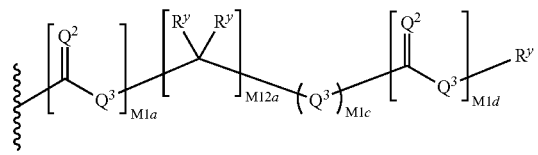

wherein:
each M1a, M1c, and M1d is independently 0 or 1;
M12c is 0, 1, 2, 3, 4, 5, 6, 7, 8, 9, 10, 11 or 12;

$Z^3$ is $Z^4$ or $Z^5$;
$Z^4$ is R, —C(Q$^2$)R$^y$, —C(Q$^2$)Z$^5$, —SO$_2$R$^y$, or —SO$_2$Z$^5$; and
$Z^5$ is a carbocycle or a heterocycle wherein $Z^5$ is independently substituted with 0 to 3 R$^y$ groups;
R$^8$ is halogen, NR$^{11}$R$^{12}$, N(R$^{11}$)OR$^{11}$, NR$^{11}$NR$^{11}$R$^{12}$, N$_3$, NO, NO$_2$, CHO, CN, —CH(=NR$^{11}$), —CH=NNHR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl, (C$_6$-C$_{20}$)aryl(C$_1$-C$_8$)alkyl, OR$^{11}$ or SR$^{11}$;
each R$^9$ or R$^{10}$ is independently H, halogen, NR$^{11}$R$^{12}$, N(R$^{11}$)OR$^{11}$, NR$^{11}$NR$^{11}$R$^{12}$, N$_3$, NO, NO$_2$, CHO, CN, —CH(=NR$^{11}$), —CH=NHNR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, R$^{11}$, OR$^{11}$ or SR$^{11}$;
each R$^{11}$ or R$^{12}$ is independently H, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl or (C$_6$-C$_{20}$)aryl(C$_1$-C$_8$)alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S— or —NR$^a$—;
each R$^a$ is independently H, (C$_1$-C$_8$)alkyl, (C$_2$-C$_8$)alkenyl, (C$_2$-C$_8$)alkynyl, (C$_6$-C$_{20}$)aryl(C$_1$-C$_8$)alkyl, (C$_4$-C$_8$)carbocyclylalkyl, —C(=O)R, —C(=O)OR, —C(=O)NR$_2$, —C(=O)SR, —S(O)R, —S(O)$_2$R, —S(O)(OR), —S(O)$_2$(OR), or —SO$_2$NR$_2$; wherein
each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, (C$_6$-C$_{20}$)aryl, (C$_6$-C$_{20}$)substituted aryl, (C$_2$-C$_{20}$)heterocyclyl, (C$_2$-C$_{20}$)substituted heterocyclyl, (C$_6$-C$_{20}$)aryl(C$_1$-C$_8$)alkyl or substituted (C$_6$-C$_{20}$)aryl(C$_1$-C$_8$)alkyl;
each n is independently 0, 1, or 2; and
wherein each (C$_1$-C$_8$)alkyl, (C$_2$-C$_8$)alkenyl, (C$_2$-C$_8$)alkynyl or (C$_6$-C$_{20}$)aryl(C$_1$-C$_8$)alkyl of each R$^2$, R$^3$, R$^5$, R$^6$, R$^{11}$ or R$^{12}$ is, independently, optionally substituted with one or more halo, hydroxy, CN, N$_3$, N(R$^a$)$_2$ or OR$^a$; and wherein one or more of the non-terminal carbon atoms of each said (C$_1$-C$_8$)alkyl may be optionally replaced with —O—, —S— or —NR$^a$—.

In another embodiment, provided is a method of treating an Arenaviridae infection in a human in need thereof comprising administering a therapeutically effective amount of a compound of Formula I represented by Formula II:

Formula II or a pharmaceutically acceptable salt or ester, thereof; wherein
R$^1$, R$^3$, R$^5$, R$^7$, R$^8$ and R$^9$ are as defined above for Formula I;
each R$^2$ is OR$^a$ or halogen; and
R$^6$ is OR$^a$, N(R$^a$)$_2$, N$_3$, CN, S(O)$_n$R$^a$, —C(=O)R$^{11}$, —C(=O)OR$^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), —SO$_2$NR$^{11}$R$^{12}$, halogen, (C$_1$-C$_8$)alkyl, (C$_4$-C$_8$)carbocyclylalkyl, (C$_1$-C$_8$)substituted alkyl, (C$_2$-C$_8$)alkenyl, (C$_2$-C$_8$)substituted alkenyl, (C$_2$-C$_8$)alkynyl, or (C$_2$-C$_8$)substituted alkynyl.

In one embodiment of the method of treating an Arenaviridae infection by administering a compound of Formula II, R$^1$ of Formula II is H. In another aspect of this embodiment R$^6$ of Formula II is N$_3$, CN, halogen, (C$_1$-C$_8$)alkyl, (C$_1$-C$_8$)substituted alkyl, (C$_2$-C$_8$)alkenyl, (C$_2$-C$_8$)substituted alkenyl, (C$_2$-C$_8$)alkynyl, or (C$_2$-C$_8$)substituted alkynyl. In another aspect of this embodiment, R$^6$ of Formula II is CN, methyl, ethenyl, or ethynyl. In another aspect of this embodiment, R$^6$ of Formula II is CN. In another aspect of this embodiment, R$^6$ of Formula II is methyl. In another aspect of this embodiment, R$^5$ of Formula II is H. In another aspect of this embodiment, R$^2$ of Formula II is OR$^a$. In another aspect of this embodiment, R$^2$ of Formula II is OH. In another aspect of this embodiment, R$^2$ of Formula II is F. In another aspect of this embodiment, R$^3$ of Formula II is OR$^a$. In another aspect of this embodiment, R$^3$ of Formula II is OH, —OC(=O)R$^{11}$, or —OC(=O)OR$^{11}$. In another aspect of this embodiment, R$^3$ of Formula II is OH. In another aspect of this embodiment, R$^8$ of Formula II is N$^{11}$R$^{12}$. In another aspect of this embodiment, R$^8$ of Formula II is NH$_2$. In another aspect of this embodiment, R$^8$ of Formula II is OR$^{11}$. In another aspect of this embodiment, R$^8$ of Formula II is OH. In another aspect of this embodiment, R$^9$ of Formula II is H. In another aspect of this embodiment, R$^9$ of Formula II is NR$^{11}$R$^{12}$. In another aspect of this embodiment, R$^9$ of Formula II is NH$_2$. In another aspect of this embodiment, R$^7$ of Formula II is H, —C(=O)R$^{11}$, —C(=O)OR$^{11}$ or In another aspect of this embodiment, R$^7$ of Formula II is H. In another aspect of this embodiment, R$^7$ of Formula II is In another embodiment of the method of treating an Arenaviridae infection comprising administering a compound of Formula II, the Arenaviridae infection is caused by an Arenaviridae virus. In another aspect of this embodiment, the Arenaviridae virus is a Lassa virus or Junin virus. In another aspect of this embodiment, the Arenaviridae virus is a Lassa virus. In another aspect of this embodiment, the Arenaviridae virus is a Junin virus. In another aspect of this embodiment, the Arenaviridae virus is caused by a Lassa virus caused by a strain selected from Josiah, NL, z148, Macenta, AV, and CSF.

In another aspect of this embodiment, the Arenaviridae infection is caused by Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), or Whitewater Arroyo virus (WWAV).

In another embodiment, provided is a method of treating an Arenaviridae infection in a human in need thereof comprising administering a therapeutically effective amount of a compound of Formula I represented by Formula III:

Formula III or a pharmaceutically acceptable salt or ester, thereof; wherein $R^6$, $R^7$, $R^8$ and $R^9$ are as defined above for Formula II;

each $R^2$ is $OR^a$ or F; and each $R^3$ is $OR^a$.

In one embodiment of the method of treating an Arenaviridae infection comprising administering a compound of Formula III, $R^6$ of Formula III is $N_3$, CN, halogen, $(C_1\text{-}C_8)$alkyl, $(C_1\text{-}C_8)$substituted alkyl, $(C_2\text{-}C_8)$alkenyl, $(C_2\text{-}C_8)$substituted alkenyl, $(C_2\text{-}C_8)$alkynyl, or $(C_2\text{-}C_8)$substituted alkynyl. In another aspect of this embodiment, $R^6$ of Formula III is CN, methyl, ethenyl, or ethynyl. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH. In another aspect of this embodiment, $R^2$ of Formula III is F. In another aspect of this embodiment, $R^3$ of Formula III is OH, $—OC(=O)R^{11}$, or $—OC(=O)OR^{11}$. In another aspect of this embodiment, $R^3$ of Formula III is OH. In another aspect of this embodiment, $R^8$ of Formula III is $NR^{11}R^{12}$. In another aspect of this embodiment, $R^8$ of Formula III is $NH_2$. In another aspect of this embodiment, $R^8$ of Formula III is $OR^{11}$. In another aspect of this embodiment, $R^8$ of Formula III is OH. In another aspect of this embodiment, $R^9$ of Formula III is H. In another aspect of this embodiment, $R^9$ of Formula III is $NR^{11}R^{12}$. In another aspect of this embodiment, $R^9$ of Formula III is $NH_2$. In another aspect of this embodiment, $R^7$ of Formula III is H, $—C(=O)R^{11}$, $—C(=O)OR^{11}$ or In another aspect of this embodiment, $R^7$ of Formula III is H. In another aspect of this embodiment, $R^7$ of Formula III is In another embodiment of the method of treating an Arenaviridae infection comprising administering a compound of Formula III, $R^6$ of Formula III is $N_3$, CN, halogen, $(C_1\text{-}C_8)$alkyl, $(C_1\text{-}C_8)$substituted alkyl, $(C_2\text{-}C_8)$alkenyl, $(C_2\text{-}C_8)$substituted alkenyl, $(C_2\text{-}C_8)$alkynyl, or $(C_2\text{-}C_8)$substituted alkynyl and $R^8$ is $NH_2$. In another aspect of this embodiment, $R^6$ of Formula III is CN, methyl, ethenyl, or ethynyl. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH, $—OC(=O)R^{11}$, or $—OC(=O)OR^{11}$. In another aspect of this embodiment, $R^2$ of Formula III is OH. In another aspect of this embodiment, $R^2$ of Formula III is F. In another aspect of this embodiment, $R^3$ of Formula III is OH, $—OC(=O)R^{11}$, or $—OC(=O)OR^{11}$. In another aspect of this embodiment, $R^3$ of Formula III is OH. In another aspect of this embodiment, $R^9$ of Formula III is H. In another aspect of this embodiment, $R^9$ of Formula III is $NR^{11}R^{12}$. In another aspect of this embodiment, $R^9$ of Formula III is $NH_2$. In another aspect of this embodiment, $R^7$ of Formula III is H, $—C(=O)R^{11}$, $—C(=O)OR^{11}$ or In another aspect of this embodiment, $R^7$ of Formula III is H. In another aspect of this embodiment, $R^7$ of Formula III is In another embodiment of the method of treating an Arenaviridae infection comprising administering a compound of Formula III, $R^6$ of Formula III is CN, methyl, ethenyl, or ethynyl, $R^8$ is $NH_2$, and $R^9$ is H. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH, $—OC(=O)R^{11}$, or $—OC(=O)OR^{11}$. In another aspect of this embodiment, $R^2$ of Formula III is OH. In another aspect of this embodiment, $R^2$ of Formula III is F. In another aspect of this embodiment, $R^3$ of Formula III is OH, —OC($=$O)$R^{11}$, or —OC($=$O)O$R^{11}$. In another aspect of this embodiment, $R^3$ of Formula III is OH. In another aspect of this embodiment, $R^7$ of Formula III is H, —C($=$O)$R^{11}$, —C($=$O)O$R^{11}$ or

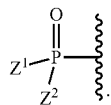

In another aspect of this embodiment, $R^7$ of Formula III is H. In another aspect of this embodiment, $R^7$ of Formula III is

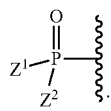

In another embodiment of the method of treating an Arenaviridae infection comprising administering a compound of Formula III, the Arenaviridae infection is caused by an Arenaviridae virus. In another aspect of this embodiment, the Arenaviridae virus is a Lassa virus or Junin virus. In another aspect of this embodiment, the Arenaviridae virus is a Lassa virus. In another aspect of this embodiment, the Arenaviridae virus is a Junin virus. In another aspect of this embodiment, the Arenaviridae virus is caused by a Lassa virus caused by a strain selected from Josiah, NL, z148, Macenta, AV, and CSF.

In another aspect of this embodiment, the Arenaviridae infection is caused by Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), or Whitewater Arroyo virus (WWAV).

In another embodiment, provided is a method of treating an Arenaviridae infection in a human in need thereof comprising administering a therapeutically effective amount of a compound of Formula I represented by Formula IV:

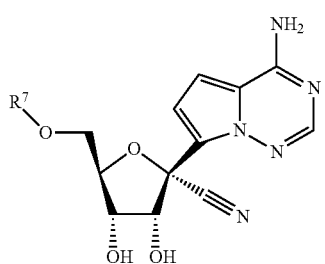

Formula IV or a pharmaceutically acceptable salt or ester, thereof; wherein $R^7$ is as defined above for Formula I.

In another embodiment of the method of treating an Arenaviridae infection comprising administering a compound of Formula IV, $R^7$ can be H. In another embodiment of the method of treating an Arenaviridae infection comprising administering a compound of Formula IV, $R^7$ is selected from the group of a), b), or c) as defined for Formula I.

In another embodiment of the method of treating an Arenaviridae infection comprising administering a compound of Formula IV, $R^7$ is

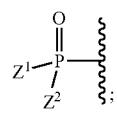

wherein $Z^1$ and $Z^2$ are each, independently, a group having the structure:

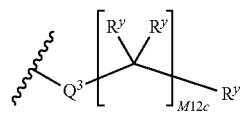

and $Z^3$ is $Z^5$.

In another embodiment of the method of treating an Arenaviridae infection comprising administering a compound of Formula IV, $R^7$ is

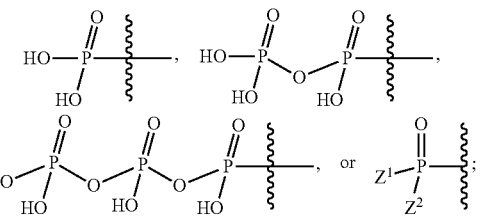

wherein $Z^1$ and $Z^2$ are each, independently, a group having the structure:

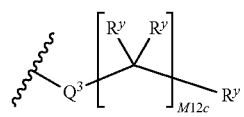

and $Z^3$ is $Z^5$.

In another embodiment of the method of treating an Arenaviridae infection comprising administering a compound of Formula IV, $R^7$ is

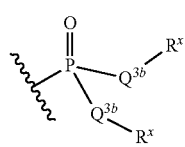

wherein each $Q^{3b}$ is, independently, O or N(R). In another embodiment, each $Q^{3b}$ is O and each $R^x$ is independently:

[Structure: chain with R groups, M12c, Q³, C(=O), Q³, R]

wherein M12c is 1, 2 or 3 and each $Q^3$ is independently a bond, O, $CR_2$, or S.

In some embodiments, $R^{e1}$ and $R^{e2}$ can each independently be H, $C_1$-$C_6$ alkyl or benzyl. In some embodiments, $R^{e1}$ can be H, $C_1$-$C_6$ alkyl or benzyl, and $R^{e2}$ can be H or $C_1$-$C_6$ alkyl. In some embodiments, $R^{e1}$ and $R^{e2}$ can each independently be H or $C_1$-$C_6$ alkyl. In some embodiments, $R^{e1}$ and $R^{e2}$ can each independently be H or benzyl. In some embodiments, $R^{e1}$ can be H, methyl or benzyl, and $R^{e2}$ can be H or methyl. In some embodiments, $R^{e1}$ can be H or methyl, and $R^{e2}$ can be H or methyl. In some embodiments, $R^{e1}$ can be methyl, and $R^{e2}$ can be H or methyl. In some embodiments, $R^{e1}$ can be H or benzyl, and $R^{e2}$ can be H or methyl.

In another embodiment of the method of treating an Arenaviridae infection comprising administering a compound of Formula IV, $R^7$ is

[Structure: phosphoramidate with phenoxy, alanine-OR, $(R^y)_{0-3}$]

In another embodiment of the method of treating an Arenaviridae infection comprising administering a compound of Formula IV, $R^7$ is

[Structures: HO-P(=O)(OH)-, HO-P(=O)(OH)-O-P(=O)(OH)-, HO-P(=O)(OH)-O-P(=O)(OH)-O-P(=O)(OH)-, bis-SATE thioester phosphate, phenyl phosphoramidate alanine ester]

or

In another embodiment of the method of treating an Arenaviridae infection comprising administering a compound of Formula IV, $R^7$ is

[Two phosphoramidate structures with phenoxy, $CH_3$, $NH$, $C(=O)OR^f$]

wherein $R^f$ is selected from the group of from H, $C_1$-$C_8$ alkyl, benzyl, $C_3$-$C_6$ cycloalkyl, and —$CH_2$—$C_3$-$C_6$ cycloalkyl. In another embodiment of a compound of Formula IV, $R^f$ is $C_1$-$C_8$ alkyl. In another embodiment of a compound of Formula IV, $R^f$ is 2-ethylbutyl.

In another embodiment of the method of treating an Arenaviridae infection comprising administering a compound of Formula IV, $R^7$ is

[Structures: HO-P(=O)(OH)-, diphosphate, triphosphate]

[Structures: bis-SATE thioester phosphate with $R^g$; phenyl phosphoramidate alanine ester with $R^f$]

or

[Structure: phenyl phosphoramidate with gem-dimethyl amino acid ester]

wherein
$R^f$ is selected from H, $C_1$-$C_8$ alkyl, benzyl, $C_3$-$C_6$ cycloalkyl, and —$CH_2$—$C_3$-$C_6$ cycloalkyl; and
$R^g$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$.

In another embodiment of the method of treating an Arenaviridae infection comprising administering a compound of Formula IV, $R^7$ is

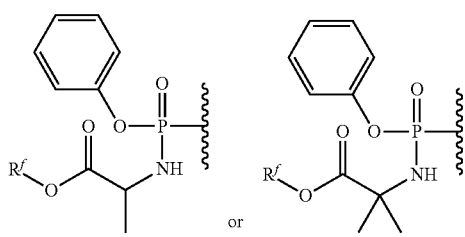

wherein $R^f$ is selected from H, $C_1$-$C_8$ alkyl, benzyl, $C_3$-$C_6$ cycloalkyl, and —$CH_2$—$C_3$-$C_6$ cycloalkyl. In another embodiment of a compound of Formula IV, $R^f$ is $C_1$-$C_8$ alkyl. In another embodiment of a compound of Formula IV, $R^f$ is $C_1$-$C_6$ alkyl. In another embodiment of a compound of Formula IV, $R^f$ is 2-ethylbutyl.

In another embodiment of the method of treating an Arenaviridae infection comprising administering a compound of Formula IV, $R^7$ is:

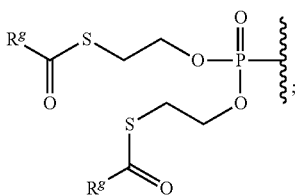

wherein $R^g$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$. In another embodiment of a compound of Formula IV, $R^f$ is $C_1$-$C_8$ alkyl. In another embodiment of a compound of Formula IV, $R^f$ is $C_1$-$C_6$ alkyl.

In another embodiment of the method of treating an Arenaviridae infection comprising administering a compound of Formula IV, $R^7$ is selected from the group of:

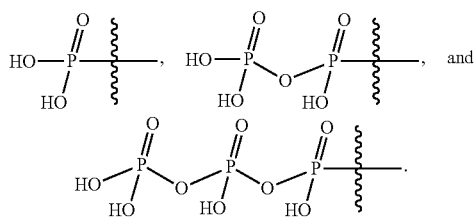

In another embodiment of the method of treating an Arenaviridae infection comprising administering a compound of Formula IV, $R^7$ is

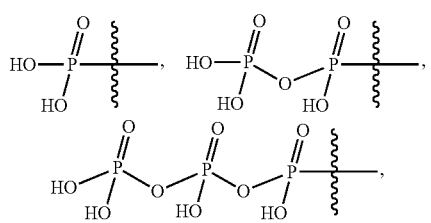

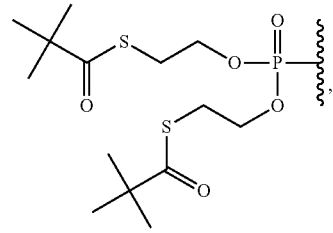

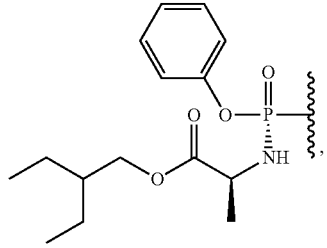

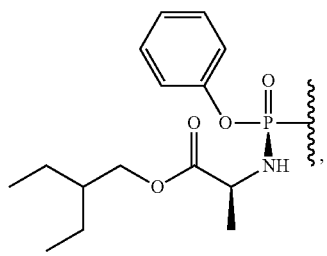

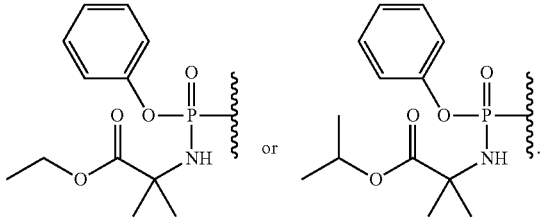

In another embodiment of the method of treating an Arenaviridae infection comprising administering a compound of Formula IV, $Z^1$ and $Z^2$ can each be:

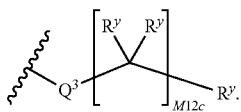

In another embodiment, provided is a method of treating an Arenaviridae infection in a human in need thereof comprising administering a therapeutically effective amount of a compound of Formulas I-IV, wherein $R^{11}$ or $R^{12}$ is independently H, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, —C(=O)($C_1$-$C_8$)alkyl, —S(O)$_n$($C_1$-$C_8$)alkyl or aryl($C_1$-$C_8$)alkyl. In another embodiment, $R^{11}$ and $R^{12}$ taken together with a nitrogen to which they are both attached, form a 3 to 7 membered heterocyclic ring wherein any one carbon atom of said heterocyclic ring can optionally be replaced with —O—, —S— or —$NR^a$—. Therefore, by way of example and not limitation, the moiety —$NR^{11}R^{12}$ can be represented by the heterocycles:

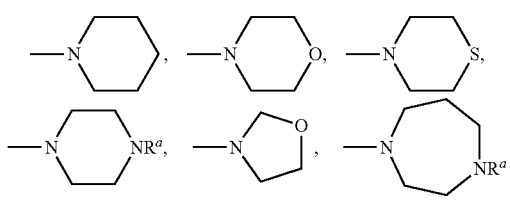

and the like.

In another embodiment, provided is a method of treating an Arenaviridae infection in a human in need thereof comprising administering a therapeutically effective amount of a compound of Formula I-IV, wherein each $R^3$, $R^4$, $R^5$, $R^6$, $R^{11}$ or $R^{12}$ is, independently, $(C_1$-$C_8)$alkyl, $(C_2$-$C_8)$alkenyl, $(C_2$-$C_8)$alkynyl or aryl$(C_1$-$C_8)$alkyl, wherein said $(C_1$-$C_8)$alkyl, $(C_2$-$C_8)$alkenyl, $(C_2$-$C_8)$alkynyl or aryl$(C_1$-$C_8)$alkyl are, independently, optionally substituted with one or more halo, hydroxy, CN, $N_3$, $N(R^a)_2$ or $OR^a$. Therefore, by way of example and not limitation, $R^3$, $R^4$, $R^5$, $R^6$, $R^{11}$ or $R^{12}$ could represent moieties such as —CH(NH$_2$)CH$_3$, —CH(OH)CH2CH3, —CH(NH$_2$)CH(CH$_3$)$_2$, —CH$_2$CF$_3$, —(CH$_2$)$_2$CH(N$_3$)CH$_3$, —(CH$_2$)$_6$NH$_2$ and the like.

In another embodiment, provided is a method of treating an Arenaviridae infection in a human in need thereof comprising administering a therapeutically effective amount of a compound of Formula I-IV, wherein $R^3$, $R^4$, $R^5$, $R^6$, $R^{11}$ or $R^{12}$ is $(C_1$-$C_8)$alkyl wherein one or more of the non-terminal carbon atoms of each said $(C_1$-$C_8)$alkyl may be optionally replaced with —O—, —S— or —NR$^a$—. Therefore, by way of example and not limitation, $R^3$, $R^4$, $R^5$, $R^6$, $R^{11}$ or $R^{12}$ could represent moieties such as —CH$_2$OCH$_3$, —CH$_2$OCH$_2$CH$_3$, —CH$_2$OCH(CH$_3$)$_2$, —CH$_2$SCH$_3$, —(CH$_2$)$_6$OCH$_3$, —(CH$_2$)$_6$N(CH$_3$)$_2$ and the like.

In another embodiment of the method of treating an Arenaviridae infection comprising administering a compound of Formula I, the compound is

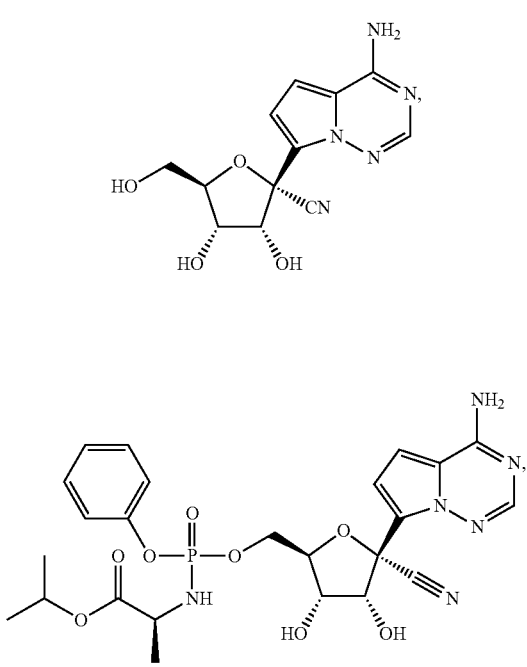

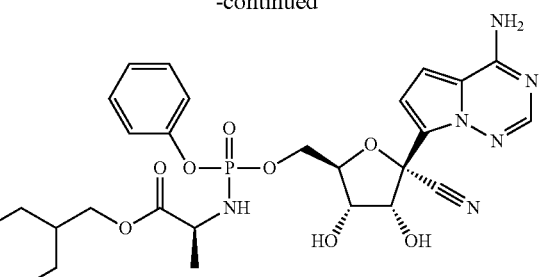

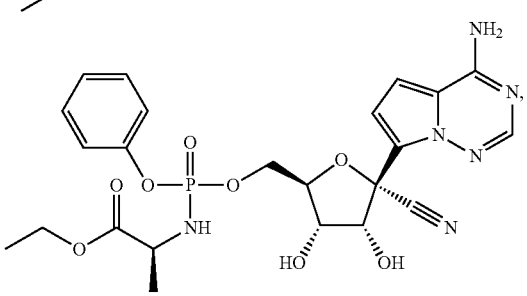

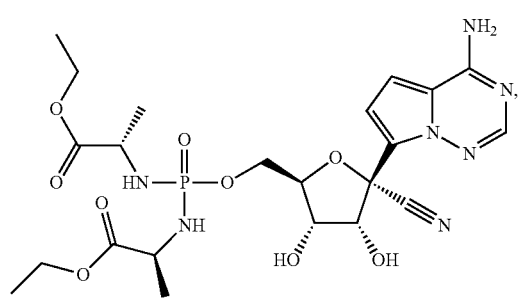

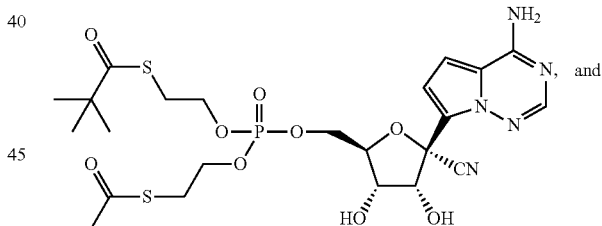

and

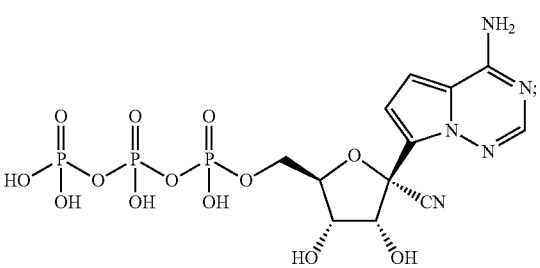

or a pharmaceutically acceptable salt or ester thereof.

In another embodiment of the method of treating an Arenaviridae infection comprising administering a compound of Formula I, the compound is

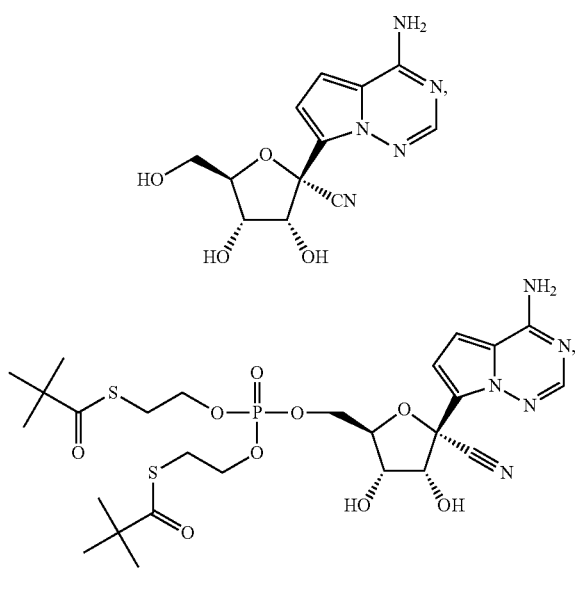
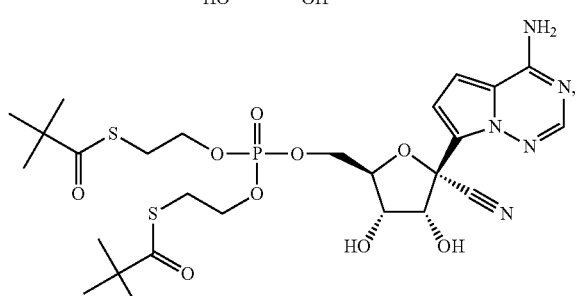
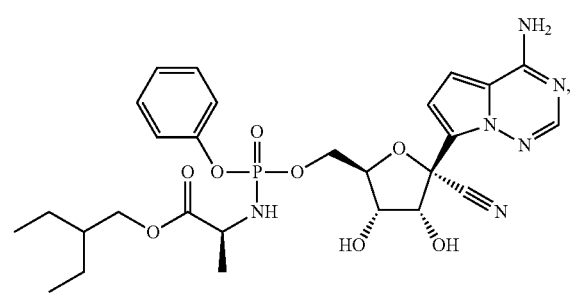
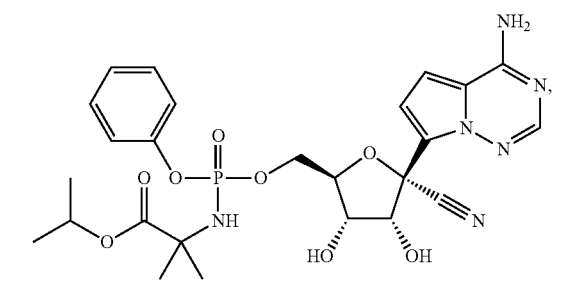
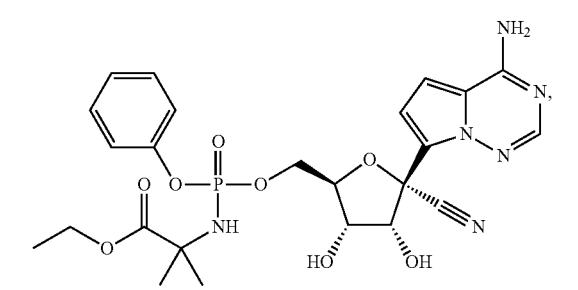
-continued
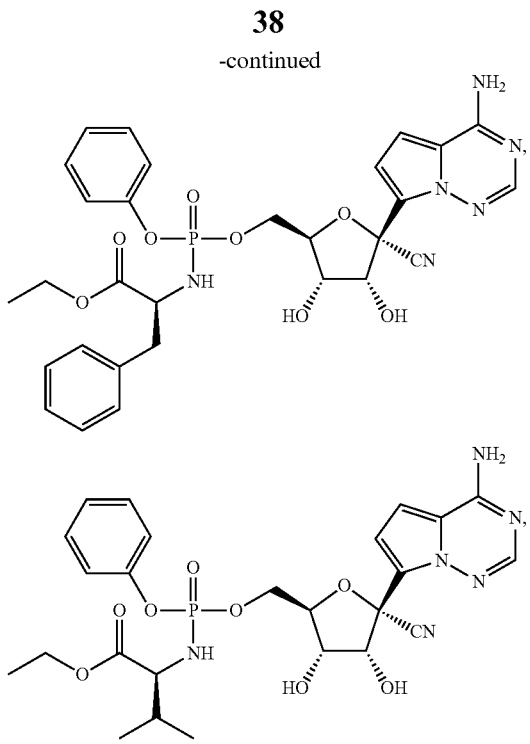

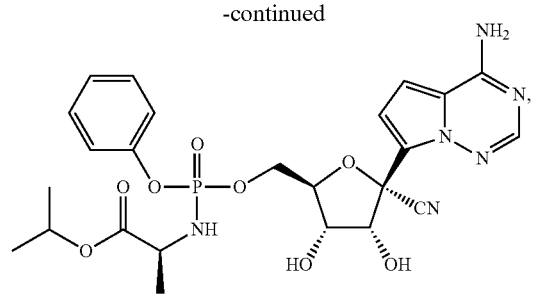
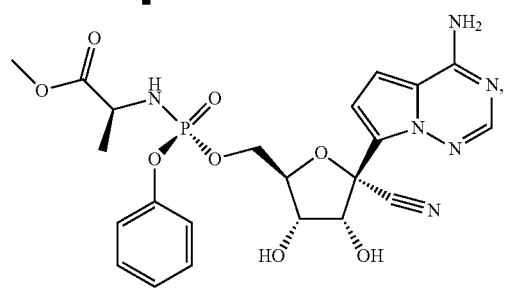
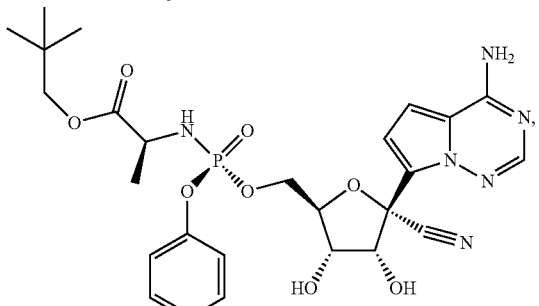
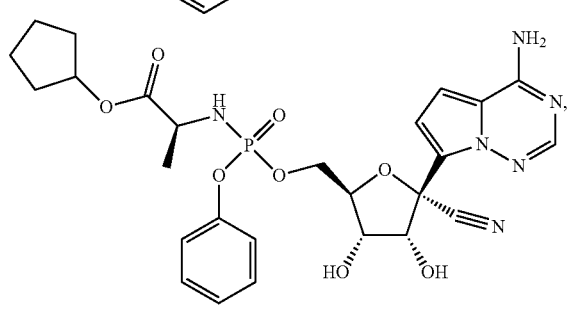
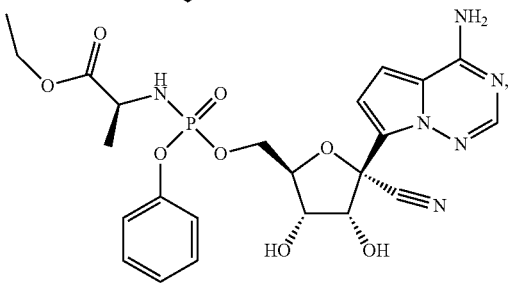
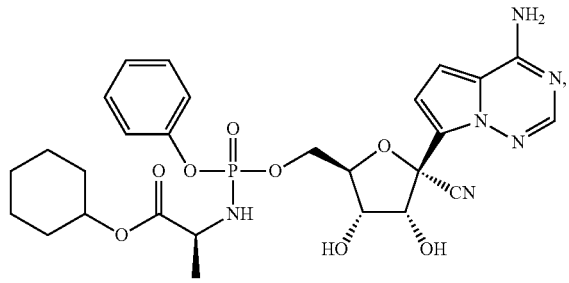
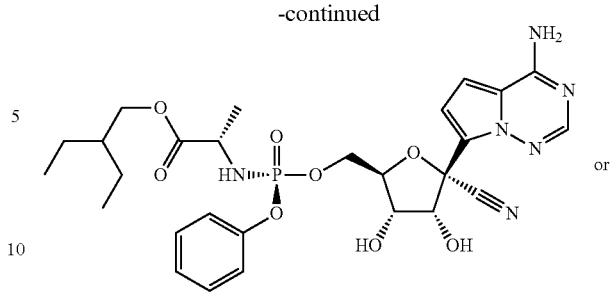
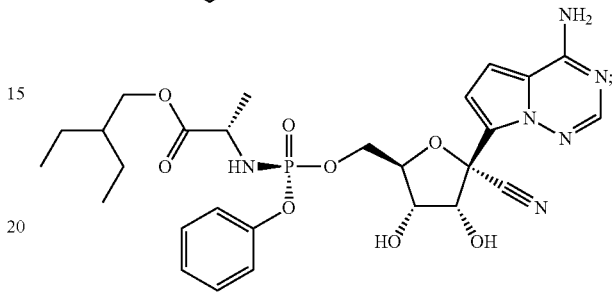
or a pharmaceutically acceptable salt or ester thereof.
In another embodiment of the method of treating an Arenaviridae infection comprising administering a compound of Formula IV, the compound is:
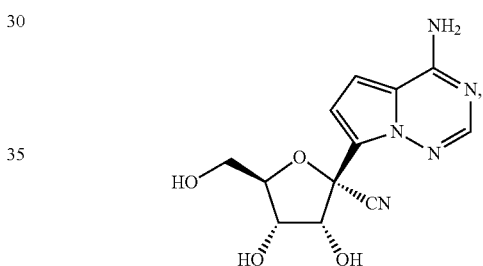
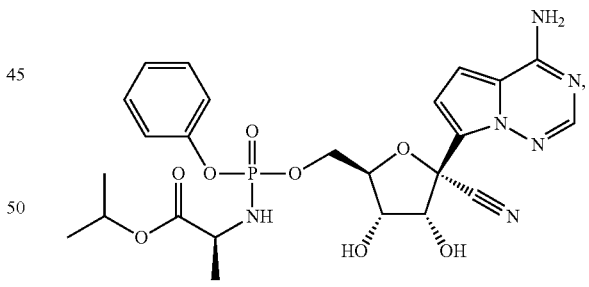
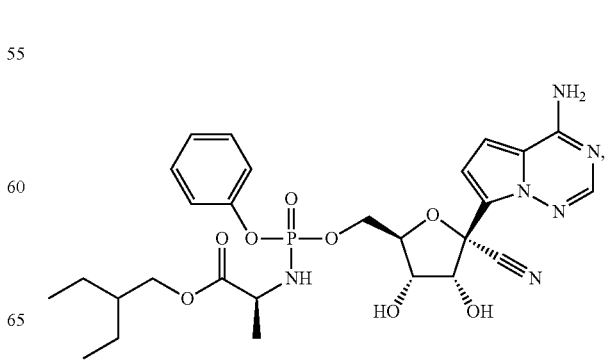

-continued

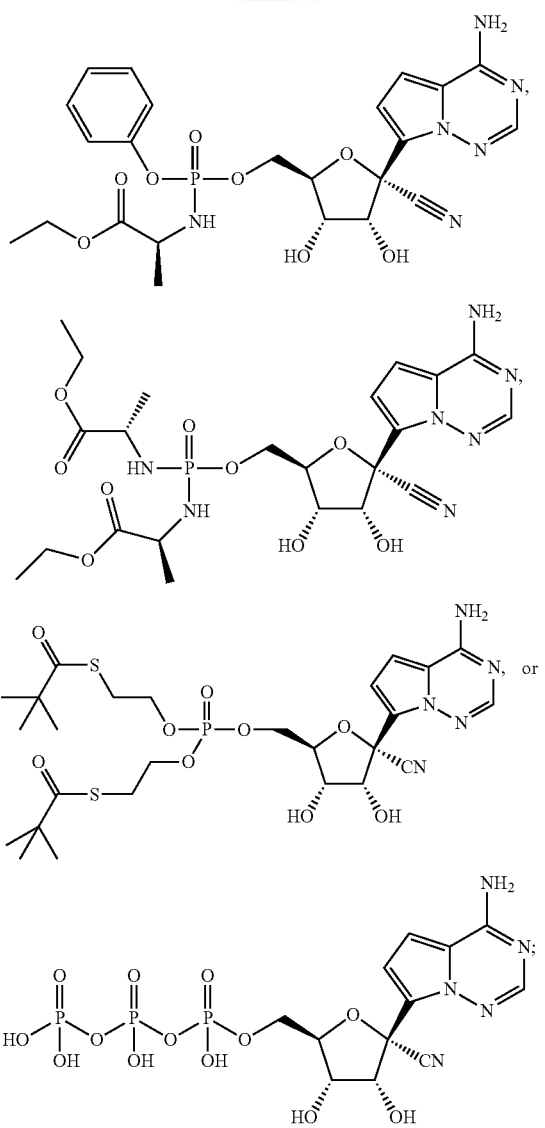

or a pharmaceutically acceptable salt or ester thereof.

In another embodiment of the method of treating an Arenaviridae infection comprising administering a compound of Formula IV, the compound is:

-continued

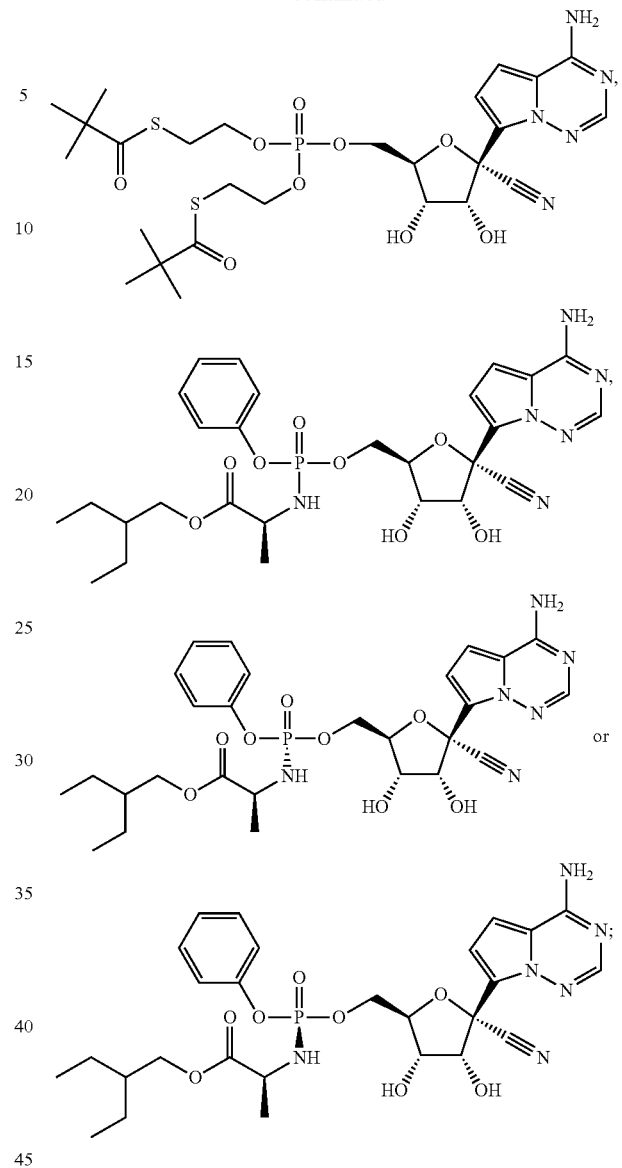

or a pharmaceutically acceptable salt or ester thereof.

In another embodiment of the method of treating an Arenaviridae infection comprising administering a compound of Formula I-IV, the compound is

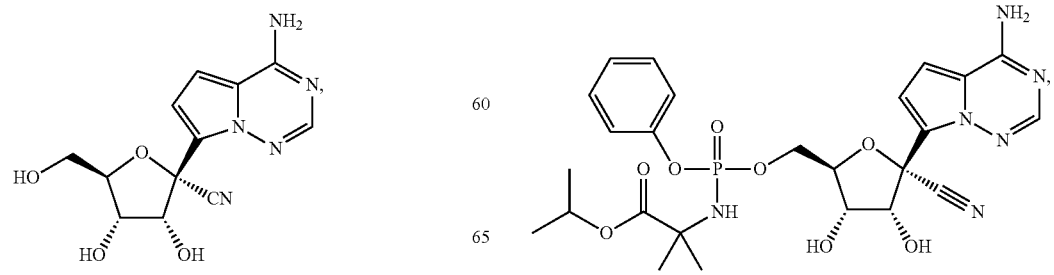

43
-continued
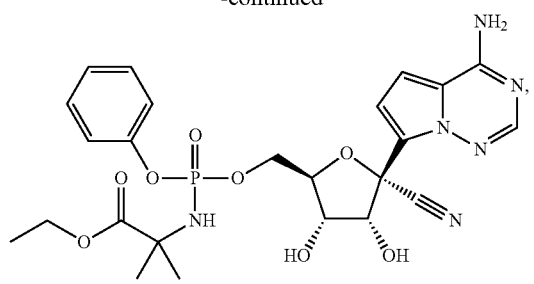
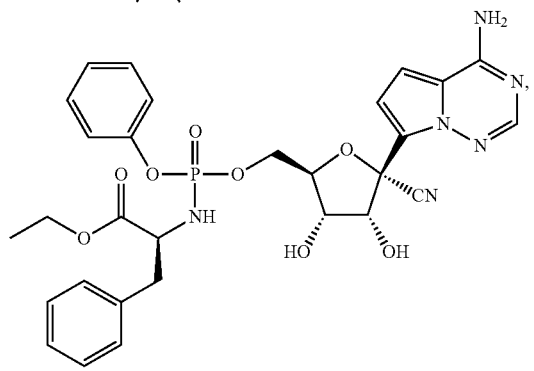
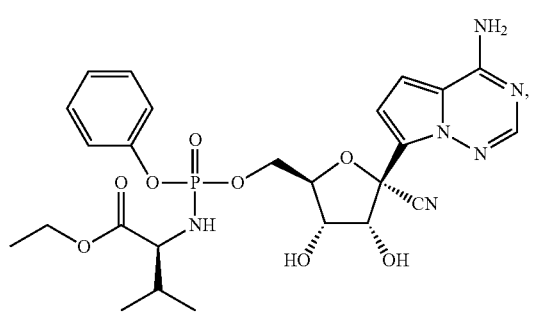
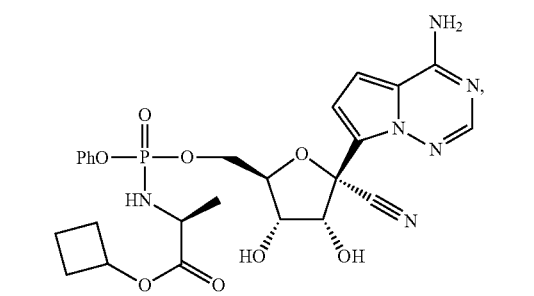
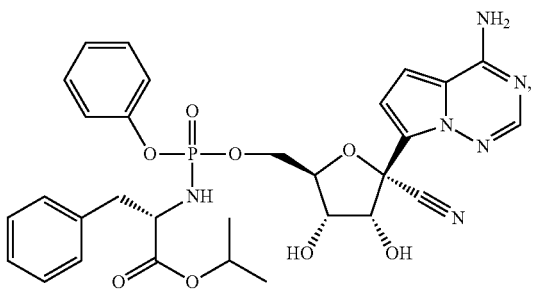
44
-continued
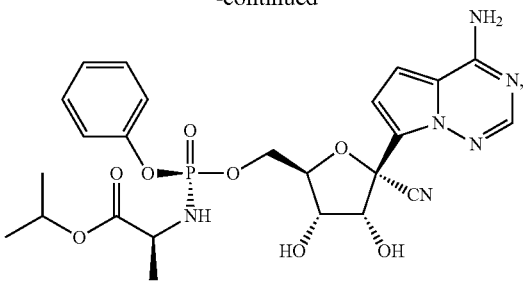
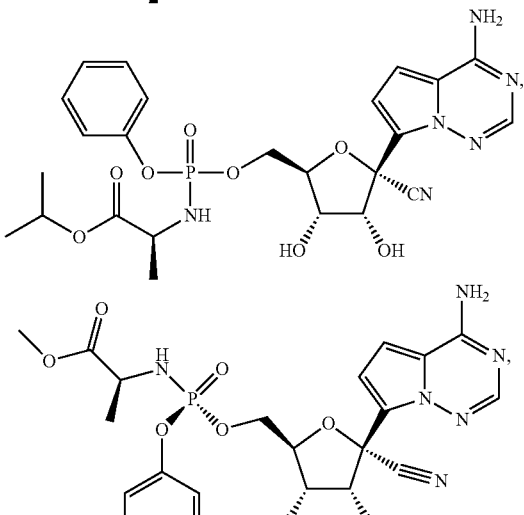
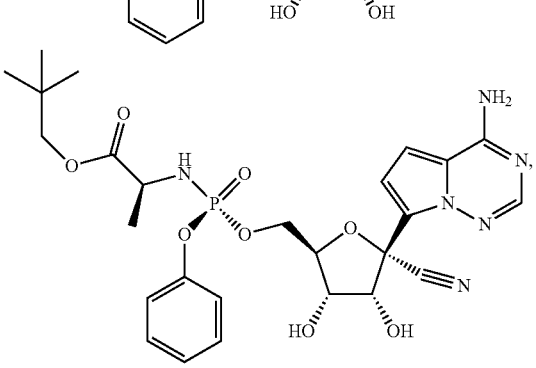
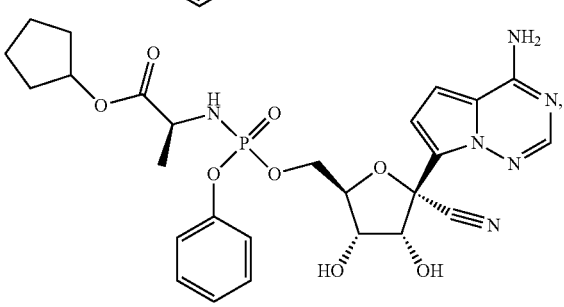
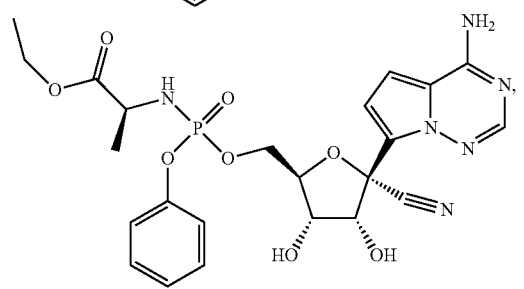

-continued

[Chemical structure: phosphoramidate prodrug with cyclohexyl ester, phenoxy, alanine linker, and pyrrolo[2,1-f][1,2,4]triazin-4-amine ribonucleoside with 1'-CN]

[Chemical structure: phosphoramidate prodrug with 2-ethylbutyl ester, alanine, phenoxy, nucleoside with 1'-CN]

or

[Chemical structure: phosphoramidate prodrug with 2-ethylbutyl ester, alanine, phenoxy, nucleoside with 1'-CN]

or a pharmaceutically acceptable salt or ester thereof.

In another embodiment of the method of treating an Arenaviridae infection comprising administering a compound of Formula I-IV, the compound is

[Chemical structure: phosphoramidate prodrug]

or

[Chemical structure: phosphoramidate prodrug]

or a pharmaceutically acceptable salt or ester thereof.

Provided is a method for treating a Coronaviridae infection in a human in need thereof comprising administering a therapeutically effective amount of a compound of Formula I:

[Chemical structure: Formula I - nucleoside analog with substituents $R^1$ through $R^{10}$]

Formula I or a pharmaceutically acceptable salt or ester, thereof;
wherein:
each $R^1$ is H or halogen;
each $R^2$, $R^3$, $R^4$ or $R^5$ is independently H, $OR^a$, $N(R^a)_2$, $N_3$, CN, $NO_2$, $S(O)_nR^a$, halogen, ($C_1$-$C_8$)alkyl, ($C_4$-$C_8$)carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl or ($C_2$-$C_8$)substituted alkynyl;
or any two $R^2$, $R^3$, $R^4$ or $R^5$ on adjacent carbon atoms when taken together are —O(CO)O— or when taken together with the ring carbon atoms to which they are attached form a double bond;
$R^6$ is $OR^a$, $N(R^a)_2$, $N_3$, CN, $NO_2$, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, halogen, ($C_1$-$C_8$)alkyl, ($C_4$-$C_8$)carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl, ($C_2$-$C_8$)substituted alkynyl, or ($C_6$-$C_{20}$)aryl($C_1$-$C_8$)alkyl;
$R^7$ is selected from a group consisting of
a) H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), or —SO$_2NR^{11}R^{12}$, wherein each ($C_1$-$C_8$)alkyl, ($C_2$-$C_8$)alkenyl, ($C_2$-$C_8$)alkynyl or ($C_6$-$C_{20}$)aryl($C_1$-$C_8$)alkyl of each $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said ($C_1$-$C_8$)alkyl may be optionally replaced with —O—, —S— or —$NR^a$—, b) [Chemical structures: mono-, di-, triphosphate groups]

, or c) [Chemical structures: phosphoramidate groups with $R^c$, $R^{e1}$, $R^{e2}$, $R^d$, $R^f$]

, or

-continued

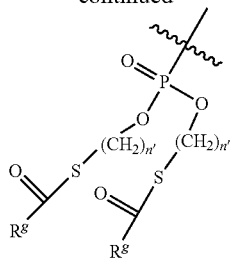

wherein:

R$^c$ is selected from phenyl, 1-naphthyl, 2-naphthyl,

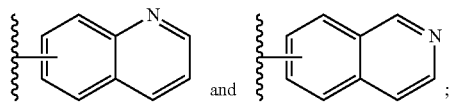

R$^d$ is H or CH$_3$;

R$^{e1}$ and R$^{e2}$ are each independently H, (C$_1$-C$_6$) alkyl or benzyl;

R$^f$ is selected from H, (C$_1$-C$_8$)alkyl, benzyl, (C$_3$-C$_6$)cycloalkyl, and —CH$_2$—(C$_3$-C$_6$)cycloalkyl;

R$^g$ is selected from (C$_1$-C$_8$)alkyl, —O—(C$_1$-C$_8$) alkyl, benzyl, —O-benzyl, —CH$_2$—(C$_3$-C$_6$)cycloalkyl, —O—CH$_2$—(C$_3$-C$_6$)cycloalkyl, and CF$_3$; and n' is selected from 1, 2, 3, and 4; and d) a group of the formula:

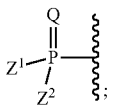

wherein:

Q is O, S, NR, $^+$N(O)(R), N(OR), $^+$N(O)(OR), or N—NR$_2$;

Z$^1$ and Z$^2$, when taken together, are -Q$^1$(C(R$^y$)$_2$)$_3$Q$^1$-;

wherein each Q$^1$ is independently O, S, or NR; and each R$^y$ is independently H, F, Cl, Br, I, OH, R, —C(=Q$^2$)R, —C(=Q$^2$)OR, —C(=Q$^2$)N(R)$_2$, —N(R)$_2$, —$^+$N(R)$_3$, —SR, —S(O)R, —S(O)$_2$R, —S(O)(OR), —S(O)$_2$(OR), —OC(=Q$^1$)R, —OC(=Q$^2$)OR, —OC(=Q$^2$)(N(R)$_2$), —SC(=Q$^2$)R, —SC(=Q$^2$)OR, —SC(=Q$^2$)(N(R)$_2$), —N(R)C(=Q$^2$)R, —N(R)C(=Q$^2$)OR, —N(R)C(=Q$^2$)N(R)$_2$, —SO$_2$NR$_2$, —CN, —N$_3$, —NO$_2$, —OR, or Z$^3$; or when taken together, two R$^y$ on the same carbon atom form a carbocyclic ring of 3 to 7 carbon atoms;

each Q$^2$ is independently, O, S, NR, $^+$N(O)(R), N(OR), $^+$N(O)(OR), or N—NR$_2$; or Z$^1$ and Z$^2$ are each, independently, a group of the Formula Ia:

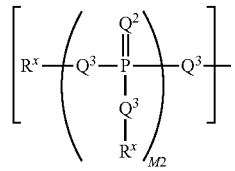

wherein:

each Q$^3$ is independently a bond, O, CR$_2$, NR, $^+$N(O)(R), N(OR), $^+$N(O)(OR), N—NR$_2$, S, S—S, S(O), or S(O)$_2$;

M2 is 0, 1 or 2;

each R$^x$ is independently R$^y$ or the formula:

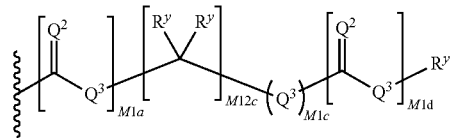

wherein:

each M1a, M1c, and M1d is independently 0 or 1; M12c is 0, 1, 2, 3, 4, 5, 6, 7, 8, 9, 10, 11 or 12;

Z$^3$ is Z$^4$ or Z$^5$;

Z$^4$ is R, —C(Q$^2$)R$^y$, —C(Q$^2$)Z$^5$, —SO$_2$R$^y$, or —SO$_2$Z$^5$; and

Z$^5$ is a carbocycle or a heterocycle wherein Z$^5$ is independently substituted with 0 to 3 R$^y$ groups;

R$^8$ is halogen, NR$^{11}$R$^{12}$, N(R$^{11}$)OR$^{11}$, NR$^{11}$NR$^{11}$R$^{12}$, N$_3$, NO, NO$_2$, CHO, CN, —CH(=NR$^{11}$), —CH=NNHR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl, (C$_6$-C$_{20}$)aryl(C$_1$-C$_8$)alkyl, OR$^{11}$ or SR$^{11}$;

each R$^9$ or R$^{10}$ is independently H, halogen, NR$^{11}$R$^{12}$, N(R$^{11}$)OR$^{11}$, NR$^{11}$NR$^{11}$R$^{12}$, N$_3$, NO, NO$_2$, CHO, CN, —CH(=NR$^{11}$), —CH=NHNR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, R$^{11}$, OR$^{11}$ or SR$^{11}$;

each R$^{11}$ or R$^{12}$ is independently H, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl or (C$_6$-C$_{20}$)aryl(C$_1$-C$_8$)alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S— or —NR$^a$—;

each R$^a$ is independently H, (C$_1$-C$_8$)alkyl, (C$_2$-C$_8$)alkenyl, (C$_2$-C$_8$)alkynyl, (C$_6$-C$_{20}$)aryl(C$_1$-C$_8$)alkyl, (C$_4$-C$_8$)carbocyclylalkyl, —C(=O)R, —C(=O)OR, —C(=O)NR$_2$, —C(=O)SR, —S(O)R, —S(O)$_2$R, —S(O)(OR), —S(O)$_2$(OR), or —SO$_2$NR$_2$; wherein each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, ($C_6$-$C_{20}$)aryl, ($C_6$-$C_{20}$)substituted aryl, ($C_2$-$C_{20}$)heterocyclyl, ($C_2$-$C_{20}$)substituted heterocyclyl, ($C_6$-$C_{20}$)aryl($C_1$-$C_8$)alkyl or substituted ($C_6$-$C_{20}$)aryl($C_1$-$C_8$)alkyl;

each n is independently 0, 1, or 2; and wherein each ($C_1$-$C_8$)alkyl, ($C_2$-$C_8$)alkenyl, ($C_2$-$C_8$)alkynyl or ($C_6$-$C_{20}$)aryl($C_1$-$C_8$)alkyl of each $R^2$, $R^3$, $R^5$, $R^6$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said ($C_1$-$C_8$)alkyl may be optionally replaced with —O—, —S— or —$NR^a$—.

In another embodiment, provided is a method of treating a Coronaviridae infection in a human in need thereof comprising administering a therapeutically effective amount of a compound of Formula I represented by Formula II:

Formula II or a pharmaceutically acceptable salt or ester, thereof; wherein $R^1$, $R^3$, $R^5$, $R^7$, $R^8$ and $R^9$ are as defined above for Formula I;

each $R^2$ is $OR^a$ or halogen; and $R^6$ is $OR^a$, $N(R^a)_2$, $N_3$, CN, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, halogen, ($C_1$-$C_8$)alkyl, ($C_4$-$C_8$)carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl, or ($C_2$-$C_8$)substituted alkynyl.

In one embodiment of the method of treating a Coronaviridae infection by administering a compound of Formula II, $R^1$ of Formula II is H. In another aspect of this embodiment $R^6$ of Formula II is $N_3$, CN, halogen, ($C_1$-$C_8$)alkyl, ($C_1$-$C_8$)substituted alkyl, ($C_2$-$C_8$)alkenyl, ($C_2$-$C_8$)substituted alkenyl, ($C_2$-$C_8$)alkynyl, or ($C_2$-$C_8$)substituted alkynyl. In another aspect of this embodiment, $R^6$ of Formula II is CN, methyl, ethenyl, or ethynyl. In another aspect of this embodiment, $R^6$ of Formula II is CN. In another aspect of this embodiment, $R^6$ of Formula II is methyl. In another aspect of this embodiment, $R^5$ of Formula II is H. In another aspect of this embodiment, $R^2$ of Formula II is $OR^a$. In another aspect of this embodiment, $R^2$ of Formula II is OH. In another aspect of this embodiment, $R^2$ of Formula II is F. In another aspect of this embodiment, $R^3$ of Formula II is $OR^a$. In another aspect of this embodiment, $R^3$ of Formula II is OH, —OC(=O)$R^{11}$, or —OC(=O)$OR^{11}$. In another aspect of this embodiment, $R^3$ of Formula II is OH. In another aspect of this embodiment, $R^8$ of Formula II is $NR^{11}R^{12}$. In another aspect of this embodiment, $R^8$ of Formula II is $NH_2$. In another aspect of this embodiment, $R^8$ of Formula II is $OR^{11}$. In another aspect of this embodiment, $R^8$ of Formula II is OH. In another aspect of this embodiment, $R^9$ of Formula II is H. In another aspect of this embodiment, $R^9$ of Formula II is $NR^{11}R^{12}$. In another aspect of this embodiment, $R^9$ of Formula II is $NH_2$. In another aspect of this embodiment, $R^7$ of Formula II is H, —C(=O)$R^{11}$, —C(=O)$OR^{11}$ or In another aspect of this embodiment, $R^7$ of Formula II is H. In another aspect of this embodiment, $R^7$ of Formula II is In another embodiment of the method of treating a Coronaviridae infection comprising administering a compound of Formula II, the Coronaviridae infection is caused by a Coronaviridae virus. In another aspect of this embodiment, the Coronaviridae virus is a MERS virus or SARS virus. In another aspect of this embodiment, the Coronaviridae virus is a MERS virus. In another aspect of this embodiment, the Coronaviridae virus is a SARS virus. In another aspect of this embodiment, the Coronaviridae virus is caused by a MERS virus caused by a strain selected from known strains.

In another embodiment, provided is a method of treating a Coronaviridae infection in a human in need thereof comprising administering a therapeutically effective amount of a compound of Formula I represented by Formula III:

Formula III or a pharmaceutically acceptable salt or ester, thereof; wherein $R^6$, $R^7$, $R^8$ and $R^9$ are as defined above for Formula II;

each $R^2$ is $OR^a$ or F; and each $R^3$ is $OR^a$.

In one embodiment of the method of treating a Coronaviridae infection comprising administering a compound of Formula III, $R^6$ of Formula III is $N_3$, CN, halogen, ($C_1$-$C_8$)alkyl, ($C_1$-$C_8$)substituted alkyl, ($C_2$-$C_8$)alkenyl, ($C_2$-$C_8$)substituted alkenyl, ($C_2$-$C_8$)alkynyl, or ($C_2$-$C_8$)substituted alkynyl. In another aspect of this embodiment, $R^6$ of Formula III is CN, methyl, ethenyl, or ethynyl. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH. In another aspect of this embodiment, $R^2$ of Formula III is F. In another aspect of this embodiment, $R^3$ of Formula III is OH, —OC(=O)R$^{11}$, or —OC(=O)OR$^{11}$. In another aspect of this embodiment, R$^3$ of Formula III is OH. In another aspect of this embodiment, R$^8$ of Formula III is NR$^{11}$R$^{12}$. In another aspect of this embodiment, R$^8$ of Formula III is NH$_2$. In another aspect of this embodiment, R$^8$ of Formula III is OR$^{11}$. In another aspect of this embodiment, R$^8$ of Formula III is OH. In another aspect of this embodiment, R$^9$ of Formula III is H. In another aspect of this embodiment, R$^9$ of Formula III is NR$^{11}$R$^{12}$. In another aspect of this embodiment, R$^9$ of Formula III is NH$_2$. In another aspect of this embodiment, R$^7$ of Formula III is H, —C(=O)R$^{11}$, —C(=O)OR$^{11}$ or $$Z^1-\overset{\overset{O}{\|}}{\underset{Z^2}{P}}-\xi.$$

In another aspect of this embodiment, R$^7$ of Formula III is H. In another aspect of this embodiment, R$^7$ of Formula III is $$Z^1-\overset{\overset{O}{\|}}{\underset{Z^2}{P}}-\xi.$$

In another embodiment of the method of treating a Coronaviridae infection comprising administering a compound of Formula III, R$^6$ of Formula III is N$_3$, CN, halogen, (C$_1$-C$_8$)alkyl, (C$_1$-C$_8$)substituted alkyl, (C$_2$-C$_8$)alkenyl, (C$_2$-C$_8$)substituted alkenyl, (C$_2$-C$_8$)alkynyl, or (C$_2$-C$_8$)substituted alkynyl and R$^8$ is NH$_2$. In another aspect of this embodiment, R$^6$ of Formula III is CN, methyl, ethenyl, or ethynyl. In another aspect of this embodiment, R$^6$ of Formula III is CN. In another aspect of this embodiment, R$^6$ of Formula III is methyl. In another aspect of this embodiment, R$^2$ of Formula III is OR$^a$. In another aspect of this embodiment, R$^2$ of Formula III is OH, —OC(=O)R$^{11}$, or —OC(=O)OR$^{11}$. In another aspect of this embodiment, R$^2$ of Formula III is OH. In another aspect of this embodiment, R$^2$ of Formula III is F. In another aspect of this embodiment, R$^3$ of Formula III is OH, —OC(=O)R$^{11}$, or —OC(=O)OR$^{11}$. In another aspect of this embodiment, R$^3$ of Formula III is OH. In another aspect of this embodiment, R$^9$ of Formula III is H. In another aspect of this embodiment, R$^9$ of Formula III is NR$^{11}$R$^{12}$. In another aspect of this embodiment, R$^9$ of Formula III is NH$_2$. In another aspect of this embodiment, R$^7$ of Formula III is H, —C(=O)R$^{11}$, —C(=O)OR$^{11}$ or $$Z^1-\overset{\overset{O}{\|}}{\underset{Z^2}{P}}-\xi.$$

In another aspect of this embodiment, R$^7$ of Formula III is H. In another aspect of this embodiment, R$^7$ of Formula III is $$Z^1-\overset{\overset{O}{\|}}{\underset{Z^2}{P}}-\xi.$$

In another embodiment of the method of treating a Coronaviridae infection comprising administering a compound of Formula III, R$^6$ of Formula III is CN, methyl, ethenyl, or ethynyl, R$^8$ is NH$_2$, and R$^9$ is H. In another aspect of this embodiment, R$^6$ of Formula III is CN. In another aspect of this embodiment, R$^6$ of Formula III is methyl. In another aspect of this embodiment, R$^2$ of Formula III is OR$^a$. In another aspect of this embodiment, R$^2$ of Formula III is OH, —OC(=O)R$^{11}$, or —OC(=O)OR$^{11}$. In another aspect of this embodiment, R$^2$ of Formula III is OH. In another aspect of this embodiment, R$^2$ of Formula III is F. In another aspect of this embodiment, R$^3$ of Formula III is OH, —OC(=O)R$^{11}$, or —OC(=O)OR$^{11}$. In another aspect of this embodiment, R$^3$ of Formula III is OH. In another aspect of this embodiment, R$^7$ of Formula III is H, —C(=O)R$^{11}$, —C(=O)OR$^{11}$ or $$Z^1-\overset{\overset{O}{\|}}{\underset{Z^2}{P}}-\xi.$$

In another aspect of this embodiment, R$^7$ of Formula III is H. In another aspect of this embodiment, R$^7$ of Formula III is $$Z^1-\overset{\overset{O}{\|}}{\underset{Z^2}{P}}-\xi.$$

In another embodiment of the method of treating a Coronaviridae infection comprising administering a compound of Formula III, the Coronaviridae infection is caused by a Coronaviridae virus. In another aspect of this embodiment, the Coronaviridae virus is a MERS virus or SARS virus. In another aspect of this embodiment, the Coronaviridae virus is a MERS virus. In another aspect of this embodiment, the Coronaviridae virus is a SARS virus. In another aspect of this embodiment, the Coronaviridae virus is caused by a MERS virus caused by a strain selected from known strains.

In another embodiment, provided is a method of treating a Coronaviridae infection in a human in need thereof comprising administering a therapeutically effective amount of a compound of Formula I represented by Formula IV:

Formula IV or a pharmaceutically acceptable salt or ester, thereof; wherein R$^7$ is as defined above for Formula I.

In another embodiment of the method of treating a Coronaviridae infection comprising administering a compound of Formula IV, $R^7$ can be H. In another embodiment of the method of treating a Coronaviridae infection comprising administering a compound of Formula IV, $R^7$ is selected from the group of a), b), or c) as defined for Formula I.

In another embodiment of the method of treating a Coronaviridae infection comprising administering a compound of Formula IV, $R^7$ is

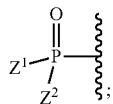

wherein $Z^1$ and $Z^2$ are each, independently, a group having the structure:

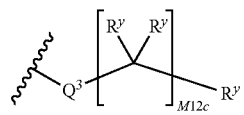

and $Z^3$ is $Z^5$.

In another embodiment of the method of treating a Coronaviridae infection comprising administering a compound of Formula IV, $R^7$ is

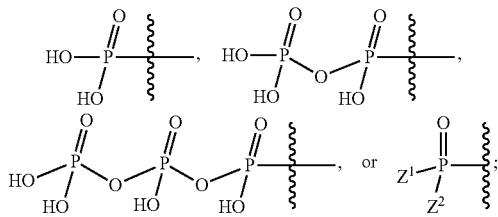

wherein $Z^1$ and $Z^2$ are each, independently, a group having the structure:

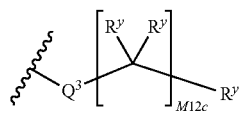

and $Z^3$ is $Z^5$.

In another embodiment of the method of treating a Coronaviridae infection comprising administering a compound of Formula IV, $R^7$ is

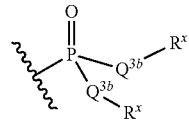

wherein each $Q^{3b}$ is, independently, O or N(R). In another embodiment, each $Q^{3b}$ is O and each $R^x$ is independently:

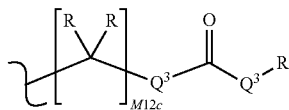

wherein M12c is 1, 2 or 3 and each $Q^3$ is independently a bond, O, $CR_2$, or S.

In some embodiments, $R^{e1}$ and $R^{e2}$ can each independently be H, $C_1$-$C_6$ alkyl or benzyl. In some embodiments, $R^{e1}$ can be H, $C_1$-$C_6$ alkyl or benzyl, and $R^{e2}$ can be H or $C_1$-$C_6$ alkyl. In some embodiments, $R^{e1}$ and $R^{e2}$ can each independently be H or $C_1$-$C_6$ alkyl. In some embodiments, $R^{e1}$ and $R^{e2}$ can each independently be H or benzyl. In some embodiments, $R^{e1}$ can be H, methyl or benzyl, and $R^{e2}$ can be H or methyl. In some embodiments, $R^{e1}$ can be H or methyl, and $R^{e2}$ can be H or methyl. In some embodiments, $R^{e1}$ can be methyl, and $R^{e2}$ can be H or methyl. In some embodiments, $R^{e1}$ can be H or benzyl, and $R^{e2}$ can be H or methyl.

In another embodiment of the method of treating a Coronaviridae infection comprising administering a compound of Formula IV, $R^7$ is

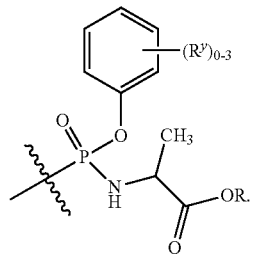

In another embodiment of the method of treating a Coronaviridae infection comprising administering a compound of Formula IV, $R^7$ is

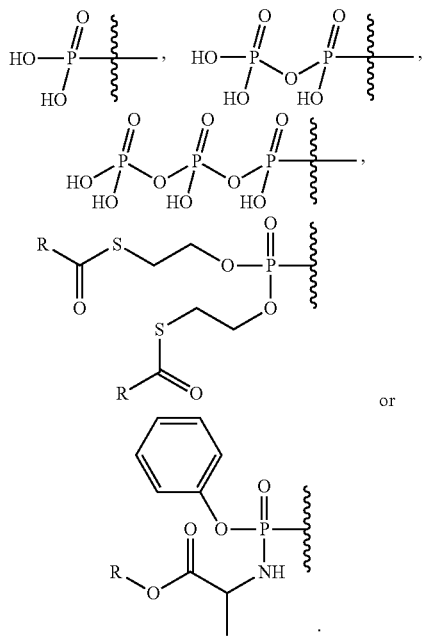

In another embodiment of the method of treating a Coronaviridae infection comprising administering a compound of Formula IV, R$^7$ is

[chemical structures]

or wherein R$^f$ is selected from the group of from H, C$_1$-C$_8$ alkyl, benzyl, C$_3$-C$_6$ cycloalkyl, and —CH$_2$—C$_3$-C$_6$ cycloalkyl. In another embodiment of a compound of Formula IV, R$^f$ is C$_1$-C$_8$ alkyl. In another embodiment of a compound of Formula IV, R$^f$ is 2-ethylbutyl.

In another embodiment of the method of treating a Coronaviridae infection comprising administering a compound of Formula IV, R$^7$ is

[chemical structures]

wherein
R$^f$ is selected from H, C$_1$-C$_8$ alkyl, benzyl, C$_3$-C$_6$ cycloalkyl, and —CH$_2$—C$_3$-C$_6$ cycloalkyl; and
R$^g$ is selected from C$_1$-C$_8$ alkyl, —O—C$_1$-C$_8$ alkyl, benzyl, —O-benzyl, —CH$_2$—C$_3$-C$_6$ cycloalkyl, —O—CH$_2$—C$_3$-C$_6$ cycloalkyl, and CF$_3$.

In another embodiment of the method of treating a Coronaviridae infection comprising administering a compound of Formula IV, R$^7$ is

[chemical structures]

or wherein R$^f$ is selected from H, C$_1$-C$_8$ alkyl, benzyl, C$_3$-C$_6$ cycloalkyl, and —CH$_2$—C$_3$-C$_6$ cycloalkyl. In another embodiment of a compound of Formula IV, R$^f$ is C$_1$-C$_8$ alkyl. In another embodiment of a compound of Formula IV, R$^f$ is C$_1$-C$_6$ alkyl. In another embodiment of a compound of Formula IV, R$^f$ is 2-ethylbutyl.

In another embodiment of the method of treating a Coronaviridae infection comprising administering a compound of Formula IV, R$^7$ is:

[chemical structure]

wherein R$^g$ is selected from C$_1$-C$_8$ alkyl, —O—C$_1$-C$_8$ alkyl, benzyl, —O-benzyl, —CH$_2$—C$_3$-C$_6$ cycloalkyl, —O—CH$_2$—C$_3$-C$_6$ cycloalkyl, and CF$_3$. In another embodiment of a compound of Formula IV, R$^f$ is C$_1$-C$_8$ alkyl. In another embodiment of a compound of Formula IV, R$^f$ is C$_1$-C$_6$ alkyl.

In another embodiment of the method of treating a Coronaviridae infection comprising administering a compound of Formula IV, R$^7$ is selected from the group of:

[chemical structures] , and

In another embodiment of the method of treating a Coronaviridae infection comprising administering a compound of Formula IV, R$^7$ is

[chemical structures]

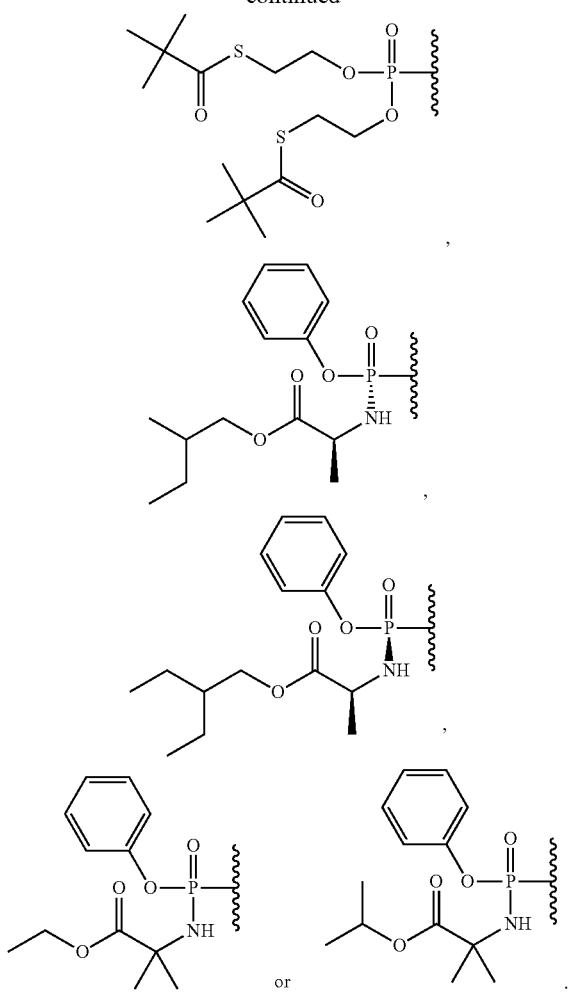

In another embodiment of the method of treating a Coronaviridae infection comprising administering a compound of Formula IV, $Z^1$ and $Z^2$ can each be:

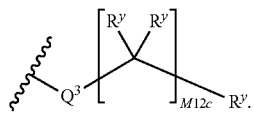

In another embodiment, provided is a method of treating a Coronaviridae infection in a human in need thereof comprising administering a therapeutically effective amount of a compound of Formulas I-IV, wherein $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$carbocyclylalkyl, optionally substituted aryl, optionally substituted heteroaryl, —C(=O)$(C_1\text{-}C_8)$alkyl, —S(O)$_n$$(C_1\text{-}C_8)$alkyl or aryl$(C_1\text{-}C_8)$alkyl. In another embodiment, $R^{11}$ and $R^{12}$ taken together with a nitrogen to which they are both attached, form a 3 to 7 membered heterocyclic ring wherein any one carbon atom of said heterocyclic ring can optionally be replaced with —O—, —S— or —NR$^a$—. Therefore, by way of example and not limitation, the moiety —NR$^{11}$R$^{12}$ can be represented by the heterocycles:

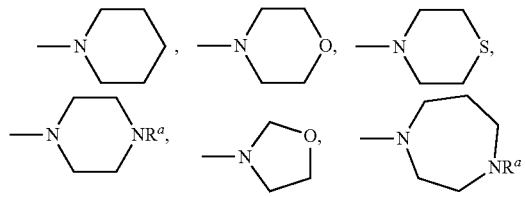

and the like.

In another embodiment, provided is a method of treating a Coronaviridae infection in a human in need thereof comprising administering a therapeutically effective amount of a compound of Formula I-IV, wherein each $R^3$, $R^4$, $R^5$, $R^6$, $R^{11}$ or $R^{12}$ is, independently, $(C_1\text{-}C_8)$alkyl, $(C_2\text{-}C_8)$alkenyl, $(C_2\text{-}C_8)$alkynyl or aryl$(C_1\text{-}C_8)$alkyl, wherein said $(C_1\text{-}C_8)$alkyl, $(C_2\text{-}C_8)$alkenyl, $(C_2\text{-}C_8)$alkynyl or aryl$(C_1\text{-}C_8)$alkyl are, independently, optionally substituted with one or more halo, hydroxy, CN, $N_3$, $N(R^a)_2$ or OR$^a$. Therefore, by way of example and not limitation, $R^3$, $R^4$, $R^5$, $R^6$, $R^{11}$ or $R^{12}$ could represent moieties such as —CH(NH$_2$)CH$_3$, —CH(OH)CH2CH3, —CH(NH$_2$)CH(CH$_3$)$_2$, —CH$_2$CF$_3$, —(CH$_2$)$_2$CH(N$_3$)CH$_3$, —(CH$_2$)$_6$NH$_2$ and the like.

In another embodiment, provided is a method of treating a Coronaviridae infection in a human in need thereof comprising administering a therapeutically effective amount of a compound of Formula I-IV, wherein $R^3$, $R^4$, $R^5$, $R^6$, $R^{11}$ or $R^{12}$ is $(C_1\text{-}C_8)$alkyl wherein one or more of the non-terminal carbon atoms of each said $(C_1\text{-}C_8)$alkyl may be optionally replaced with —O—, —S— or —NR$^a$—. Therefore, by way of example and not limitation, $R^3$, $R^4$, $R^5$, $R^6$, $R^{11}$ or $R^{12}$ could represent moieties such as —CH$_2$OCH$_3$, —CH$_2$OCH$_2$CH$_3$, —CH$_2$OCH(CH$_3$)$_2$, —CH$_2$SCH$_3$, —(CH$_2$)$_6$OCH$_3$, —(CH$_2$)$_6$N(CH$_3$)$_2$ and the like.

In another embodiment of the method of treating a Coronaviridae infection comprising administering a compound of Formula I, the compound is

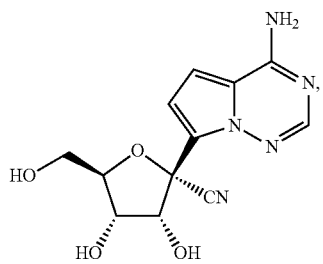

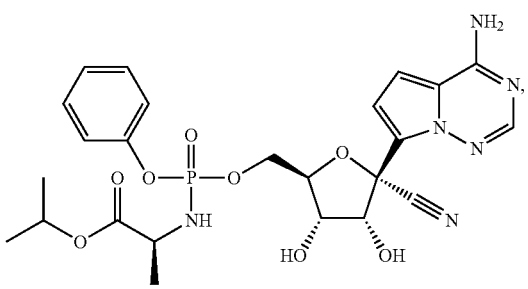

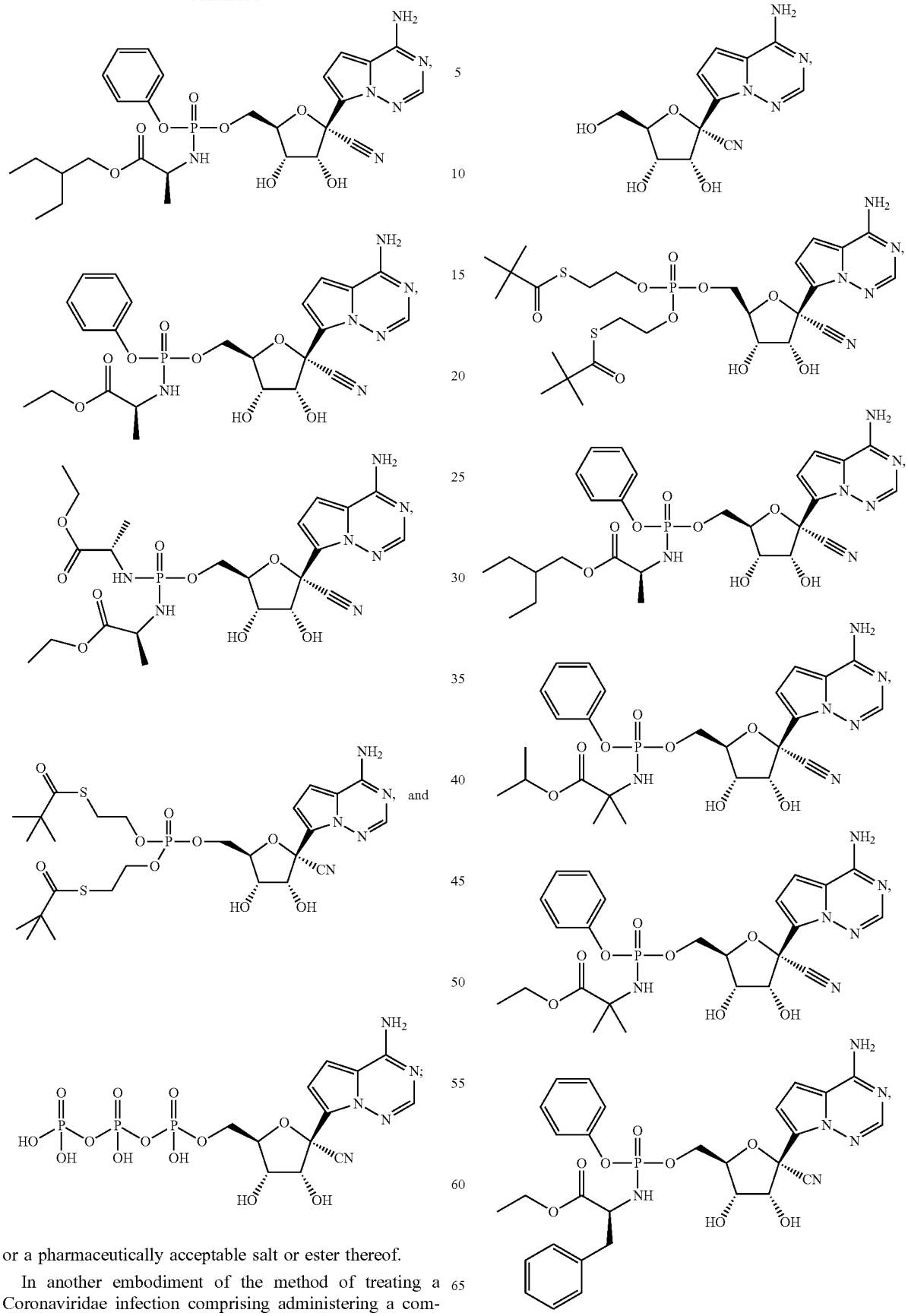
or a pharmaceutically acceptable salt or ester thereof.
In another embodiment of the method of treating a Coronaviridae infection comprising administering a compound of Formula I, the compound is

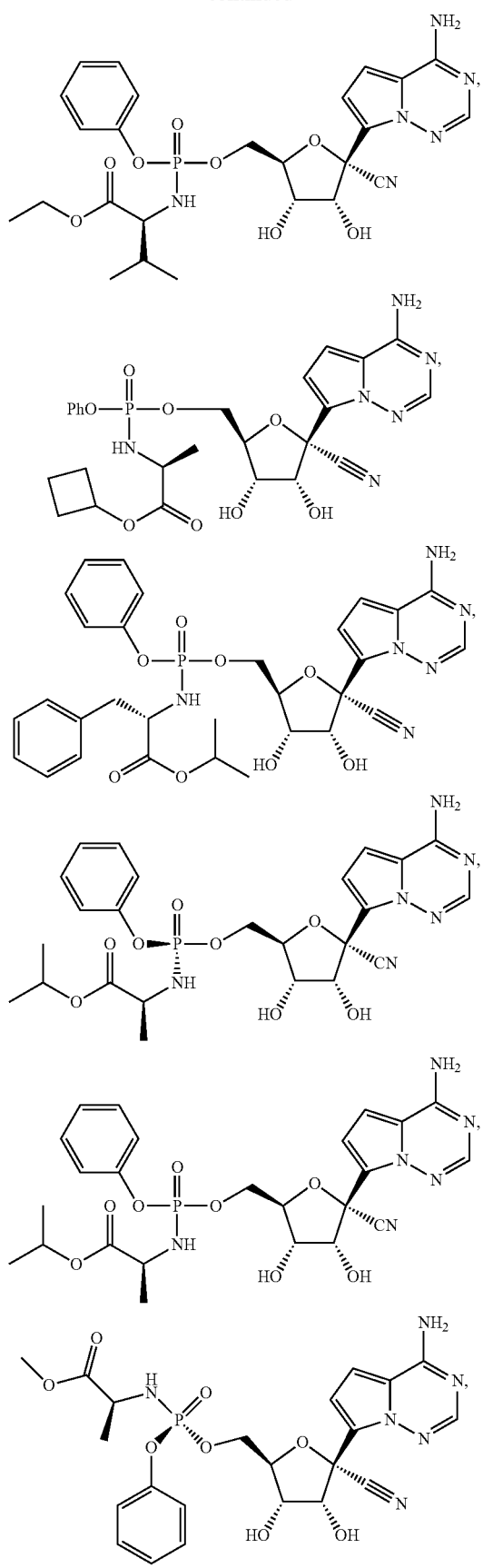
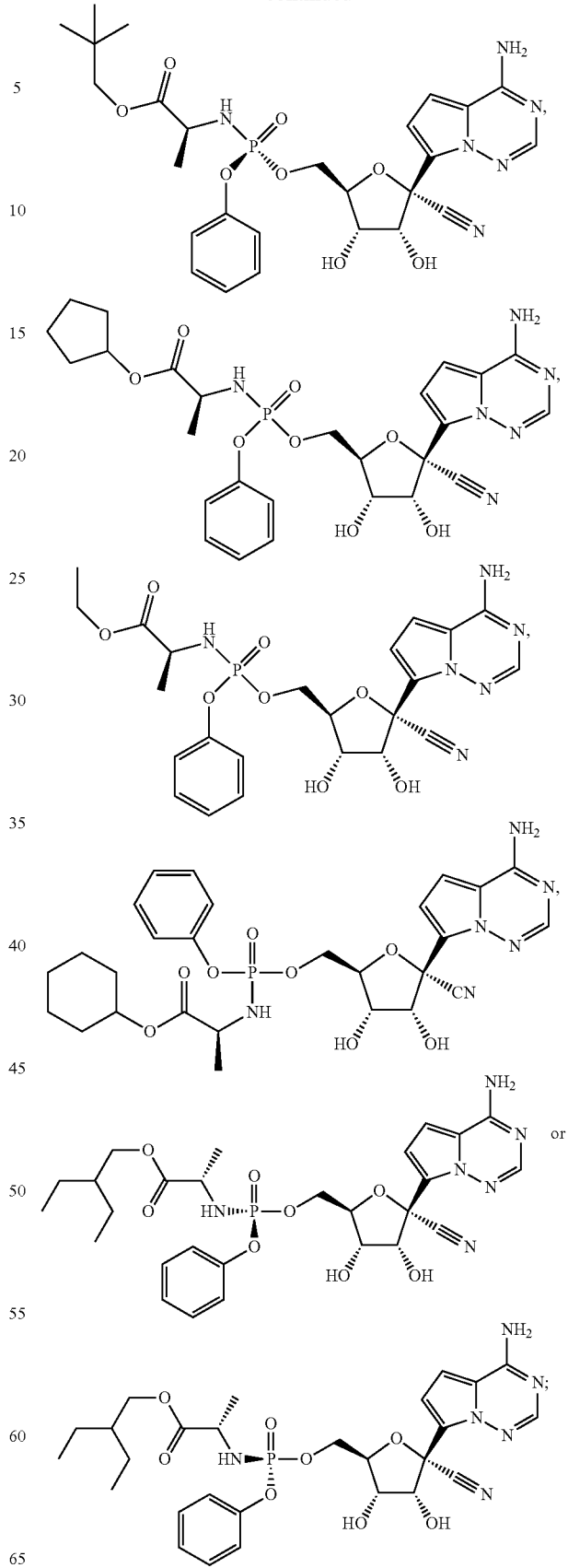
or a pharmaceutically acceptable salt or ester thereof.

In another embodiment of the method of treating a Coronaviridae infection comprising administering a compound of Formula IV, the compound is:

or a pharmaceutically acceptable salt or ester thereof.

In another embodiment of the method of treating a Coronaviridae infection comprising administering a compound of Formula IV, the compound is:

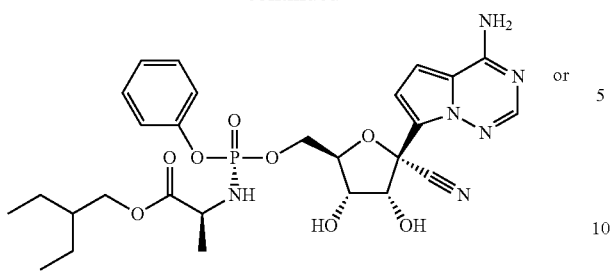
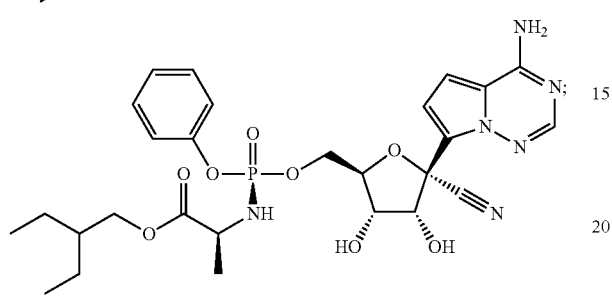
or a pharmaceutically acceptable salt or ester thereof.
In another embodiment of the method of treating a Coronaviridae infection comprising administering a compound of Formula I-IV, the compound is
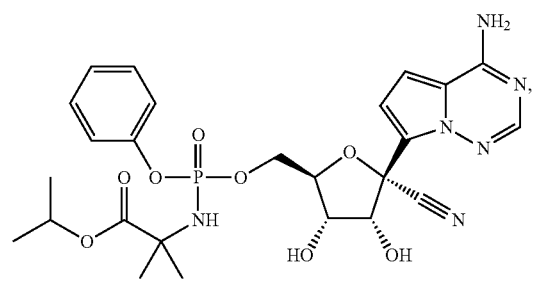
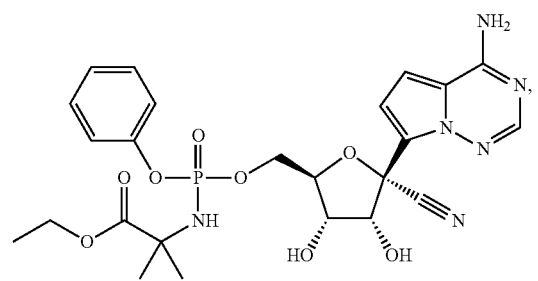
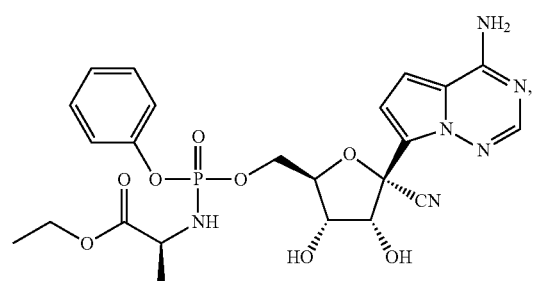
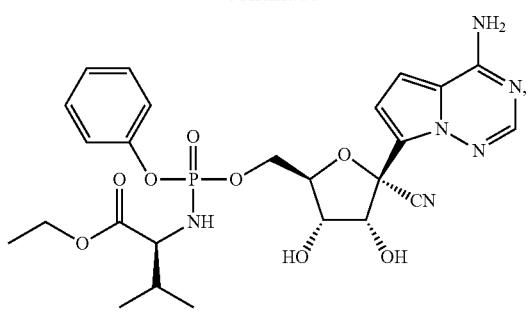
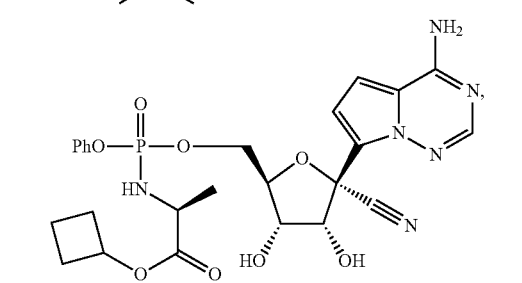
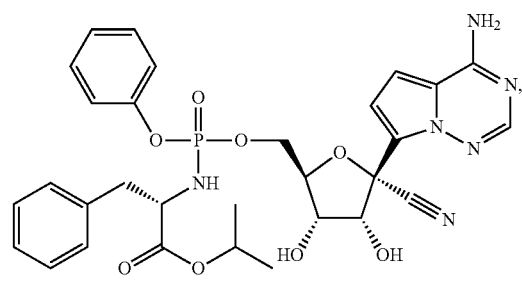
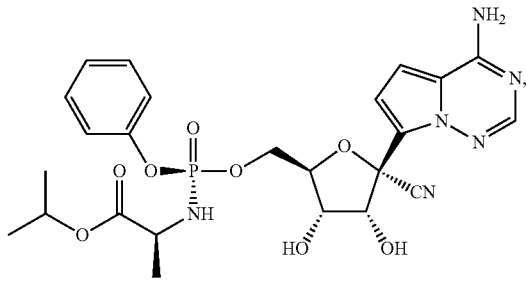
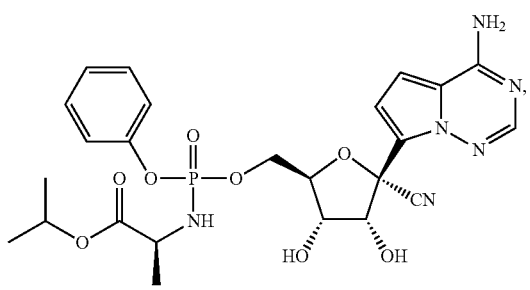
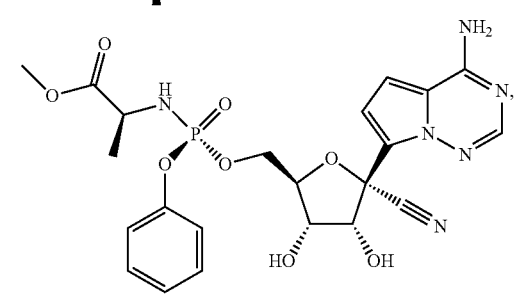

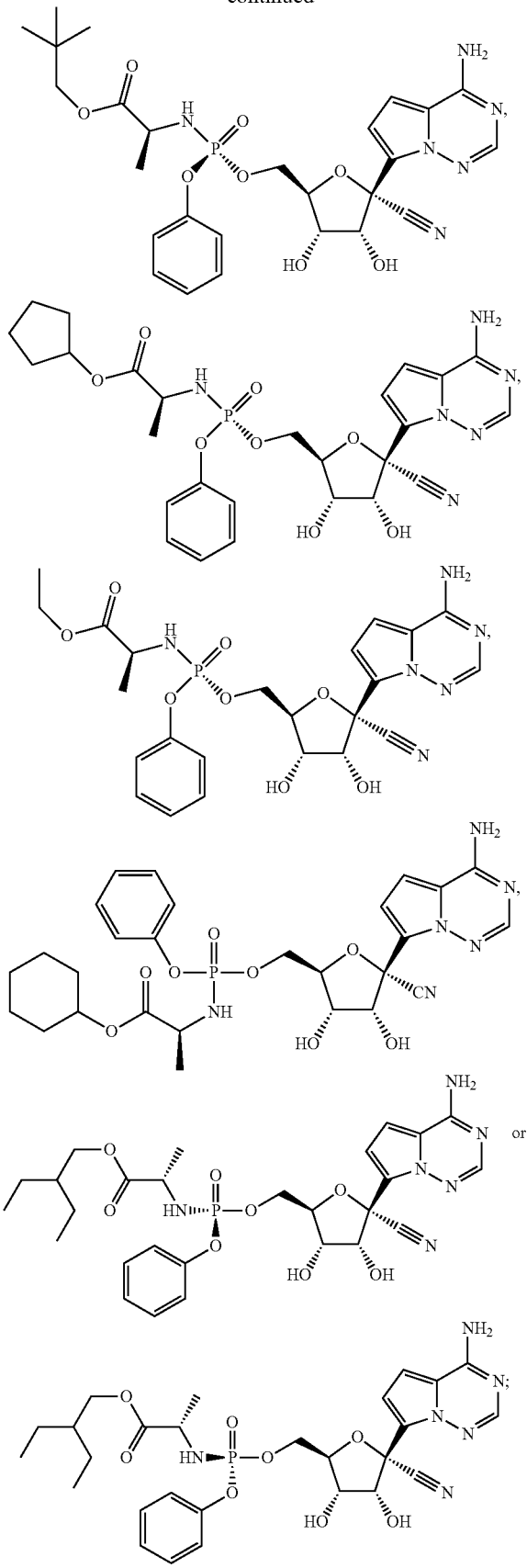

or a pharmaceutically acceptable salt or ester thereof.

In another embodiment of the method of treating a Coronaviridae infection comprising administering a compound of Formula I-IV, the compound is

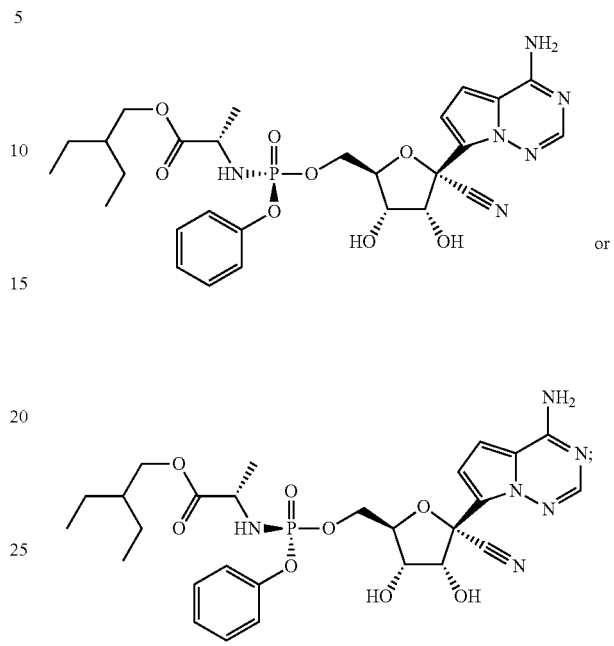

or a pharmaceutically acceptable salt or ester thereof.

Methods of treatment herein include those for treating coronavirus infections in a human, including infections caused by alpha coronaviruses 229E (HCoV-229E) and NL63 (HCoV-NL63, New Haven coronavirus), beta coronaviruses OC43 (HCoV-OC43), HKU1, SARS-CoV (the coronavirus responsible for Severe Acute Respiratory Syndrome, or SARS), and MERS-CoV (the coronavirus responsible for Middle East Respiratory Syndrome), previously known as Novel coronavirus 2012 and HCoV-EMC.

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

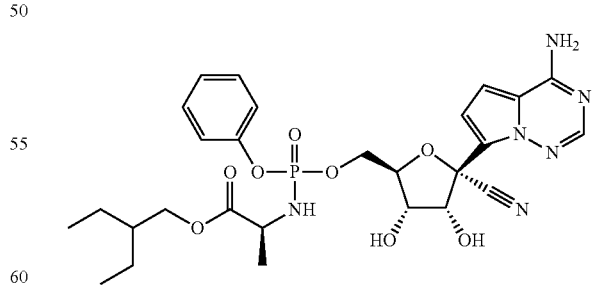

which is named (2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate. Other compounds of the present invention include:

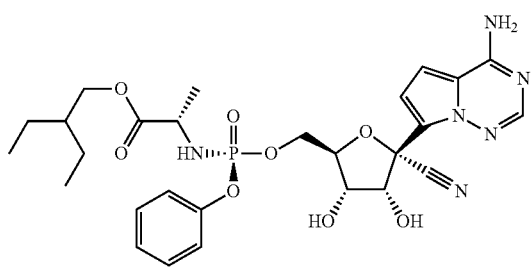 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

which is named (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate, and

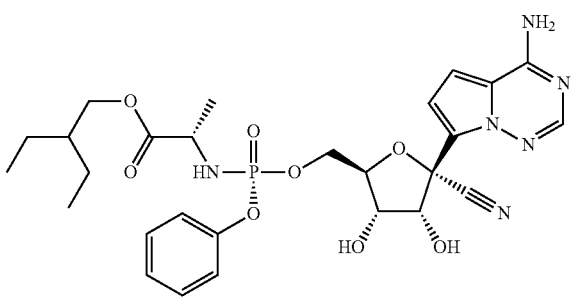 [SMILES: CCC(CC)COC(=O)[C@H](C)N[P@@](=O)(OC[C@H]1O[C@@](C#N)(c2ccc3c(N)ncnn23)[C@H](O)[C@@H]1O)Oc1ccccc1]

which is named (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate.

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

A compound of Formula I-IV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-III and their pharmaceutically acceptable salts.

A compound of Formula I-IV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IV and their pharmaceutically acceptable salts.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula I-IV and pharmaceutically acceptable salts thereof are embraced by the present invention. All mixtures of such enantiomers and diastereomers are within the scope of the present invention.

The compounds of the invention, exemplified by Formula I-IV may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R$^1$", then it will be understood that the groups may be the same or different, i.e., each group is independently selected. Wavy lines, ∿∿∿∿, indicate the site of covalent bond attachments to the adjoining substructures, groups, moieties, or atoms.

Selected substituents comprising the compounds of Formula I-IV are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $Z^3$. $Z^3$ can be $Z^4$ and $Z^4$ can be R or comprise substituents comprising $R^y$. Alternatively, $Z^3$ can be $Z^5$ which can comprise substituents comprising $R^y$. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $Z^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $Z^3$ will occur 0 to 8 times, $R^y$ will occur 0 to 6 times in a given embodiment. Even more typically, $Z^3$ will occur 0 to 6 times and $R^y$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

The compounds of the present invention can be prepared by methods known to one of skill in the art. For example, the compounds of the present invention can be prepared according to the methods described in U.S. Pat. No. 8,008,264 and U.S. Application Publication No. US 2012/0027752.

A. Substituted Forms of the Compounds

The compounds of the Formula I-IV may comprise a phosphate group as $R^7$, $R^7$ is selected from the group of a) H, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, $-SO_2NR^{11}R^{12}$ wherein each $R^{11}$ or $R^{12}$ is independently H, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, $-C(=O)(C_1$-$C_8)$alkyl, $-S(O)_n(C_1$-$C_8)$alkyl or aryl$(C_1$-$C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S-$ or $-NR^a-$;

each $R^a$ is independently H, $(C_1$-$C_8)$alkyl, $(C_2$-$C_8)$alkenyl, $(C_2$-$C_8)$alkynyl, aryl$(C_1$-$C_8)$alkyl, $(C_4$-$C_8)$carbocyclylalkyl, $-C(=O)R$, $-C(=O)OR$, $-C(=O)NR_2$, $-C(=O)SR$, $-S(O)R$, $-S(O)_2R$, $-S(O)(OR)$, $-S(O)_2(OR)$, or $-SO_2NR_2$;

wherein each R is independently H, $(C_1$-$C_8)$ alkyl, $(C_1$-$C_8)$ substituted alkyl, $(C_2$-$C_8)$alkenyl, $(C_2$-$C_8)$ substituted alkenyl, $(C_2$-$C_8)$ alkynyl, $(C_2$-$C_8)$ substituted alkynyl, $C_6$-$C_{20}$ aryl, $C_6$-$C_{20}$ substituted aryl, $C_2$-$C_{20}$ heterocyclyl, $C_2$-$C_{20}$ substituted heterocyclyl, arylalkyl or substituted arylalkyl; and wherein each $(C_1$-$C_8)$alkyl, $(C_2$-$C_8)$alkenyl, $(C_2$-$C_8)$alkynyl or aryl$(C_1$-$C_8)$alkyl of each $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1$-$C_8)$alkyl may be optionally replaced with $-O-$, $-S-$ or $-NR^a-$, b)

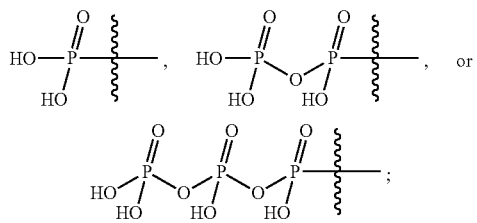

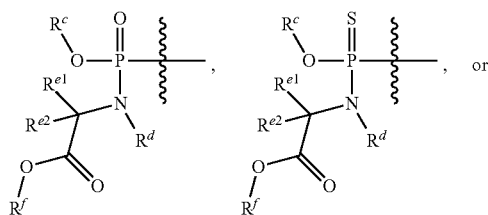

c)

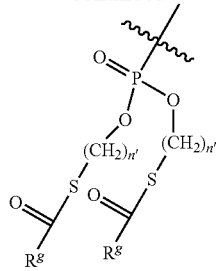

wherein:

$R^c$ is selected from phenyl, 1-naphthyl, 2-naphthyl,

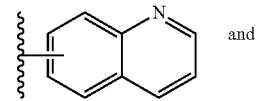 and 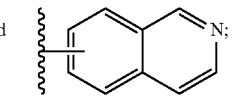

$R^d$ is H or $CH_3$;

$R^{e1}$ and $R^{e2}$ are each independently H, $C_1$-$C_6$ alkyl or benzyl;

$R^f$ is selected from H, $C_1$-$C_8$ alkyl, benzyl, $C_3$-$C_6$ cycloalkyl, and $-CH_2-C_3$-$C_6$ cycloalkyl;

$R^g$ is selected from $C_1$-$C_8$ alkyl, $-O-C_1$-$C_8$ alkyl, benzyl, $-O$-benzyl, $-CH_2-C_3$-$C_6$ cycloalkyl, $-O-CH_2-C_3$-$C_6$ cycloalkyl, and $CF_3$; and n' is selected from 1, 2, 3, and 4; and d) a group of the formula:

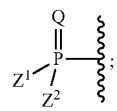

wherein

Q is O, S, NR, $^+N(O)(R)$, N(OR), $^+N(O)(OR)$, or $N-NR_2$;

$Z^1$ and $Z^2$, when taken together, are $-Q^1(C(R^y)_2)_3Q^1-$;

wherein each $Q^1$ is independently O, S, or NR; and each $R^y$ is independently H, F, Cl, Br, I, OH, R, $-C(=Q^2)R$, $-C(=Q^2)OR$, $-C(=Q^2)N(R)_2$, $-N(R)_2$, $-^+N(R)_3$, $-SR$, $-S(O)R$, $-S(O)_2R$, $-S(O)(OR)$, $-S(O)_2(OR)$, $-OC(=Q^2)R$, $-OC(=Q^2)OR$, $-OC(=Q^2)(N(R)_2)$, $-SC(=Q^2)R$, $-SC(=Q^2)OR$, $-SC(=Q^2)(N(R)_2)$, $-N(R)C(=Q^2)R$, $-N(R)C(=Q^2)OR$, $-N(R)C(=Q^2)N(R)_2$, $-SO_2NR_2$, $-CN$, $-N_3$, $-NO_2$, $-OR$, or $Z^3$; or when taken together, two $R^y$ on the same carbon atom form a carbocyclic ring of 3 to 7 carbon atoms;

each $Q^2$ is independently, O, S, NR, $^+N(O)(R)$, N(OR), $^+N(O)(OR)$, or $N-NR_2$; or $Z^1$ and $Z^2$ are each, independently, a group of the Formula Ia:

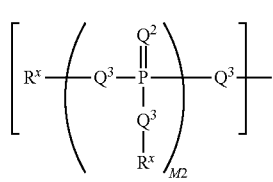

Formula Ia wherein:
each $Q^3$ is independently a bond, O, $CR_2$, NR, $^+N(O)(R)$, N(OR), $^+N(O)(OR)$, N—$NR_2$, S, S—S, S(O), or $S(O)_2$;
M2 is 0, 1 or 2;
each $R^x$ is independently $R^y$ or the formula:

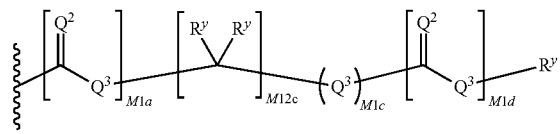

wherein:
each M1a, M1c, and M1d is independently 0 or 1;
M12c is 0, 1, 2, 3, 4, 5, 6, 7, 8, 9, 10, 11 or 12;
$Z^3$ is $Z^4$ or $Z^5$;
$Z^4$ is R, —$C(Q^2)R^y$, —$C(Q^2)Z^5$, —$SO_2R^y$, or —$SO_2Z^5$; and
$Z^5$ is a carbocycle or a heterocycle wherein $Z^5$ is independently substituted with 0 to 3 $R^y$ groups.

$Z^5$ carbocycles and $Z^5$ heterocycles may be independently substituted with 0 to 3 $R^y$ groups. $Z^5$ may be a saturated, unsaturated or aromatic ring comprising a mono- or bicyclic carbocycle or heterocycle. $Z^5$ may have 3 to 10 ring atoms, e.g., 3 to 7 ring atoms. The $Z^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $Z^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $Z^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $Z^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $Z^5$ heterocycle may be bonded to $Q^2$ through a carbon, nitrogen, sulfur or other atom by a stable covalent bond.

$Z^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $Z^5$ also includes, but is not limited to, examples such as:

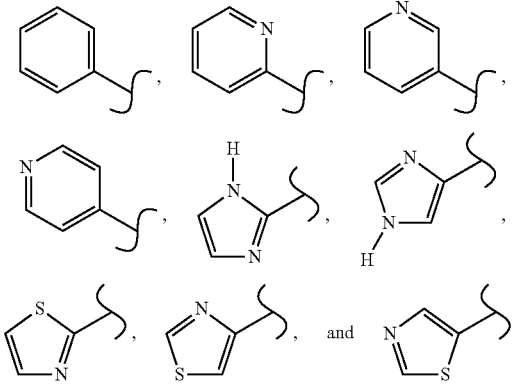

$Z^5$ carbocycles and heterocycles may be independently substituted with 0 to 3 R groups, as defined above. For example, substituted $Z^5$ carbocycles include:

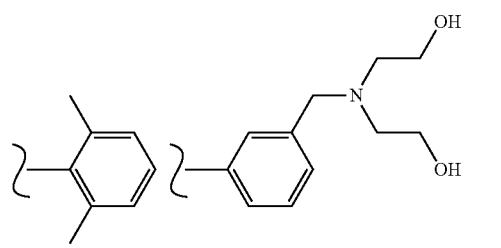

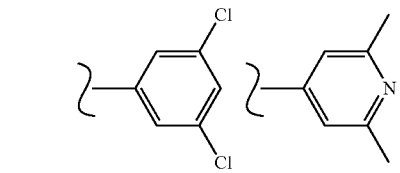

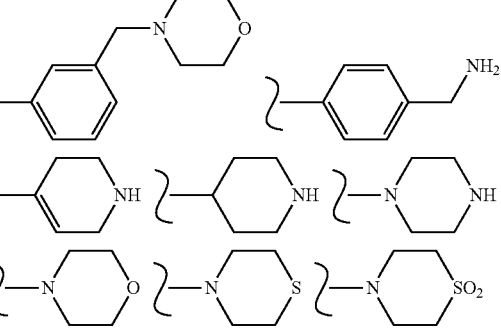

Examples of substituted phenyl carbocycles include:

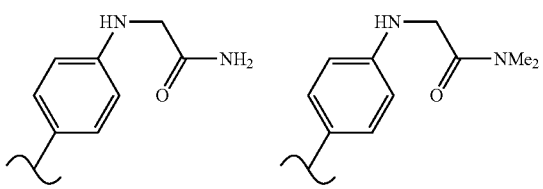

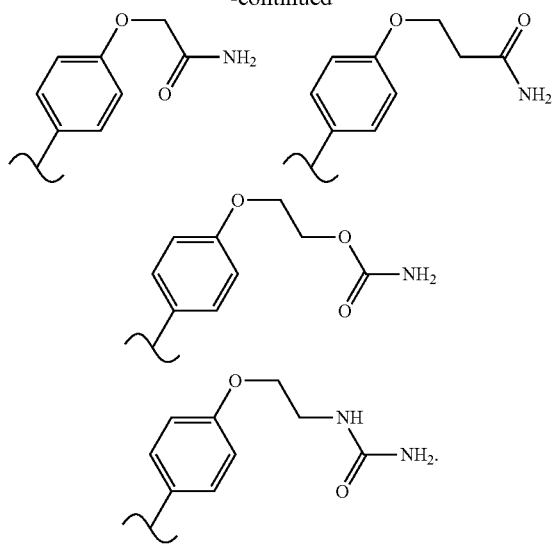

In another embodiment, $Z^5$ of the compounds of Formula I-IV is a carbocycle or a heterocycle wherein $Z^5$ is independently substituted with 0 to 3 $R^z$ groups, wherein each $R^z$ is independently H, F, Cl, Br, I, OH, R, —C(=$Q^2$)R, —C(=$Q^2$)OR, —C(=$Q^2$)N(R)$_2$, —N(R)$_2$, —$^+$N(R)$_3$, —SR, —S(O)R, —S(O)$_2$R, —S(O)(OR), —S(O)$_2$(OR), —OC(=$Q^1$)R, —OC(=$Q^2$)OR, —OC(=$Q^2$)(N(R)$_2$), —SC(=$Q^2$)R, —SC(=$Q^2$)OR, —SC(=$Q^2$)(N(R)$_2$), —N(R)C(=$Q^2$)R, —N(R)C(=$Q^2$)OR, —N(R)C(=$Q^2$)N(R)$_2$, —SO$_2$NR$_2$, —CN, —N$_3$, —NO$_2$, or —OR.

Embodiments of

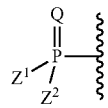

of Formula I-IV compounds include substructures such as:

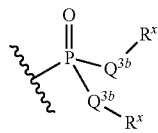

wherein each $Q^{3b}$ is, independently, O or N(R). In another aspect of this embodiment, each $Q^{3b}$ is O and each $R^x$ is independently:

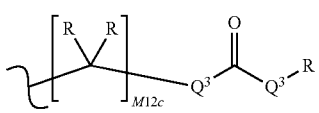

wherein M12c is 1, 2 or 3 and each $Q^3$ is independently a bond, O, CR$_2$, or S. In another aspect of this embodiment, one $Q^{3b}$-$R^x$ is NH(R) and the other $Q^{3b}$-$R^x$ is O—$R^x$ wherein $R^x$ is:

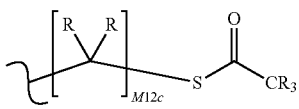

wherein M12c is 2. In another aspect of this embodiment, each $Q^{3b}$ is O and each $R^x$ is independently:

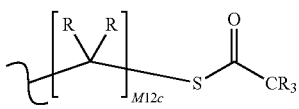

wherein M12c is 2. In another aspect of this embodiment, each $Q^{3b}$ is O and each $R^x$ is independently:

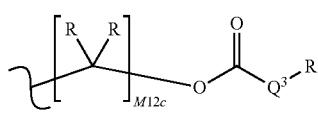

wherein M12c is 1 and $Q^3$ is a bond, O, or CR$_2$.

Other embodiments of

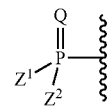

of Formulas I-IV compounds include substructures such as:

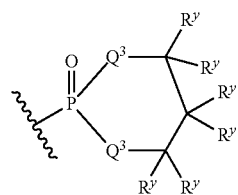

wherein each $Q^3$ is, independently, O or N(R). In another aspect of this embodiment, each $Q^3$ is O. In another aspect of this embodiment, the substructure is:

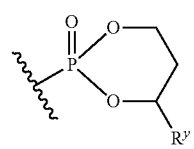

wherein $R^y$ is $Z^5$ as defined herein.

Another embodiment of

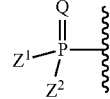

of Formula I-IV includes the substructures:

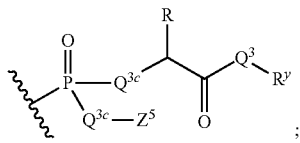

wherein each $Q^{2c}$ is, independently, O, $N(R^y)$ or S.

Another embodiment of

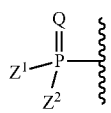

of Formula I-IV compounds includes the substructures wherein one of $Z^1$ or $Z^2$ together with either $R^3$ or $R^4$ is $-Q^3-$ and the other of $Z^1$ or $Z^2$ is Formula Ia. Such an embodiment is represented by a compound of Formula Ib selected from:

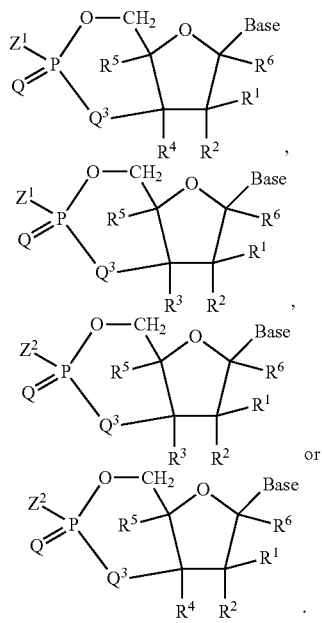

Formula Ib

In another aspect of the embodiment of Formula Ib, each Q and $Q^3$ is O. In another aspect of the embodiment of Formula Ib, $Z^1$ or $Z^2$ is $Q^{3b}$-$R^x$; each Q, $Q^3$ and $Q^{3b}$ is O and $R^x$ is:

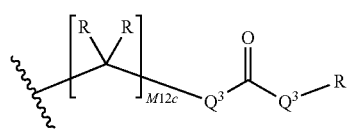

wherein M12c is 1, 2 or 3 and each $Q^3$ is independently a bond, O, $CR_2$, or S. In another aspect of the embodiment of Formula Ib, $Z^1$ or $Z^2$ is $Q^{3b}$-$R^x$; each Q, $Q^3$ and $Q^{3b}$ is O and $R^x$ is:

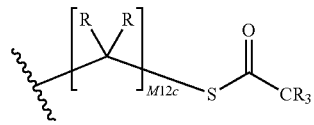

wherein M12c is 2. In another aspect of the embodiment of Formula Ib, $Z^1$ or $Z^2$ is $Q^{3b}$-$R^x$; each Q, $Q^3$ and $Q^{3b}$ is O and $R^x$ is:

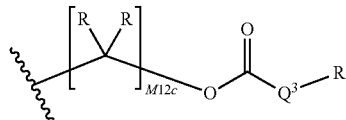

wherein M12c is 1 and $Q^3$ is a bond, O, or $CR_2$.

Another embodiment of

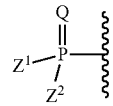

of Formula I-IV compounds includes a substructure:

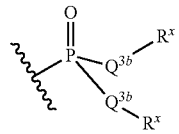

wherein $Z^5$ is a carbocycle such as phenyl or substituted phenyl. In another aspect of this embodiment, the substructure is:

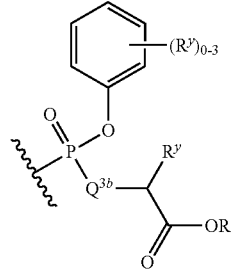

wherein $Q^{3b}$ is O or N(R) and the phenyl carbocycle is substituted with 0 to 3 R groups. In another aspect of this embodiment of the substructure, $R^x$ is:

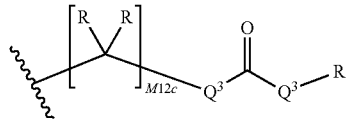

wherein M12c is 1, 2 or 3 and each $Q^3$ is independently a bond, O, $CR_2$, or S.

Another embodiment of

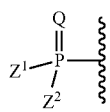

of Formula I-IV includes substructures:

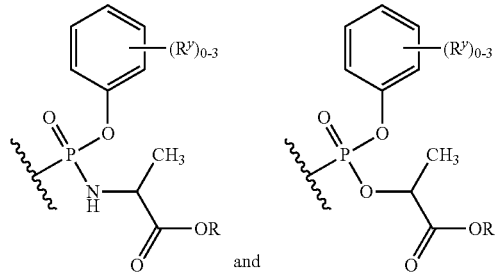

The chiral carbon of the amino acid and lactate moieties may be either the R or S configuration or the racemic mixture.

Another embodiment of

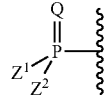

of Formula I-IV is substructure

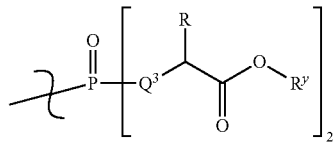

wherein each $Q^3$ is, independently, —O— or —NH—. In another aspect of this embodiment, $R^y$ is $(C_1-C_8)$ alkyl, $(C_1-C_8)$ substituted alkyl, $(C_2-C_8)$ alkenyl, $(C_2-C_8)$ substituted alkenyl, $(C_2-C_8)$ alkynyl or $(C_2-C_8)$ substituted alkynyl. In another aspect of this embodiment, $R^y$ is $(C_1-C_8)$ alkyl, $(C_1-C_8)$ substituted alkyl, $(C_2-C_8)$ alkenyl, $(C_2-C_8)$ substituted alkenyl, $(C_2-C_8)$ alkynyl or $(C_2-C_8)$ substituted alkynyl; and R is $CH_3$. In another aspect of this embodiment, $R^y$ is $(C_1-C_8)$ alkyl, $(C_1-C_8)$ substituted alkyl, $(C_2-C_8)$ alkenyl, $(C_2-C_8)$ substituted alkenyl, $(C_2-C_8)$ alkynyl or $(C_2-C_8)$ substituted alkynyl; R is $CH_3$; and each $Q^3$ is —NH—. In another aspect of this embodiment, $Z^1$ and $Z^2$ are, independently, nitrogen-linked, naturally occurring amino acids or naturally occurring amino acid esters. In another aspect of this embodiment, $Z^1$ and $Z^2$ are, independently, naturally-occurring 2-hydroxy carboxylic acids or naturally-occurring 2-hydroxy carboxylic acid esters wherein the acid or ester is linked to P through the 2-hydroxy group.

Another embodiment of

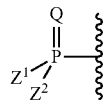

of Formula I-IV is substructure:

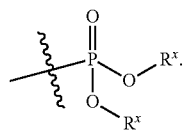

In one aspect of this embodiment, each $R^x$ is, independently, $(C_1-C_8)$ alkyl. In another aspect of this embodiment, each $R^x$ is, independently, $C_6-C_{20}$ aryl or $C_6-C_{20}$ substituted aryl.

In a preferred embodiment,

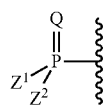

is selected from

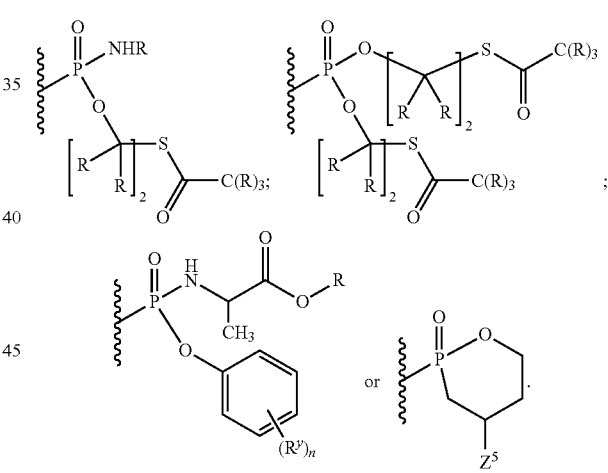

Embodiments of $R^x$ include esters, carbamates, carbonates, thioesters, amides, thioamides, and urea groups:

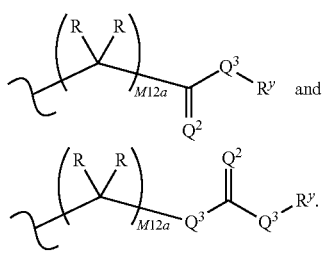

B. Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}$C or $^{3}$H) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti arenaviridae activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

III. Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s)

make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin and Captisol (=Sulfobutyl ether beta-cyclodextrin; SEB-beta-CD).

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Arenaviridae infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

IV. Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

In the methods of the present invention for the treatment of Arenaviridae infection, the compounds of the present invention can be administered at any time to a human who may come into contact with humans suffering from Arenaviridae infection or is already suffering from Arenaviridae infection. In some embodiments, the compounds of the present invention can be administered prophylactically to humans coming into contact with humans suffering from Arenaviridae infection. In some embodiments, administration of the compounds of the present invention can be to humans testing positive for Arenaviridae infection but not yet showing symptoms of Arenaviridae infection. In some embodiments, administration of the compounds of the present invention can be to humans upon commencement of symptoms of Arenaviridae infection.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

The effective dose of a compound of the present invention for treating the Arenaviridae infection can depend on whether the dose is to be used prophylactically or to treat a human already suffering from Arenaviridae infection. Moreover, the dose can depend on whether the human suffering from Arenaviridae infection does not yet show symptoms or is already showing symptoms of Arenaviridae infection. Larger doses may be necessary for treating humans testing positive for Arenaviridae infection and for humans showing symptoms of Arenaviridae infection as compared to humans receiving prophylactic treatment.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated. The time for administration can depend on whether the compound is being administered prophylactically or to treat a human suffering from an Arenaviridae infection. For example, a prophylactic administration can be for a period of time while the human is in regular contact with other humans suffering from an Arenaviridae infection, and for a suitable period of time following the last contact with a human suffering from an Arenaviridae infection. For humans already suffering from an Arenaviridae infection, the period of administration can be for any length of time necessary to treat the patient and a suitable period of time following a negative test for Arenaviridae infection to ensure the Arenaviridae infection does not return.

V. Combination Therapy

Compositions of the invention are also used in combination with other active ingredients. For the treatment of Arenaviridae virus infections, preferably, the other active therapeutic agent is active against Arenaviridae virus infections, particularly Lassa virus and Junin virus infections. Non-limiting examples of these other active therapeutic agents are ribavirin, favipiravir (also known as T-705 or Avigan), T-705 monophosphate, T-705 diphosphate, T-705 triphosphate, ST-193, and mixtures thereof. The compounds and compositions of the present invention are also intended for use with general care provided patients with Arenaviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting Arenaviridae polymerase in a cell, comprising: contacting a cell infected with an arenavirus with an effective amount of a compound of Formula I-IV, or a pharmaceutically acceptable salt, solvate, and/or ester thereof, whereby Arenaviridae polymerase is inhibited.

In still yet another embodiment, the present application provides for methods of inhibiting Arenaviridae polymerase in a cell, comprising: contacting a cell infected with arenavirus with an effective amount of a compound of Formula I-IV, or a pharmaceutically acceptable salt, solvate, and/or ester thereof, and at least one additional active therapeutic agent, whereby Arenaviridae polymerase is inhibited.

In still yet another embodiment, the present application provides for methods of inhibiting Arenaviridae polymerase in a cell, comprising: contacting a cell infected with Arenaviridae virus with an effective amount of a compound of Formula I-IV, or a pharmaceutically acceptable salt, solvate, and/or ester thereof, and at least one additional active therapeutic agent selected In still yet another embodiment, the present application provides for methods of treating Arenaviridae virus infection in a human, comprising: administering to the patient a therapeutically effective amount of a compound of Formula I-IV, or a pharmaceutically acceptable salt, solvate, and/or ester thereof.

In still yet another embodiment, the present application provides for methods of treating Arenaviridae virus infection in a human, comprising: administering to the patient a therapeutically effective amount of a compound of Formula I-IV, or a pharmaceutically acceptable salt, solvate, and/or ester thereof, and at least one additional active therapeutic agent, whereby Arenaviridae polymerase is inhibited.

In still yet another embodiment, the present application provides for methods of treating Arenaviridae virus infection in a human, comprising: administering to the patient a therapeutically effective amount of a compound of Formula I-IV, or a pharmaceutically acceptable salt, solvate, and/or ester thereof, and at least one additional active therapeutic agent.

Also provided is a kit that includes a compound of Formula I, or a pharmaceutically acceptable salt, pharmaceutically acceptable ester, stereoisomer, mixture of stereoisomers or tautomer thereof. In separate embodiments individual kits are provided includes a compound selected from the group of each of the Formulas herein, as well as each subgroup and embodiment thereof, including Formula II, Formula II, Formula IV, and individual Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32 (Compounds 1-32), or a pharmaceutically acceptable salt, pharmaceutically acceptable ester, stereoisomer, mixture of stereoisomers or tautomer thereof. In one aspect, the kit comprises a compound of Formula I, or a pharmaceutically acceptable salt thereof. Each of the individual kits described herein may comprise a label and/or instructions for use of the compound in the treatment of a disease or condition in a subject (e.g., human) in need thereof. In some embodiments, the disease or condition is a human Arenaviridae viral infection, including a Lassa viral infection or a Junin viral infection. In other embodiments, each separate kit may also contain instructions for use of additional medical agents in combination with the compound of Formula I in the treatment of a disease or condition in a subject (e.g., human) in need thereof. In certain of these embodiments, the disease or condition is a human Arenaviridae viral infection, including a Lassa viral infection or a Junin viral infection. In each of the kits herein there is a further embodiment in which the kit comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula I, or a pharmaceutically acceptable salt, pharmaceutically acceptable ester, stereoisomer, mixture of stereoisomers or tautomer thereof; and a container. In one aspect, the article of manufacture comprises a compound of Formula I, Formula II, Formula II, Formula IV, and individual Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32 (Compounds 1-32), or a pharmaceutically acceptable salt thereof, and a container. In separate embodiments, the container of the article of manufacture may be a vial, jar, ampoule, preloaded syringe, blister package, tin, can, bottle, box, or an intravenous bag.

Also provided as separate embodiments are the uses of a compound selected from each of the Formulas herein, as well as each subgroup and embodiment thereof, including a compound selected from the group of Formula (I), Formula (II), Formula (III), Formula (IV), or one of the specific compounds of the examples herein, including Compounds 1-32, or a pharmaceutically acceptable salt, solvate, and/or ester thereof, in the preparation of a medicament for use in treating an Arenaviridae infection in a human.

VI. Methods of Inhibition of an Arena Viridae Polymerase

Another aspect of the invention relates to methods of inhibiting the activity of Arenaviridae polymerase comprising the step of treating a sample suspected of containing Arenaviridae with a compound or composition of the invention.

Arenaviridae that can be treated using the methods of the present invention are single-stranded negative sense RNA viruses that typically infect primates. Arenaviruses are able to multiply in virtually all cell types.

Based upon studies in nonhuman primates infected with Lassa virus, the first cells infected appear to be dendritic cells in the lymphoid tissues. Infection progresses to infection of Kupffer cells in liver and parenchymal cells in liver and adrenal gland, endothelial cells in a variety of tissues including nervous tissue, and finally to infection of the epithelium. Evidence of liver infection in humans leading to hepatitis has also been documented) (Hensley, L., 2011, Virology Journal; Yun, N. E., 2012 Viruses).

There are 30 identified genera of Arenaviruses: Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV; six strains—Josiah, NL, z148, Macenta, AV, and CSF), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), or Whitewater Arroyo virus (WWAV).

The arenavirus virions are heterogeneous in size from 40 to more than 200 nm in diameter that consist of nucleocapsid surrounded by a lipid envelope. Electron micrographs of the interior of virions show a characteristic granular appearance due to incorporation of host cell ribosomes in virus particles during assembly. The genome of arenaviruses consists of two single-stranded RNA segments, small (S) and large (L). Both genomic segments have an ambisense gene organization and encode two genes in opposite orientation. The L RNA (~7 kb) encodes the viral RNA-dependent RNA polymerase (L) and the small RING finger zinc-binding protein (Z). The S RNA (~3.4 kb) encodes the glycoprotein precursor protein (GPC) and the nucleoprotein (NP). GPC is posttranslationally cleaved to yield two envelope glycoproteins GP1 and GP2 and the stable signal peptide (SSP) (Yun, N. E., 2012 Viruses).

Compositions of the invention may act as inhibitors of arenavirus polymerase, as intermediates for such inhibitors or have other utilities as described below. The inhibitors will bind to locations on the surface or in a cavity of Arenaviridae polymerase having a geometry unique to Arenaviridae polymerase. Compositions binding Arenaviridae polymerase may bind with varying degrees of reversibility. Those compounds binding substantially irreversibly are ideal candidates for use in this method of the invention. Once labeled, the substantially irreversibly binding compositions are useful as probes for the detection of Arenaviridae polymerase. Accordingly, the invention relates to methods of detecting Arenaviridae polymerase in a sample suspected of containing Arenaviridae polymerase comprising the steps of: treating a sample suspected of containing Arenaviridae polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing Arenaviridae polymerase include natural or manmade materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces Arenaviridae polymerase, frequently a pathogenic organism such as an Arenaviridae virus. Samples can be contained in any medium including water and organic solvent\water mixtures. Samples include living organisms such as humans, and manmade materials such as cell cultures.

The treating step of the invention comprises adding the composition of the invention to the sample or it comprises adding a precursor of the composition to the sample. The addition step comprises any method of administration as described above.

If desired, the activity of Arenaviridae polymerase after application of the composition can be observed by any method including direct and indirect methods of detecting Arenaviridae polymerase activity. Quantitative, qualitative, and semiquantitative methods of determining Arenaviridae polymerase activity are all contemplated. Typically one of the screening methods described above are applied, however, any other method such as observation of the physiological properties of a living organism are also applicable.

Organisms that contain Arenaviridae polymerase include the Arenaviridae virus. The compounds of this invention are useful in the treatment or prophylaxis of Arenaviridae infections in animals or in man.

However, in screening compounds capable of inhibiting human Arenaviridae viruses, it should be kept in mind that the results of enzyme assays may not correlate with cell culture assays. Thus, a cell based assay should be the primary screening tool.

In another embodiment, the present application provides for methods of treating Arenaviridae virus infection in a human, comprising: administering to the patient a therapeutically effective amount of a compound of Formula I-IV, or a pharmaceutically acceptable salt, solvate, and/or ester thereof. In some embodiments, the Arenaviridae infection is caused by an Arenaviridae virus. In some embodiments, the Arenaviridae infection is caused by a Junin virus. In some embodiments, the Arenaviridae infection is caused by Lassa virus strains Josiah, NL, z148, Macenta, AV, or CSF. In some embodiments, an Arenaviridae polymerase is inhibited.

The compounds of the present invention can be used in the treatment of a human already suffering from an Arenaviridae infection, or can be administered prophylactically to reduce or prevent the chance of an Arenaviridae infection. Physical examination of patients infected with arenavirus after the onset of fever often reveals purulent pharyngitis, bilateral conjunctival hemorrhages, facial edema, and generalized abdominal tenderness. Macroscopic pathological changes can include pleural effusions, pulmonary edema, ascites, and hemorrhagic manifestations in the gastrointestinal mucosa. Mortality rates for hospitalized patients vary between 5-10%.

VII. Screens for Arena Viridae Polymerase Inhibitors

Compositions of the invention are screened for inhibitory activity against Arenaviridae polymerase by any of the conventional techniques for evaluating enzyme activity. Within the context of the invention, typically compositions are first screened for inhibition of Arenaviridae polymerase in vitro and compositions showing inhibitory activity are then screened for activity in vivo. Compositions having in vitro Ki (inhibitory constants) of less than about $5 \times 10^{-6}$ M and preferably less than about $1 \times 10^{-7}$ M are preferred for in vivo use.

Useful in vitro screens have been described in detail and will not be elaborated here. However, the examples describe suitable in vitro assays.

VIII. Preparation of Compounds

The compounds of the present invention can be prepared by a variety of means. For example, protected nucleosides of Formula V can be prepared by reaction of a protected lactone with an iodo-substituted base under suitable coupling conditions. The nucleosides can then be modified with a prodrug moiety by reaction of a partially protected nucleoside with a suitable prodrug moiety, following be removal of the protecting groups, to afford the compounds of the present invention.

A. Preparation of Nucleosides via Iodo-Base

In some embodiments, the present invention provides a method of preparing a compound of Formula V:

Formula (V)

The method of making the compound of Formula V includes forming a reaction mixture having a coupling agent, a halo-silane, a compound of Formula VI:

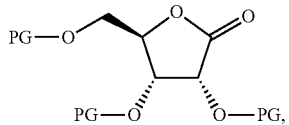

Formula (VI)

and a compound of Formula VII:

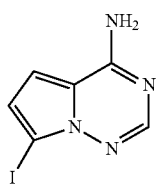

Formula (VII)

under conditions suitable to prepare the compound of Formula V, wherein each PG is independently a hydroxy protecting group, alternatively, two PG groups on adjacent carbons can be combined to form a —C($R^{19}$)$_2$— group, $R^{10}$ is H or a silyl group, and $R^{19}$ is H, $C_1$-$C_8$ alkyl, phenyl or substituted phenyl.

Any suitable coupling agent can be used in the method of making the compound of Formula V. The coupling agent can be a lithium coupling agent, a sodium coupling agent, a magnesium coupling agent, or others. For example, the coupling agent can be a deprotonating agent such as n-butyl lithium (n-BuLi), sodium hydride (NaH), lithium aluminum hydride (LAH or LiAlH$_4$), and others. The coupling agent can also be a magnesium based coupling agent such as, but not limited to, MgCl$_2$, iPrMgCl, tBuMgCl, PhMgCl, or combinations thereof. In some embodiments, the coupling agent can be a lithium coupling agent or a magnesium coupling agent. In some embodiments, the coupling agent can be n-BuLi, MgCl$_2$, iPrMgCl, tBuMgCl, PhMgCl, or combinations thereof. In some embodiments, the coupling agent can be n-BuLi. In some embodiments, the coupling agent can be PhMgCl and iPrMgCl.

The coupling agent can be present in any suitable amount. For example, the coupling agent can be present in an amount of at least 1.0 eq. (mol/mol) to the compound of Formula V, such as about 1.0, 2, 3, 4, 5, 6, 7, 8, 9, or about 10.0 eq. (mol/mol). The coupling agent can also be present in an amount of from about 1.0 to about 10.0 eq. (mol/mol) to the compound of Formula V, such as of from about 1.0 to about 5.0 eq. (mol/mol), or of from about 1.0 to about 2.0 eq. (mol/mol). In some embodiments, the coupling agent can be present in an amount of from about 1.0 to about 5.0 eq. (mol/mol) to the compound of Formula V. In some embodiments, the coupling agent can be present in an amount of from about 1.0 to about 2.0 eq. (mol/mol) to the compound of Formula V.

Any suitable halo-silane can be used in the method of making the compound of Formula V. For example, the halo-silane can be a fluoro-silane, a chloro-silane, a bromo-silane or an iodo-silane. The silane portion can have any suitable substituents, such as alkyl, alkenyl, alkynyl, cycloalkyl, or phenyl. Exemplary halo-silanes include, but are not limited to, Cl—Si(CH$_3$)$_3$, or Cl—Si(CH$_3$)$_2$CH$_2$CH$_2$Si(CH$_3$)$_2$—Cl. In some embodiments, the halo-silane can be a chloro-silane. In some embodiments, the halo-silane can be Cl—Si(CH$_3$)$_3$, or Cl—Si(CH$_3$)$_2$CH$_2$CH$_2$Si(CH$_3$)$_2$—Cl. In some embodiments, the halo-silane can be TMS-Cl.

The silyl group of $R^{10}$ can be any suitable group, but can depend on the choice of the halo-silane. For example, when the halo-silane is TMS-Cl, the silyl group can be trimethylsilyl.

The halo-silane can be present in any suitable amount. For example, the halo-silane can be present in an amount of at least 1.0 eq. (mol/mol) to the compound of Formula V, such as about 1.0, 2, 3, 4, 5, 6, 7, 8, 9, or about 10.0 eq. (mol/mol). The halo-silane can also be present in an amount of from about 1.0 to about 10.0 eq. (mol/mol) to the compound of Formula V, such as of from about 1.0 to about 5.0 eq. (mol/mol), or of from about 1.0 to about 2.0 eq. (mol/mol). In some embodiments, the halo-silane can be present in an amount of from about 1.0 to about 5.0 eq. (mol/mol) to the compound of Formula V. In some embodiments, the halo-silane can be present in an amount of from about 1.0 to about 2.0 eq. (mol/mol) to the compound of Formula V.

The hydroxy protecting group can be any protecting group suitable for a hydroxy functional group. Representative hydroxy protecting groups include, but are not limited to, silanes such as trimethyl silane (TMS), t-butyl dimethyl silane (TBDMS), or t-butyl diphenyl silane (TBDPS), ethers such as methyl-methoxy (MOM), tetrahydropyran (THP), t-butyl, allyl, or benzyl, and esters such as acetyl, pivaloyl, or benzoyl. In some embodiments, the hydroxy protecting group can be trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be benzyl.

Hydroxy groups on adjacent carbons, referred to as 1,2-hydroxy groups, can form a cyclic protecting group called an acetonide by reaction with a ketone of di-ether. Exemplary acetonides include, but are not limited to acetonide and benzylidene acetal. In some embodiments, the hydroxy protecting groups of hydroxy groups on adjacent carbons can be combined to form acetonide.

When the $R^{19}$ group is $C_1$-$C_8$ alkyl, $R^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^{19}$ group can be methyl.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran, or combinations thereof. In some embodiments, the solvent can be tetrahydrofuran. Further representative solvents include, but are not limited to 2-Methyltetrahydrofuran, Dibutyl ether, Methyl tert-butyl ether, Dimethoxyethane, Dioxanes (1.4 dioxane), N-methyl pyrrolidinone (NMP), or combinations thereof.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C. In some embodiments, the temperature of the reaction mixture can be of from about −30° C. to about −10° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula V in any suitable yield. For example, the compound of Formula V can be prepared in a yield of at least about 50%, 55, 60, 65, 70, 75, 80, 85, 90 or at least about 95%.

The method of the present invention can provide the compound of Formula V in any suitable purity. For example, the compound of Formula V can be prepared in a purity of at least about 90, 95, 96, 97, 98 or at least about 99%. In some embodiments, the compound of Formula V can be prepared in at least 95% purity. In some embodiments, the compound of Formula V can be prepared in at least 98% purity. In some embodiments, the compound of Formula V can be prepared in at least 99% purity.

In some embodiments, the method including preparing the compound of Formula V:

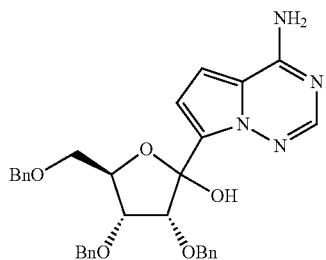

wherein the method includes forming the reaction mixture having TMS-Cl, PhMgCl, iPrMgCl, the compound of Formula VI:

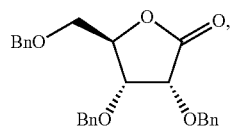

and the compound of Formula VII:

under conditions suitable to prepare the compound of Formula V.

In some embodiments, the present invention provides the compound:

B. Addition of Prodrug Moiety

The present invention also provides a method of coupling a prodrug moiety to a nucleoside to provide a compound of the present invention. In some embodiments, the present invention provides a method of preparing a compound of Formula VIII:

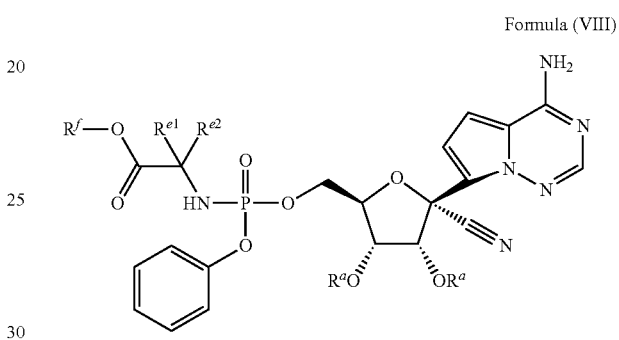

Formula (VIII)

wherein the method includes forming a reaction mixture including a coupling agent, a non-nucleophilic base, a compound of Formula IX:

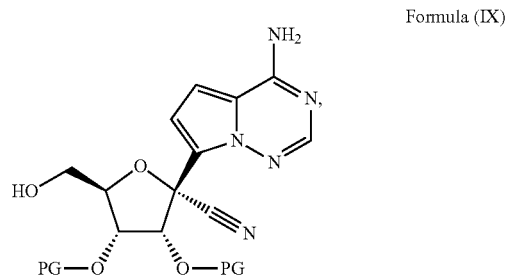

Formula (IX)

and a compound of Formula X:

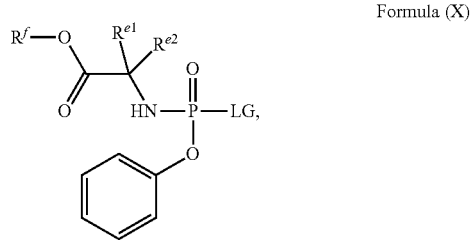

Formula (X)

under conditions suitable to form the compound of Formula VIII, wherein each $R^a$ is H or PG, each PG group is a hydroxy protecting group, or both PG groups are combined to form —$C(R^{19})_2$—, $R^{e1}$ and $R^{e2}$ are each independently H, $C_1$-$C_6$ alkyl or benzyl, $R^f$ is H, $C_1$-$C_8$ alkyl, benzyl, $C_3$-$C_6$ cycloalkyl, or —CH$_2$—C$_3$-C$_6$ cycloalkyl, R$^{19}$ is H, C$_1$-C$_8$ alkyl, phenyl or substituted phenyl, and LG is a leaving group.

Any suitable coupling agent can be used in the method of making the compound of Formula VIII, as described above for the method of making the compound of Formula V. In some embodiments, the coupling agent can be a magnesium coupling agent. In some embodiments, the coupling agent can be MgCl$_2$, iPrMgCl, tBuMgCl, PhMgCl, or combinations thereof. In some embodiments, the coupling agent can be MgCl$_2$.

Any suitable non-nucleophilic base can be used in the method of making the compound of Formula VIII. Representative non-nucleophilic bases include, but are not limited to, triethylamine, diisopropylethyl amine, N,N-diethylaniline, pyridine, 2,6-lutidine, 2,4,6-collidine, 4-dimethylaminopyridine, and quinuclidine. In some embodiments, the non-nucleophilic base can be di-isopropyl ethyl amine (DIPEA).

The protecting groups PG can be any suitable hydroxy protecting groups, as described above for the method of making the compound of Formula V. Exemplary protecting groups PG can be benzyl, or the PG groups can be combined to form an acetonide. Exemplary acetonides include, but are not limited to acetonide and benzylidene acetal. In some embodiments, the hydroxy protecting groups of hydroxy groups on adjacent carbons can be combined to form acetonide. In some embodiments, the PG groups are combined to form —C(R$^{19}$)$_2$—. In some embodiments, each R$^a$ is the protecting group PG where the PG groups are combined to form —C(Me)$_2$-.

When the R$^e$ group is C$_1$-C$_8$ alkyl, each R$^e$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, each R$^e$ group can be methyl.

When the R$^f$ group is C$_1$-C$_8$ alkyl, R$^f$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the R$^f$ group can be methyl, ethyl, isopropyl, t-butyl, or iso-hexyl. When the R$^f$ group is C$_3$-C$_6$ cycloalkyl, R$^f$ can be cyclopropyl, cyclobutyl, cyclopentyl or cyclohexyl. In some embodiments, R$^f$ can be cyclobutyl, cyclopentyl or cyclohexyl.

When the R$^{19}$ group is C$_1$-C$_8$ alkyl, R$^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the R$^{19}$ group can be methyl.

The leaving group can be any suitable leaving group. Suitable leaving groups LG include, but are not limited to, chloride, bromide, mesylate, tosylate, triflate, 4-nitrobenzenesulfonate, 4-chlorobenzenesulfonate, 4-nitrophenoxy, pentafluorophenoxy, etc. In some embodiments, the leaving group LG can be 4-nitrophenoxy or pentafluorophenoxy. In some embodiments, the leaving group LG can be 4-nitrophenoxy.

In some embodiments, each R$^a$ is PG where the PG groups are combined to form —C(R)$_2$—, R$^f$ is C$_1$-C$_8$ alkyl, R$^{19}$ is C$_1$-C$_8$ alkyl, and the leaving group LG is 4-nitrophenoxy or pentafluorophenoxy.

In some embodiments, the coupling agent is MgCl$_2$, and the non-nucleophilic base is di-isopropyl ethyl amine.

In some embodiments, the compound of Formula VIII can be

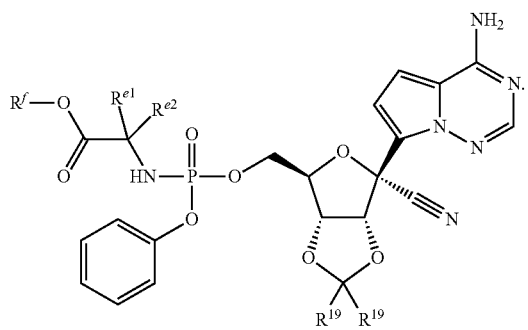

In some embodiments, the compound of Formula VIII can be

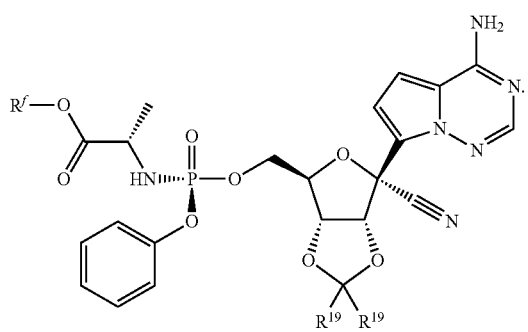

In some embodiments, the compound of Formula VIII can be

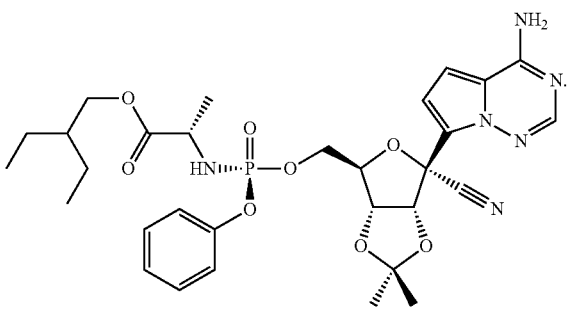

In some embodiments, the method of making the compound Formula VIII includes forming the reaction mixture including MgCl$_2$, DIPEA, the compound of Formula IX:

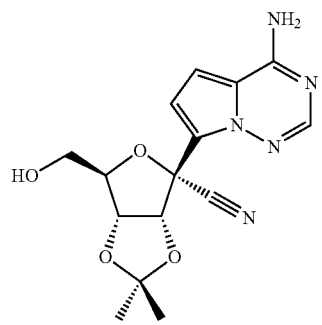

and the compound of Formula X:

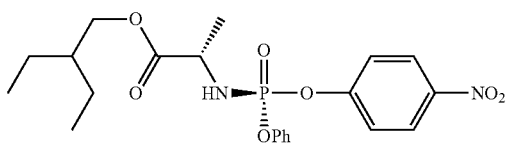

under conditions suitable to form the compound of Formula VIII:

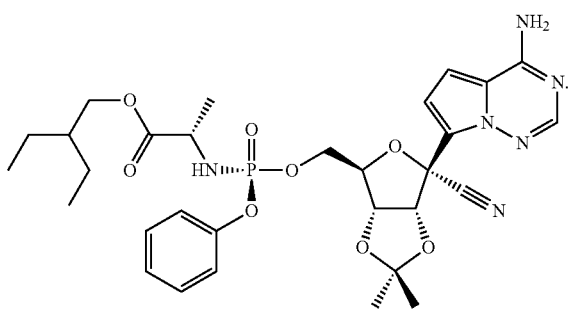

When the $R^a$ groups of the compound of Formula VIII are the hydroxy protecting groups PG, the method can include the additional step of removing the protecting groups to form the compound of Formula VIII where each $R^a$ is H. In some embodiments, the method of preparing the compound of Formula VIII includes forming a second reaction mixture including a deprotection agent and the compound Formula VIII wherein each $R^a$ group is the protecting group PG, under suitable conditions to form the compound of Formula VIII where each $R^a$ is H. The deprotection agent can be any suitable agent to remove the protecting groups PG such as hydrogen and a hydrogenation catalyst, or acid. For example, if the protecting group PG is benzyl, the deprotection agent can be hydrogen and platinum on carbon. Alternatively, when the protecting group PG is an acetonide, the deprotection agent can be an acid. Representative acids include, but are not limited to, acetic acid, glacial acetic acid, trifluoroacetic acid (TFA), hydrochloric acid, concentrated hydrochloric acid, and others. In some embodiments, the method of preparing the compound of Formula VIII includes forming a second reaction mixture including an acid and the compound Formula VIII wherein the $R^a$ groups are combined to form $—C(R^{19})_2—$, under suitable conditions to form the compound of Formula VIII where each $R^a$ is H. In some embodiments, the acid can be hydrochloric acid.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran, acetonitrile, or combinations thereof. In some embodiments, the solvent can be acetonitrile.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula VIII in any suitable yield. For example, the compound of Formula VIII can be prepared in a yield of at least about 50%, 55, 60, 65, 70, 75, 80, 85, 90 or at least about 95%.

The method of the present invention can provide the compound of Formula VIII in any suitable purity. For example, the compound of Formula VIII can be prepared in a purity of at least about 90, 95, 96, 97, 98 or at least about 99%. In some embodiments, the compound of Formula VIII can be prepared in at least 95% purity. In some embodiments, the compound of Formula VIII can be prepared in at least 98% purity. In some embodiments, the compound of Formula VIII can be prepared in at least 99% purity.

In some embodiments, the present invention provides the compound

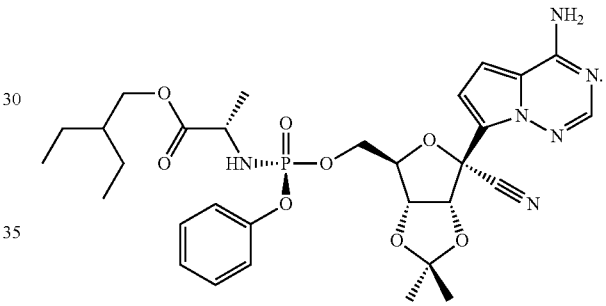

IX. Examples

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Ac₂O | acetic anhydride |
| AIBN | 2,2′-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |

TABLE 1-continued

List of abbreviations and acronyms.

| Abbreviation | Meaning |
|---|---|
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH+ | mass plus 1 |
| MH− | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

A. Preparation of Compounds

Example 1. (2S)-ethyl 2-(chloro(phenoxy)phosphorylamino)propanoate (Chloridate A)

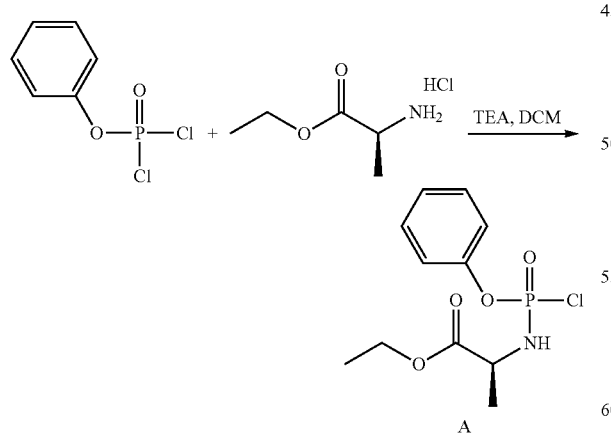

Ethyl alanine ester hydrochloride salt (1.69 g, 11 mmol) was dissolved in anhydrous $CH_2Cl_2$ (10 mL) and the mixture stirred with cooling to 0° C. under $N_2$(g). Phenyl dichlorophosphate (1.49 mL, 10 mmol) was added followed by dropwise addition of $Et_3N$ over 10 min. The reaction mixture was then slowly warmed to RT and stirred for 12 h. Anhydrous $Et_2O$ (50 mL) was added and the mixture stirred for 30 min. The solid that formed was removed by filtration, and the filtrate concentrated under reduced pressure. The residue was subjected to silica gel chromatography eluting with 0-50% EtOAc in hexanes to provide intermediate A (1.13 g, 39%). $^1$H NMR (300 MHz, $CDCl_3$) δ 7.39-7.27 (m, 5H), 4.27 (m, 3H), 1.52 (m, 3H), 1.32 (m, 3H). $^{31}$P NMR (121.4 MHz, $CDCl_3$) δ 8.2, 7.8.

Example 2. (2S)-2-ethylbutyl 2-(chloro(phenoxy)phosphorylamino)propanoate (Chloridate B)

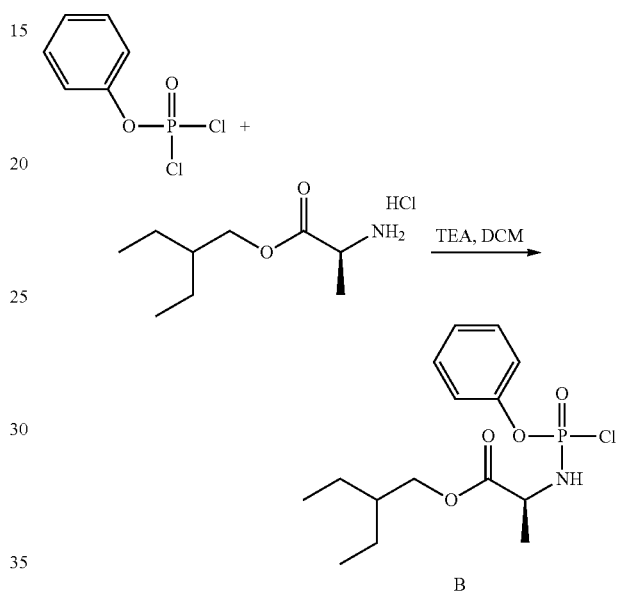

The 2-ethylbutyl alanine chlorophosphoramidate ester B was prepared using the same procedure as chloridate A except substituting 2-ethylbutyl alanine ester for ethyl alanine ester. The material is used crude in the next reaction. Treatment with methanol or ethanol forms the displaced product with the requisite LCMS signal.

Example 3. (2S)-isopropyl 2-(chloro(phenoxy)phosphorylamino)propanoate (Chloridate C)

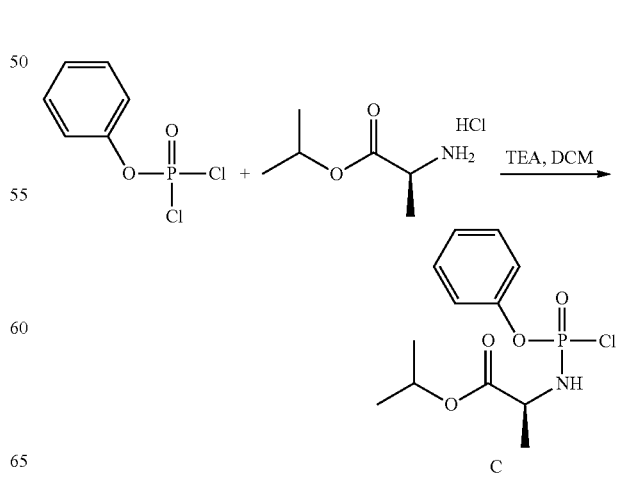

The isopropyl alanine chlorophosphoramidate ester C was prepared using the same procedure as chloridate A except substituting isopropyl alanine ester for the ethyl alanine ester. The material is used crude in the next reaction. Treatment with methanol or ethanol forms the displaced product with the requisite LCMS signal.

Example 4. (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile (Compound 1)

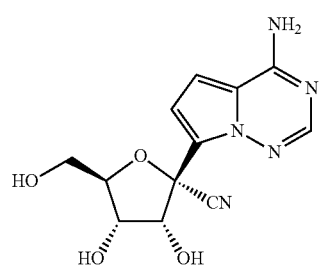

The preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile is described below.

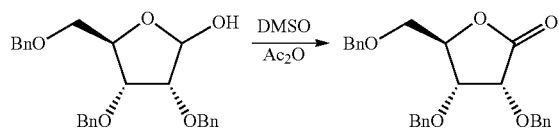 [SMILES: "Ac2O" ; OC1O[C@H](COCc2ccccc2)[C@@H](OCc2ccccc2)[C@H]1OCc1ccccc1 ; O=C1O[C@H](COCc2ccccc2)[C@@H](OCc2ccccc2)[C@H]1OCc1ccccc1]

The commercially available lactol (10 g, 23.8 mmol) was dissolved in anhydrous DMSO (30 mL) under $N_2(g)$. $Ac_2O$ (20 mL) was added and the resultant reaction mixture stirred at RT for 48 h. The reaction mixture was poured onto ice $H_2O$ (500 mL) and the mixture stirred for 20 min. The mixture was extracted with EtOAc (3×200 mL) and the combined organic extracts were then washed with $H_2O$ (3×200 mL). The organic extract was dried over anhydrous $MgSO_4$, filtered and concentrated under reduced pressure. The residue was dissolved in $CH_2Cl_2$ and subjected to silica gel chromatography eluting with 25% EtOAc in hexanes to provide the lactone (9.55 g, 96%). $^1$H NMR (400 MHz, DMSO) δ 7.30-7.34 (m, 13H), 7.19-7.21 (m, 2H), 4.55-4.72 (m, 6H), 4.47 (s, 2H), 4.28 (d, J=3.9 Hz, 1H), 3.66 (m, 2H). LCMS m/z 436.1 [M+$H_2O$], 435.2 [M+OH]– Tr=2.82 min. HPLC Tr=4.59 [2-98% ACN in H2] over 5 min @ 2 ml/min flow.

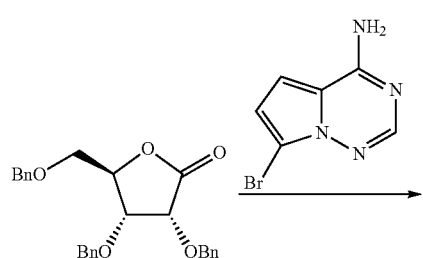

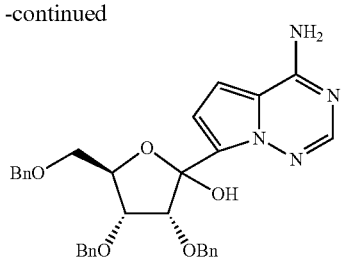

The bromopyrazole (prepared according to WO2009/132135) (0.5 g, 2.4 mmol) was suspended in anhydrous THF (10 mL) under $N_2(g)$. The suspension was stirred and TMSCl (0.67 mL, 5.28 mmol) was added. The mixture was stirred for 20 min. at RT and then cooled to −78° C. after which time a solution of n-BuLi (6 mL, 1.6 N in hexanes, 9.6 mmol) was added slowly. The reaction mixture was stirred for 10 min. at −78° C. and then the lactone (1 g, 2.4 mmol) was added via syringe. When the reaction was complete as measured by LCMS, AcOH was added to quench the reaction. The mixture was concentrated under reduced pressure and the residue dissolved in a mixture of $CH_2Cl_2$ and $H_2O$ (100 mL, 1:1). The organic layer was separated and washed with $H_2O$ (50 mL). The organic layer was then dried over anhydrous $MgSO_4$, filtered and concentrated under reduced pressure. The residue was subjected to silica gel chromatography eluting with 0-50% EtOAc in hexanes to provide the product as a 1:1 mixture of anomers (345 mg, 26% yield). LCMS m/z 553 [M+H].

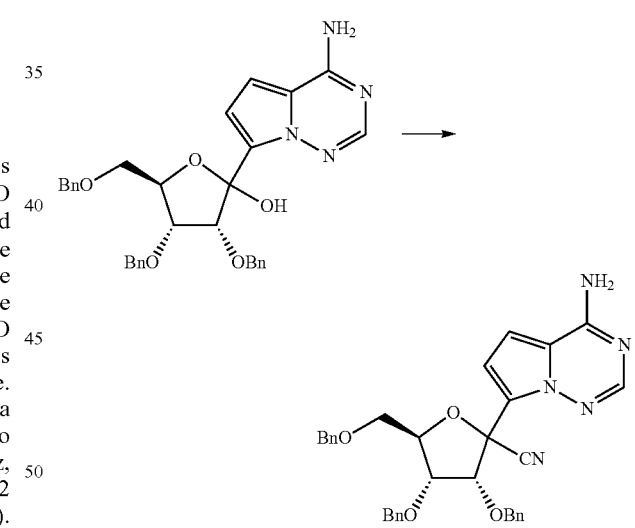

The hydroxy nucleoside (1.1 g, 2.0 mmol) was dissolved in anhydrous $CH_2Cl_2$ (40 mL) and the solution cooled with stirring to 0° C. under $N_2(g)$. TMSCN (0.931 mL, 7 mmol) was added and the mixture stirred for a further 10 min. TMSOTf (1.63 mL, 9.0 mmol) was slowly added to the reaction and the mixture stirred for 1 h. The reaction mixture was then diluted with $CH_2Cl_2$ (120 mL) and aqueous $NaHCO_3$ (120 mL) was added to quench the reaction. The reaction mixture was stirred for a further 10 min and the organic layer separated. The aqueous layer was extracted with $CH_2Cl_2$ (150 mL) and the combined organic extracts dried over anhydrous $MgSO_4$, filtered and concentrated under reduced pressure. The residue was dissolved in a minimal amount of $CH_2Cl_2$ and subjected to silica gel chromatography eluting with a gradient of 0-75% EtOAc and hexanes to provide the tribenzyl cyano nucleoside as a mixture of anomers. (0.9 g, 80%). $^1$H NMR (300 MHz, CD$_3$CN) δ 7.94 (s, 0.5H), 7.88 (s, 0.5H), 7.29-7.43 (m, 13H), 7.11-7.19 (m, 1H), 6.82-6.88 (m, 1H), 6.70-6.76 (m, 1H), 6.41 (bs, 2H), 5.10 (d, J=3.9 Hz, 0.5H), 4.96 (d, J=5.1 Hz, 0.5H), 4.31-4.85 (m, 7H), 4.09-4.18 (m, 2H), 3.61-3.90 (m, 2H). LCMS m/z 562 [M+H].

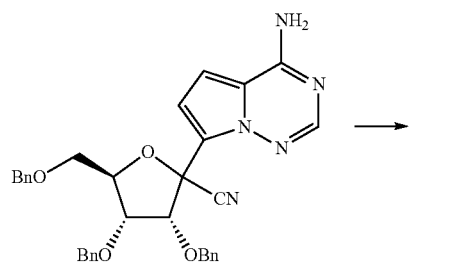

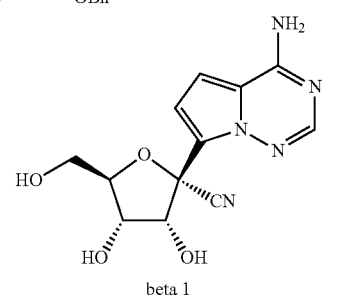

beta 1

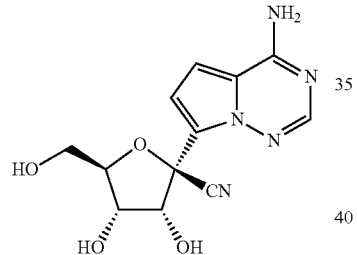

The tribenzyl cyano nucleoside (70 mg, 0.124 mmol) was dissolved in anhydrous CH$_2$Cl$_2$ (2 mL) and cooled to −78° C. under N$_2$(g). A solution of BCl$_3$ (1N in CH$_2$Cl$_2$, 0.506 mL, 0.506 mmol) was added and the reaction mixture stirred for 1 h. at −78° C. When the reaction was complete by LC/MS, MeOH was added to quench the reaction. The reaction mixture was allowed to warm to room RT and the solvent removed under reduced pressure. The residue was subjected to C18 reverse phase HPLC, eluting for 5 min with H$_2$O (0.1% TFA), followed by a gradient of 0-70% MeCN in H$_2$O (0.1% TFA) over 35 min, to elute the α-anomer (20 mg, 37%), and β-anomer 1 (20 mg, 37%). (α-anomer)$^1$H NMR (300 MHz, D$_2$O) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H). (β-anomer)$^1$H NMR (400 MHz, DMSO) δ 7.91 (s, 1H), 7.80-8.00 (br s, 2H), 6.85-6.89 (m, 2H), 6.07 (d, J=6.0 Hz, 1H), 5.17 (br s, 1H), 4.90 (br s, 1H), 4.63 (t, J=3.9 Hz, 1H), 4.02-4.06 (m, 1H), 3.94 (br s, 1H), 3.48-3.64 (m, 2H). LCMS m/z 292.2 [M+H], 290.0 [M−H]. Tr=0.35 min. 13C NMR (400 MHZ, DMSO), 156.0, 148.3, 124.3, 117.8, 117.0, 111.2, 101.3, 85.8, 79.0, 74.7, 70.5, 61.4. HPLC Tr=1.32 min Example 5. (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (Compound 2)

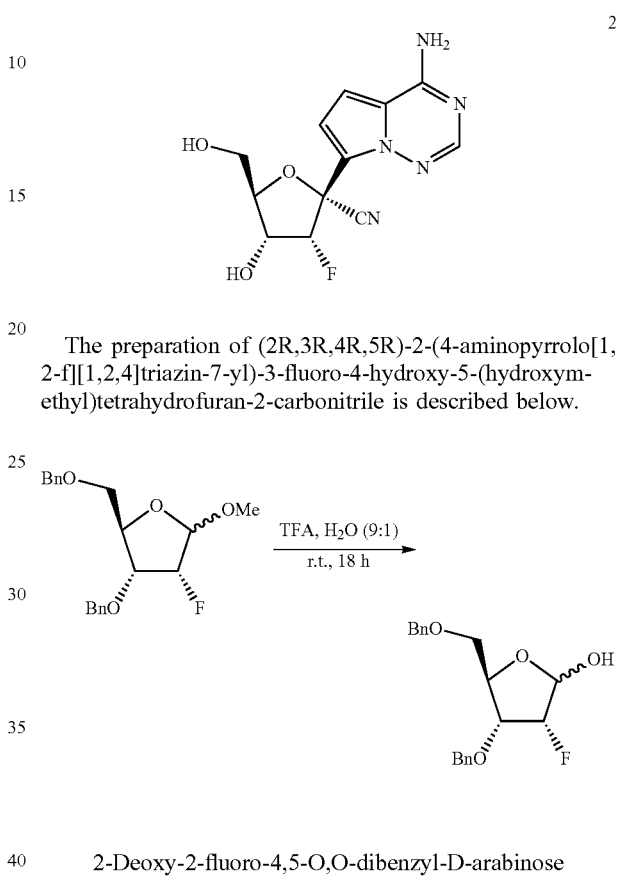

The preparation of (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile is described below.

2-Deoxy-2-fluoro-4,5-O,O-dibenzyl-D-arabinose

1'-Methoxy-2-deoxy-2-fluoro-4,5-O,O-dibenzyl-D-arabinose (1.0 g, 2.88 mmol) in TFA (13.5 mL) was treated with H$_2$O (1.5 mL) and the resultant mixture stirred for 5 h. The mixture was then diluted with EtOAc (100 mL) and treated with saturated NaHCO$_3$ (50 mL). The organic layer was separated and washed with NaCl (50 mL), dried over anhydrous MgSO$_4$, filtered and concentrated under reduced pressure. The residue was subjected to silica gel chromatography (80 g SiO$_2$ Combiflash HP Gold Column) eluting with 0-100% EtOAc in hexanes to afford 2-deoxy-2-fluoro-4,5-O,O-dibenzyl-D-arabinose (695 mg, 72%) as a white solid: R$_f$=0.52 (25% EtOAc in hexanes). $^1$H NMR (300 MHz, CDCl$_3$) δ 7.30 (m, 10H), 5.35 (m, 1H), 4.68-4.29 (m, 7H), 3.70 (d, J=10.5 Hz, 1H), 3.50 (d, J=10.5 Hz, 2H). $^{19}$F NMR (282.2 MHz, CDCl$_3$) δ −207 (m), −211 (m). LCMS m/z 350 [M+H$_2$O].

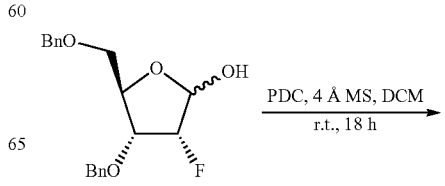

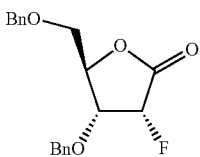

(3R,4R,5R)-4-(benzyloxy)-5-(benzyloxymethyl)-3-fluorodihydrofuran-2(3H)-one

2-Deoxy-2-fluoro-4, 5-O,O-dibenzyl-D-arabinose (4.3 g, 12.8 mmol) was dissolved in CH$_2$Cl$_2$ (85 mL) was treated with 4 Å MS (10 g) and pyridinium dichromate (14.4 g, 38.3 mmol). The resultant mixture was stirred for 24 h and then filtered through a pad of Celite. The eluant was concentrated under reduced pressure and the residue subjected to silica gel chromatography (120 g SiO$_2$ HP Gold Combiflash Column) eluting with 0-100% EtOAc in hexanes to afford (3R,4R, 5R)-4-(benzyloxy)-5-(benzyloxymethyl)-3-fluorodihydrofuran-2(3H)-one as a clear oil (3.5 g, 83%): R$_f$=0.25 (25% EtOAc in hexanes). $^1$H NMR (300 MHz, CDCl$_3$) δ 7.37 (m, 10H), 5.45 (dd, J=49, 5.7, Hz, 1H), 4.85 (d, J=11.7 Hz, 1H), 4.52 (m, 4H), 4.29 (d, J=5.4 Hz, 1H), 2.08 (dd, J=15.3, 10.2 Hz, 2H). $^{19}$F NMR (282.2 MHz, CDCl$_3$) δ −216. LCMS m/z 348 [M+H$_2$O]. HPLC (6-98% MeCN—H$_2$O gradient, 0.05% TFA modifier) t$_R$=5.29 min. Phenomenex Synergi 4 m Hydro-RP 80 A, 50×4.60 mm, 4 micron; 2 mL/min flow rate

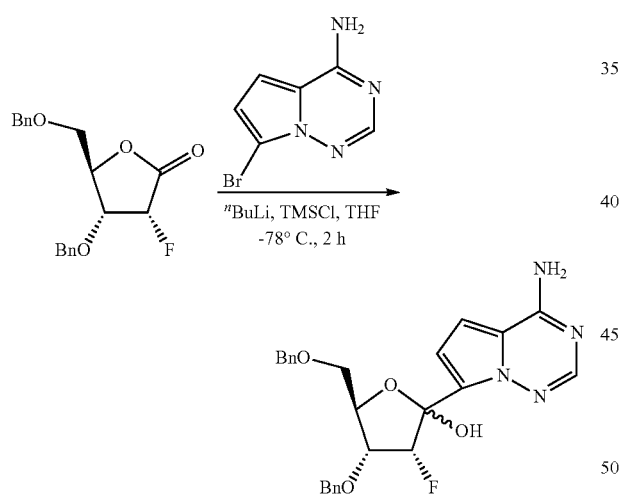

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol 7-Bromopyrrolo[1,2-f][1,2,4]-triazin-4-amine (68 mg, 0.319 mmol) in THF (1.4 mL) was treated with TMSCl (89 µL, 0.703 mmol) and the mixture stirred for 2 h. The mixture was then cooled to −78° C. and treated with nBuLi (1.0 M in hexanes, 1.09 mL, 1.09 mmol). The solution was stirred for 30 min and then treated with (3R,4R, 5R)-4-(benzyloxy)-5-(benzyloxymethyl)-3-fluorodihydrofuran-2(3H)-one (106 mg, 0.319 mmol) dropwise in THF (1.4 mL). The resultant mixture was stirred for 30 min and then AcOH (83 µL, 1.44 mmol) in THF (1.0 mL) was added to quench the reaction. The mixture was warmed to RT and then concentrated under reduced pressure. The residue was diluted with EtOAc (100 mL) and washed with saturated NaCl solution (50 mL). The organic layer was dried over anhydrous MgSO$_4$, filtered and concentrated under reduced pressure. The residue was subjected to silica gel chromatography (40 g SiO$_2$ HP Gold Combiflash Column) eluting with 0-100% EtOAc in hexanes followed by a 0-100% gradient of (20% MeOH in EtOAc) in EtOAc to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol as a white solid (68 mg, 44%, 60/40 mixture of α/β isomers). R$_f$=0.32 (EtOAc). $^1$H NMR (300 MHz, CDCl$_3$) δ 8.05 (s, 1H), 7.86 (s, 1H), 7.81 (s, 1H), 7.64 (s, 1H), 7.26 (m, 10H), 6.95 (m, 1H), 6.71 (m, 1H), 6.08 (m, 1H), 5.34 (m, 1H), 4.65 (m, 6H), 4.71 (m, 2H). $^{19}$F NMR (282.2 MHz, CDCl$_3$) δ −211 (m). LCMS m/z 465 [M+H]. HPLC (6-98% MeCN—H$_2$O gradient, 0.05% TFA modifier) t$_R$=4.37 min. (α-isomer), 4.54 min. (β-isomer).

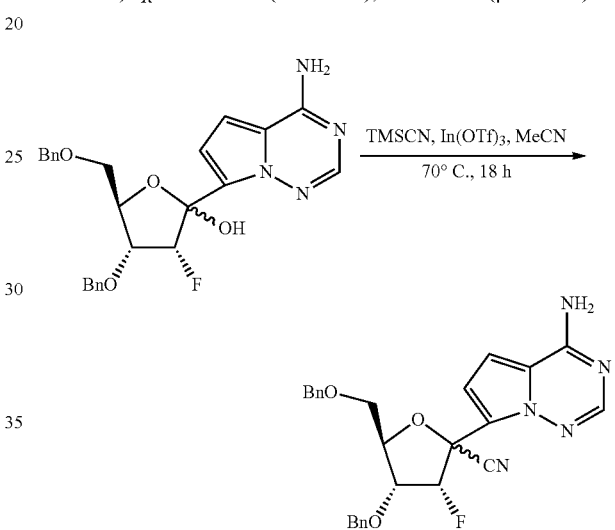

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol (195 mg, 0.42 mmol) was dissolved in MeCN (1.4 mL) was treated with TMSCN (336 µL, 2.52 mmol) and In(OTf)$_3$ (708 mg, 1.26 mmol). The solution was stirred at 70° C. for 18 h and then cooled to 0° C. The mixture was treated with saturated NaHCO$_3$ solution (20 drops) then warmed to RT and diluted with EtOAc (100 mL) and H$_2$O (50 mL). The organic layer was separated and washed with saturated NaCl solution (50 mL), dried over MgSO$_4$, filtered and concentrated under reduced pressure. The residue was subjected to silica gel chromatography (40 g SiO$_2$ HP Gold Combiflash Column) eluting with 0-100% EtOAc in hexanes to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile as a white solid (110 mg, 55%, 60/40 mixture of a/0 isomers). Data for both isomers: R$_f$=0.53 (EtOAc). $^1$H NMR (300 MHz, CDCl$_3$) δ 8.01 (s, 1H), 7.94 (s, 1H), 7.30 (m, 10H), 7.00 (d, J=4.5 Hz, 1H), 6.93 (d, J=4.8 Hz, 1H), 6.87 (d, J=5.4 Hz, 1H), 6.70 (d, J=4.8 Hz, 1H), 5.85 (dd, J=52, 3.3 Hz, 1H), 5.55 (dd, J=53, 4.5 Hz, 1H), 4.71 (m, 7H), 3.87 (m, 2H), 3.72 (m, 2H). $^{19}$F NMR (282.2 MHz, CDCl$_3$) δ −196 (m), −203 (m). LCMS m/z 474 [M+H]. HPLC (6-98% MeCN—H$_2$O gradient, 0.05% TFA modifier) $t_R$=4.98 min.

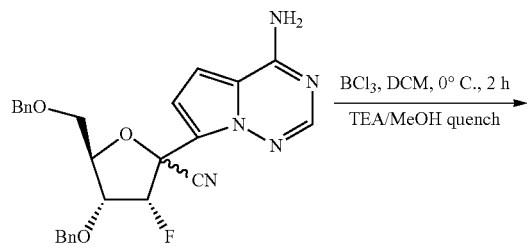

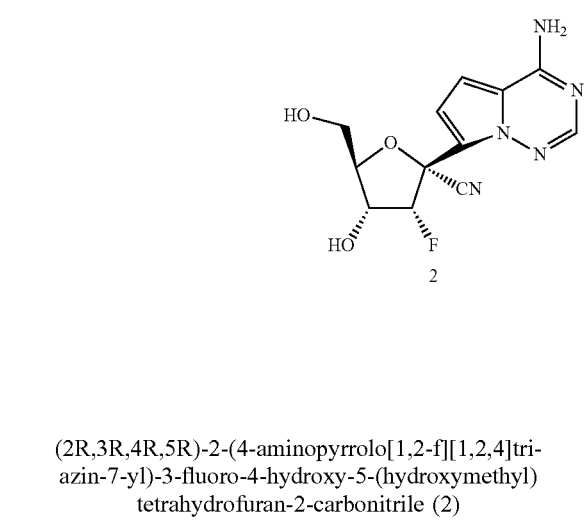

(2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (2)

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile (110 mg, 0.23 mmol) was dissolved in CH$_2$Cl$_2$ (1.5 mL) and cooled to 0° C. The reaction mixture was treated with BCl$_3$ (1.0 M in CH$_2$Cl$_2$, 766 µL, 0.77 mmol) and stirred for 2 h. The mixture was then cooled to −78° C. and treated with Et$_3$N (340 µL, 2.44 mmol) followed by MeOH (2 mL) before allowing to warm to RT. The reaction was concentrated under reduced pressure and then co-evaporated with MeOH (3×5 mL). The residue was then suspended in H$_2$O (5 mL) and treated with NaHCO$_3$ (1 g). The solution was stirred for 10 min and then concentrated under reduced pressure. The residue was filtered and washed with MeOH (3×10 mL) on a fritted glass funnel (coarse) and the eluant concentrated under reduced pressure. The residue was subjected to reverse phase HPLC (6-98% MeCN in H$_2$O gradient with 0.05% TFA modifier) to afford (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile 2 as a white solid (16.8 mg, 25%) and the α-isomer. Data for the β-isomer: R$_f$=0.13 (10% MeOH in EtOAc). $^1$H NMR (300 MHz, CD$_3$OD) δ 8.09 (s, 1H), 7.28 (d, J=5.1 Hz, 1H), 7.17 (d, J=5.1 Hz, 1H), 5.42 (dd, J=53, 3.3 Hz, 1H), 4.20 (m, 2H), 3.99 (d, J=3.6 Hz, 1H), 3.77 (d, J=3.6 Hz, 1H). $^{19}$F NMR (282.2 MHz, CDCl$_3$) δ −197 (m). LCMS m/z 294 [M+H]. HPLC (2-98% MeCN—H$_2$O gradient, 0.05% TFA modifier) $t_R$=1.49 min.

Example 6. (2R,3R,4R,5S)-5-(4-aminopyrrolo[1,2-f][1,2,4]triazin-7-yl)-4-fluoro-2-(hydroxymethyl)-5-methyltetrahydrofuran-3-ol (Compound 3)

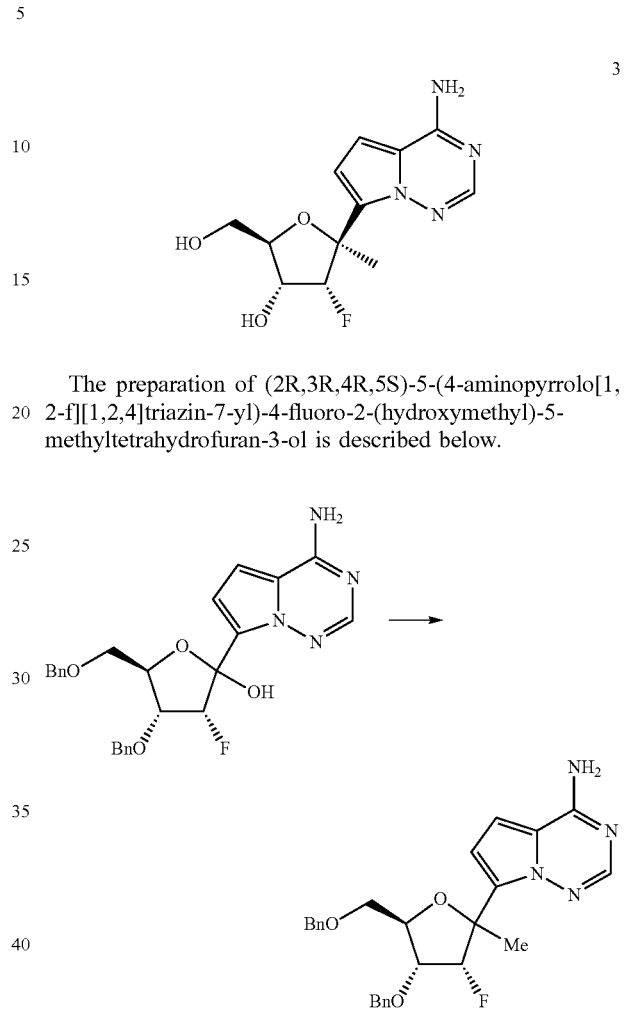

The preparation of (2R,3R,4R,5S)-5-(4-aminopyrrolo[1,2-f][1,2,4]triazin-7-yl)-4-fluoro-2-(hydroxymethyl)-5-methyltetrahydrofuran-3-ol is described below.

The starting nucleoside (prepared as described in the synthesis of compound 2) (0.355 g, 0.765 mmol) was dissolved in anhydrous THF (35 mL) and cooled to 0° C. with stirring under N$_2$(g). A solution of methyl magnesium chloride (2 mL, 6 mmol) (3N in THF) was added and the resultant mixture stirred overnight. Acetic acid (7 mmol) was added to quench the reaction and then the solvents were removed by rotory under reduced pressure. The residue was re-dissolved in CH$_2$Cl$_2$ and the solution subjected to a plug of silica gel to isolate the product (0.355 g) as a crude mixture. LC/MS (m/z: 480, M$^{+1}$). The crude material was dissolved in anhydrous CH$_2$Cl$_2$ (20 mL) and placed under N$_2$(g). The solution was stirred and treated with methanesulfonic acid (0.2 mL, 2.74 mmol). The reaction mixture was stirred for 12 h at RT and then quenched by the addition of Et$_3$N (3.5 mmol). The mixture was concentrated under reduced pressure and the residue subjected to silica gel chromatography to provide the methyl substituted nucleoside (0.174 g, 0.377 mmol, 44% yield) as a 4:1 mixture of beta- and alpha-anomers respectively. $^1$H NMR (300 MHz, CD$_3$CN) major anomer δ 7.87 (s, 1H), 7.27-7.40 (m, 10H), 6.77 (d, J=4.5 HZ, 1H), 6.70 (d, J=4.5 Hz, 1H), 6.23 (br s, 2H), 5.53 (dd, J=55, 3.3 Hz, 1H), 4.42-4.75 (m, 4H), 4.19-4.26 (m, 1H), 3.65-4.00 (m, 3H), 1.74 (d, J=3.9 Hz, 3H). $^{19}$F NMR (282.2 MHz, CD$_3$CN) major anomer δ-207 (m, 1F). LCMS m/z 463 [M+H].

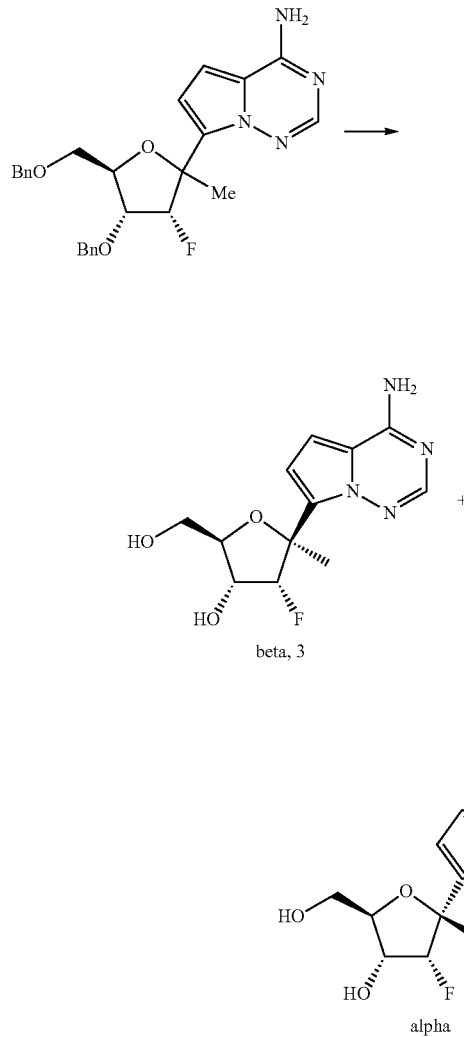

beta, 3 alpha

The benzylated nucleoside material (0.134 g, 0.290 mmol), Degussa catalyst (0.268 g) and AcOH (30 mL) were mixed together. The reaction atmosphere was charged with H$_2$ (g) and the reaction stirred for 2 h. The catalyst was removed by filtration and the mixture concentrated under reduced pressure. The residue was dissolved in a minimal amount of H$_2$O and subjected to reverse phase HPLC (C$^{18}$ hydro RP column) to isolate the β-anomer 3 (0.086 g, 0.217 mmol, 57% yield). $^1$H NMR (300 MHz, D$_2$O) δ 7.87 (s, 1H), 7.22 (d, J=4.8 Hz, 1H), 6.87 (d, J=4.8 Hz, 1H), 5.35 (dd, J=54, 3.6 Hz, 1H), 3.97-4.10 (m, 2H), 3.81 (dd, J=12.6, 2.1 Hz, 1H), 3.64 (dd, J=12.6, 4.8 Hz, 1H), 1.65 (d, J=4.2 Hz, 3H). $^{19}$F NMR (282.2 MHz, CD$_3$CN) δ −207 (m, 1F).

A small amount of alpha anomer was characterized as follows. $^1$H NMR (300 MHz, D$_2$O) δ 7.86 (s, 1H), 7.26 (d, J=4.8 Hz, 1H), 6.85 (d, J=4.8 Hz, 1H), 5.31 (dd, J=54, 3.9 Hz, 1H), 4.39 (ddd, J=26.1, 9.9, 3.6 Hz, 2H), 4.00-4.05 (m, 1H), 3.90 (dd, J=12.3, 2.1 Hz, 1H), 3.66 (dd, J=12.6, 4.8, 1H), 1.56 (s, 3H). $^{19}$F NMR (282.2 MHz, CD$_3$CN) δ −198 (dd, J=54, 26 Hz, 1F).

Example 7. (2R)-isopropyl 2-((((2R,3R,4R,5S)-5-(4-aminopyrrolo[1,2-f][1,2,4]triazin-7-yl)-4-fluoro-3-hydroxy-5-methyltetrahydrofuran-2-yl)methoxy)-(phenoxy)phosphorylamino)propanoate (Compound 4)

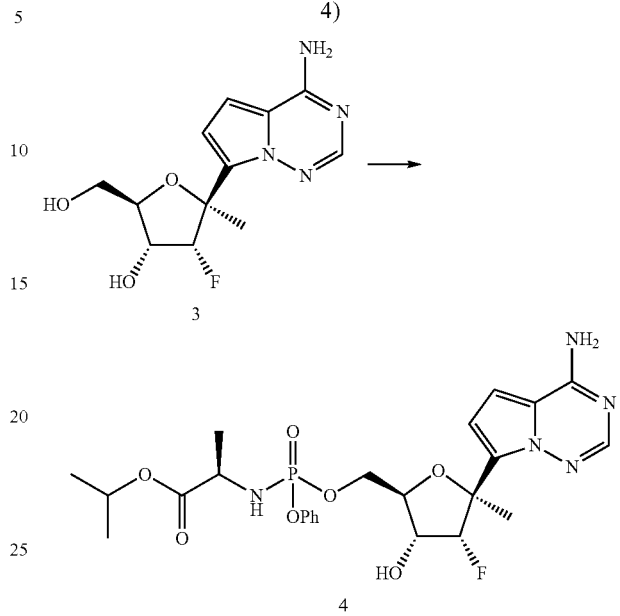

The nucleoside 3 (0.011 g, 0.04 mmol) was dissolved in trimethylphosphate (2 mL) and cooled to 0° C. The mixture was stirred under an atmosphere of N$_2$(g) and 1-Methylimidazole (0.320 mL, 5 mmol) followed by the alaninylmonoisopropyl, monophenol phosphorchloridate C (0.240 mL, 4.4 mmol) was added. The reaction mixture was stirred for 2 h. at 0° C. and then allowed to warm slowly to RT. while monitoring by LC/MS. When complete by LCMS, the reaction mixture was treated with H$_2$O (5 mL) and then concentrated under reduced pressure. The residue was dissolved in CH$_2$Cl$_2$ and subjected to silica gel chromatography eluting with 0-100% EtOAc in hexanes. The product fractions were collected and concentrated. The residue was subjected to prep HPLC to yield the alanine isopropyl monoamidate prodrug 4 as a mixture of isomers (4.7 mg, 0.003 mmol, 6%). $^1$H NMR (300 MHz, CD3CN) δ 7.87 (s, 1H), 7.17-7.44 (m, 5H), 6.71-6.83 (m, 2H), 6.14 (br, s, 2H), 5.38 (dd, J=56, 3.3 Hz, 1H), 4.92-5.01 (m, 1H), 3.86-4.46 (m, 6H), 3.58 (m, 1H), 1.73 (m, 3H), 1.18-1.34 (m, 9H). LCMS m/z 552 [M+H].

Example 8. (2R)-ethyl 2-((((2R,3R,4R,5S)-5-(4-aminopyrrolo[1,2-f][1,2,4]triazin-7-yl)-4-fluoro-3-hydroxy-5-methyltetrahydrofuran-2-yl)methoxy)(phenoxy)phosphorylamino)propanoate (Compound 5)

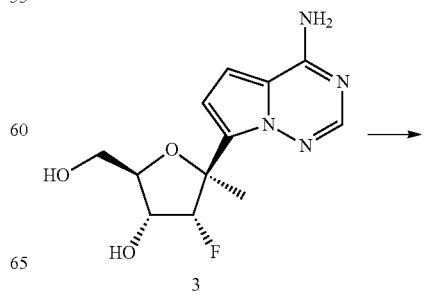

3

-continued

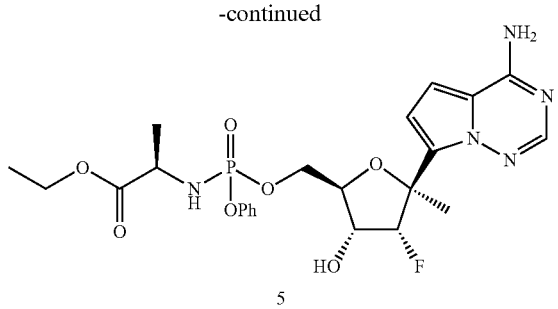

5

The nucleoside 3 (0.026 g, 0.092 mmol) was dissolved in trimethylphosphate (2 mL) and cooled to 0° C. The mixture was stirred under $N_2(g)$ and 1-methylimidazole (0.062 mL, 0.763 mmol) followed by the chloridate A (0.160 g, 0.552 mmol) were added. The reaction mixture was stirred for 2 h. at 0° C. and then allowed to warm slowly to RT. $H_2O$ (5 mL) was added to quench the reaction and then the mixture concentrated under reduced pressure. The residue was dissolved in $CH_2Cl_2$ and subjected to silica gel chromatography eluting with 0-100% EtOAc in hexanes. The product fractions were collected and concentrated. Crude product was eluted using 0 to 100 percent EtOAc in hexanes. The crude product was collected and concentrated under reduced pressure. The residue was subjected to prep HPLC to yield 5 (2.0 mg, 4% yield). LCMS m/z 538 [M+H].

Example 9. ((2R,3R,4R,5S)-5-(4-aminopyrrolo[1,2-f][1,2,4]triazin-7-yl)-4-fluoro-3-hydroxy-5-methyl-tetrahydrofuran-2-yl)methyl tetrahydrogen triphosphate (Compound 6)

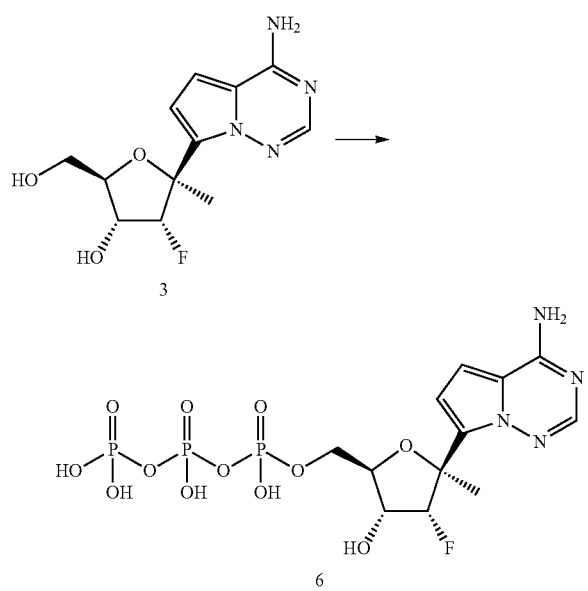

The nucleoside 3 (0.022 g, 0.056 mmol) was dissolved in trimethylphosphate (1 mL) and stirred under $N_2(g)$. Phosphorous oxychloride (0.067 mL, 0.73 mmol) was added and the mixture stirred for 2 h. Monitoring by analytical ion-exchange column determined the time at which >80 percent of monophosphate was formed. A solution of tributylamine (0.44 mL, 1.85 mmol) and triethylammonium pyrophosphate (0.327 g, 0.72 mmol) dissolved in anhydrous DMF (1 mL) was added. The reaction mixture was stirred for 20 min and then quenched by the addition of 1N triethylammonium bicarbonate solution in $H_2O$ (5 mL). The mixture was concentrated under reduced pressure and the residue redissolved in $H_2O$. The solution was subjected to ion exchange chromatography to yield the title product 6 (1.7 mg, 6% yield). LCMS m/z 521 [M–H]. Tr=0.41. HPLC ion exchange TR=9.40 min Example 10. (2R,3R,5S)-2-(4-aminopyrrolo[1,2-f][1,2,4]triazin-7-yl)-3-hydroxy-5-(hydroxymethyl)-tetrahydrofuran-2-carbonitrile (Compound 7)

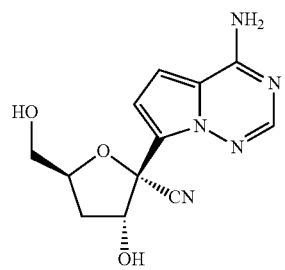

The preparation of (2R,3R,5S)-2-(4-aminopyrrolo[1,2-f][1,2,4]triazin-7-yl)-3-hydroxy-5-(hydroxymethyl)-tetrahydrofuran-2-carbonitrile is described below.

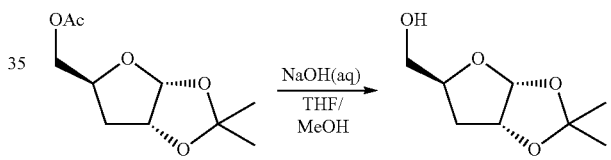

((3αR,5S,6αR)-2,2-dimethyl-tetrahydrofuro[2,3-d][1,3]dioxol-5-yl)methanol

The acetate material (1.2 g, 5.5 mmol) (J. Org. Chem. 1985, 50, 3547, De Bernardo et al) was dissolved in a 1:1 mixture MeOH and THF (10 mL). A 1N solution of NaOH (aq) (10 mL) was added until the pH was 13. The reaction mixture was stirred for 2 h and then neutralized to pH 8-9 by the addition of AcOH. The mixture was extracted with EtOAc (10×30 mL) and the combined organic extracts dried over anhydrous $Na_2SO_4$, filtered and concentrated under reduced pressure. The residue was subjected to silica gel chromatography eluting with 0-70% EtOAc in hexanes to give the desired product (866 mg, 90%). $^1$H NMR (300 MHz, $CDCl_3$) δ 5.84 (d, J=3.6 Hz, 1H), 4.78 (t, J=4.5 Hz, 1H), 4.38 (m, 1H), 3.93-3.54 (m, 2H), 2.04-1.84 (m, 2H), 1.52 (s, 3H), 1.33 (s, 3H).

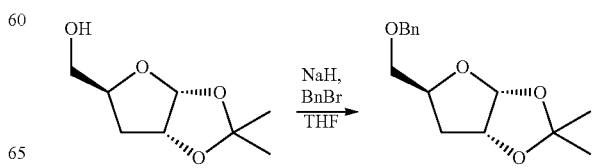

(3αR,5S,6αR)-5-(benzyloxymethyl)-2,2-dimethyl-tetrahydrofuro[2,3-d][1,3]dioxole Sodium hydride (188 mg, 7.46 mmol) was dissolved in anhydrous THF (5 mL) and stirred under N₂(g) at RT. The alcohol (866 mg, 4.97 mmol) was dissolved in anhydrous THF (3 mL) and then added in portions over 5 min. to the sodium hydride mixture. The resultant mixture was stirred for 20 min. and then benzyl bromide (892 µL, 7.46 mmol) was added. The reaction was stirred for 2 h and then poured onto a mixture of ice cold aqueous NaHCO₃ and EtOAc (30 mL). The organic layer was separated and then the aqueous layer re-extracted with EtOAc (30 mL). The combined organic extracts were dried over anhydrous Na₂SO₄, filtered and concentrated under reduced pressure. The residue was subjected to silica gel chromatography eluting with 0-40% EtOAc in hexanes to give the benzyl ether product (912 mg, 69%). ¹H NMR (300 MHz, CDCl₃) δ 7.35-7.27 (m, 5H), 5.86 (d, J=3.6 Hz, 1H), 4.74 (t, J=4.2 Hz, 1H), 4.60 (s, 2H), 4.42 (m, 1H), 3.69-3.53 (m, 2H), 2.10-2.04 (m, 1H), 1.83-1.77 (m, 1H), 1.52 (s, 3H), 1.33 (s, 3H).

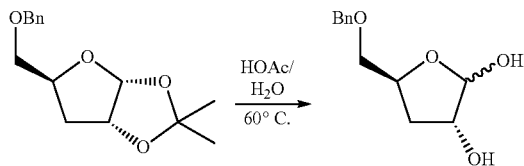 [SMILES: CC1(C)O[C@H]2O[C@H](COCc3ccccc3)C[C@H]2O1 ; OC1O[C@H](COCc2ccccc2)C[C@H]1O]

(3R,5S)-5-(benzyloxymethyl)-tetrahydrofuran-2,3-diol

The benzyl ether (910 mg, 3.44 mmol) was dissolved in a 1:1 AcOH and H₂O (20 mL) mixture and stirred at 60° C. for 7 h. The mixture was concentrated under reduced pressure and the residue subjected to silica gel chromatography eluting with 0-70% EtOAc in hexanes to give the diol product (705 mg, 91%). ¹H NMR (300 MHz, CDCl₃) δ 7.36-7.27 (m, 5H), 5.40 (d, J=3.9 Hz, 0.5H), 5.17 (s, 0.5H), 4.67-4.56 (m, 3H), 4.33 (m, 0.5H), 4.24 (d, J=4.8 Hz, 0.5H), 3.71-3.67 (m, 1H), 3.56-3.42 (m, 2H), 2.31-2.22 (m, 1H), 2.08-1.89 (m, 2H).

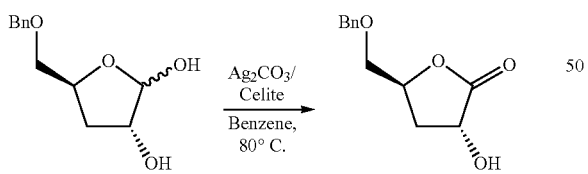

(3R,5S)-5-(benzyloxymethyl)-3-hydroxy-dihydrofuran-2(3H)-one

The diol (705 mg, 3.14 mmol) was dissolved in benzene (30 mL) and treated with a silver carbonate celite mixture (3.46 g, 6.28 mmol). The resultant mixture was stirred at 80° C. under N₂(g) for 2 h. The mixture was then cooled to RT, filtered and concentrated under reduced pressure. The residue was subjected to silica gel chromatography eluting with 0-70% EtOAc in hexanes to give the lactone product (600 mg, 86%). ¹H NMR (300 MHz, CDCl₃) δ 7.39-7.27 (m, 5H), 4.75-4.68 (m, 1H), 4.60-4.49 (m, 2H), 3.74-3.54 (m, 2H), 2.61-2.35 (m, 2H), 2.38-2.28 (m, 1H).

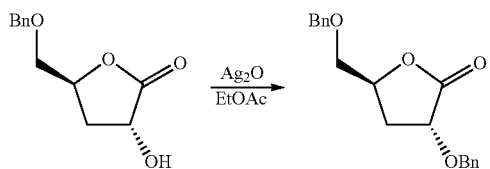

(3R,5S)-3-(benzyloxy)-5-(benzyloxymethyl)-dihydrofuran-2(3H)-one

The lactone (600 mg, 2.7 mmol) was dissolved in EtOAc (30 mL) and treated with silver oxide (626 mg, 2.7 mmol) followed by benzyl bromide (387 µL, 3.24 mmol). The reaction mixture was then stirred at 50° C. under N₂(g) for 8 h. Additional silver oxide (300 mg) was then added and the resultant mixture stirred at 50° C. for 16 h. Additional benzyl bromide (50 uL) and silver oxide (150 mg) were added and the mixture stirred for an additional 8 h. The reaction mixture was allowed to cool, filtered and then concentrated under reduced pressure. The residue was subjected to silica gel chromatography eluting with 0-20% EtOAc in hexanes to give the title product (742 mg, 88%). ¹H NMR (300 MHz, CDCl₃) δ 7.39-7.27 (m, 10H), 4.99 (d, J=11.4 Hz, 1H), 4.72 (m, 2H), 4.56 (m, 2H), 4.39 (t, J=8.1 Hz, 1H), 3.72-3.51 (m, 2H), 2.42-2.25 (m, 2H).

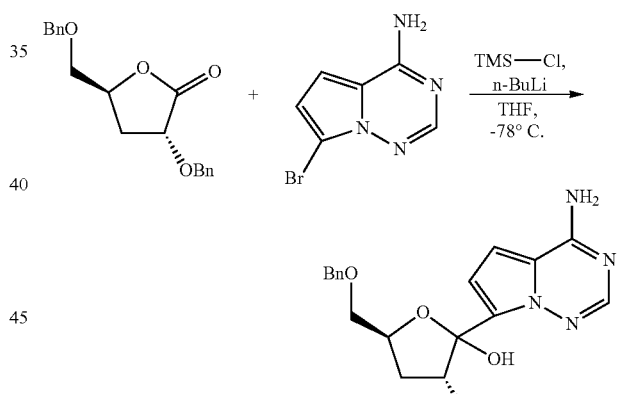

(3R,5S)-2-(4-aminopyrrolo[1,2-f][1,2,4]triazin-7-yl)-3-(benzyloxy)-5-(benzyloxymethyl)-tetrahydrofuran-2-ol The 7-bromopyrrolo[1,2-f][1,2,4]triazin-4-amine (607 mg, 2.85 mmol) was dissolved in anhydrous THF (10 mL) and stirred under Ar(g) at RT. TMSCl (1.1 mL, 8.55 mmol) was added dropwise and the mixture stirred for 2 h. The reaction was concentrated under reduced pressure and then dried under high vacuum. The residue was suspended in THF (20 mL) and stirred under Ar(g) at −78° C. A 2.5M n-BuLi solution in hexane (2.28 mL, 5.7 mmol) was added dropwise over 10 min. and the resultant mixture stirred for 60 min. The lactone (742 mg, 2.37 mmol) dissolved in anhydrous THF (7 mL) was added to the above mixture over 20 min. The reaction mixture was stirred for 2 h. and then quenched with AcOH until pH was 5-6. The mixture was allowed to warm to RT and then diluted with EtOAc. The solution was washed with saturated NaHCO₃ solution, saturated NaCl, dried over anhydrous Na₂SO₄ and concentrated under reduced pressure. The residue was subjected to silica gel chromatography eluting with 0-80% EtOAc in hexanes to give the title product (250 mg, 24%). LCMS m/z 447.2 [M+H], 445.1 [M−H].

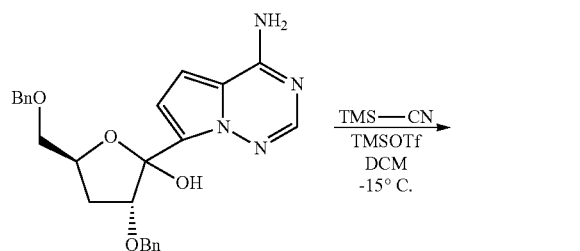

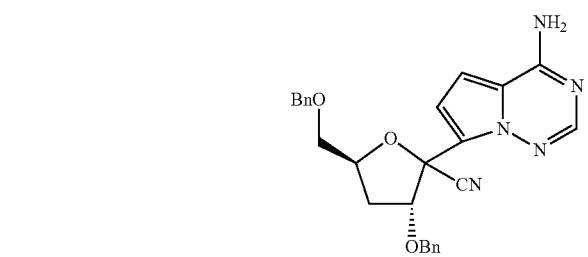

(3R,5S)-2-(4-aminopyrrolo[1,2-f][1,2,4]triazin-7-yl)-3-(benzyloxy)-5-(benzyloxymethyl)-tetrahydrofuran-2-carbonitrile The alcohol (250 mg, 0.56 mmol) was dissolved in anhydrous CH₂Cl₂(10 mL) and stirred under Ar(g) at −15° C. TMSCN (448 µL, 3.36 mmol) was added dropwise and the mixture stirred for 10 min. TMSOTf (466 µL, 2.58 mmol) was added dropwise over 10 min and the resultant mixture stirred for 90 min. at −15° C. Additional TMSCN (224 µL, 3 eq.) and TMSOTf (202 µL, 2 eq.) was added and stirring continued for 5 h. Saturated aqueous NaHCO₃ solution was added to quench the reaction and the mixture stirred for 10 min. The organic layer was separated and washed with saturated aqueous NaHCO₃ solution, saturated NaCl solution, dried over anhydrous Na₂SO₄, filtered and concentrated under reduced pressure. The residue was subjected to silica gel chromatography eluting with 0-70% EtOAc in hexanes to give the title product (150 mg, 59%). LCMS m/z 456.3 [M+H], 454.1 [M−H].

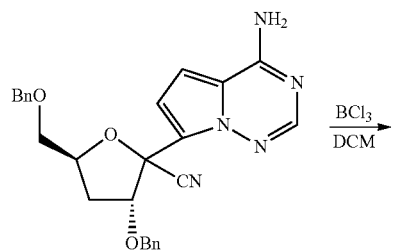

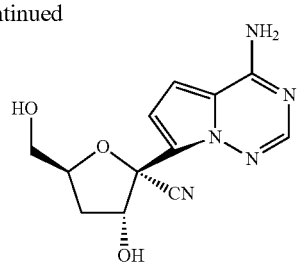

(2R,3R,5S)2-(4-aminopyrrolo[1,2-f][1,2,4]triazin-7-yl)-3-hydroxy-5-(hydroxymethyl)-tetrahydrofuran-2-carbonitrile (7)

The benzyl ether (150 mg, 0.329 mmol) was dissolved in anhydrous CH₂Cl₂ (2 mL) and the mixture stirred under Ar(g) at −20° C. A 1M BCl₃ solution in CH₂Cl₂ (724 µL, 0.724 mmol) was added dropwise and the resultant mixture stirred for 2 h. Additional 1M BCl₃ in CH₂Cl₂ (724 µL, 0.724 mmol) was added and stirring continued for 2 h. The mixture was then cooled to −78° C. and slowly treated with a 2:1 mixture of Et₃N and MeOH (3 mL). The mixture was stirred for 10 min and then treated with MeOH (10 mL). The reaction was allowed to warm to RT and then concentrated under reduced pressure. The residue was dissolved in MeOH and concentrated under reduced pressure. The residue was dissolved in MeOH again and treated with solid NaHCO₃. The mixture was stirred for 5 min and then the solid removed by filtration. The solution was concentrated under reduced pressure and subjected to preparative HPLC to provide the desired product 7 (10 mg, 11%). ¹H NMR (300 MHz, D₂O) δ 7.71 (s, 1H), 6.75 (d, J=4.5 Hz, 1H), 6.65 (d, J=4.8 Hz, 1H), 4.91 (t, J=6.3 Hz, 1H), 4.57 (m, 1H), 3.67-3.47 (m, 2H), 2.18 (m, 2H). LCMS m/z 276.1 [M+H], 274.0 [M−H].

Example 11. (2S)-isopropyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)-phosphorylamino)propanoate (Compound 8)

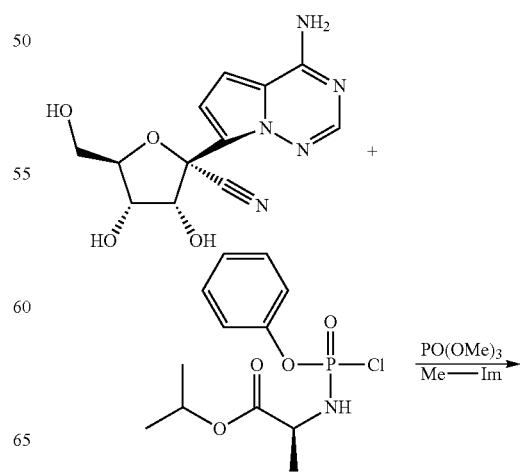

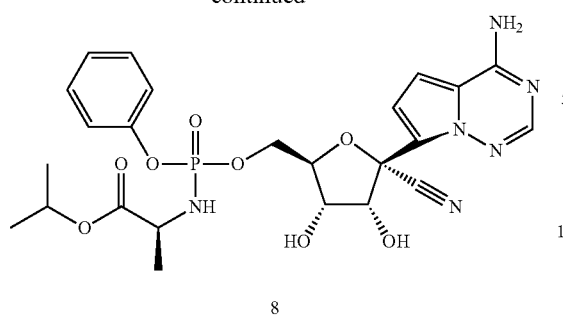

8

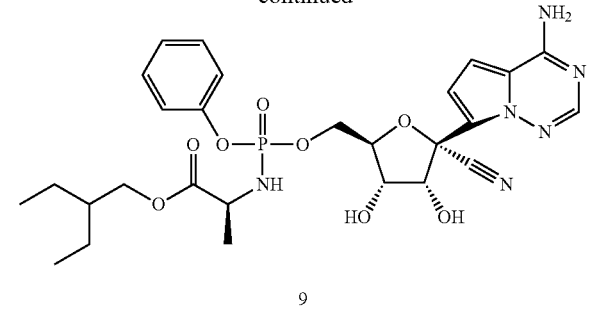

9

The nucleoside 1 (45 mg, 0.15 mmol) was dissolved in anhydrous trimethyl phosphate (0.5 mL) and the solution stirred under $N_2$(g) at 0° C. Methyl imidazole (36 μL, 0.45 mmol) was added to the solution. Chlorophosphoramidate C (69 mg, 0.225 mmol) was dissolved in anhydrous THF (0.25 mL) and added dropwise to the nucleoside mixture. When the reaction was complete by LCMS, the reaction mixture was diluted with EtOAc and washed with saturated aqueous $NaHCO_3$ solution, saturated NaCl, dried over anhydrous $Na_2SO_4$, filtered and concentrated under reduced pressure. The residue was subjected to silica gel chromatography eluting with 0-5% MeOH in $CH_2Cl_2$ followed by preparative HPLC to give the product (20.9 mg, 25%). $^1$H NMR (300 MHz, $CD_3OD$) δ 7.95 (m, 1H), 7.31-6.97 (m, 7H), 4.94 (m, 1H), 4.78 (m, 1H), 4.43 (m, 3H), 4.20 (m, 1H), 3.80 (d, 1H), 1.30-1.18 (m, 9H). $^{31}$P NMR (121.4 MHz, $CD_3OD$) δ 3.8. LCMS m/z 561.0 [M+H], 559.0 [M−H].

Example 12. (2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 9)

Compound 9 can be prepared by several methods described below.

Procedure 1

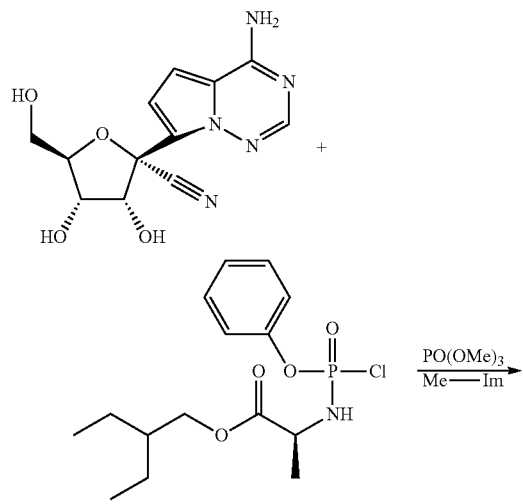

Prepared from Compound 1 and chloridate B according to the same method as for the preparation of compound 8. $^1$H NMR (300 MHz, $CD_3OD$) δ 7.87 (m, 1H), 7.31-7.16 (m, 5H), 6.92-6.89 (m, 2H), 4.78 (m, 1H), 4.50-3.80 (m, 7H), 1.45-1.24 (m, 8H), 0.95-0.84 (m, 6H). $^{31}$P NMR (121.4 MHz, $CD_3OD$) δ 3.7. LCMS m/z 603.1 [M+H], 601.0 [M−H].

Procedure 2

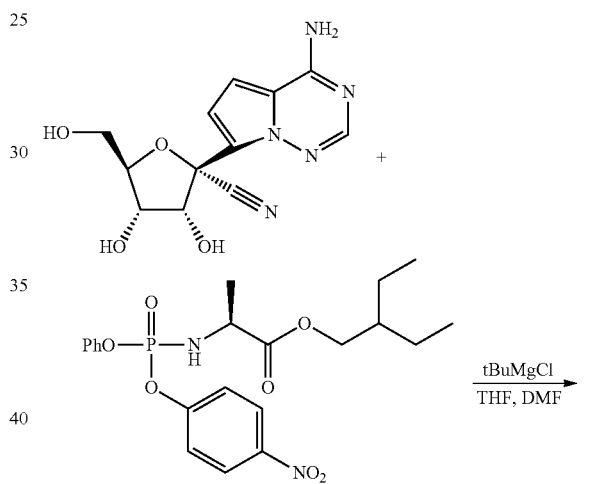

(2S)-2-ethylbutyl 2-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (2S)-2-ethylbutyl 2-(((4-nitrophenoxy)(phenoxy)phosphoryl)amino)propanoate (1.08 g, 2.4 mmol) was dissolved in anhydrous DMF (9 mL) and stirred under a nitrogen atmosphere at RT. (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (350 mg, 1.2 mmol) was added to the reaction mixture in one portion. A solution of t-butylmagnesium chloride in THF (1M, 1.8 mL, 1.8 mmol) was then added to the reaction dropwise over 10 minutes. The reaction was stirred for 2 h, at which point the reaction mixture was diluted with ethyl acetate (50 mL) and washed with saturated aqueous sodium bicarbonate solution (3×15 mL) followed by saturated aqueous sodium chloride solution (15 mL). The organic layer was dried over anhydrous sodium sulfate and concentrated under reduced pressure. The resulting oil was purified with silica gel column chromatography (0-10% MeOH in DCM) to afford (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (311 mg, 43%, 1:0.4 diastereomeric mixture at phosphorus) as a white solid. $^1$H NMR (400 MHz, CD$_3$OD) δ 7.85 (m, 1H), 7.34-7.23 (m, 2H), 7.21-7.09 (m, 3H), 6.94-6.84 (m, 2H), 4.78 (d, J=5.4 Hz, 1H), 4.46-4.33 (m, 2H), 4.33-4.24 (m, 1H), 4.18 (m, 1H), 4.05-3.80 (m, 3H), 1.52-1.39 (m, 1H), 1.38-1.20 (m, 7H), 0.85 (m, 6H). $^{31}$P NMR (162 MHz, CD$_3$OD) δ 3.71, 3.65. LCMS m/z 603.1 [M+H], 600.9 [M−H]. HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.544 min, 5.601 min Separation of the (S) and (R) Diastereomers (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate was dissolved in acetonitrile. The resulting solution was loaded onto Lux Cellulose-2 chiral column, equilibrated in acetonitrile, and eluted with isocratic acetonitrile/methanol (95:5 vol/vol). The first eluting diastereomer had a retention time of 17.4 min, and the second eluting diastereomer had a retention time of 25.0 min.

First Eluting Diastereomer is (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate:

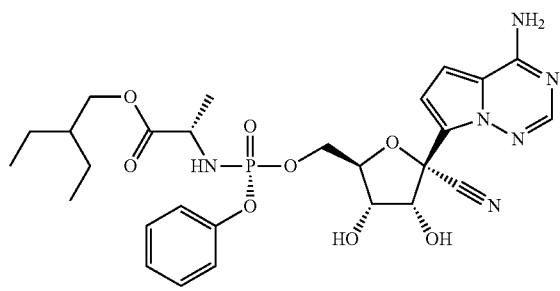 [SMILES: CCC(CC)COC(=O)[C@H](C)N[P@@](=O)(OC[C@H]1O[C@@](C#N)(c2ccc3c(N)ncnn23)[C@H](O)[C@@H]1O)Oc1ccccc1]

$^1$HNMR (400 MHz, CD$_3$OD) δ 8.05 (s, 1H), 7.36 (d, J=4.8 Hz, 1H), 7.29 (br t, J=7.8 Hz, 2H), 7.19-7.13 (m, 3H), 7.11 (d, J=4.8 Hz, 1H), 4.73 (d, J=5.2 Hz, 1H), 4.48-4.38 (m, 2H), 4.37-4.28 (m, 1H), 4.17 (t, J=5.6 Hz, 1H), 4.08-3.94 (m, 2H), 3.94-3.80 (m, 1H), 1.48 (sep, J=12.0, 6.1 Hz, 1H), 1.34 (p, J=7.3 Hz, 4H), 1.29 (d, J=7.2 Hz, 3H), 0.87 (t, J=7.4 Hz, 6H). $^{31}$PNMR (162 MHz, CD$_3$OD) δ 3.71 (s). HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.585 min.

Second Eluting Diastereomer is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate:

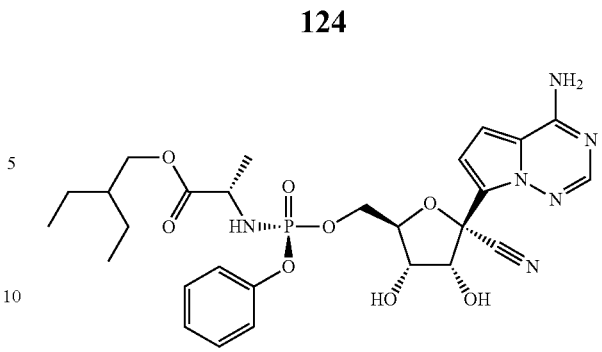

$^1$HNMR (400 MHz, CD$_3$OD) δ 8.08 (s, 1H), 7.36-7.28 (m, 3H), 7.23-7.14 (m, 3H), 7.08 (d, J=4.8 Hz, 1H), 4.71 (d, J=5.3 Hz, 1H), 4.45-4.34 (m, 2H), 4.32-4.24 (m, 1H), 4.14 (t, J=5.8 Hz, 1H), 4.08-3.94 (m, 2H), 3.93-3.85 (m, 1H), 1.47 (sep, J=6.2 Hz, 1H), 1.38-1.26 (m, 7H), 0.87 (t, J=7.5 Hz, 6H). $^{31}$PNMR (162 MHz, CD$_3$OD) δ 3.73 (s). HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.629 min.

Example 13. (2S)-ethyl 2-(((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 10)

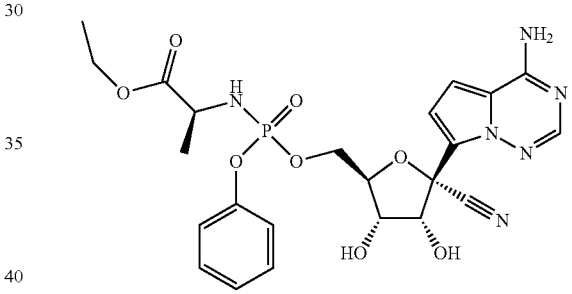

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Procedure 1. Preparation Via Chloridate A

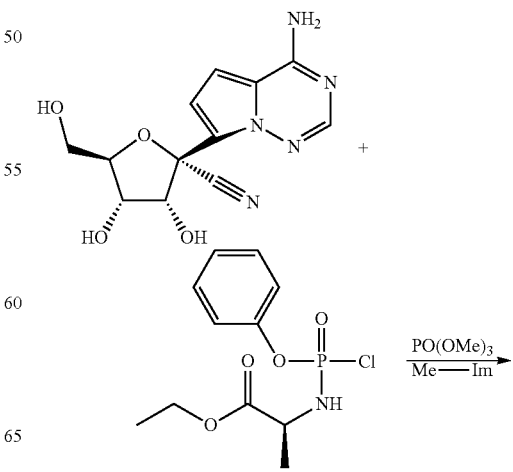

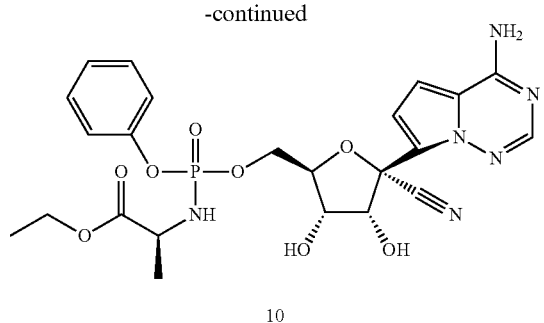

10

Prepared from Compound 1 and chloridate A using same method as for the preparation of compound 8. $^1$H NMR (300 MHz, CD$_3$OD) δ 7.95 (m, 1H), 7.32-6.97 (m, 7H), 4.78 (m, 1H), 4.43-4.08 (m, 6H), 3.83 (m, 1H), 1.31-1.18 (m, 6H). $^{31}$P NMR (121.4 MHz, CD$_3$OD) δ 3.7. LCMS m/z 547.0 [M+H], 545.0 [M−H].

Procedure 2. Preparation Via Nitro-Benzene Compound L was purified by HPLC (acetonitrile 10 to 80% in water) to give compound 29 as a yellow solid. The solid was further purified with silica gel chromatography (MeOH 0 to 20% DCM) to afford compound 29 (23 mg, 24% as a 2.5:1 mixture of diastereomers). $^1$H NMR (400 MHz, CD$_3$OD) δ 7.76 (d, J=6.0 Hz, 1H), 7.25-7.14 (m, 2H), 7.11-6.99 (m, 3H), 6.87-6.72 (m, 2H), 4.70 (d, J=5.4 Hz, 1H), 4.39-4.24 (m, 2H), 4.20 (dddd, J=9.7, 7.9, 5.1, 2.8 Hz, 1H), 4.10 (dt, J=12.8, 5.5 Hz, 1H), 4.06-3.91 (m, 2H), 3.72 (ddq, J=14.3, 9.3, 7.1 Hz, 1H), 1.17 (dd, J=7.1, 1.0 Hz, 1H), 1.14-1.06 (m, 5H). $^{31}$P NMR (162 MHz, CD$_3$OD) δ 3.73, 3.68. MS m/z=547 (M+1)$^+$.

Example 14. (2S)-ethyl 2-((((2R,3R,4R,5R)-5-(4-aminopyrrolo[1,2-f][1,2,4]triazin-7-yl)-5-cyano-4-fluoro-3-hydroxytetrahydrofuran-2-yl)methoxy)(phenoxy)phosphorylamino)propanoate (Compound 11)

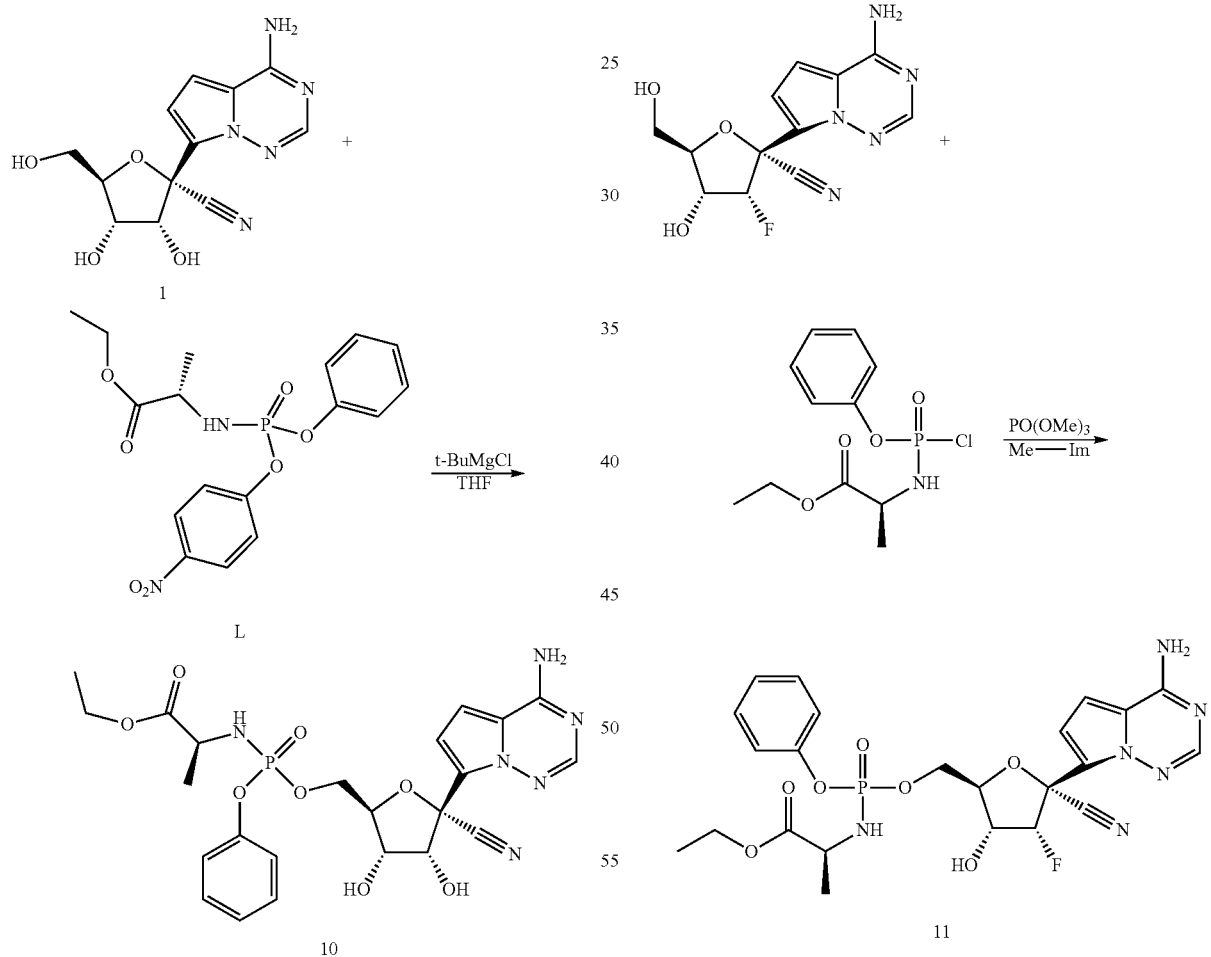

Compound 1 (50 mg, 0.17 mmol) was dissolved in NMP-THF (1:1 mL)) and cooled with ice bath. tBuMgCl (0.257 mL, 0.257 mmol) was then added over 5 min. The resulting mixture was allowed to warm to RT and was stirred for 30 min. Then a solution of compound L (Prepared according to US20120009147, 74.6 mg, 0.189 mmol) in THF (2 mL) was added. After 30 min, the reaction mixture Compound 11 was prepared from Compound 2 and chloridate A using same method as for the preparation of compound 8. $^1$H NMR (300 MHz, CD$_3$OD) δ 7.91 (m, 1H), 7.33-7.16 (m, 5H), 6.98-6.90 (m, 2H), 5.59 (m, 1H), 4.50-4.15 (m, 4H), 4.12-3.90 (m, 3H), 1.33-1.18 (m, 6H). $^{31}$P NMR (121.4 MHz, CD$_3$OD) δ 3.8. LCMS m/z 549.0 [M+H], 547.1 [M−H].

Example 15. (2S,2'S)-diethyl 2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(azanediyl)dipropanoate (Compound 12)

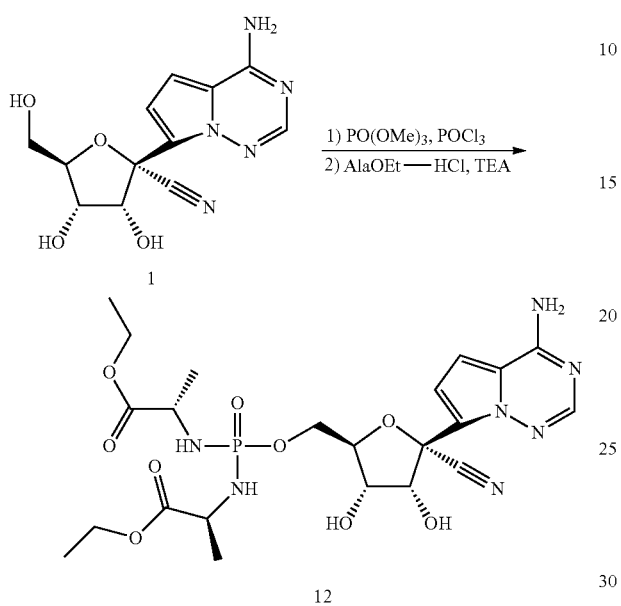

The nucleoside 1 (14.6 mg, 0.05 mmol) was dissolved in anhydrous trimethyl phosphate (0.5 mL) and stirred under $N_2(g)$ at RT. $POCl_3$ (9.2 µL, 0.1 mmol) was added and the mixture stirred for 60 min. Alanine ethyl ester hydrochloride (61 mg, 0.4 mmol) and then $Et_3N$ (70 µL, 0.5 mmol) was added. The resultant mixture was stirred for 15 min. and then additional $Et_3N$ (70 µl, 0.5 mmol) was added to give a solution pH of 9-10. The mixture was stirred for 2 h. and then diluted with EtOAc, washed with saturated aqueous $NaHCO_3$ solution followed by saturated aqueous NaCl solution. The organic layer was dried over anhydrous $Na_2SO_4$ and concentrated under reduced pressure. The residue was subjected to preparative HPLC ($C_{18}$ column) to yield the product 12 (5.5 mg, 16%). $^1$H NMR (400 MHz, $CD_3OD$) δ 8.13 (s, 1H), 7.41 (d, J=4.8 Hz, 1H), 7.18 (d, J=4.8 Hz, 1H), 4.78 (d, J=5.6 Hz, 1H), 4.36 (m, 1H), 4.25-4.08 (m, 7H), 3.83 (m, 2H), 1.33-1.23 (m, 12H). $^{31}$P NMR (121.4 MHz, $CD_3OD$) δ 13.8. LCMS m/z 570.0 [M+H], 568.0 [M−H].

Example 16. (2S,3R,4S,5R)-2-(4-aminopyrrolo[1,2-f][1,2,4]triazin-7-yl)-2-ethynyl-5-(hydroxymethyl)tetrahydrofuran-3,4-diol (Compound 13)

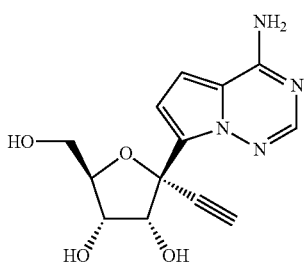

The preparation of (2S,3R,4S,5R)-2-(4-aminopyrrolo[1,2-f][1,2,4]triazin-7-yl)-2-ethynyl-5-(hydroxymethyl)tetrahydrofuran-3,4-diol is described below.

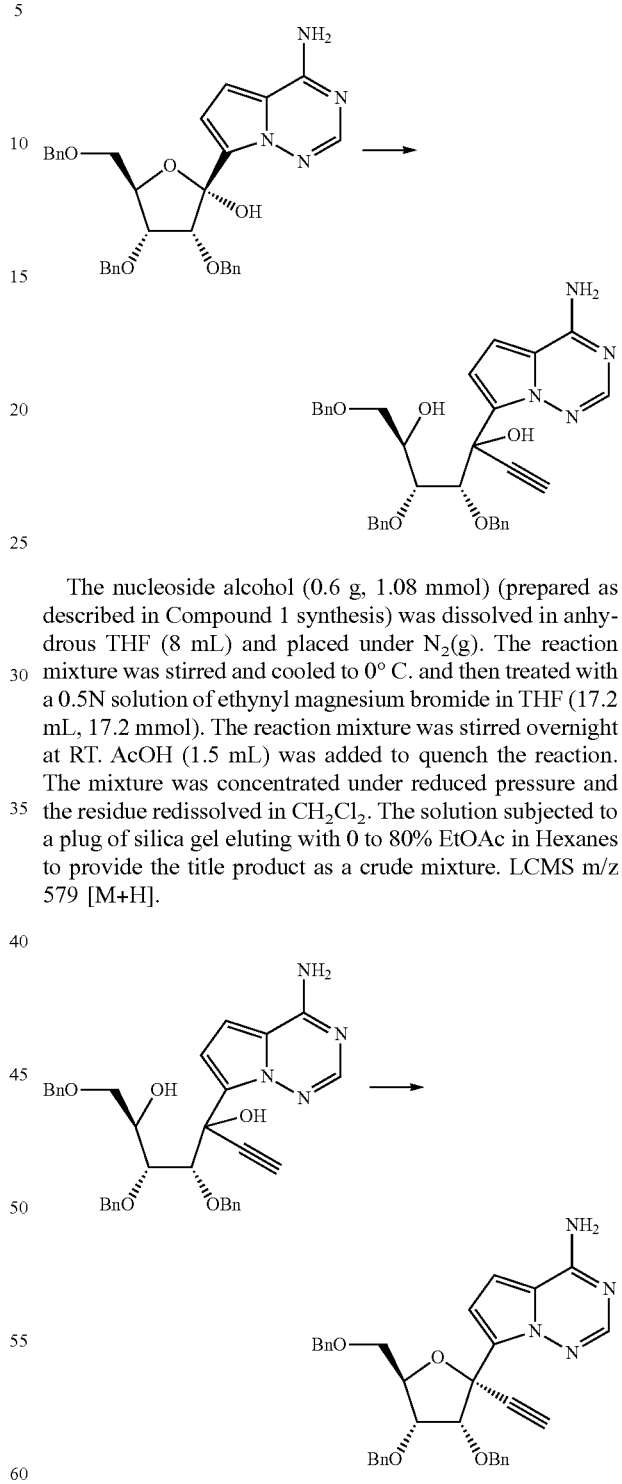

The nucleoside alcohol (0.6 g, 1.08 mmol) (prepared as described in Compound 1 synthesis) was dissolved in anhydrous THF (8 mL) and placed under $N_2(g)$. The reaction mixture was stirred and cooled to 0° C. and then treated with a 0.5N solution of ethynyl magnesium bromide in THF (17.2 mL, 17.2 mmol). The reaction mixture was stirred overnight at RT. AcOH (1.5 mL) was added to quench the reaction. The mixture was concentrated under reduced pressure and the residue redissolved in $CH_2Cl_2$. The solution subjected to a plug of silica gel eluting with 0 to 80% EtOAc in Hexanes to provide the title product as a crude mixture. LCMS m/z 579 [M+H].

The crude ethynyl alcohol (0.624 g, 1.08 mmol) was dissolved in anhydrous $CH_2Cl_2$ (10 mL) and placed under $N_2(g)$. The mixture was stirred and sulfonic acid (0.2 mL, 2.74 mmol) was added. The reaction mixture was stirred for 12 h. at RT. When complete by LCMS, $Et_3N$ (0.56 mL) was added to quench the reaction. The reaction was concentrated under reduced pressure and the residue subjected to silica gel chromatography eluting with 0 to 75% EtOAc in Hexanes to yield the ethynyl nucleoside as a mixture of anomers (0.200 g, 33% over 2 steps). LCMS m/z 561 [M+H].

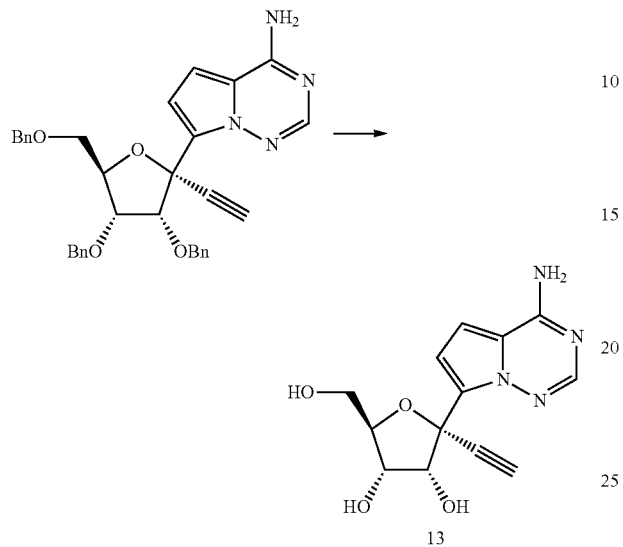

The tribenzyl nucleoside (0.650 g, 1.16 mmol) was dissolved in anhydrous CH$_2$Cl$_2$ (30 mL) and cooled to –78° C. under N$_2$(g). A solution of boron tribromide (1 N in CH$_2$Cl$_2$, 5.5 mL) was added and the reaction mixture stirred for 1 h. at –78° C. A solution of MeOH (10 mL) and pyridine (2 mL) was added to quench the reaction and the mixture was allowed to rise to RT. The mixture was concentrated under reduced pressure and subjected to preparative HPLC to provide the α-anomer (20 mg) and β-anomer 13 (110 mg). (β-anomer) $^1$H NMR (300 MHz, DMSO) δ 7.81 (s, 1H), 7.76 (br s, 2H), 6.80-6.85 (m, 2H), 5.11 (d, J=7.2 Hz, 1H), 4.90 (d, J=6.0 Hz, 1H), 4.82 (dd, J=7.2, 4.8 Hz, 1H), 4.62 (t, J=6.3 Hz, 1H), 3.95-3.99 (m, 1H), 3.85-3.91 (dd, J=11.4, 5.7 Hz, 1H), 3.61-3.67 (m, 1H), 3.47-3.55 (m, 1H), 3.52 (d, J=0.9 Hz, 1H). (α-anomer) $^1$H NMR (300 MHz, DMSO) δ 7.80 (s, 1H), 7.59 (bs, 2H), 6.80 (d, J=4.5 Hz, 1H), 6.54 (d, J=4.2 Hz, 1H), 5.00 (d, J=7.2 Hz, 1H), 4.89 (d, J=4.8 Hz, 1H), 4.74 (t, J=5.7 Hz, 1H), 4.58 (t, J=4.5 Hz, 1H), 4.27 (m, 1H), 3.88 (m, 1H), 3.64-3.72 (m, 1H), 3.51-3.59 (m, 1H), 3.48 (d, J=0.6 Hz, 1H). LCMS m/z 291 [M+H].

Example 17. (2R,3R,4R)-5-(4-aminopyrrolo[1,2-f][1,2,4]triazin-7-yl)-1,3,4-tris(benzyloxy)hexane-2,5-diol (Compound 14)

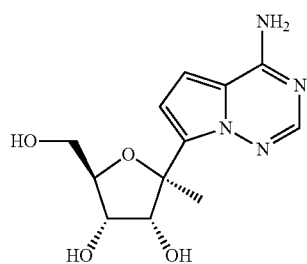

14

The preparation of (2R,3R,4R)-5-(4-aminopyrrolo[1,2-f][1,2,4]triazin-7-yl)-1,3,4-tris(benzyloxy)hexane-2,5-diol is described below.

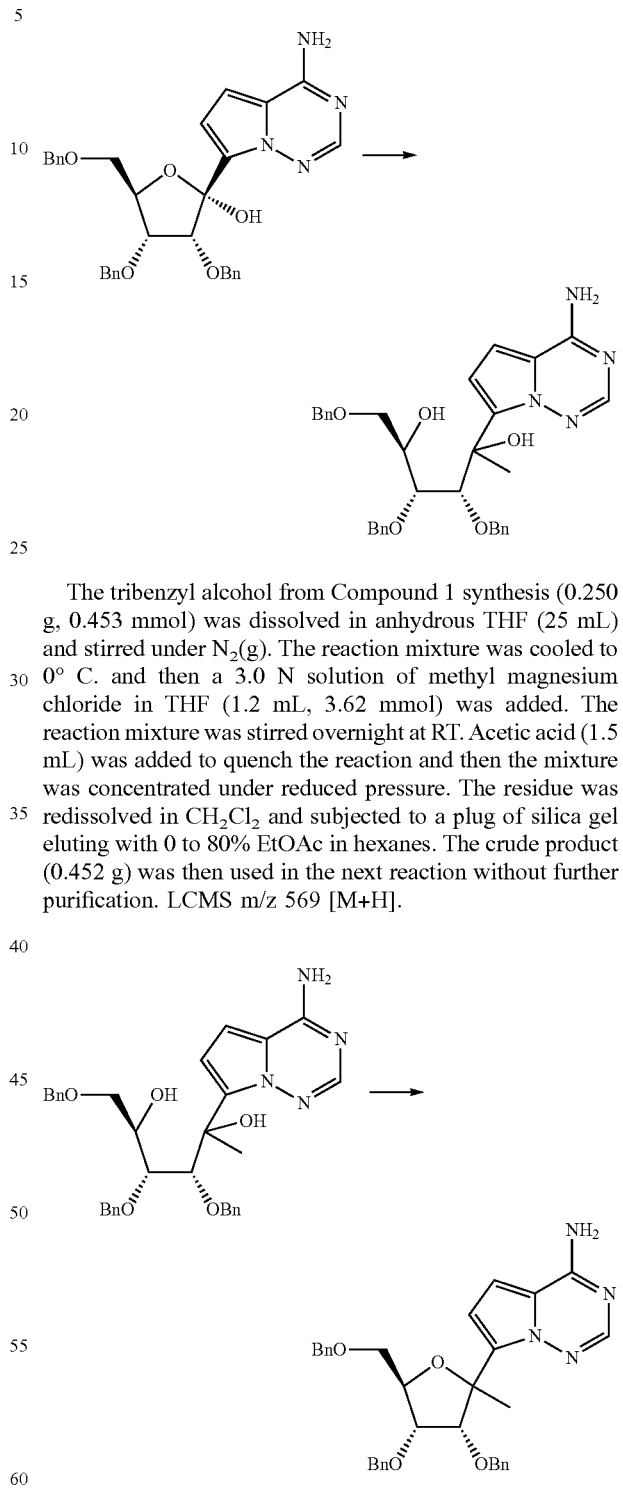

The tribenzyl alcohol from Compound 1 synthesis (0.250 g, 0.453 mmol) was dissolved in anhydrous THF (25 mL) and stirred under N$_2$(g). The reaction mixture was cooled to 0° C. and then a 3.0 N solution of methyl magnesium chloride in THF (1.2 mL, 3.62 mmol) was added. The reaction mixture was stirred overnight at RT. Acetic acid (1.5 mL) was added to quench the reaction and then the mixture was concentrated under reduced pressure. The residue was redissolved in CH$_2$Cl$_2$ and subjected to a plug of silica gel eluting with 0 to 80% EtOAc in hexanes. The crude product (0.452 g) was then used in the next reaction without further purification. LCMS m/z 569 [M+H].

The crude methyl nucleoside (0.452 g, 0.796 mmol) was dissolved in anhydrous CH$_2$Cl$_2$ (20 mL) and stirred under N$_2$(g). Methanesulfonic acid (0.2 mL, 2.78 mmol) was added and the reaction stirred for 12 hr at RT. Et$_3$N (0.56 mL) was added to quench the reaction and then the mixture concentrated under reduced pressure. The residue was subjected to silica gel chromatography eluting with 0 to 75% EtOAc in Hexanes to yield the product as a mixture of anomers (0.20 g, 46% over 2 steps). LCMS m/z 551 [M+H].

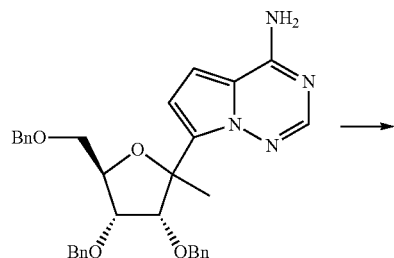

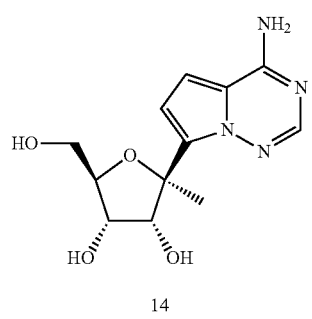

14

The tribenzyl nucleoside (0.20 g, 0.364 mmol) was dissolved in AcOH (30 mL). and charged with Pd/C (Degussa) (400 mg). The stirred mixture was flushed with N₂(g) three times and then H₂ (g) was introduced, The reaction was stirred under H₂ (g) for 2 h. and then the catalyst removed by filtration. The solution was concentrated under reduced pressure and under the residue was re-dissolved in H₂O. The solution was subjected to preparative HPLC under neutral conditions to provide the α-anomer and β-anomer 14 in 81% yield. (α-anomer)¹H NMR (300 MHz, D₂O) δ 7.81 (s, 1H), 7.22 (d, 1H), 6.75 (d, 1H), 4.47 (d, 1H), 4.25-4.31 (m, 1H), 3.88-4.95 (m, 1H), 3.58-3.86 (dd, 2H), 1.50 (s, 3H). (β-anomer)¹H NMR (300 MHz, D₂O) δ 7.91 (s, 1H), 7.26 (d, 1H), 6.90 (d, 1H), 4.61 (d, 1H), 4.00-4.09 (m, 2H), 3.63-3.82 (dd, 2H), 1.67 (s, 3H). LCMS m/z 281 [M+H].

Example 18. S,S'-2,2'-(4(2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(oxy)bis(ethane-2,1-diyl) bis(2,2-dimethylpropanethioate) (Compound 15)

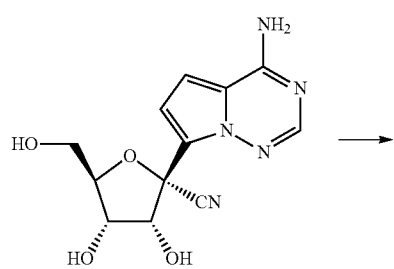

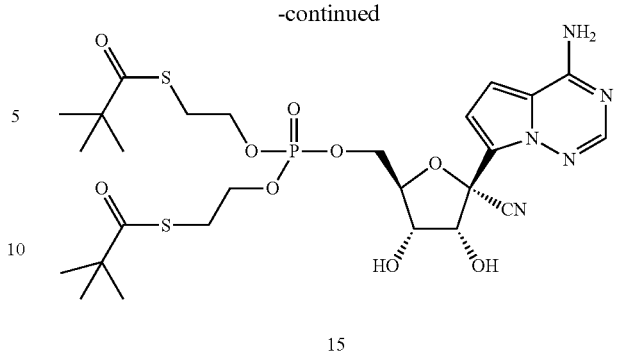

15

The nucleoside 1 (0.028 g, 0.096 mmol) was dissolved in trimethylphosphate (1 mL). The reaction was stirred under N₂(g) and then treated with 1H-tetrazole (0.021 g, 0.29 mmol). The reaction mixture was cooled to 0° C. and the phosphane (Nucleoside Nucleotides, Nucleic acids; 14; 3-5; 1995; 763-766. Lefebvre, Isabelle; Pompon, Alain; Perigaud, Christian; Girardet, Jean-Luc; Gosselin, Gilles; et al.) (87 mg, 0.192 mmol) was added. The reaction was stirred for 2 h. and then quenched with 30% hydrogen peroxide (0.120 mL). The mixture was stirred for 30 min at RT and then treated with saturated aqueous sodium thiosulfate (1 mL). The mixture was stirred for 10 min. and then concentrated under reduced pressure. The residue was subjected to preparative HPLC to isolate the title product 15. ¹H NMR (300 MHz, CD₃CN) δ 7.98 (s, 1H), 6.92 (d, 1H), 6.81 (d, 1H), 6.44 (bs, 2H), 4.82 (m, 2H), 4.47 (m, 1H), 4.24 (m, 2H), 4.00 (m, 4H), 3.80 (bs, 1H), 3.11 (m, 4H), 1.24 (s, 9H). ³¹P NMR (121.4 MHz, CD₃CN) δ −1.85 (s). LCMS m/z 661 [M+H].

Example 19. S,S'-2,2'-((((2R,3S,4R,5S)-5-(4-aminopyrrolo[1,2-f][1,2,4]triazin-7-yl)-5-ethynyl-3,4-dihydroxytetrahydrofuran-2-yl)methoxy)phosphoryl)bis(oxy)bis(ethane-2,1-diyl) bis(2,2-dimethylpropanethioate) (Compound 16)

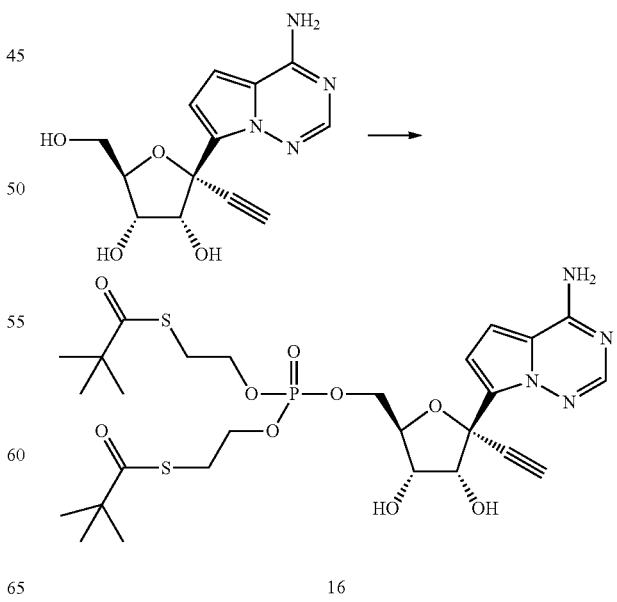

16

Compound 16 was prepared using the same method as compound 15 except substituting compound 13 as the starting nucleoside. ¹H NMR (300 MHz, CD₃CN) δ 7.91 (s, 1H), 6.86 (d, J=4.8 Hz, 1H), 6.76 (d, J=4.5 Hz, 1H), 6.29 (bs, 2H), 4.69 (t, J=2.7 Hz, 1H), 4.58 (d, J=5.7 Hz, 1H), 4.14-4.33 (m, 5H), 3.99-4.07 (m, 4H), 3.53 (d, J=5.4 Hz, 1H), 3.11 (q, J=5.7 Hz, 4H), 1.22 (s, 18H). LCMS m/z 658.9 [M+]. Tr=2.31

Example 20. ((2R,3S,4R,5R)-5-(4-aminopyrrolo[1,2-f][1,2,4]triazin-7-yl)-5-cyano-3,4-dihydroxytetrahydrofuran-2-yl)methyl tetrahydrogen triphosphate (Compound 17)

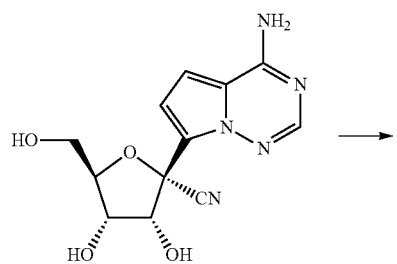

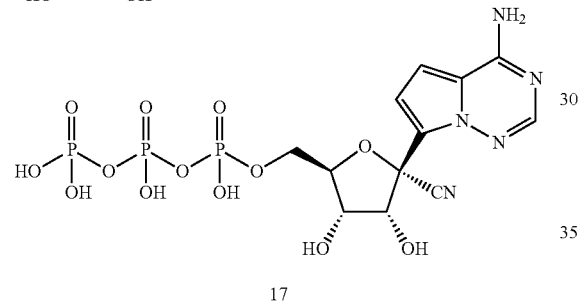

17

Compound 17 was prepared from compound 1 using a similar procedure to the preparation of compound 6. The product was isolated as the sodium salt. ¹H NMR (400 MHz, D₂O) δ 7.76 (s, 1H), 6.88 (d, J=4.8 Hz, 1H), 6.73 (d, J=4.4 Hz, 1H), 4.86 (d, J=5.2 Hz, 1H), 4.43 (m, 1H), 4.39 (m, 1H), 4.05 (m, 1H), 3.94 (m, 1H). ³¹P NMR (121.4 MHz, D₂O) δ −5.4 (d, 1P), −10.8 (d, 1P), −21.1 (t, 1P). LCMS m/z 530 [M−H], 531.9 [M+H] Tr=0.22 min. HPLC ion exchange Tr=9.95 min.

Example 21. ((2R,3S,4R,5S)-5-(4-aminopyrrolo[1,2-f][1,2,4]triazin-7-yl)-5-ethynyl-3,4-dihydroxytetrahydrofuran-2-yl)methyl tetrahydrogen triphosphate (Compound 18)

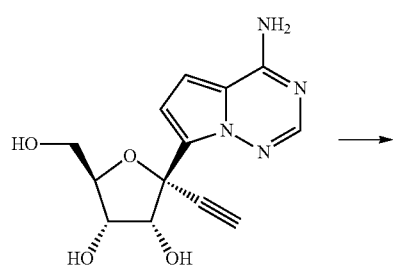

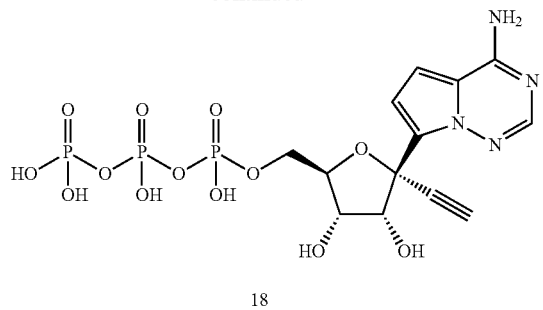

18

Compound 18 was prepared from compound 13 using a similar procedure to the preparation of compound 6. The product was isolated as the TEA salt. ¹H NMR (300 MHz, D₂O) δ 7.85 (s, 1H), 7.09 (d, J=4.6 Hz, 1H), 6.95 (d, J=4.7 Hz, 1H), 4.23 (m, 2H), 4.08 (m, 2H), 3.06 (q, J=7.4 Hz, 20H), 1.14 (t, J=7.3 Hz, 30H). ³¹P NMR (121.4 MHz, D₂O) δ −10.8 (d, 1P), −11.2 (d, 1P), −23.2 (t, 1P). LCMS m/z 530.8 [M+H], Tr=0.46. HPLC ion exchange Tr=9.40 min.

Example 22. ((2R,3S,4R,5S)-5-(4-aminopyrrolo[1,2-f][1,2,4]triazin-7-yl)-3,4-dihydroxy-5-methyltetrahydrofuran-2-yl)methyl tetrahydrogen triphosphate (Compound 19)

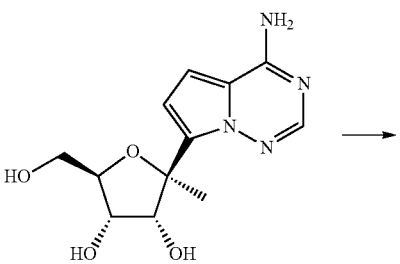

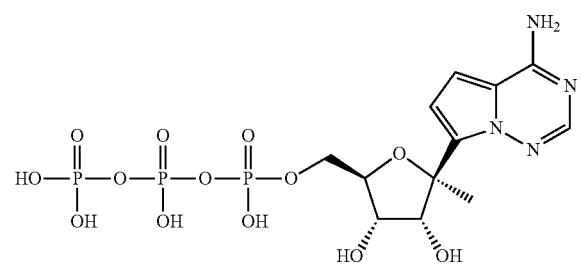

19

Compound 19 was prepared from compound 14 using a similar procedure to the preparation of compound 6. ¹H NMR (400 MHz, D₂O) δ 7.78 (s, 1H), 6.98 (m, 1H), 6.84 (m, 1H), 4.45 (m, 1H), 4.04 (m, 4H), 1.54 (s, 3H). ³¹P NMR (161 MHz, D₂O) δ −10.6 (m), −23.0 (m). LCMS m/z 521.0 [M+H].

Example 23. ((2R,3R,4R,5R)-5-(4-aminopyrrolo[1,2-f][1,2,4]triazin-7-yl)-5-cyano-4-fluoro-3-hydroxytetrahydrofuran-2-yl)methyl tetrahydrogen triphosphate (Compound 20)

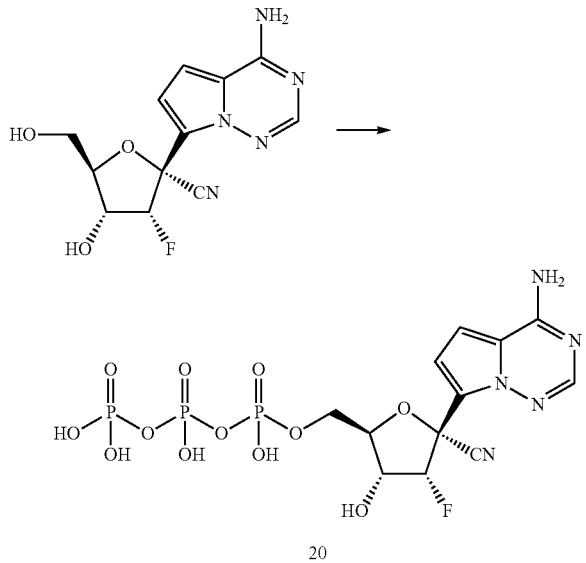

20

Compound 20 was prepared from compound 2 using a similar procedure to the preparation of compound 6. $^1$H NMR (400 MHz, D$_2$O) δ 7.78 (s, 1H), 6.93 (d, J=4.4 Hz, 1H), 6.78 (d, J=4.8 Hz, 1H), 5.45 (dd, J=53, 4.4 Hz, 1H), 4.38-4.50 (m, 2H), 4.13-4.20 (m, 2H). $^{31}$P NMR (161 MHz, D$_2$O) δ −5.7 (d, 1P), −11.0 (d, 1P), −21.5 (t, 1P). LCMS m/z 533.9.0 [M+H], 532.0 [M−H] Tr=1.25 min. HPLC ion exchange Tr=11.0 min.

Example 24. (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (21

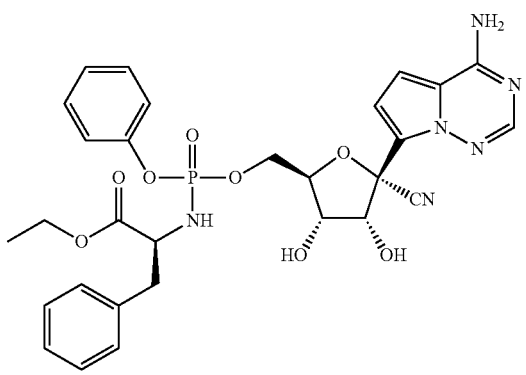 [SMILES: CCOC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate is described below.

Preparation of (S)-ethyl 2-amino-3-phenylpropanoate hydrochloride

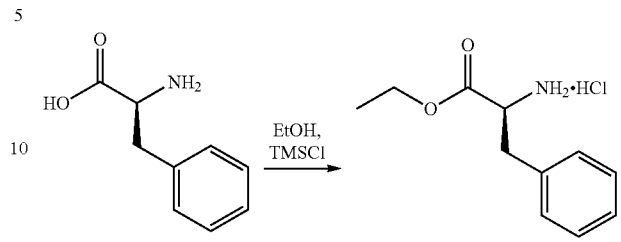

L-Phenylalanine (5 g, 30 mmol) was taken up in EtOH (30 mL). TMSCl (6.915 mL, 54 mmol) was added to the reaction at RT. The reaction vessel was fitted with a reflux condenser and the reaction was placed in an 80° C. bath. The reaction was stirred overnight. The next day the reaction was cooled to RT, concentrated under reduced pressure and the resulting residue was taken up in Et$_2$O. The resulting slurry was filtered and the isolate solids were further washed with Et$_2$O. The washed solids were placed under high vacuum to yield example (S)-ethyl 2-amino-3-phenylpropanoate hydrochloride (6.86 g, 99%). $^1$H NMR (400 MHz, DMSO-d$_6$) δ 8.52 (s, 3H), 7.30 (m, 5H), 4.24 (AB$\underline{X}$, J$_{AX}$=7.8 Hz, J$_{BX}$=6.2 Hz, 1H), 4.11 (m, 2H), 3.17, 3.05 ($\underline{AB}$X, J$_{AB}$=−14 Hz, J$_{BX}$=5.8 Hz, J$_{AX}$=7.6 Hz, 2H), 1.09 (t, J=6.8 Hz, 3H).

Preparation of (2S)-ethyl 2-(((4-nitrophenoxy)(phenoxy)phosphoryl)amino)-3-phenylpropanoate (Compound D)

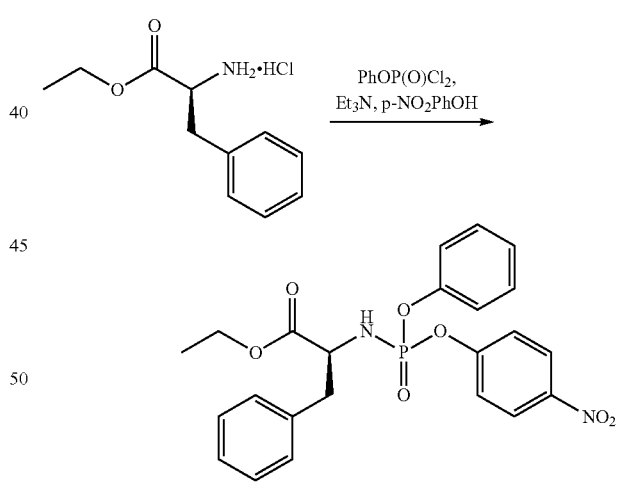

(S)-ethyl 2-amino-3-phenylpropanoate hydrochloride (1.01 g, 4.41 mmol) was dissolved in DCM (50 mL). This solution was cooled to 0° C. and PhOP(O)Cl$_2$ (0.656 mL, 4.41 mmol) was added, followed by the slow addition of Et$_3$N (1.62 mL, 11.5 mmol) over 5 min. The cold bath was removed and the reaction was allowed to warm to RT and stir over a period of 80 min. p-NO$_2$PhOH (0.583 g, 4.19 mmol) was added, followed by more Et$_3$N (0.3 mL, 2.1 mmol). The reaction progress was monitored by LC/MS. Upon completion of the reaction, it was diluted with Et$_2$O, and the resulting solids were removed by filtration. The filtrate was concentrated and compound D (1.25 g, 60%, as a mixture of diastereomers) was isolated by silica gel column chromatography (25 g dry load cartridge, 120 g column; eluent: 100% hexanes ramping to 55% EtOAc in hexanes). $^1$H NMR (400 MHz, CD$_3$OD) δ 8.17 (m, 2H), 7.33 (m, 2H), 7.09-7.25 (m, 10H), 4.17 (m, 1H), 4.07 (m, 2H), 3.08 (m, 1H), 2.84 (m, 1H), 1.14 (m, 3H). $^{31}$P NMR (162 MHz, DMSO-d$_6$) δ −1.479 (s), −1.719 (s). MS m/z=471.01 [M+1].

Preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)-3-phenylpropanoate (Compound 21)

(70 μL). The reaction was concentrated and compound 21 (22 mg, 34%, as a 2.6:1 mixture of diastereomers) was isolated from the residue by reverse phase HPLC. $^1$H NMR (400 MHz, DMSO-d$_6$) δ 7.91 (d, J=4 Hz, 1H), 7.90 (brs, 2H), 7.09-7.30 (m, 8H), 7.01, (t, J=8.2 Hz, 2H), 6.89 (d, J=4.4 Hz, 1H), 6.82 (t, J=4.4 Hz, 1H), 6.27 (m, 1H), 6.14 (m, 1H), 5.34 (m, 1H), 4.62 (t, J=5.6 Hz, 1H), 4.15 (m, 1H), 3.78-4.01 (m, 6H), 2.92 (m, 1H), 2.78 (m, 1H), 1.04 (m, 3H). $^{31}$P NMR (162 MHz, DMSO-d$_6$) δ 3.69 (s), 3.34 (s). MS m/z=623.0 [M+H].

Example 25. (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)-3-methylbutanoate (22)

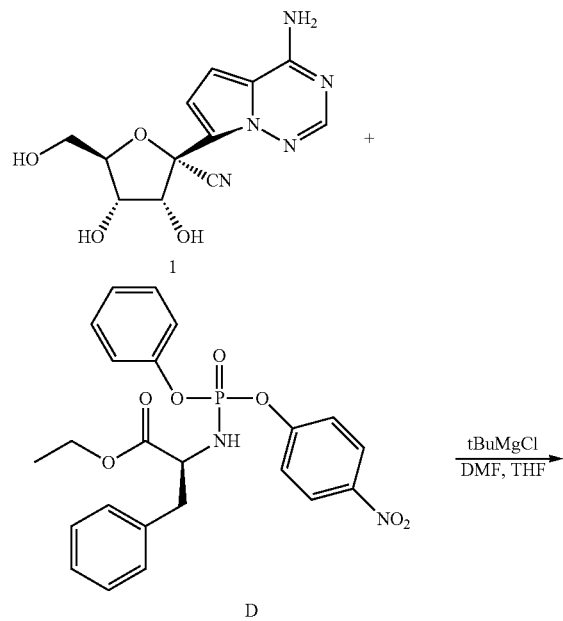

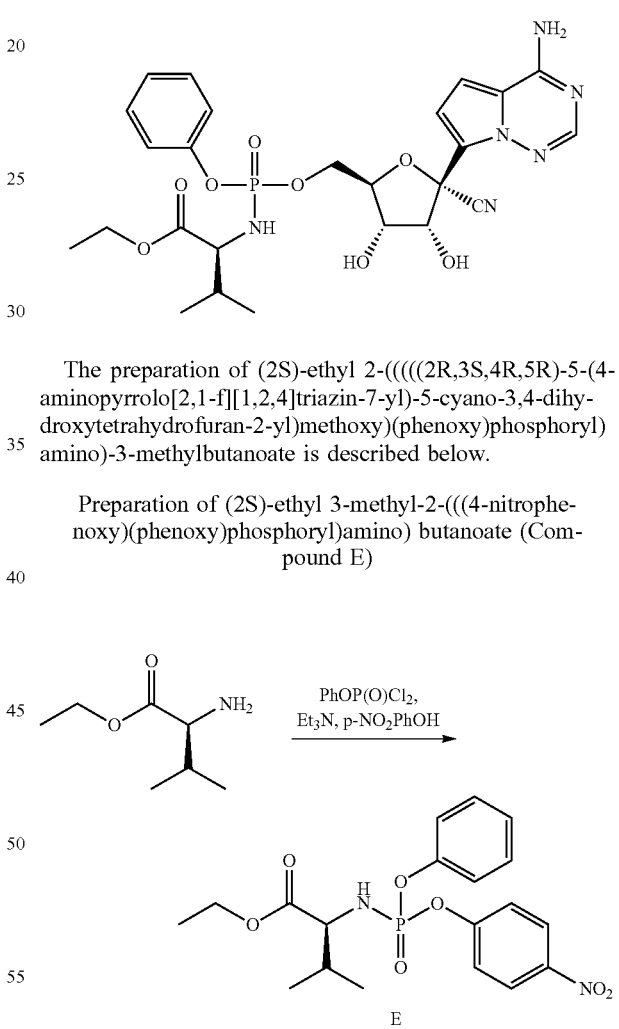

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)-3-methylbutanoate is described below.

Preparation of (2S)-ethyl 3-methyl-2-(((4-nitrophenoxy)(phenoxy)phosphoryl)amino) butanoate (Compound E)

Compound 1 (0.030 g, 0.103 mmol) was dissolved in DMF (1 mL) and then THF (0.5 mL) was added. t-BuMgCl (1M/THF, 154.5 μL, 0.154 μmol) was added to the reaction in a drop-wise manner with vigorous stirring. The resulting white slurry was stirred at RT for 30 min. A solution of compound D (0.058 g, 0.124 mmol) in THF (1 mL) was added in a drop-wise manner to the reaction at RT. The reaction progress was monitored by LC/MS. When the reaction progressed to 50% conversion, the reaction was cooled in an ice bath and quenched with glacial acetic acid The (S)-ethyl 2-amino-3-methylbutanoate (0.351 g, 1.932 mmol) was dissolved in DCM (17 mL). This solution was cooled in an ice bath and PhOP(O)Cl$_2$ (0.287 mL, 1.932 mmol) was added, followed by the slow addition of Et$_3$N (1.62 mL, 11.4 mmol) over 5 min. The cold bath was removed and the reaction was allowed to warm to RT and stir over a period of 1 h. p-NO$_2$PhOH (0.255 g, 1.836 mmol) was added, and the reaction progress was monitored by LC/MS. Upon completion of the reaction, the mixture was diluted with Et$_2$O, and the resulting solids were removed by filtration. The filtrate was concentrated and compound E (0.642 g, 79% as a mixture of diastereomers) was isolated by silica gel column chromatography (12 g dry load cartridge, 80 g column; eluent: 100% hexanes ramping to 55% EtOAc in hexanes). $^1$H NMR (400 MHz, DMSO-d$_6$) δ 8.30 (d, J=9.2 Hz, 2H), 7.48 (t, J=9.6 Hz, 2H), 7.40 (t, J=7.8 Hz, 2H), 7.20-7.27 (m, 3H), 6.60 (quart, J=11.6 Hz, 1H), 4.01 (m, 2H), 3.61 (m, 1H), 1.93 (m, 1H), 1.11 (m, 3H), 0.79 (m, 6H). $^{31}$P NMR (162 MHz, DMSO-d$_6$) δ −0.342 (s), −0.578 (s). MS m/z=422.9 [M+H].

Preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate (Compound 22)

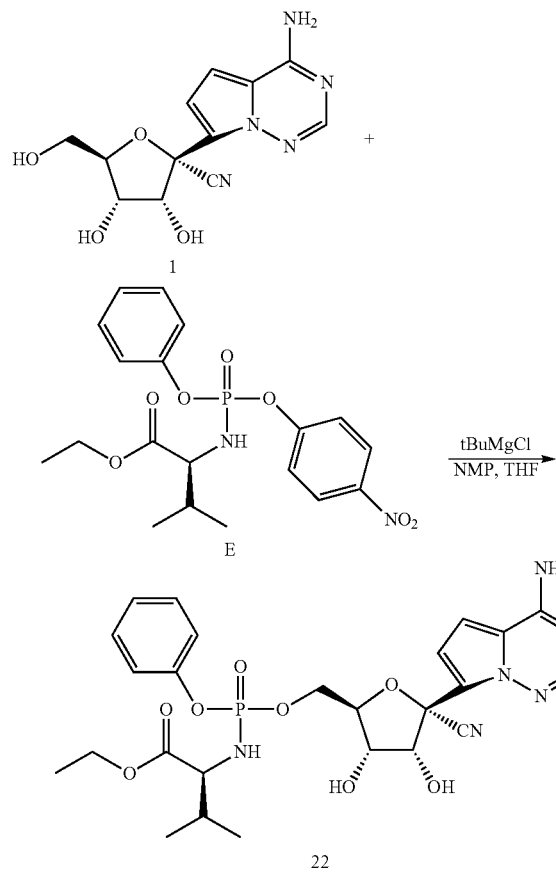

Compound 1 (0.040 g, 0.137 mmol) was dissolved in NMP (1.5 mL) and then THF (0.25 mL) was added. This solution was cooled in an ice bath and t-BuMgCl (1M/THF, 425.7 μL, 0.426 μmol) was added in a drop-wise manner with vigorous stirring. The ice bath was removed and the resulting white slurry was stirred at RT for 15 min. A solution of compound E (0.081 g, 0.192 mmol) in THF (0.5 mL) was added in a drop-wise manner to the reaction at RT. The reaction progress was monitored by LC/MS. When the reaction progressed to 50% conversion, the reaction was cooled in an ice bath and quenched with glacial acetic acid (70 μL). The reaction was concentrated and compound 22 (22 mg, 34%) was semi-purified from the residue by reverse phase HPLC. The semi-pure material was further purified by silica gel column chromatography (12 g dry load cartridge, 40 g column; eluent: 100% EtOAc ramping to 10% MeOH in EtOAc) to yield compound 22 (0.034 g, 43% as a 1.8:1 mixture of diastereomers). $^1$H NMR (400 MHz, DMSO-d$_6$) δ 7.91 (d, J=1.6 Hz, 1H), 7.88 (brs, 2H), 7.32 (m, 2H), 7.15 (m, 3H), 6.90 (t, J=4.2 Hz, 1H), 6.84 (d, J=4.8 Hz, 1H), 6.26 (dd, J=13.4, 6.2 Hz, 1H), 5.87 (quart. J=11.2 Hz, 1H), 5.35 (m, 1H), 4.64 (m, 1H), 4.25 (m, 2H), 3.93-4.15 (m, 4H), 3.45 (m, 1H), 1.87 (m, 1H), 1.09-1.16 (m, 3H), 0.70-0.83 (m, 6H). $^{31}$P NMR (162 MHz, DMSO-d$_6$) δ 4.59 (s), 4.47 (s). MS m/z=575.02 [M+H].

Example 26. (S)-isopropyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (23)

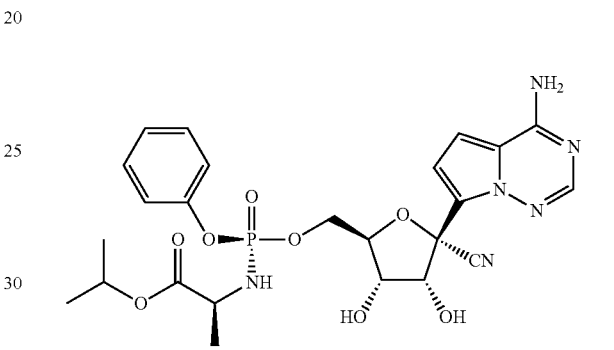

The preparation of (S)-isopropyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

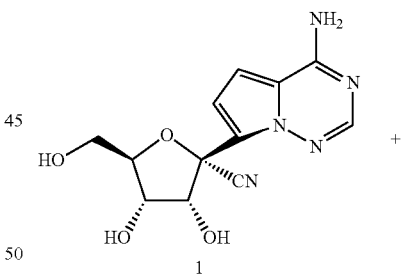

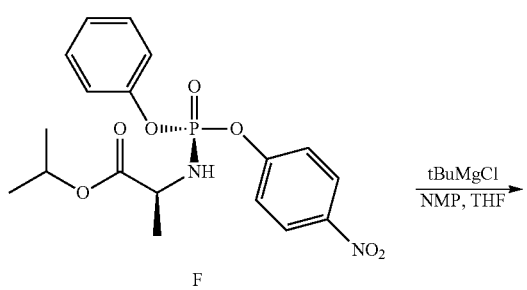

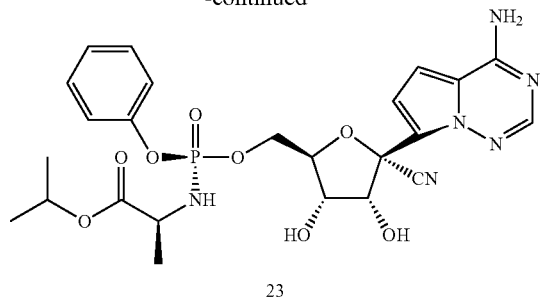

23

Compound 1 (60.0 mg, 206 μmol) was dissolved in NMP (0.28 mL). THF (0.2 mL) was added followed by tert-butyl magnesium chloride (1.0M solution in tetrahydrofuran, 0.309 mL) at RT under an argon atmosphere. After 20 min, a solution of compound F (Prepared according to Cho, A. et al *J. Med. Chem.* 2014, 57, 1812-1825, 81 mg, 206 μmol) in THF (0.2 mL) was added, and the resulting mixture was warmed to 50° C. After 3 h, the reaction mixture was allowed to cool to RT and was purified directly by preparatory HPLC (Phenominex Synergi 4u Hydro-RR 80 Å 150×30 mm column, 5-100% acetonitrile/water gradient) to afford compound 23 (44 mg, 38% as a single diastereomer). $^1$H NMR (400 MHz, CD$_3$OD) δ 7.86 (s, 1H), 7.34-7.26 (m, 2H), 7.21-7.12 (m, 3H), 6.91 (d, J=4.6 Hz, 1H), 6.87 (d, J=4.6 Hz, 1H), 4.92 (sept, J=6.3 Hz, 1H), 4.80 (d, J=5.4 Hz, 1H), 4.43-4.34 (m, 1H), 4.33-4.24 (m, 1H), 4.18 (t, J=5.6 Hz, 1H), 3.82 (dq, J=9.7, 7.1 Hz, 2H), 1.27 (dd, J=7.1, 1.0 Hz, 3H), 1.18 (dd, J=6.3, 4.8 Hz, 6H). $^{31}$P NMR (162 MHz, CD$_3$OD) δ 3.72 (s). LC/MS: t$_R$=1.39 min, MS m/z=561.11 [M+H]; LC system: Thermo Accela 1250 UHPLC; MS system: Thermo LCQ Fleet; Column: Kinetex 2.6μ XB-C18 100 A, 50×4.6 mm; Solvents: ACN with 0.1% acetic acid, water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 20/min. HPLC: t$_R$=2.523 min; HPLC system: Agilent 1100 series; Column: Gemini 5μ C18 110 A, 50×4.6 mm; Solvents: ACN with 0.1% TFA, Water with 0.1% TFA; Gradient: 0 min-5.0 min 2-98% ACN, 5.0 min-6.0 min 98% ACN at 2 mL/min.

Example 27. (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (24)

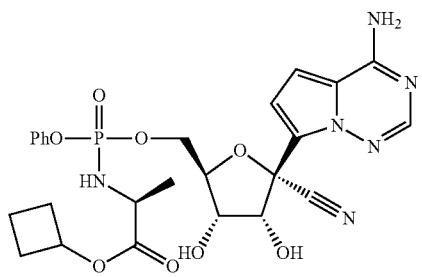 [SMILES: C[C@H](NP(=O)(OC[C@H]1O[C@@](C#N)(c2ccc3c(N)ncnn23)[C@H](O)[C@@H]1O)Oc1ccccc1)C(=O)OC1CCC1]

The preparation of (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Preparation of (2S)-cyclobutyl 2-(((4-nitrophenoxy)(phenoxy)phosphoryl)amino)propanoate (Compound G)

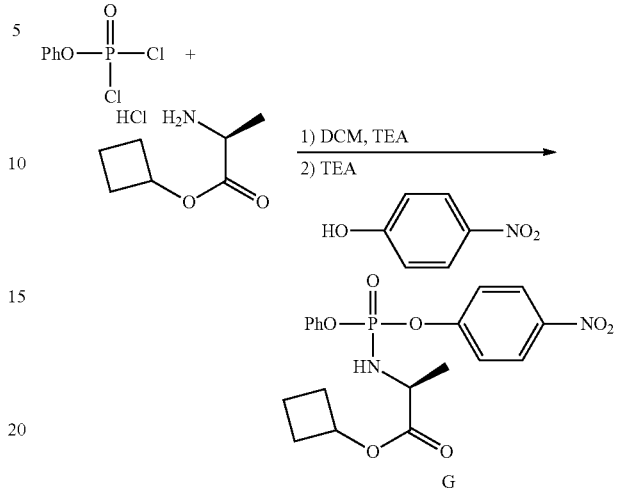

G

Phenyl dichlorophosphate (1.49 mL, 10 mmol) was dissolved in 10 mL of anhydrous DCM and stirred under atmosphere nitrogen in an ice bath. L-Alanine isobutyl ester hydrochloride (0.9 g, 5 mmol) was added in one portion. Triethylamine (765 μL, 5.5 mmol) was then added dropwise. Reaction stirred for 1 h. More Triethylamine (765 μL, 5.5 mmol) was added dropwise and the reaction was stirred for 45 min. p-Nitrophenol (1.25 g, 9 mmol) was added in one portion and stirred for 30 min. Triethylamine (765 μL, 5.5 mmol) was added and the reaction mixture was stirred for 2 h. Additional p-nitrophenol (1.25 g, 9 mmol) and triethylamine (765 μL, 5.5 mmol) were then added, and the reaction was stirred for another 2 h. The reaction mixture was concentrated under reduced pressure. The resulting crude was diluted with EtOAc and washed twice with 5% aqueous citric acid solution, followed with saturated aqueous sodium chloride solution. The organic layer was then dried over anhydrous sodium sulfate and concentrated under reduced pressure. The crude residue was purified with silica gel column (0-20-50% EtOAc in hexanes) to give compound G (1.48 g, 70% yield as a mixture of diastereomers). $^1$H NMR (400 MHz, CD$_3$OD) δ 8.33-8.23 (m, 2H), 7.52-7.33 (m, 4H), 7.33-7.17 (m, 3H), 4.96-4.85 (m, 1H), 4.07-3.96 (m, 1H), 2.27 (m, 2H), 2.07-1.91 (m, 2H), 1.83-1.70 (m, 1H), 1.70-1.55 (m, 1H), 1.32 (m, 3H). $^{31}$P NMR (162 MHz, CD$_3$OD) δ −1.36, −1.59. MS m/z=420.9 [M+H].

Preparation (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 24)

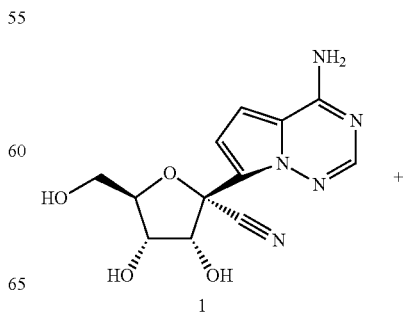

1

143

-continued

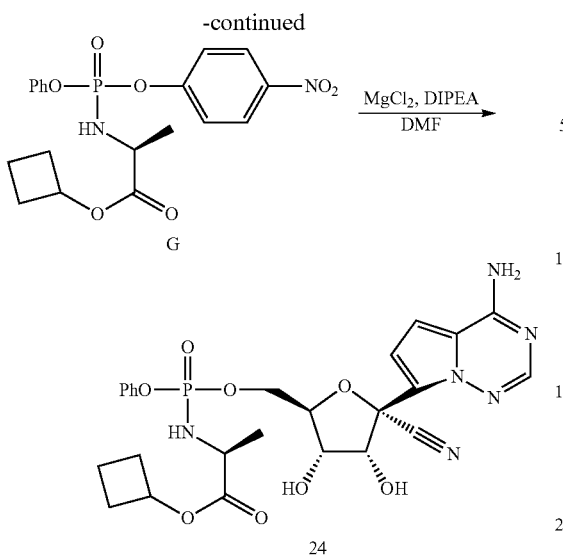

144
Preparation of (2S)-isopropyl 2-(((4-nitrophenoxy)(phenoxy)phosphoryl)amino)-3-phenylpropanoate (Compound H)

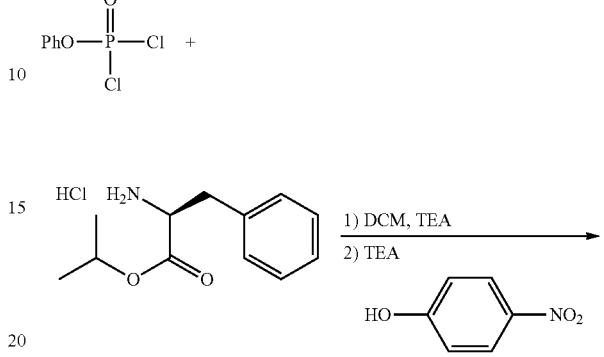

Compound 1 (58 mg, 0.2 mmol) was mixed with compound G (101 mg, 0.24 mmol) in 2 mL of anhydrous DMF. Magnesium chloride (42 mg, 0.44 mmol) was added in one portion. The reaction mixture was heated to 50° C. DIPEA (87 µL, 0.5 mmol) was added, and the reaction was stirred for 2 h at 50° C. The reaction mixture was cooled to room temperature, was diluted with EtOAc and was washed with 5% aqueous citric acid solution followed by saturated aqueous sodium chloride solution. The organic layer was then dried over anhydrous sodium sulfate and concentrated under reduced pressure. The crude residue was purified with silica gel column (0-2-5% MeOH in DCM) to afford compound 24 (42 mg, 37% yield, as a mixture of diastereomers). $^1$H NMR (400 MHz, Methanol-d4) δ 7.85 (m, 1H), 7.34-7.22 (m, 2H), 7.22-7.08 (m, 3H), 6.94-6.84 (m, 2H), 4.95-4.85 (m, 1H), 4.79 (m, 1H), 4.46-4.34 (m, 2H), 4.34-4.24 (m, 1H), 4.19 (m, 1H), 3.81 (m, 1H), 2.27 (m, 2H), 2.01 (m, 2H), 1.84-1.68 (m, 1H), 1.62 (m, 1H), 1.30-1.16 (m, 3H). $^{31}$P NMR (162 MHz, cd$_3$od) δ 3.70, 3.65. MS m/z=573.0 [M+H].

Example 28. (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (25)

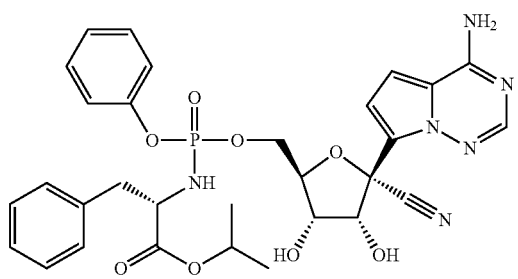 [SMILES: CC(C)OC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate is described below.

Phenyl dichlorophosphate (718 µL, 4.8 mmol) was dissolved in 10 mL of anhydrous DCM and stirred under a nitrogen atmosphere in an ice bath. L-Phenylalanine isopropyl ester hydrochloride (1 g, 4.1 mmol) was added in one portion. Another 10 mL of anhydrous DCM was added. Triethylamine (736 µL, 5.3 mmol) was added dropwise and the reaction mixture was stirred for 30 min. More triethylamine (736 µL, 5.3 mmol) was then added dropwise and the reaction mixture was stirred for 30 min. Additional triethylamine (736 µL, 5.3 mmol) was then added dropwise and the reaction mixture was stirred for 15 min. p-Nitrophenol (600 mg, 4.32 mmol) was then added. The ice bath was then removed and the reaction mixture was allowed to warm to room temperature and stirred for 2 h. More p-nitrophenol (50 mg) and triethylamine (736 µL, 5.3 mmol) were the added and the reaction mixture was stirred for 1 h.

The reaction mixture was then concentrated under reduced pressure, and was diluted with EtOAc and washed twice with 5% aqueous citric acid solution, followed with saturated aqueous sodium chloride solution. The organic layer was dried over anhydrous sodium sulfate and was concentrated under reduced pressure. The crude was purified with silica gel column (0-15% EtOAc in hexanes) to give compound H (1.57 g, 68% yield as a mixture of diastereomers). $^1$H NMR (400 MHz, CDCl$_3$) δ 8.17 (m, 2H), 7.38-7.13 (m, 10H), 7.13-7.02 (m, 2H), 4.95 (m, 1H), 4.31 (m, 1H), 3.69 (m, 1H), 3.02 (dd, J=6.1, 1.8 Hz, 2H), 1.21-1.08 (m, 6H). $^{31}$P NMR (162 MHz, cdcl3) δ −2.96, −2.98. MS m/z=485.0 [M+H].

Preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (Compound 25)

Example 29. (S)-methyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (26)

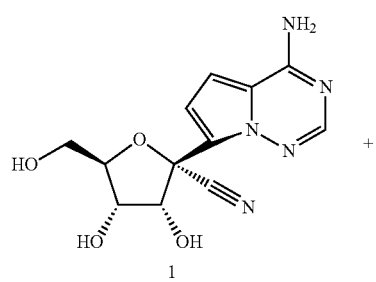

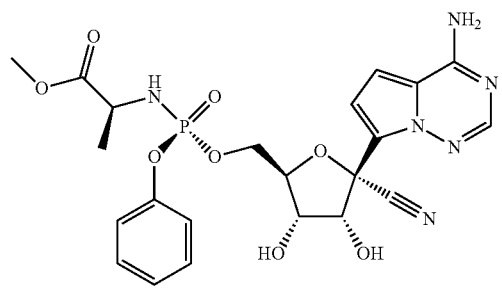 [SMILES: COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-methyl 2-(((S)-(((2R,3S,4R,5R)-5-(4-aminopyrrolo[2, 1-f][1,2,4]triazin-7-yl)-5-cyano-3,4-dihydroxytetrahydrofuran-2-yl)methoxy)(phenoxy)phosphoryl)amino)propanoate is described below.

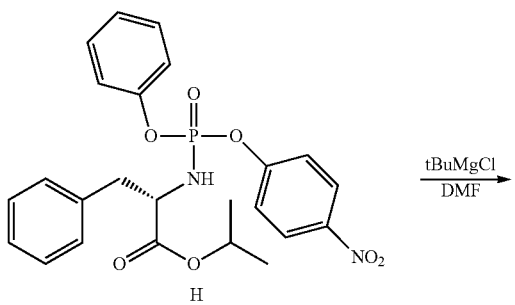

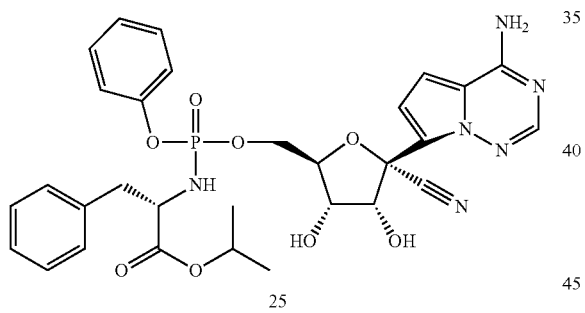

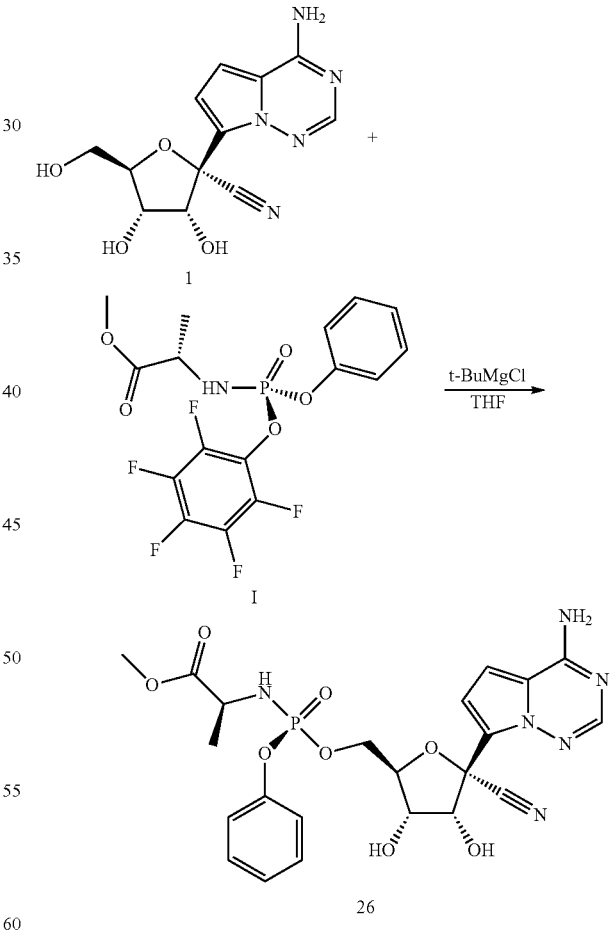

Compound 1 (58 mg, 0.2 mmol) and compound H (116 mg, 0.24 mmol) were mixed and 2 mL of anhydrous DMF was added. The reaction mixture was stirred under a nitrogen atmosphere at room temperature. 1M tBuMgCl in THF (300 μL, 0.3 mmol) was added dropwise over 3 minutes and the reaction mixture was then stirred for 16 h. The reaction mixture was diluted with EtOAc and washed with 5% aqueous citric acid solution, saturated aqueous sodium bicarbonate solution and then saturated aqueous sodium chloride solution. The organic layer was dried over anhydrous sodium sulfate and concentrated under reduced pressure. The crude residue was purified with silica gel column (0-5% MeOH in DCM) to give compound 25 (40 mg, 32% yield as a mixture of diastereomers). $^1$H NMR (400 MHz, CD$_3$OD) δ 7.84 (m, 1H), 7.27-7.08 (m, 8H), 7.08-6.97 (m, 2H), 6.88 (m, 2H), 4.91-4.84 (m, 1H), 4.74 (m, 1H), 4.26 (m, 1H), 4.19-4.04 (m, 2H), 4.04-3.91 (m, 2H), 2.97 (m, 1H), 2.82 (m, 1H), 1.14 (m, 3H), 1.06 (m, 3H). $^{31}$P NMR (162 MHz, CD$_3$OD) δ 3.63, 3.25. MS m/z=637.0 [M+H].

Compound 1 (100 mg, 0.34 mmol) was dissolved in THF (2 mL) and cooled with an ice water bath. Then 1M t-BuMgCl (0.52 mL, 0.77 mmol) was added dropwise slowly. The resulting mixture was stirred for 30 min at room temperature. Then compound I (Prepared according to WO 2012142085, 219 mg, 0.52 mmol) in THF (2 mL) was added over 5 min and the resulting mixture was stirred for 24 h at room temperature. The reaction mixture was then diluted with EtOAc, cooled under ice-water bath, washed with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give compound 26 (12 mg, 6.6% as a single diastereomer). 1H NMR (400 MHz, CD$_3$OD) δ 7.86 (s, 1H), 7.29 (dd, J=8.6, 7.2 Hz, 2H), 7.21-7.09 (m, 3H), 6.94-6.81 (m, 2H), 4.79 (d, J=5.4 Hz, 1H), 4.38 (ddq, J=10.8, 5.3, 2.7 Hz, 2H), 4.33-4.23 (m, 1H), 4.18 (t, J=5.5 Hz, 1H), 3.86 (dq, J=9.9, 7.1 Hz, 1H), 3.62 (s, 3H), 1.27 (dd, J=7.2, 1.1 Hz, 3H). MS m/z=533 (M+1)$^+$.

Example 30. (S)-neopentyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (27)

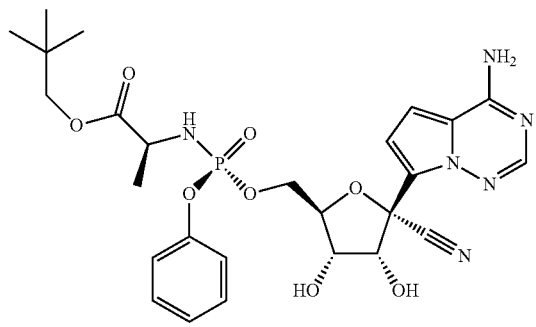 [SMILES: C[C@H](N[P@](=O)(OC[C@H]1O[C@@](C#N)(c2ccc3c(N)ncnn23)[C@H](O)[C@@H]1O)Oc1ccccc1)C(=O)OCC(C)(C)C]

The preparation of (S)-neopentyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

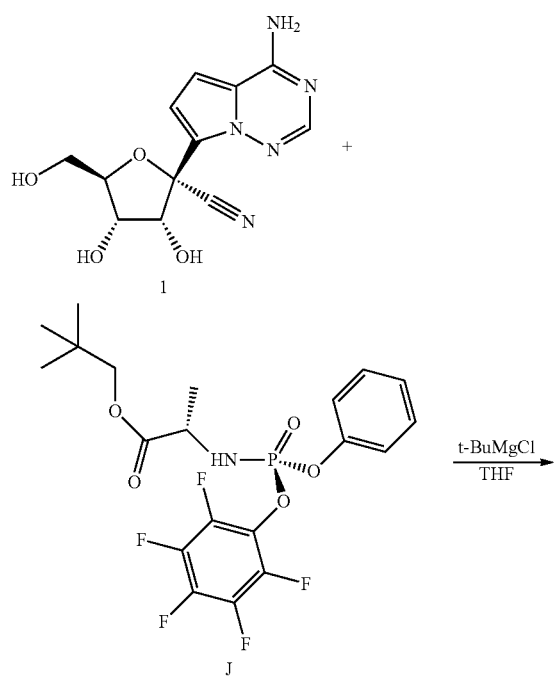

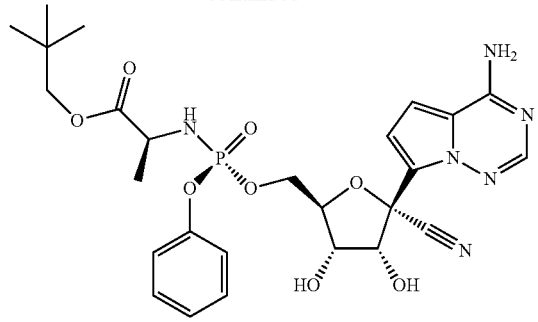

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for 30 min at room temperature. Then compound J (Prepared according to WO2012075140, 248 mg, 0.52 mmol) was added over 5 min and the resulting mixture was stirred for 24 h at room temperature, diluted with EtOAc, cooled under ice-water bath, treated with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give Compound 27 (12 mg, 10% as a single diastereomer). $^1$H NMR (400 MHz, CD$_3$OD) δ 7.86 (s, 1H), 7.36-7.24 (m, 2H), 7.23-7.10 (m, 3H), 6.96-6.85 (m, 2H), 4.78 (d, J=5.4 Hz, 1H), 4.38 (tdd, J=10.0, 4.9, 2.5 Hz, 2H), 4.32-4.24 (m, 1H), 4.17 (t, J=5.6 Hz, 1H), 3.91 (dq, J=9.8, 7.1 Hz, 1H), 3.81 (d, J=10.5 Hz, 1H), 3.69 (d, J=10.5 Hz, 1H), 1.31 (dd, J=7.2, 1.1 Hz, 3H), 0.89 (s, 9H). MS m/z=589 (M+1)$^+$.

Example 31. (2S)-cyclopentyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (28)

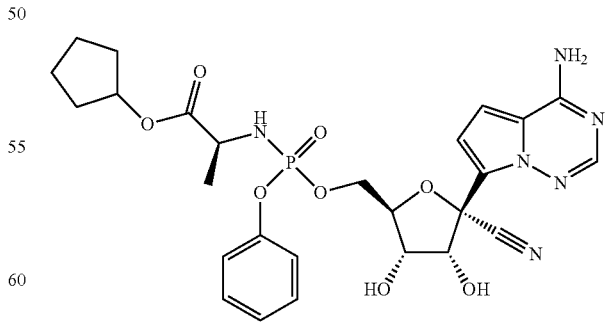

The preparation of (2S)-cyclopentyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

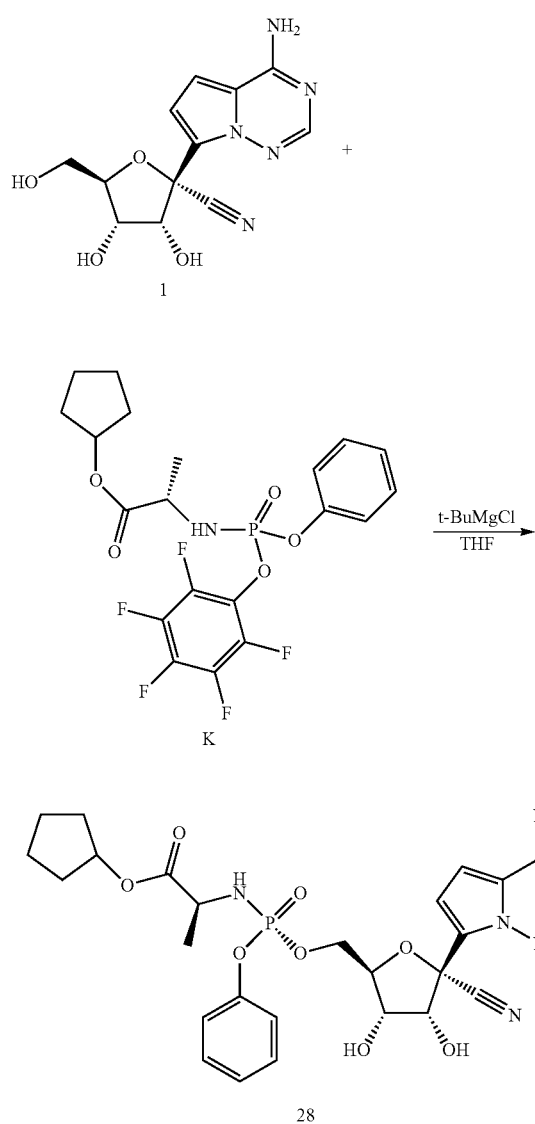

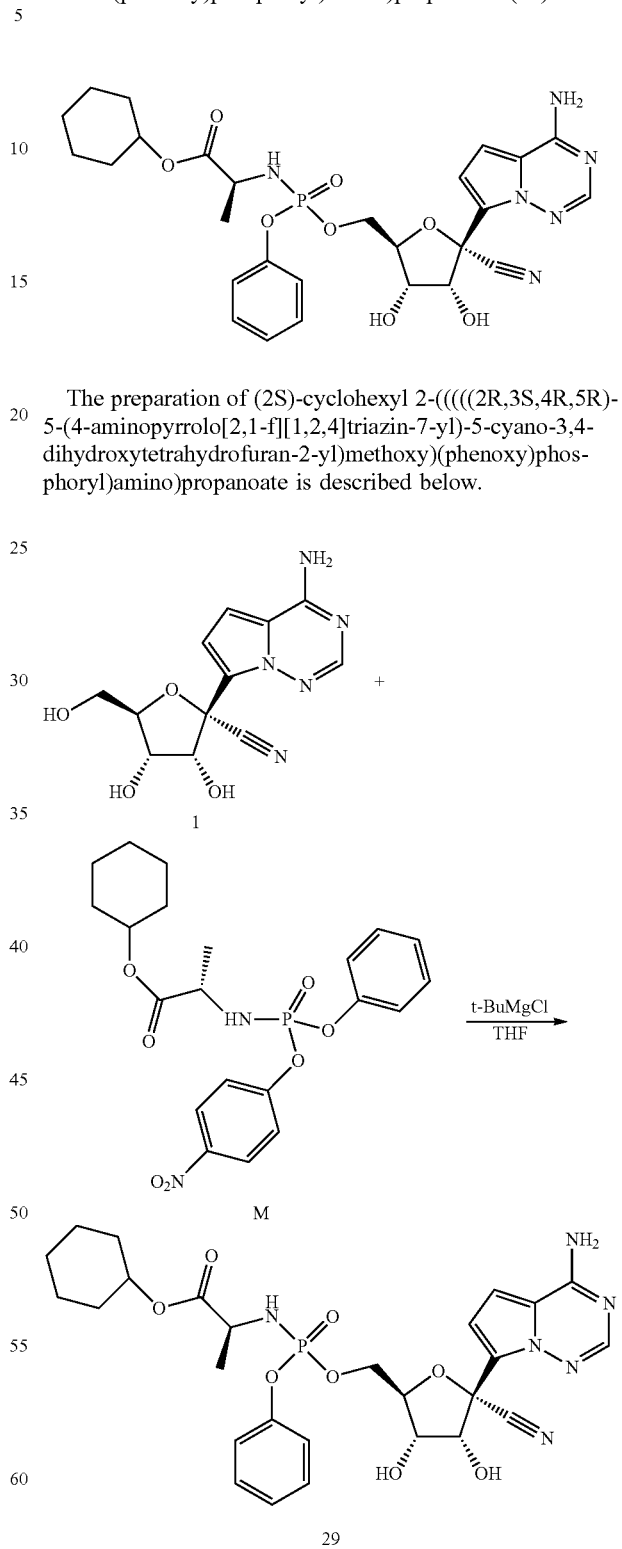

Example 32. (2S)-cyclohexyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (29)

The preparation of (2S)-cyclohexyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for 30 min at room temperature. Then compound K (Prepared according to WO2012075140, 247 mg, 0.52 mmol) in THF (2 mL) was added over 5 min and the resulting mixture was stirred for 24 h at room temperature, diluted with EtOAc, cooled under ice-water bath, treated with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give example 28 (47 mg, 23% as a 27:1 mixture of diastereomers). 1H NMR (400 MHz, CD$_3$OD) δ 7.85 (s, 1H), 7.33-7.22 (m, 2H), 7.14 (tdd, J=7.6, 2.1, 1.1 Hz, 3H), 6.95-6.87 (m, 2H), 5.13-5.00 (m, 1H), 4.78 (d, J=5.4 Hz, 1H), 4.48-4.35 (m, 2H), 4.30 (ddd, J=10.6, 5.7, 3.6 Hz, 1H), 4.19 (t, J=5.4 Hz, 1H), 3.78 (dq, J=9.2, 7.1 Hz, 1H), 1.81 (dtd, J=12.5, 5.9, 2.4 Hz, 2H), 1.74-1.49 (m, 6H), 1.21 (dd, J=7.1, 1.2 Hz, 3H). MS m/z=587 (M-1)$^+$.

To a mixture of compound 1 (50 mg, 0.343 mmol), compound M (Prepared according to US20130143835, 93 mg, 0.209 mmol), and MgCl$_2$ (24.5 mg, 0.257 mmol) in DMF (1 mL) was added diisopropylethylamine (0.075 mL, 0.43 mmol) dropwise over 5 min at 0° C. The resulting mixture was stirred at 50° C. for 1 h. The reaction mixture was then cooled with an ice-water bath, treated with 1M citric acid (0.5 mL), and was purified directly by prep-HPLC (ACN 0 to 70% in water) to afford compound 29 (20 mg, 19% as a mixture of diastereomers). $^1$H NMR (400 MHz, CD$_3$OD) δ 7.84 (s, 1H), 7.32-7.23 (m, 2H), 7.18-7.10 (m, 3H), 6.93-6.87 (m, 2H), 4.78 (d, J=5.4 Hz, 1H), 4.67 (td, J=8.7, 4.2 Hz, 1H), 4.48-4.35 (m, 2H), 4.30 (ddd, J=10.8, 5.7, 3.7 Hz, 1H), 4.20 (t, J=5.4 Hz, 1H), 3.88-3.71 (m, 1H), 1.83-1.63 (m, 4H), 1.58-1.46 (m, 1H), 1.46-1.24 (m, 5H), 1.24 (s, 3H). $^{31}$P NMR (162 MHz, CD$_3$OD) δ 3.75. MS m/z=601 (M+1)$^-$.

Example 33. Ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (30)

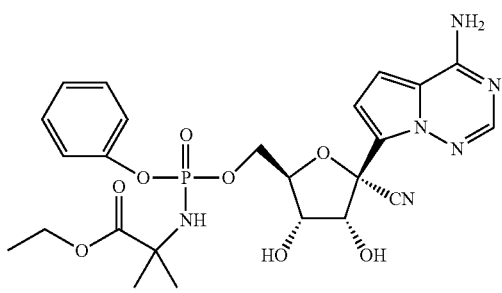 [SMILES: CCOC(=O)C(C)(C)NP(=O)(OC[C@H]1O[C@@](C#N)(c2ccc3c(N)ncnn23)[C@H](O)[C@@H]1O)Oc1ccccc1]

The preparation of ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Ethyl 2-((tert-butoxycarbonyl)amino)-2-methylpropanoate

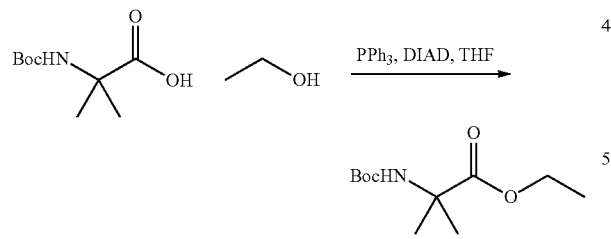

Take up triphenylphosphine (6.18 g, 25.00 mmol) in THF (30 mL). Next charge DIAD (4.92 mL, 25.00 mmol) and stir at room temperature for 10 min. Dissolve 2-((tert-butoxycarbonyl)amino)-2-methylpropanoic acid (5.08 g, 25.00 mmol) in THF (20 mL) and add to the reaction mixture followed by the addition of ethanol (2.19 mL, 37.49 mmol). Allow the reaction to stir at room temperature for 1 h. The solvents were removed under reduced pressure and the crude was taken up in 1:1 Et$_2$O:Hexanes (120 mL). The solid triphenylphosphine oxide was filtered off and the solvent was removed under reduced pressure. The crude was taken up in minimal CH$_2$Cl$_2$ and purified by silica gel chromatography 0-50% EtOAc/Hex to afford ethyl 2-((tert-butoxycarbonyl)amino)-2-methylpropanoate (2.71 g, 47%). $^1$H NMR (400 MHz, Chloroform-d) δ 4.18 (q, J=7.1 Hz, 2H), 1.49 (s, 6H), 1.43 (s, 9H), 1.27 (t, J=7.1 Hz, 3H).

Preparation of Ethyl 2-amino-2-methylpropanoate hydrochloride

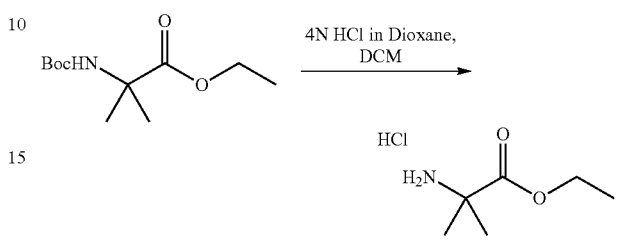

Take up ethyl 2-((tert-butoxycarbonyl)amino)-2-methylpropanoate (2.71 g, 11.72 mmol) in CH$_2$Cl$_2$ (25 mL) and slowly add 4N HCl in dioxane (25 mmol) and stir at room temperature. At 1 h, the reaction was determined to be complete by TLC. The solvents were removed under reduced pressure and the crude was coevaporated with Et$_2$O two times then placed under high vacuum to afford ethyl 2-amino-2-methylpropanoate hydrochloride (2.02 g, 102%). $^1$H NMR (400 MHz, DMSO-d$_6$) δ 8.70 (s, 3H), 4.18 (q, J=7.1 Hz, 2H), 1.46 (s, 6H), 1.21 (t, J=7.1 Hz, 3H).

Preparation of Ethyl 2-methyl-2-(((4-nitrophenoxy)(phenoxy)phosphoryl)amino)propanoate (Compound N)

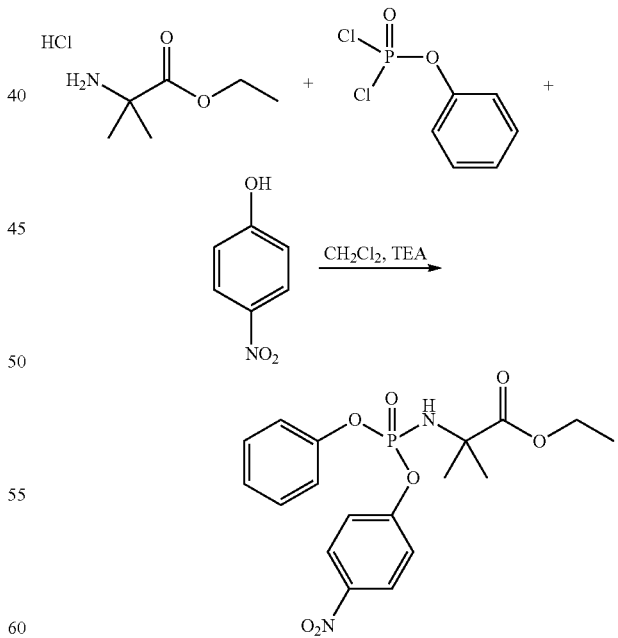

N

Take up phenyl dichlorophosphate (0.97 mL, 6.50 mmol) and ethyl 2-amino-2-methylpropanoate hydrochloride (1.09 g, 6.50 mmol) in CH$_2$Cl$_2$ (50 mL). Cool the reaction mixture to 0° C. and slowly add TEA (1.75 mL, 12.45 mmol).

Remove the cold bath and allow the reaction mixture to stir at room temperature. After 2 h, the addition of the amino acid was determined to be complete by $^{31}$P NMR. Charge p-nitrophenol (0.860 g, 6.17 mmol) followed by the addition of TEA (0.87, 7.69 mmol). Allow the reaction to stir at room temperature. After 2 h, the reaction was determined to be complete by LCMS. The reaction was diluted with Et$_2$O and the TEA*HCl salts were filtered off. The crude was concentrated and purified by silica gel chromatography (0-50% EtOAc/Hex) to afford compound N (1.79 g, 68%). $^1$H NMR (400 MHz, DMSO-d$_6$) δ 8.37-8.21 (m, 2H), 7.55-7.44 (m, 2H), 7.43-7.33 (m, 2H), 7.30-7.09 (m, 3H), 6.57 (d, J=10.1 Hz, 1H), 3.99 (q, J=7.1 Hz, 2H), 1.39 (s, 6H), 1.08 (t, J=7.1 Hz, 3H). $^{31}$P NMR (162 MHz, DMSO-d$_6$) δ −2.87. LC/MS: t$_R$=1.65 min, MS m/z=408.97 [M+1]; LC system: Thermo Accela 1250 UHPLC; MS system: Thermo LCQ Fleet; Column: Kinetex 2.6μ XB-C18 100 A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Preparation of ethyl 2-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 30)

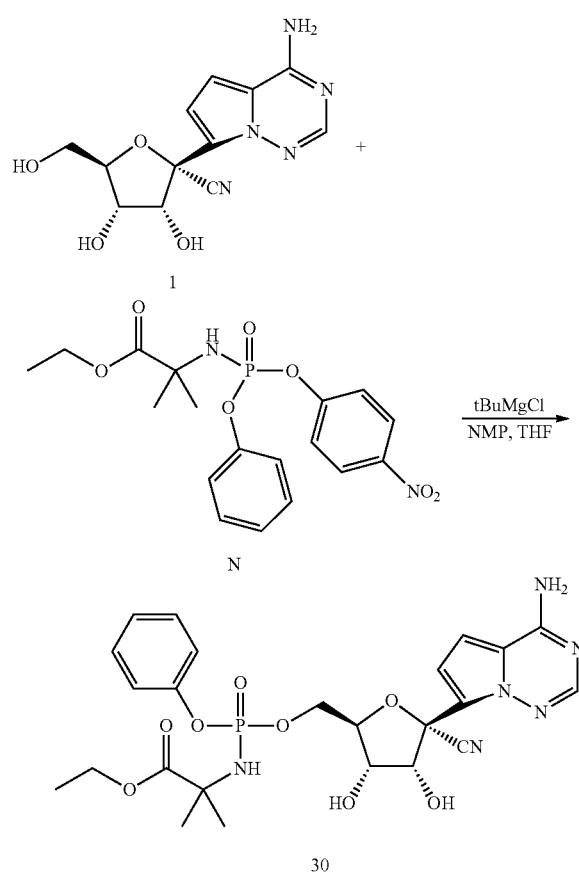

Take up compound 1 (66 mg, 0.23 mmol) in NMP (2.0 mL). Cool the mixture to 0° C. and slowly add tBuMgCl (1.0M in THF, 0.34 mL, 0.34 mmol). Allow the reaction to stir at 0° C. for 30 min, then add a solution of compound N (139 mg, 0.34 mmol) dissolved in THF (1.0 mL). Remove the cold bath and place the reaction in a 50° C. preheated oil bath. After 2 h, the reaction was cooled to room temperature and quenched with acetic acid and methanol. The crude was concentrated and purified by reverse phase HPLC without modifier to afford compound 30 (32 mg, 25% as a mixture of diastereomers). $^1$H NMR (400 MHz, DMSO-d$_6$) δ 7.89 (m, 3H), 7.31 (q, J=8.1 Hz, 2H), 7.22-7.05 (m, 3H), 6.87 (d, J=4.5, 1H), 6.80 (d, J=4.5 Hz, 1H), 6.27 (d, J=11.7, 1H), 5.81 (d, J=9.7, 1H), 5.35 (d, J=5.6 Hz, 1H), 4.64 (dt, J=9.0, 5.6 Hz, 1H), 4.24 (m, 2H), 4.11 (m, 1H), 4.04-3.90 (m, 3H), 1.39-1.23 (m, 6H), 1.10 (t, J=7.1, 3H). $^{31}$P NMR (162 MHz, DMSO-d$_6$) δ 2.45, 2.41. LC/MS: t$_R$=1.03 min, MS m/z=561.03 [M+1]; LC system: Thermo Accela 1250 UHPLC; MS system: Thermo LCQ Fleet; Column: Kinetex 2.6μ XB-C18 100 A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 34. Isopropyl 2-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (31)

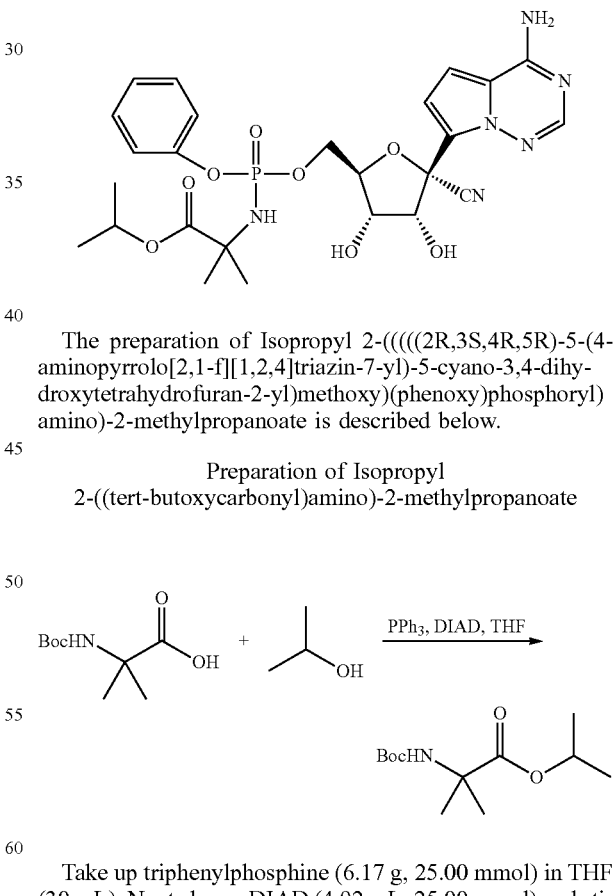

The preparation of Isopropyl 2-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Isopropyl 2-((tert-butoxycarbonyl)amino)-2-methylpropanoate

Take up triphenylphosphine (6.17 g, 25.00 mmol) in THF (30 mL). Next charge DIAD (4.92 mL, 25.00 mmol) and stir at room temperature for 10 min. Dissolve 2-((tert-butoxycarbonyl)amino)-2-methylpropanoic acid (5.07 g, 25.00 mmol) in THF (20 mL) and add to the reaction mixture followed by the addition of isopropanol (1.91 mL, 25.00 mmol). Allow the reaction to stir at room temperature for 1 h. The solvents were removed under reduced pressure and the crude was taken up in 1:1 Et$_2$O:Hexanes (120 mL). The solid triphenylphosphine oxide was filtered off and the solvent was removed under reduced pressure. The crude was taken up in minimal CH$_2$Cl$_2$ and purified by silica gel chromatography (0-50% EtOAc/Hex) to afford isopropyl 2-((tert-butoxycarbonyl)amino)-2-methylpropanoate (4.09 g, 67%). $^1$H NMR (400 MHz, Chloroform-d) δ 5.03 (p, J=6.2 Hz, 1H), 1.48 (s, 6H), 1.40 (d, J=6.2 Hz, 9H), 1.24 (d, J=6.3 Hz, 6H).

Preparation of Isopropyl 2-amino-2-methylpropanoate hydrochloride

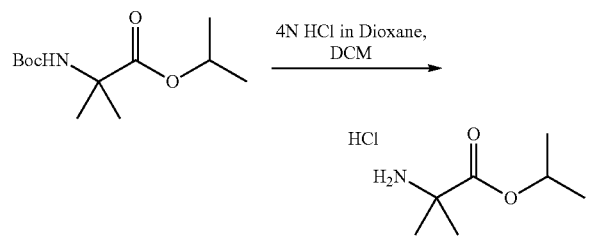

Take up isopropyl 2-((tert-butoxycarbonyl)amino)-2-methylpropanoate (4.09 g, 16.67 mmol) in CH$_2$Cl$_2$ (50 mL) and slowly add 4N HCl in dioxane (50 mmol) and stir at room temperature. At 1 h, the reaction was determined to be complete by TLC. The solvents were removed under reduced pressure and the crude was coevaporated with Et$_2$O two times then placed under high vacuum to afford isopropyl 2-amino-2-methylpropanoate hydrochloride (3.06 g, 101%). $^1$H NMR (400 MHz, DMSO-d$_6$) δ 8.61 (s, 3H), 4.96 (p, J=6.2 Hz, 1H), 1.44 (s, 6H), 1.22 (d, J=6.2 Hz, 6H).

Preparation of Isopropyl 2-methyl-2-(((4-nitrophenoxy)(phenoxy)phosphoryl)amino) propanoate (Compound O)

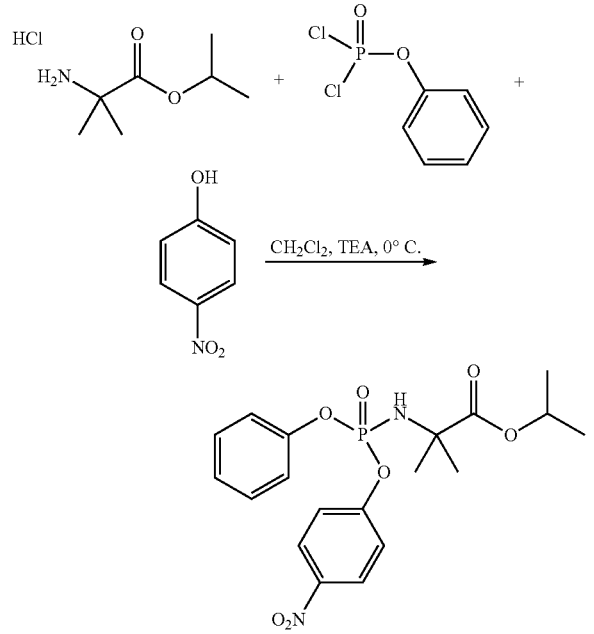

Take up phenyl dichlorophosphate (0.83 mL, 5.58 mmol) and isopropyl 2-amino-2-methylpropanoate hydrochloride (1.01 g, 5.58 mmol) in CH$_2$Cl$_2$ (50 mL). Cool the reaction mixture to 0° C. and slowly add TEA (1.61 mL, 11.45 mmol). Remove the cold bath and allow the reaction mixture to stir at room temperature. After 2 h, the addition of the amino acid was determined to be complete by $^{31}$P NMR. Charge p-nitrophenol (0.74 g, 5.30 mmol) followed by the addition of TEA (0.81, 5.84 mmol). Allow the reaction to stir at room temperature. After 2 h, the reaction was determined to be complete by LCMS. The reaction was diluted with Et$_2$O and the TEA*HCl salts were filtered off. The crude was concentrated and purified by silica gel chromatography (0-50% EtOAc/Hex) to afford compound O (1.45 g, 62%). $^1$H NMR (400 MHz, DMSO-d$_6$) δ 8.42-8.19 (m, 2H), 7.55-7.43 (m, 2H), 7.39 (dd, J=8.6, 7.2 Hz, 2H), 7.30-7.12 (m, 3H), 6.53 (d, J=10.1 Hz, 1H), 4.82 (hept, J=6.3 Hz, 1H), 1.38 (s, 6H), 1.09 (d, J=6.3, 6H). $^{31}$P NMR (162 MHz, DMSO-d$_6$) δ −2.84. LC/MS: t$_R$=1.73 min, MS m/z=422.92 [M+1]; LC system: Thermo Accela 1250 UHPLC; MS system: Thermo LCQ Fleet; Column: Kinetex 2.6μ. XB-C18 100 A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Preparation of Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 31)

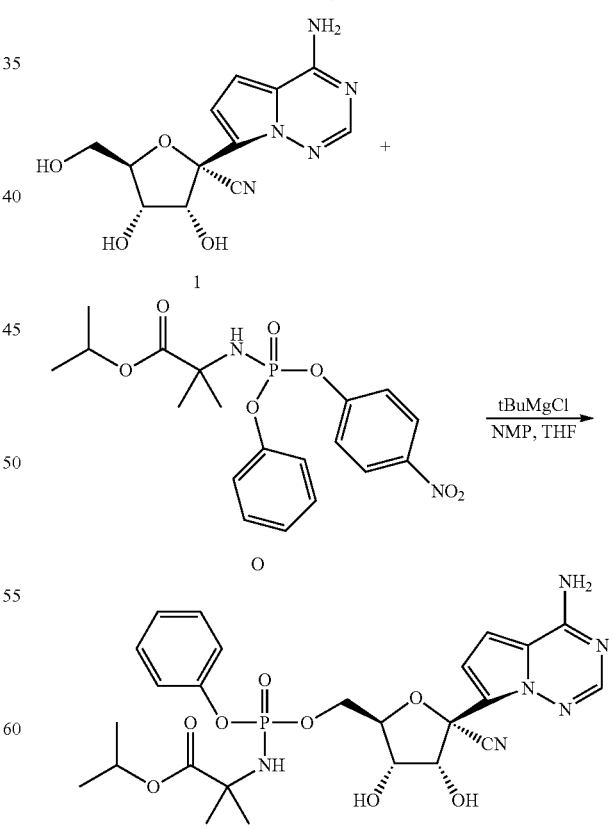

Take up compound 1 (66 mg, 0.23 mmol) in NMP (2.0 mL). Cool the mixture to 0° C. and slowly add tBuMgCl (1.0M in THF, 0.57 mL, 0.57 mmol). Allow the reaction to stir at 0° C. for 30 min, then add a solution of compound O (143 mg, 0.34 mmol) dissolved in THF (1.0 mL). Remove the cold bath and place the reaction in a 50° C. preheated oil bath. After 2 h, the reaction was cooled to room temperature and was quenched with acetic acid and methanol. The crude was concentrated and purified by reverse phase HPLC without modifier to afford compound 31 (48 mg, 37% as a mixture of diastereomers). $^1$H NMR (400 MHz, DMSO-d$_6$) δ 7.88 (m, 3H), 7.30 (td, J=8.5, 7.0 Hz, 2H), 7.20-7.04 (m, 3H), 6.87 (d, J=4.5, 1H), 6.80 (d, J=4.5 Hz, 1H), 6.27 (d, 6.1 Hz, 1H), 5.75 (t, J=9.1 Hz, 1H), 5.34 (d, J=5.7 Hz, 1H), 4.81 (p, J=6.3 Hz, 1H), 4.71-4.50 (m, 1H), 4.23 (m, 2H), 4.11 (m, 1H), 4.03-3.83 (m, 1H), 1.37-1.23 (m, 6H), 1.18-1.04 (m, 6H). $^{31}$P NMR (162 MHz, dmso) δ 2.47, 2.43. LC/MS: t$_R$=1.08 min, MS m/z=575.06 [M+1]; LC system: Thermo Accela 1250 UHPLC; MS system: Thermo LCQ Fleet; Column: Kinetex 2.6μ XB-C18 100 A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 35. (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (32)

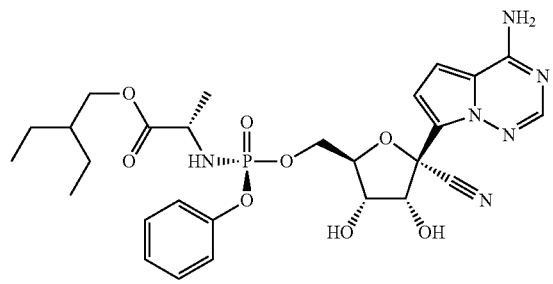 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Preparation of (3R,4R,5R)-3,4-bis(benzyloxy)-5-((benzyloxy)methyl)dihydrofuran-2(3H)-one

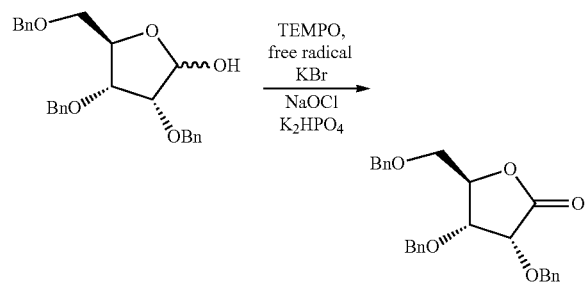

(3R,4R,5R)-3,4-bis(benzyloxy)-5-((benzyloxy)methyl)tetrahydrofuran-2-ol (15.0 g) was combined with MTBE (60.0 mL), KBr (424.5 mg), aqueous K$_2$HPO$_4$ solution (2.5M, 14.3 mL), and TEMPO (56 mg). This mixture was cooled to about 1° C. Aqueous bleach solution (7.9% wt.) was slowly charged in portions until complete consumption of starting material as indicated through a starch/iodide test. The layers were separated, and the aqueous layer was extracted with MTBE. The combined organic phase was dried over MgSO$_4$ and concentrated under reduced pressure to yield the product as a solid.

Preparation (4-amino-7-iodopyrrolo[2,1-f][1,2,4]triazine)

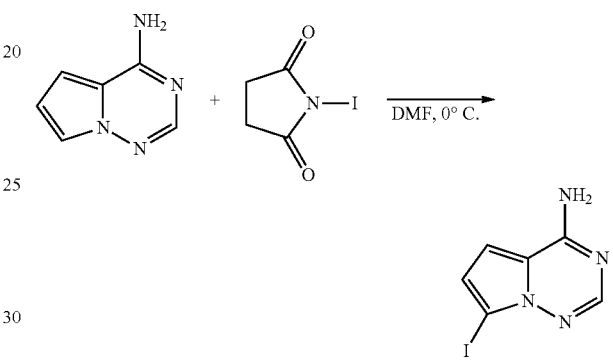

To a cold solution of 4-aminopyrrolo[2,1-f][1,2,4]-triazine (10.03 g; 74.8 mmol) in N,N-dimethylformamide (70.27 g), N-iodosuccinimide (17.01 g; 75.6 mmol) was charged in portions, while keeping the contents at about 0° C. Upon reaction completion (about 3 h at about 0° C.), the reaction mixture was transferred into a 1 M sodium hydroxide aqueous solution (11 g NaOH and 276 mL water) while keeping the contents at about 20-30° C. The resulting slurry was agitated at about 22° C. for 1.5 h and then filtered. The solids are rinsed with water (50 mL) and dried at about 50° C. under vacuum to yield 4-amino-7-iodopyrrolo[2,1-f][1,2,4]triazine as a solid. $^1$H NMR (400 MHz, DMSO-d6) δ 7.90 (s, 1H), 7.78 (br s, 2H), 6.98 (d, J=4.4 Hz, 1H), 6.82 (d, J=4.4 Hz, 1H). $^{13}$C NMR (101 MHz, DMSO-d6) δ 155.7, 149.1, 118.8, 118.1, 104.4, 71.9. MS m/z=260.97 [M+H].

Preparation (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol via (4-amino-7-iodopyrrolo[2,1-f][1,2,4]triazine)

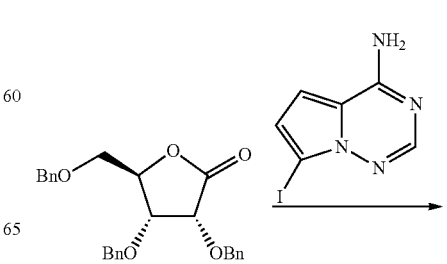

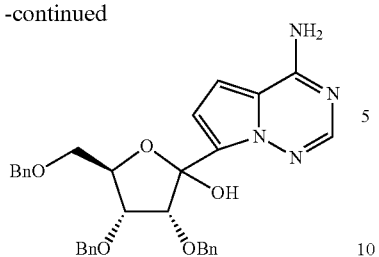

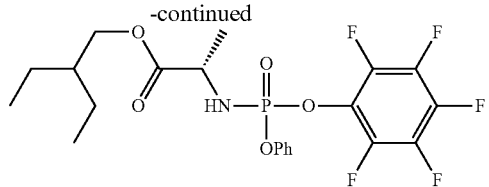

To a reactor under a nitrogen atmosphere was charged iodobase 2 (81 g) and THF (1.6 LV). The resulting solution was cooled to about 5° C., and TMSCl (68 g) was charged. PhMgCl (345 mL, 1.8 M in THF) was then charged slowly while maintaining an internal temperature at about ≤5° C. The reaction mixture was stirred at about 0° C. for 30 min, and then cooled to about −15° C. iPrMgCl-LiCl (311 mL, 1.1 M in THF) was charged slowly while maintaining an internal temperature below about −12° C. After about 10 minutes of stirring at about −15° C., the reaction mixture was cooled to about −20° C., and a solution of lactone 1 (130 g) in THF (400 mL) was charged. The reaction mixture was then agitated at about −20° C. for about 1 h and quenched with AcOH (57 mL). The reaction mixture was warmed to about 0° C. and adjusted to pH 7-8 with aqueous NaHCO$_3$ (5 wt %, 1300 mL). The reaction mixture was then diluted with EtOAc (1300 mL), and the organic and aqueous layers were separated. The organic layer was washed with 1N HCl (1300 mL), aqueous NaHCO$_3$ (5 wt %, 1300 mL), and brine (1300 mL), and then dried over anhydrous Na$_2$SO$_4$ and concentrated to dryness. Purification by silica gel column chromatography using a gradient consisting of a mixture of MeOH and EtOAc afforded the product.

Preparation ((2S)-2-ethylbutyl 2-(((perfluorophenoxy)(phenoxy)phosphoryl)amino)propanoate) (Mixture of Sp and Rp)

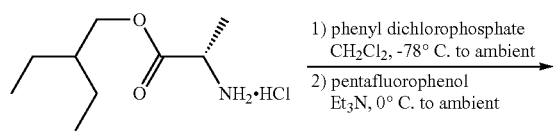

L-Alanine 2-ethylbutyl ester hydrochloride (5.0 g, 23.84 mmol) was combined with methylene chloride (40 mL), cooled to about −78° C., and phenyl dichlorophosphate (3.65 mL, 23.84 mmol) was added. Triethylamine (6.6 mL, 47.68 mmol) was added over about 60 min at about −78° C. and the resulting mixture was stirred at ambient temperature for 3 h. The reaction mixture was cooled to about 0° C. and pentafluorophenol (4.4 g, 23.84 mmol) was added. Triethylamine (3.3 mL, 23.84 mmol) was added over about 60 min. The mixture was stirred for about 3 h at ambient temperature and concentrated under reduced pressure. The residue was dissolved in EtOAc, washed with an aqueous sodium carbonate solution several times, and concentrated under reduced pressure. The residue was purified by silica gel column chromatography using a gradient of EtOAc and hexanes (0 to 30%). Product containing fractions were concentrated under reduced pressure to give (2S)-2-ethylbutyl 2-(((perfluorophenoxy)(phenoxy)phosphoryl)amino)propanoate as a solid. $^1$H NMR (400 MHz, Chloroform-d) δ 7.41-7.32 (m, 4H), 7.30-7.17 (m, 6H), 4.24-4.16 (m, 1H), 4.13-4.03 (m, 4H), 4.01-3.89 (m, 1H), 1.59-1.42 (m, 8H), 1.40-1.31 (m, 8H), 0.88 (t, J=7.5 Hz, 12H). $^{31}$P NMR (162 MHz, Chloroform-d) δ −1.52. $^{19}$F NMR (377 MHz, Chloroform-d) δ −153.63, −153.93 (m), −160.05 (td, J=21.9, 3.6 Hz), −162.65 (qd, J=22.4, 20.5, 4.5 Hz). MS m/z=496 [M+H].

Preparation of Title Compound (Mixture of Sp and Rp)

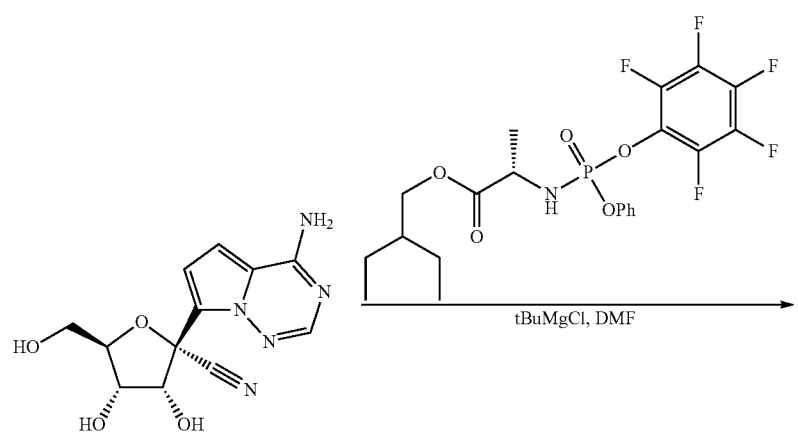

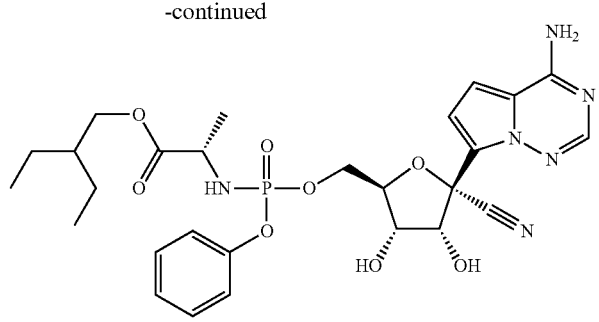

The nucleoside (29 mg, 0.1 mmol) and the phosphonamide (60 mg, 0.12 mmol) and N,N-dimethylformamide (2 mL) were combined at ambient temperature. Tert-Butyl magnesiumchloride (1M in THF, 0.15 mL) was slowly added. After about 1 h, the reaction was diluted with ethyl acetate, washed with aqueous citric acid solution (5% wt.), aqueous saturated NaHCO₃ solution and saturated brine solution. The organic phase was dried over Na₂SO₄ and concentrated under reduced pressure. The residue was purified by silica gel column chromatography using a gradient of methanol and CH₂Cl₂ (0 to 5%). Product containing fractions were concentrated under reduced pressure to provide the product.

Preparation of (3αR,4R,6R,6αR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile

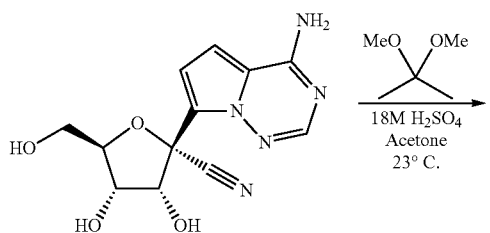

-continued

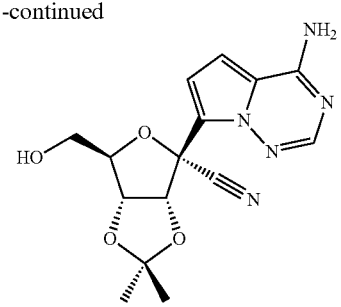

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (5.8 g, 0.02 mol), 2,2-dimethoxypropane (11.59 mL, 0.09 mol) and acetone (145 mL) at ambient temperature was added sulfuric acid (18M, 1.44 mL). The mixture was warmed to about 45° C. After about 30 min, the mixture was cooled to ambient temperature and sodium bicarbonate (5.8 g) and water 5.8 mL) were added. After 15 min, the mixture was concentrated under reduced pressure. The residue was taken up in ethyl acetate (150 mL) and water (50 mL). The aqueous layer was extracted with ethyl acetate (2×50 mL). The combined organic phase was dried over sodium sulfate and concentrated under reduced pressure to give crude (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. ¹H NMR (400 MHz, CD₃OD) δ 7.84 (s, 1H), 6.93 (d, J=4.6 Hz, 1H), 6.89 (d, J=4.6 Hz, 1H), 5.40 (d, J=6.7 Hz, 1H), 5.00 (dd, J=6.7, 3.3 Hz, 1H), 4.48-4.40 (m, 1H), 3.81-3.72 (m, 2H), 1.71 (s, 3H), 1.40 (s, 3H). MS m/z=332.23 [M+1].

Preparation of (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate

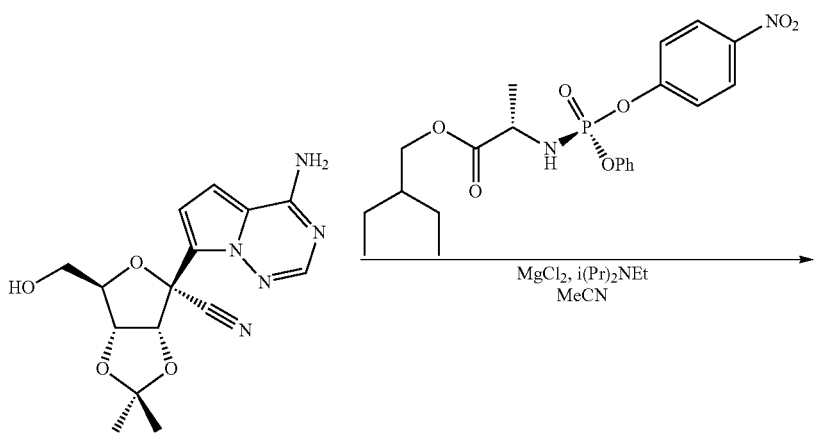

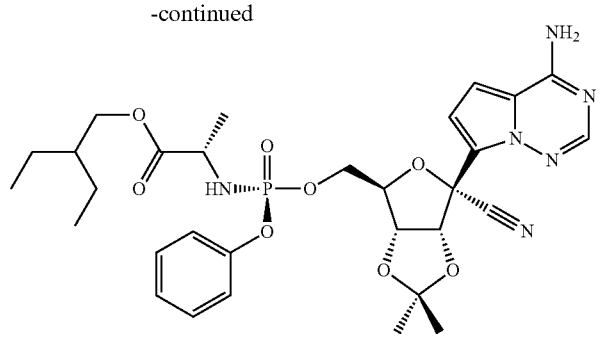

Acetonitrile (100 mL) was combined with (2S)-2-ethylbutyl 2-(((4-nitrophenoxy)(phenoxy)phosphoryl)-amino)propanoate (9.6 g, 21.31 mmol), the substrate alcohol (6.6 g, 0.02 mol), magnesium chloride (1.9 g, 19.91 mmol) at ambient temperature. The mixture was agitated for about 15 min and N,N-diisopropylethylamine (8.67 mL, 49.78 mmol) was added. After about 4 h, the reaction was diluted with ethyl acetate (100 mL), cooled to about 0° C. and combined with aqueous citric acid solution (5% wt., 100 mL). The organic phase was washed with aqueous citric acid solution (5% wt., 100 mL) and aqueous saturated ammonium chloride solution (40 mL), aqueous potassium carbonate solution (10% wt., 2×100 mL), and aqueous saturated brine solution (100 mL). The organic phase was dried with sodium sulfate and concentrated under reduced pressure to provide crude product. $^1$H NMR (400 MHz, CD$_3$OD) δ 7.86 (s, 1H), 7.31-7.22 (m, 2H), 7.17-7.09 (m, 3H), 6.93-6.84 (m, 2H), 5.34 (d, J=6.7 Hz, 1H), 4.98 (dd, J=6.6, 3.5 Hz, 1H), 4.59-4.50 (m, 1H), 4.36-4.22 (m, 2H), 4.02 (dd, J=10.9, 5.7 Hz, 1H), 3.91 (dd, J=10.9, 5.7 Hz, 1H), 3.83 (dq, J=9.7, 7.1 Hz, 1H), 1.70 (s, 3H), 1.50-1.41 (m, 1H), 1.39 (s, 3H), 1.36-1.21 (m, 7H), 0.86 (t, J=7.4 Hz, 6H). MS m/z=643.21 [M+1].

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 32)

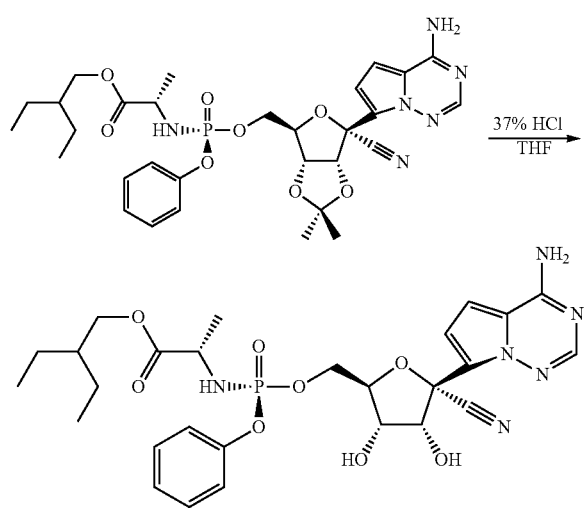

Compound 32

The crude acetonide (12.85 g) was combined with tetrahydrofuran (50 mL) and concentrated under reduced pressure. The residue was taken up in tetrahydrofuran (100 mL), cooled to about 0° C. and concentrated HCl (20 mL) was slowly added. The mixture was allowed to warm to ambient temperature. After consumption of the starting acetonide as indicated by HPLC analysis, water (100 mL) was added followed by aqueous saturated sodium bicarbonate solution (200 mL). The mixture was extracted with ethyl acetate (100 mL), the organic phase washed with aqueous saturated brine solution (50 mL), dried over sodium sulfated and concentrated under reduced pressure. The residue was purified by silica gel column chromatography using a gradient of methanol and ethyl acetate (0 to 20%). Product containing fractions were concentrated under reduced pressure to provide the product.

B. Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols:

| Virus | Cell Line | Plate Format | Cell Number | MOI (pfu/cell) | Incubation (Days) | Read Out | Values |
|---|---|---|---|---|---|---|---|
| Junin | Vero | 96 | 20,000 | 0.003 | 5 to 7 | Neutral red staining | EC50 |
| Junin | HeLa | 384 or 96 | 2,000 | 0.3 | 2 | HCS | |
| Lassa | HeLa | 384 or 96 | 2,000 | 0.3 | 2 | HCS | |

HCS: High content imaging
HeLa: Hela epithelial cell (cervical carcinoma)

Example 36. Lassa Virus and Junin Virus Antiviral Activity and Cytotoxicity Assays Antiviral activity of Compound 1, Compound 9, and Compound 32 was measured against Lassa virus (LASV) and Junin virus (JUNV). All studies conducted with wild-type virus were performed in biosafety level-4 containment (BSL-4) at the US Army Medical Research Institute for Infectious Diseases (USAMRIID). Antiviral Assays conducted with an attenuated strain of JUNV were conducted at Utah State University in a BSL-2 laboratory. Lassa virus antiviral assays were conducted HeLa cells. Junin virus antiviral assays were conducted in Vero and HeLa cells.

Antiviral assays were conducted in 384 or 96 well plates in BSL-4 containment using a high content imaging system to quantify virus antigen production as a measure of virus replication. A "no virus" control (Column 2) and a "1% DMSO" control (Column 3) were included on each plate to determine the 0% and 100% virus replication signal, respectively. The primary antibodies used for detection of viral antigens were mm L52-161-6 anti-GP; LASV and mm Y-GQC03_BF11 anti-GP; JUNV and DyLight 488 anti-mouse-IgG was used as the secondary detection antibody. The primary antibody was diluted 1000-fold in blocking buffer (1×PBS with 3% BSA) and added to each well of the assay plate. The assay plates were incubated for 60 minutes at room temperature. The primary antibody was removed and the cells were washed 3 times with 1×PBS. The secondary antibody was diluted 1000-fold in blocking buffer and was added to each well in the assay plate. The assay plates were incubated for 60 minutes at room temperature. Nuclei were stained using Draq5 (Biostatus, Shepshed Leicestershire, UK, Cat# DR05500) diluted in 1×PBS. Cell images were acquired using Perkin Elmer Opera confocal microscope (Perkin Elmer, Waltham, Mass.) using 10× air objective to collect five images per well. Virus-specific antigen was quantified by measuring fluorescence emission at a 488 nm wavelength and the nuclei were quantified by measuring fluorescence emission at a 640 nm wavelength. The Z' values for all antiviral assays were >0.3.

The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 37. Junin Virus Assay—Vero

Vero or Vero E6 cells were seeded in 96 well plates at 20,000 cells per well in 100 uL of MEM+2% FBS. Compounds diluted in DMSO were mixed with 120 uL of MEM+2% FBS. 100 uL of each test compound are transferred to 2 wells of a 96-well plate. 20 uL of virus solution in MEM+20% FBS are added so that final test concentrations are 47, 4.7, 0.47, 0.047 uM and the multiplicity of infection was 0.003 pfu/cell. Test plates were incubated until untreated virus controls approached maximum cytopathic effects (CPE) (5 to 7 days). Plates are then stained with neutral red dye for 2 hrs then eluted in Citrate/Ethanol buffer and read on a spectrophotometer at 540 nm. EC50 value is calculated by regression analysis as the concentration of test compound required to reduce viral-induced CPE by 50% measured by neutral red staining.

Example 38. Junin Virus Assay—HeLa

HeLa cells were seeded at 2000 cells per well in a 384 well plate and compounds were added to the assay plates as described in section 3.2.1. Assay plates were transferred to the BSL-4 suite and infected with 0.3 pfu per cell JUNV which resulted in ~50% of the cells expressing virus antigen in a 48 h period. The assay plates were incubated for 48 h and virus replication was quantified by immuno-staining using antibodies that recognized the viral glycoproteins.

Example 39. Lassa Virus Assay

HeLa cells were seeded at 2000 cells per well in a 384 well plate and compounds were added to the assay plates as described in section 3.2.1. Assay plates were transferred to the BSL-4 suite and infected with 0.1 pfu per cell LASV which resulted in >60% of the cells expressing virus antigen in a 48 h period. The assay plates were incubated for 48 h and virus replication was quantified by immuno-staining using antibodies that recognized the viral glycoproteins.

TABLE 2

Lassa Virus and Junin Virus antiviral assays
Table 2: In Vitro Antiviral Activity of Compounds 1, 9, and 32 against arenaviruses

| | | $EC_{50}$ (μM) | | | $EC_{90}$ (μM) | |
|---|---|---|---|---|---|---|
| Assay | | HCS | HCS | | HCS | HCS |
| Virus | Junin | Junin | Lassa | Junin | Junin | Lassa |
| Cell Line | Vero | HeLa | HeLa | Vero | HeLa | HeLa |
| Compound 1 | >47, 19 | N.D. | N.D | >47 | N.D. | N.D. |
| Compound 9 | >47 | 0.49 | 2.0 | >47 | 1.25 | 4.21 |
| Compound 32 | N.D. | 0.47 | 1.65 | N.D. | 1.26 | 3.31 |

N.D. not determined
JUNV = Junin virus,
LASV = Lassa virus

Example 40. MERS-CoV and SARS-CoV Antiviral Activity and Cytotoxicity Assays Antiviral activity of Compound 9 and Compound 32 was measured against MERS virus (MERS-CoV) and SARS virus (SARS-CoV).

Antiviral assays were conducted at USAMRIID and the University of North Carolina at Chapel Hill.

Example 41. MERS-CoV Antiviral Assay (USAMRIID)

Vero E6 cells seeded in 384-well plates and serial dilutions of Compound 32 or Compound 9 were added to the assay plates by direct titration using an HP D300 Digital Dispenser (Hewlett-Packard, Palo Alto, Calif.). The plates were transferred to the BSL-4 suite and infected with MERS-CoV (Strain Jordan N3) at a multiplicity of infection of 0.5 plaque forming unit (pfu) per cell. The infected cultures were incubated for 48 hours. The level of virus replication in compound-treated and control vehicle-treated cultures was determined by quantifying the level of virus-specific antigen following immuno-staining with antibody against the MERS-CoV spike (S) protein. The primary antibody (40069-RP02 rb-HCoV-EMC/2012 spike(S) protein) was diluted 1000-fold in blocking buffer (1× phosphate buffered saline (PBS) with 3% BSA) and added to each well of the assay plate. The assay plates were incubated for 60 minutes at room temperature. The primary antibody was removed and the cells were washed 3 times with 1×PBS. The secondary detection antibody was an anti-rabbit IgG conjugated with Dylight488 (Thermo Fisher Scientific, Waltham, Mass., Cat#405310). The secondary antibody was diluted 1000-fold in blocking buffer and was added to each well in the assay plate. The assay plates were incubated for 60 minutes at room temperature. Nuclei were stained using Draq5 (Biostatus, Shepshed Leicestershire, UK, Cat# DR05500) diluted in 1×PBS. The cells were counter-stained with CellMask Deep Red (Thermo Fisher Scientific, Waltham, Mass., Cat# C10046) to enhance detection of the cytoplasm compartment. Cell images were acquired using Perkin Elmer Opera confocal microscope (Perkin Elmer, Waltham, Mass.) using 10× air objective to collect 5 images per well. Virus-specific antigen was quantified by measuring fluorescence emission at a 488 nm wavelength and the nuclei were quantified by measuring fluorescence emission at a 640 nm wavelength. High content image analysis was performed to quantify the percent of infected cells and cell viability. Analysis of dose response to determine EC50 values was performed using GeneData Screener software applying Levenberg-Marquardt algorithm for curve fitting strategy.

Example 42. MERS-CoV and SARS-CoV Antiviral Assay

HAE cell cultures isolated from lung tissue were cultured for 6 weeks at the air liquid interface to promote differentiation. The apical surfaces of the HAE cultures were washed at 24 h and 1 h prior to infection with 1×PBS for >1 hour at 37° C. Recombinant MERS-CoV expressing red fluorescent protein (MERS-CoV RFP) and SARS-CoV expressing green fluorescent protein (SARS-CoV GFP) were used to apically infect the differentiated HAE cultures at a multiplicity of infection of 0.1 pfu per cell. To infect the HAE cultures, apical washes were removed, viral inoculum was added, and inoculated cultures were incubated at 37° C. for 2.5 hours. The inoculum was removed, and the apical surfaces of the HAE cultures were washed 3 times with 500 µL of 1×PBS to remove residual virus. Five 3-fold serial dilutions of Compound 9 starting at 10 µM were prepared in triplicate and added to HAE ALI media on the basolateral side of the culture approximately 30 minutes prior to infection. Virus replication was assessed by fluorescence imaging of cell cultures following a 48-hour incubation. In addition, virus replication was quantified by measuring the production of infectious virus in HAE apical washes by plaque assay on Vero cell monolayers and by quantifying viral RNA production from total cell RNA by real-time PCR assay.

TABLE 3

MERS antiviral assays
Table 3: In Vitro Antiviral Activity of Compound 32 against coronaviruses

| Assay | $EC_{50}$ (µM) |
|---|---|
| Virus | MERS-CoV |
| Cell Line | Vero |
| Compound 9 | 0.46 |
| Compound 32 | 0.58 |

MERS = Middle East Respiratory Syndrome

Example 43. MERS-CoV and SARS-CoV Real-Time PCR Assay

At 48 hours post-infection, primary HAE cultures from the antiviral assay described above were harvested in 500 µL TRIzol. RNA was purified using a Direct-zol RNA MiniPrep kit (Zymo Research Corporation, Irvine, Calif., USA). First-strand cDNA was generated for each sample using SuperScript III (Life Technologies, Grand Island, N.Y., USA) with incubation at 55° C. Following first-strand cDNA generation, ORF1 (genome RNA) and ORF8 or ORF9 (MERS-CoV and SARS-CoV subgenomic RNA, respectively) were quantified by real-time PCR using the following primers: MERS-CoV: Leader Forward (5'-GAA TAG CTT GGC TAT CTC AC-3' SEQ ID NO: 1), ORF1 Reverse (5'-CAC AAT CCC ACC AGA CAA-3' SEQ ID NO: 2), ORF8 Reverse (5'-TTG TTA TCG GCA AAG GAA AC-3' SEQ ID NO: 3); and SARS-CoV: Leader Forward (5'-AGC CAA CCA ACC TCG ATC TCT TGT-3' SEQ ID NO: 4), ORF1 Reverse (5'-TGA CAC CAA GAA CAA GGC TCT CCA-3' SEQ ID NO: 5), ORF9 Reverse (5'-ATT GGT GTT GAT TGG AAC GCC CTG-3' SEQ ID NO: 6). Reads were normalized to GAPDH using the following primers: GAPDH Forward (5'-TGC ACC ACC AAC TGC TTA GC-3' SEQ ID NO: 7) and GAPDH Reverse (5'-GGC ATG GAC TGT GGT CAT GAG-3' SEQ ID NO: 8). Results are expressed as log 10 fold changes in viral ORF1 and ORF8-encoding RNA (MERS-CoV)/and ORF9-encoding RNA (SARS-CoV) copy number in treated versus untreated cells using the ΔΔCt method 1104311.

Example 44. In Vitro Efficacy in Calu-3 2B4 Cells

At 48 hrs prior to infection, Calu-3 2B4 cells were plated in a 96-well black walled clear bottom plate at $5 \times 10^4$ cells/well. 24-hr prior to infection, culture medium was replaced. A 20 mM stock of Compound 32 was serially diluted in 100% DMSO in 3-fold increments to obtain a ten-point dilution series. MERS-nLUC was diluted in DMEM 10% FBS, and 1% antibiotics/antimycin to achieve a multiplicity of infection (MOI) of 0.08. Cells were infected in triplicate per drug dilution for 1 hr after which, virus was aspirated, cultures were rinsed once and fresh medium containing drug or vehicle was added. At 48 hrs post infection, virus replication was quantitated on a Spectramax (Molecular Devices) plate reader via nano-luciferase assay (Promega) according to the manufacturer's protocol. For our 100% inhibition control, diluted MERS-nLUC was exposed to short-wave UV light (LLC, Upland, Calif.) for 6 minutes to inhibit the ability of the virus to replicate. For our 0% inhibition control, cells were infected in the presence of vehicle. DMSO was kept constant in all conditions at 0.05% by volume (v/v). Values from triplicate wells per condition were averaged and compared to controls to generate a percent inhibition value for each drug dilution. The $EC_{50}$ value was defined as the concentration at which there was a 50% decrease in viral replication. Data were analyzed using GraphPad Prism 6.0 (La Jolla, Calif.). The $EC_{50}$ and $CC_{50}$ values were calculated by non-linear regression analysis using the dose-response (variable slope) equation (four parameter logistic equation): Y=Bottom+(Top-Bottom)/(1+ 10^((Log $EC_{50}$-X)*HillSlope)). The "Bottom" and "Top" values are defined by the minimum and maximum Y values. Hill slope is a parameter used to define the steepness of a dose-response curve. $EC_{50}$ and $CC_{50}$ values were calculated as an average of two to four independent experiments.

TABLE 4

Antiviral activity of Compound 1 and Compound 32 against MERS-CoV and SARS-CoV and cytotoxicity.

| | $EC_{50}$ (μM)[1] | | $CC_{50}$ (μM) |
|---|---|---|---|
| | MERS | SARS | |
| Compound 1 | 0.46 (HAE) | 0.22 (HAE) | >100 (HAE) |
| | — (Calu-3) | — (Calu-3) | >100 (Calu-3) |
| Compound 32 | 0.074 (HAE) | 0.069 (HAE) | >10 (HAE) |
| | 0.03 (Calu-3) | 0.01 (Calu-3) | >10 (Calu-3) |

[1]All values are averages from >3 independent experiments.
HAE = Human airway epithelial cell.
Calu-3 = human lung epithelial cell line Calu-3 (Calu3-2B4).
HAE studies were done from three donors.

Example 45. Evaluation of Subcutaneous Compound 32 Against Severe Acute Respiratory Syndrome Coronavirus (SARS-CoV) in Esterase Deficient (Ces1c−/−) Mice Male and female mice (25-28 week) genetically deleted for carboxylesterase 1C (Ces1c−/−) (Jackson Laboratories stock 014096). The (Ces1c−/−) mice were used since rodents express high levels of carboxylesterase activity in plasma relative to other animal species reducing the plasma half-life of Compound 32. Genetic deletion of carboxylesterase 1C improved the plasma stability of Compound 32 generating pharmacokinetic profiles similar to those observed in humans and other animal species.

The study design is captured in Table 4. Efficacy studies were performed in an animal biosafety level 3 (ABSL3) facility. All work was conducted under protocols approved by the Institutional Animal Care and Use Committee at UNC Chapel Hill according to guidelines set by the Association for the Assessment and Accreditation of Laboratory Animal Care (AAALAC) and the United States Department of Agriculture (USDA).

TABLE 4

Experimental Design (Subcutaneous Injection)

| Group | #Males/#Females | Treatment | Compound 32 Dose (mg/kg) | Timing and Duration | Challenge |
|---|---|---|---|---|---|
| 1 | 6/6 | Vehicle | 0 | Twice Daily, D −1 to D 5 | SARS-CoV |
| 2 | 4/4 | Compound 32 in vehicle | 25 | Twice Daily, D −1 to D 5 | |

TABLE 4-continued

Experimental Design (Subcutaneous Injection)

| Group | #Males/#Females | Treatment | Compound 32 Dose (mg/kg) | Timing and Duration | Challenge |
|---|---|---|---|---|---|
| 3 | 6/6 | Compound 32 in vehicle | 50 | Once Daily, D −1 to D 5 | |
| 4 | 1/2 | Vehicle | 0 | Twice Daily, D −1 to D 5 | No virus |
| 5 | 2/1 | Compound 32 in vehicle | 25 | Twice Daily, D −1 to D 5 | |

Groups 1 (vehicle), Group 2 (Compound 32 BID 25 mg/kg), and Group 3 (Compound 32 QD 50 mg/kg) were anaesthetized with ketamine/xylazine exposed to $10^4$ pfu of SARS-CoV/50 ul via the intranasal route. Group 4 (Vehicle) and Group 5 (Compound 32 BID 25 mg/kg) remained uninfected and were used as controls for whole body plethysmography evaluations. Vehicle comprised 12% sulfobutylether-β-cyclodextin in water (with HCl/NaOH) at pH 5.0). On day 0, animals were exposed to virus. On days 2 and 5 post infection, groups of animals were euthanized by isofluorane overdose and the large left lobe of the lung was placed in a 2 mL screw cap tube with 1 mL DPBS with glass beads and frozen at −80° C. until analyzed by plaque assay. The inferior right lobe was placed in 10% buffered formalin and stored at 4° C. until histological analysis.

Changes in lung function were determined by whole body plethysmography (WBP, Buxco lung function testing system, Data Sciences International). After a 30-minute acclimation in the plethysmograph chamber, 11 respiratory responses and several quality control metrics were continually measured every 2-second for 5 minutes for a total of 150 data points. Mean values for each parameter were determined within DSI Finepoint software.

Histological analysis was performed on formalin fixed samples and paraffin embedded tissues with 5 μm. To assess lung pathology, sections were stained with hematoxylin and eosin. Viral antigen in the lung was stained using polyclonal anti-nucleocapsid antibody (Imgenex). Slides were blinded to the evaluator and assessed for virus associated lung pathology as well as spatial location and prevalence of viral antigen. Images were captured using an Olympus BX41 microscope equipped with an Olympus DP71 camera.

Viral plaque assay was used to quantify infectious virus from frozen lung tissue. Vero E6 cells were seeded in 6-well plates at $5 \times 10^5$ cells/well. Lung tissue was thawed, homogenized via Roche Magnalyzer, and the tissue suspension was serially diluted and the dilutions used to infect the Vero E6 cells. At 72 h post-infection, the plates were fixed and stained and the number of plaques quantified by visual inspection.

The primary endpoint for this study was viral load in lung tissue at Day 5 post-infection. Additional endpoints included changes in animal body weight and lung function. Animal body weight was recorded daily for the duration of the in-life phase. On day −1, 1, 2, 3, and 5 after inoculation, whole body plethysmography was performed to assess lung function. On Day 5, a scheduled necropsy was performed on all remaining animals; gross lung pathology was evaluated by a board-certified veterinary pathologist. Lung tissue was collected for histopathological and virological analysis.

Figure 2A:
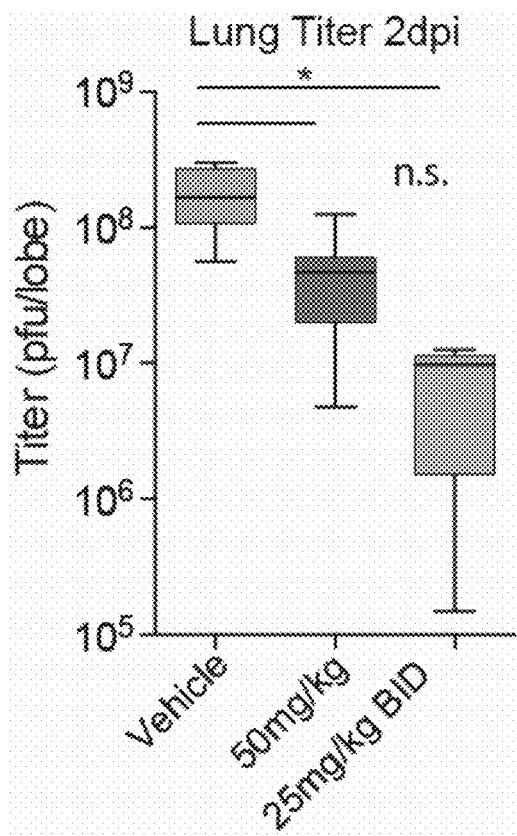
Figure 2B:
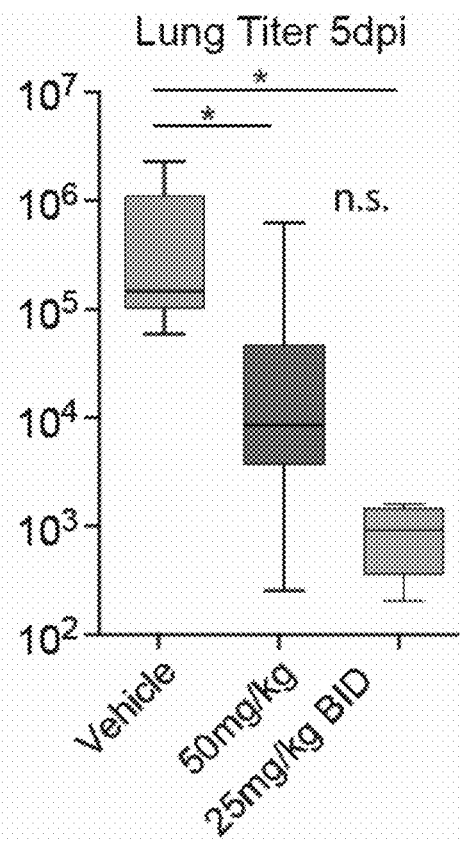

Body Weight and Viral Load:

Changes in body weight and tissue viral load for each study group at Day 5 are shown in FIG. 1, FIG. 2A and FIG. 2B. As shown in FIG. 1, animals treated with Compound 32 displayed no evidence of weight loss associated with SARS-CoV infection compared to vehicle-treated animals. Infectious virus was measured in lung tissue collected at necropsy by plaque assay. As shown in FIG. 2A and FIG. 2B, infectious virus was significantly decreased in Compound 32-treated animals at Day 2 and Day 5 post-infection relative to vehicle-treated animals. These data suggest that Compound 32 reduces replication of SARS-CoV in the lung.

Lung Function Measurements:

The effect of Compound 32 treatment on pulmonary function in SARS-CoV infected mice was evaluated by whole body plethysmography (WBP) (FIG. 3A, FIG. 3B, FIG. 3C, FIG. 3D, FIG. 3E, and FIG. 3F). WBP showed an increase in Penh values in vehicle treated mice suggesting that virus replication in the lung increased airway resistance. In animals treated with either 25 mg/kg of Compound 32 twice per day or 50 mg/kg of Compound 32 once per day, Penh values were lower compared to vehicle-treated animals and were more similar to mock-infected animals.

In vehicle-treated mice infected with SARS-CoV the length of time to release a breath (Expiration Time) or time between breaths (End Expiratory Pause) measured by WBP increased indicating labored breathing. As shown in FIG. 3A, FIG. 3B, FIG. 3C, FIG. 3D, FIG. 3E, and FIG. 3F, these breathing parameters were reduced in Compound 32-treated animals approaching values obtained from mock-infected animals.

Example 46. A Blinded, Randomized, Vehicle-Controlled Evaluation of Intravenous Compound 32 Against Middle East Respiratory Syndrome Coronavirus (MERS-CoV) in Rhesus Monkeys MERS-CoV isolate HCoV-EMC/2012 was used for the challenge virus at the Test Facility. MERS-CoV isolate HCoV-EMC/2012 was provided by the Viroscience Laboratory, Erasmus Medical Center, Rotterdam, The Netherlands, and propagated in VeroE6 cells in DMEM (Sigma) supplemented with 2% (vol/vol) FCS (Logan), 1 mM L-glutamine (Lonza), 50 U/mL penicillin, and 50 µg/mL streptomycin (Gibco). Experimentally naïve male rhesus monkeys were randomly assigned to treatment groups and balanced by body weight.

The study design is captured in Table 5.

TABLE 5

Experimental Design (Intervenous)

| Group | #Males/#Females | Treatment | Compound 32 Dose (mg/kg) | Timing and Duration* | Challenge |
|---|---|---|---|---|---|
| 1 | 6/0 | Vehicle | 0 | Once Daily, D −1 to D6 | MERS-CoV |
| 2 | 6/0 | Compound 32 in vehicle | 10 | Once Daily, D −1 to D6 | |

All animals were exposed to a target dose of $7 \times 10^6$ plaque forming units MERS-CoV virus diluted in 0.9% sodium chloride for inoculation. The animals were inoculated by multiple routes that included intranasal, ocular, and intratrachial administration. The day on which animals were challenged was designated as Day 0.

Methods to control bias included experimental blinding. Specifically, study personnel who administered Compound 32 or vehicle treatments or routinely evaluated animal health were experimentally blinded to the group assignment of all animals for the duration of the in-life phase. Unblinded personnel, who were not responsible for evaluating animal health, prepared individual doses from bulk ready-to-use formulations provided by the Sponsor. Vehicle and Compound 32 formulations were identical in physical appearance.

In Groups 1 and 2, once-daily vehicle treatment was administered for 7 days beginning on Day −1 (one day prior to virus exposure). Each dose of Compound 32 or vehicle was administered as a single bolus slow IV injection in the saphenous vein at a volume of 2.0 mL/kg body weight over the course of 1 to 2 min. Doses were administered to animals anesthetized using IM injection of a solution containing ketamine (100 mg/mL) and acepromazine (10 mg/mL) at a volume of 0.1 mL/kg body weight. The weight of each animal was obtained on Day −7, and these weights were used for dose volume determination for all administered doses of Compound 32 or vehicle.

The primary endpoint for this study was viral load in lung tissue at Day 6 post-infection. Animal health was monitored at least twice daily for the duration of the in-life phase and clinical disease signs were recorded. On day−7, 0, 1, 3, 5 and 6 after inoculation, clinical exams were performed on all animals to determine bodyweight, body temperature, respirations/minute (under anesthesia), and to collect x-rays, nose and throat swabs. Whole blood and serum were collected for hematology, biochemistry and cytokine analysis. On Day 6, a scheduled necropsy was performed on all animals; gross lung pathology was scored (as % of lung lobe affected by gross lesions) by a board-certified veterinary pathologist and lung weight was recorded to determine the lung weight/body weight ratio. Nineteen tissues were collected for histopathological and virological analysis Disease signs in vehicle-treated animals were attributed to MERS-COV infection. Cumulative clinical scores were notably higher in vehicle-treated animals compared to Compound 32-treated animals. These disease symptoms were less pronounced in the Compound 32-treated animals.

Figure 4A:
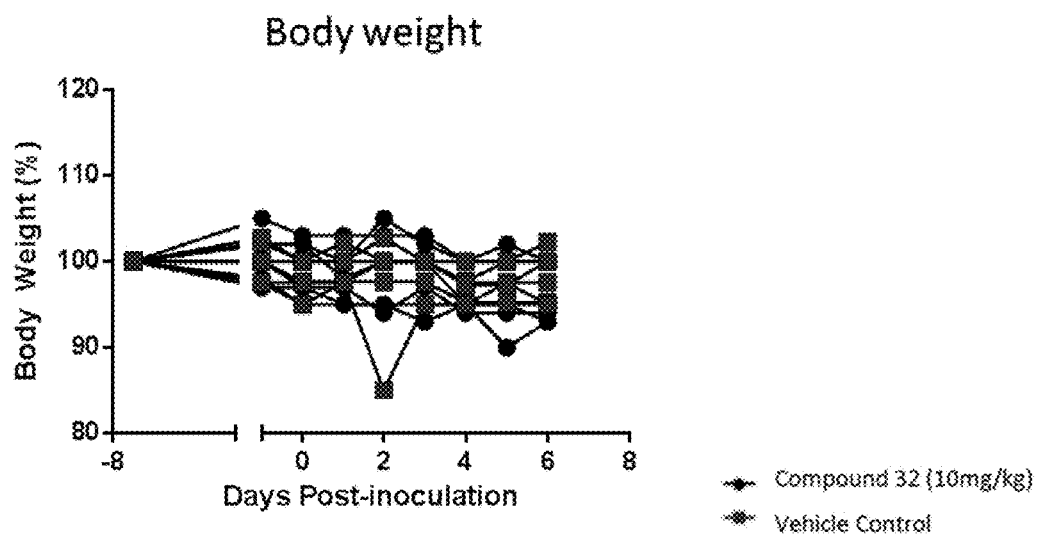
Figure 4B:
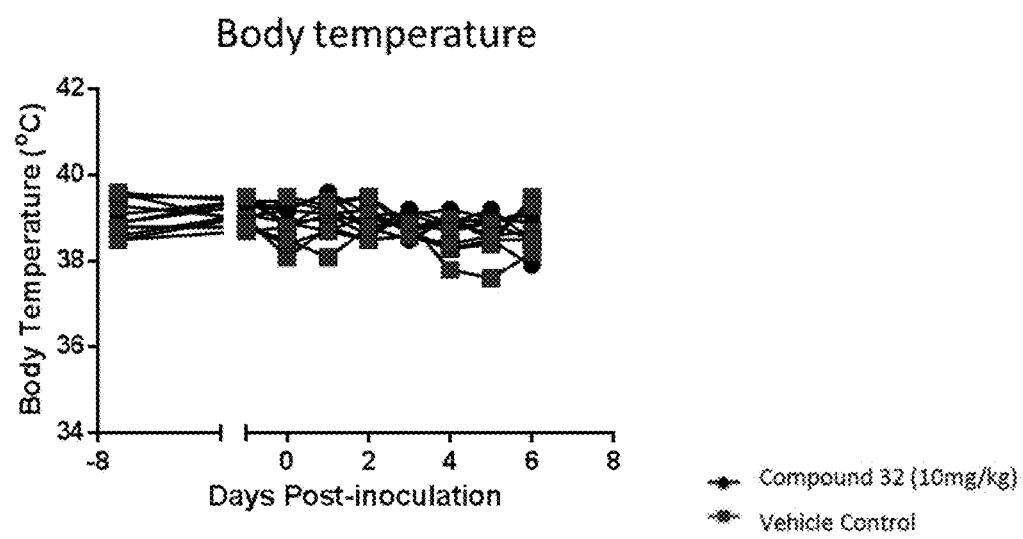
Figure 4C:
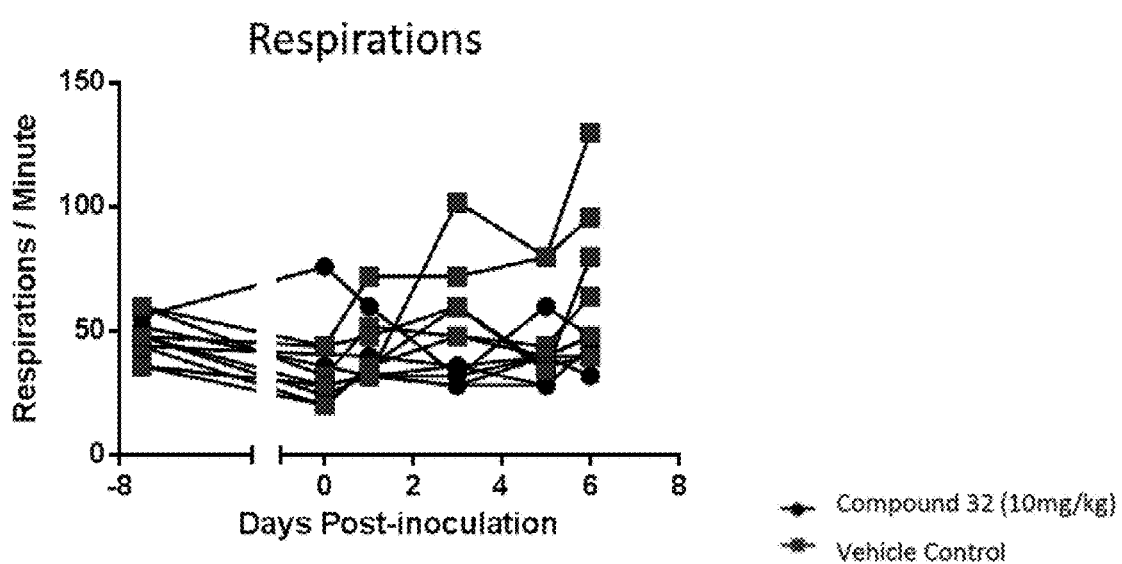

Body Weight and Viral Load:

Changes in body weight, temperature and respiration are shown in FIG. 4A, FIG. 4B, and FIG. 4C. The body weight and body temperature did not change appreciably during the course of the infection in the presence or absence of Compound 32 treatment. Respiration rates increased over the course of infection and tended to be higher at Day 6 in vehicle-treated animals compared to Compound 32-treated animals.

Figure 5:
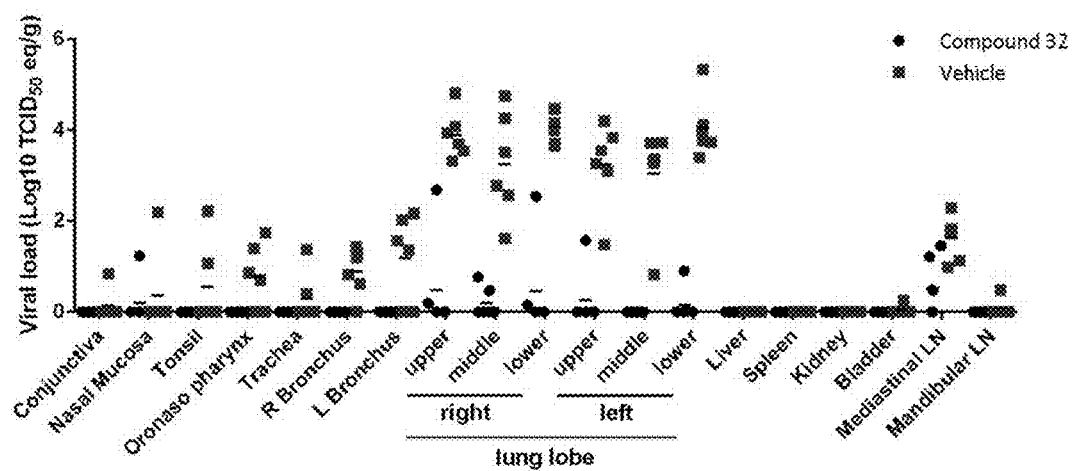

Tissue Viral Load:

Viral RNA was measured in lung tissue and other organs collected at necropsy. Changes in tissue viral RNA concentrations for each study group at Day 6 are shown in FIG. 5. Virus was detected in all respiratory tract tissues in vehicle-treated animals. Viral RNA in the respiratory tract was significantly reduced in Compound 32-treated animals. Viral RNA was below the limit of detection in treated and untreated animals in the liver, spleen, kidney and bladder tissue. Viral RNA was detected in all animals in the mediastinal lymph node, but in only one vehicle-treated animal in the mandibular lymph node.

Virus was detected in nose swabs and throat swabs at Day 1, 3, 5 and 6 post-infection There was no difference in viral load between vehicle-treated and Compound 32-treated animals. Viral RNA was detected in one vehicle-treated animal in the urine collected at Day 6. The changes in white blood cell counts, neutrophils and lymphocytes are shown in FIG. 5.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A method for treating an Arenaviridae infection in a human in need thereof comprising administering to the human a therapeutically effective amount of a compound of Formula I:

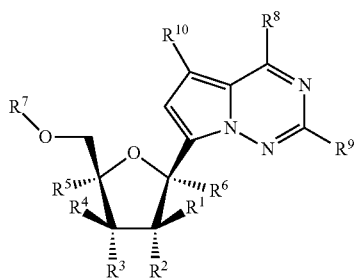

Formula I or a pharmaceutically acceptable salt or ester, thereof; wherein:

each $R^1$ is H or halogen;

each $R^2$, $R^3$, $R^4$ and $R^5$ is independently H, $OR^a$, $N(R^a)_2$, $N_3$, CN, $NO_2$, $S(O)_nR^a$, halogen, ($C_1$-$C_8$)alkyl, ($C_4$-$C_8$) carbocyclylalkyl, ($C_1$-$C_8$)substituted alkyl, ($C_2$-$C_8$)alkenyl, ($C_2$-$C_8$)substituted alkenyl, ($C_2$-$C_8$)alkynyl or ($C_2$-$C_8$)substituted alkynyl;

or any two $R^2$, $R^3$, $R^4$ and $R^5$ on adjacent carbon atoms when taken together are —O(CO)O— or when taken together with the ring carbon atoms to which they are attached form a double bond;

$R^6$ is $OR^a$, $N(R^a)_2$, $N_3$, CN, $NO_2$, $S(O)_nR^a$, —C(=O)$R^{11}$, —C(=O)O$R^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), —SO$_2$NR$^{11}$R$^{12}$, halogen, ($C_1$-$C_8$)alkyl, ($C_4$-$C_8$)carbocyclylalkyl, ($C_1$-$C_8$)substituted alkyl, ($C_2$-$C_8$) alkenyl, ($C_2$-$C_8$)substituted alkenyl, ($C_2$-$C_8$)alkynyl, ($C_2$-$C_8$)substituted alkynyl, or ($C_6$-$C_{20}$)aryl($C_1$-$C_8$) alkyl;

$R^7$ is selected from the group consisting of a) H, —C(=O)$R^{11}$, —C(=O)O$R^{11}$, —C(=O) NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), or —SO$_2$NR$^{11}$R$^{12}$, b) 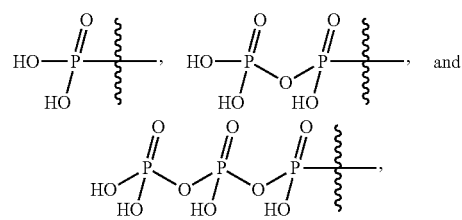

c) 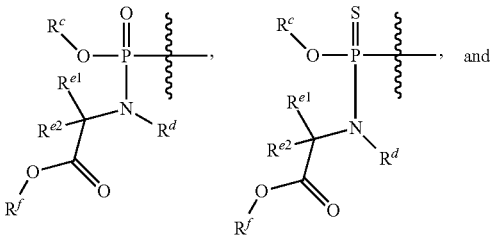

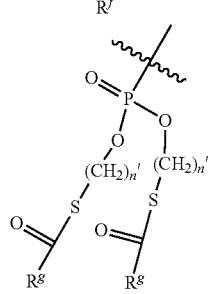

wherein:
R$^c$ is selected from phenyl, 1-naphthyl, 2-naphthyl,

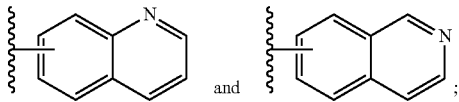

R$^d$ is H or CH$_3$;
R$^{e1}$ and R$^{e2}$ are each independently H, (C$_1$-C$_6$) alkyl or benzyl;
R$^f$ is selected from H, (C$_1$-C$_8$)alkyl, benzyl, (C$_3$-C$_6$)cycloalkyl, and —CH$_2$—(C$_3$-C$_6$)cycloalkyl;
R$^g$ is selected from (C$_1$-C$_8$)alkyl, —O—(C$_1$-C$_8$) alkyl, benzyl, —O-benzyl, —CH$_2$—(C$_3$-C$_6$)cycloalkyl, —O—CH$_2$—(C$_3$-C$_6$)cycloalkyl, and CF$_3$; and
n' is selected from 1, 2, 3, and 4; and d) a group of formula:

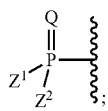

wherein:
Q is O, S, NR, $^+$N(O)(R), N(OR), $^+$N(O)(OR), or N—NR$_2$;
Z$^1$ and Z$^2$, when taken together, are -Q$^1$(C(R$^y$)$_2$)$_3$Q$^1$-;
wherein
each Q$^1$ is independently O, S, or NR; and
each R$^y$ is independently H, F, Cl, Br, I, OH, R, —C(=Q$^2$)R, —C(=Q$^2$)OR, —C(=Q$^2$)N(R)$_2$, —N(R)$_2$, —$^+$N(R)$_3$, —SR, —S(O)R, —S(O)$_2$R, —S(O)(OR), —S(O)$_2$(OR), —OC(=Q$^1$)R, —OC(=Q$^2$)OR, —OC(=Q$^2$)(N(R)$_2$), —SC(=Q$^2$)R, —SC(=Q$^2$)OR, —SC(=Q$^2$)(N(R)$_2$), —N(R)C(=Q$^2$)R, —N(R)C(=Q$^2$)OR, —N(R)C(=Q$^2$)N(R)$_2$, —SO$_2$NR$_2$, —C≡N, —N$_3$, —NO$_2$, —OR, or Z$^3$; or when taken together, two R$^y$ on the same carbon atom form a carbocyclic ring of 3 to 7 carbon atoms;
each Q$^2$ is independently, O, S, NR, $^+$N(O)(R), N(OR), $^+$N(O)(OR), or N—NR$_2$; or
Z$^1$ and Z$^2$ are each, independently, a group of Formula Ia:

Formula Ia

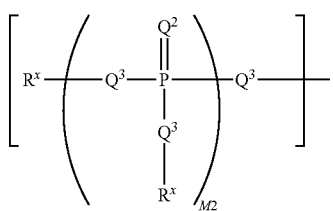

wherein:
each Q$^3$ is independently a bond, O, CR$_2$, NR, $^+$N(O)(R), N(OR), $^+$N(O)(OR), N—NR$_2$, S, S—S, S(O), or S(O)$_2$;
M2 is 0, 1 or 2;
each R$^x$ is independently R$^y$ or a formula:

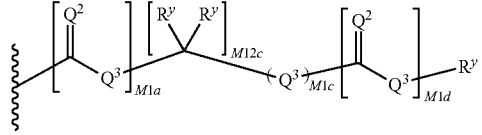

wherein:
each M1a, M1c, and M1d is independently 0 or 1;
M12c is 0, 1, 2, 3, 4, 5, 6, 7, 8, 9, 10, 11 or 12;
Z$^3$ is Z$^4$ or Z$^5$;
Z$^4$ is R, —C(Q$^2$)R$^y$, —C(Q$^2$)Z$^5$, —SO$_2$R$^y$, or —SO$_2$Z$^5$; and
Z$^5$ is a carbocycle or a heterocycle wherein Z$^5$ is independently substituted with 0 to 3 R$^y$ groups;
R$^8$ is halogen, NR$^{11}$R$^{12}$, N(R$^{11}$)OR$^{11}$, NR$^{11}$N$^{11}$R$^{12}$, N$_3$, NO, NO$_2$, CHO, CN, —CH(=NR$^{11}$), —CH=NNHR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl, (C$_6$-C$_{20}$)aryl(C$_1$-C$_8$)alkyl, OR$^{11}$ or SR$^{11}$;
each R$^9$ and R$^{10}$ is independently H, halogen, NR$^{11}$R$^{12}$, N(R$^{11}$)OR$^{11}$, NR$^{11}$NR$^{11}$R$^{12}$, N$_3$, NO, NO$_2$, CHO, CN, —CH(=NR$^{11}$), —CH=NHNR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, R$^{11}$, OR$^{11}$ or SR$^{11}$;
each R$^{11}$ and R$^{12}$ is independently H, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl or (C$_6$-C$_{20}$)aryl(C$_1$-C$_8$)alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S— or —NR$^a$—;
each R$^a$ is independently H, (C$_1$-C$_8$)alkyl, (C$_2$-C$_8$)alkenyl, (C$_2$-C$_8$)alkynyl, (C$_6$-C$_{20}$)aryl(C$_1$-C$_8$)alkyl, (C$_4$-C$_8$)carbocyclylalkyl, —C(=O)R, —C(=O)OR, —C(=O)NR$_2$, —C(=O)SR, —S(O)R, —S(O)$_2$R, —S(O)(OR), —S(O)$_2$(OR), or —SO$_2$NR$_2$; wherein
each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, (C$_6$-C$_{20}$)aryl, (C$_6$-C$_{20}$)substituted aryl, (C$_2$-C$_{20}$)heterocyclyl, (C$_2$-C$_{20}$)substituted heterocyclyl, (C$_6$-C$_{20}$)aryl(C$_1$-C$_8$)alkyl or substituted (C$_6$-C$_{20}$)aryl(C$_1$-C$_8$)alkyl;
each n is independently 0, 1, or 2; and
wherein each (C$_1$-C$_8$)alkyl, (C$_2$-C$_8$)alkenyl, (C$_2$-C$_8$) alkynyl or (C$_6$-C$_{20}$)aryl(C$_1$-C$_8$)alkyl of each R$^2$, R$^3$, R$^5$, R$^6$, R$^{11}$ and R$^{12}$ is, independently, optionally substituted with one or more halo, hydroxy, CN, N$_3$, N(R$^a$)$_2$ or OR$^a$; and wherein one or more of the non-terminal carbon atoms of each said (C₁-C₈)alkyl may be optionally replaced with —O—, —S— or —NR$^a$—.

2. The method of claim 1 wherein the compound is a compound of Formula IV:

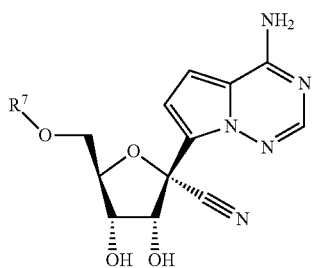

Formula IV or a pharmaceutically acceptable salt or ester, thereof.

3. The method of claim 1 wherein R$^7$ is H.

4. The method of claim 1 wherein R$^7$ is selected from the group consisting of a) H, —C(=O)R$^{11}$, —C(=O)OR$^{11}$, —C(=O)NR$^{11}$R$^{12}$, —C(=O)SR$^{11}$, —S(O)R$^{11}$, —S(O)₂R$^{11}$, —S(O)(OR$^{11}$), —S(O)₂(OR$^{11}$), —SO₂NR$^{11}$R$^{12}$, b) 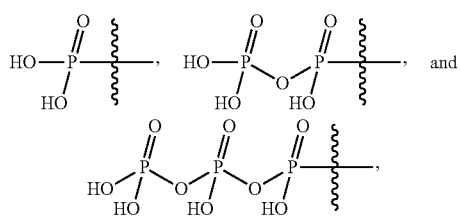

c) 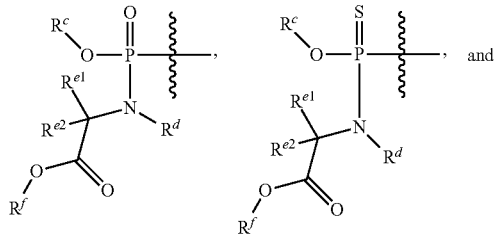

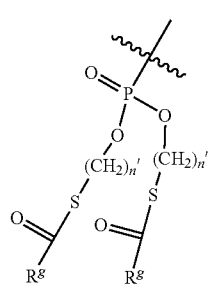

wherein:

R$^c$ is selected from phenyl, 1-naphthyl, 2-naphthyl,

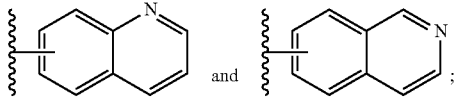

R$^d$ is H or CH₃;
R$^{e1}$ and R$^{e2}$ are each independently H or C₁-C₆ alkyl;
R$^f$ is selected from H, C₁-C₈ alkyl, benzyl, C₃-C₆ cycloalkyl, and —CH₂—C₃-C₆ cycloalkyl;
R$^g$ is selected from C₁-C₈ alkyl, —O—C₁-C₈ alkyl, benzyl, —O-benzyl, —CH₂—C₃-C₆ cycloalkyl, —O—CH₂—C₃-C₆ cycloalkyl, and CF₃; and
n' is selected from 1, 2, 3, and 4.

5. The method of claim 1 wherein R$^7$ is

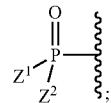

wherein Z$^1$ and Z$^2$ are each, independently, a group of structure:

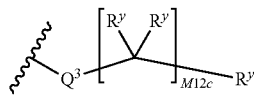

and Z$^3$ is Z$^5$.

6. The method of claim 1 wherein R$^7$ is

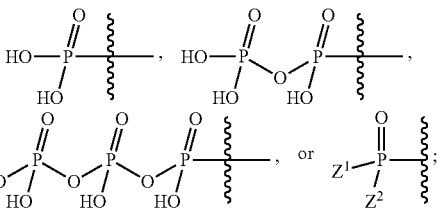

wherein Z$^1$ and Z$^2$ are each, independently, a group having the structure:

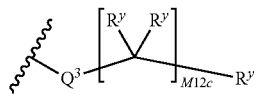

and Z$^3$ is Z$^5$.

7. The method of claim 1 wherein R$^7$ is

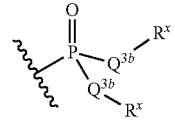

wherein each Q$^{3b}$ is, independently, O or N(R).

8. The method of claim 7 wherein each Q$^{3b}$ is O and each R$^x$ is independently:

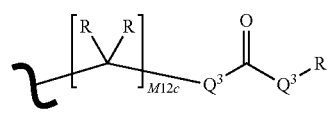

wherein M12c is 1, 2 or 3 and each $Q^3$ is independently a bond, O, $CR_2$, or S.

9. The method of claim 1 wherein $R^7$ is

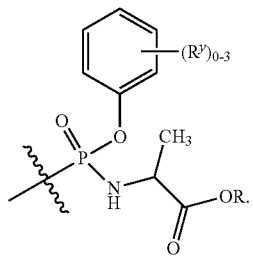

10. The method of claim 1 wherein $R^7$ is

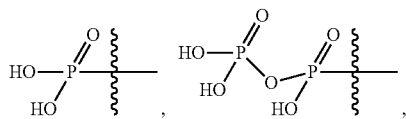

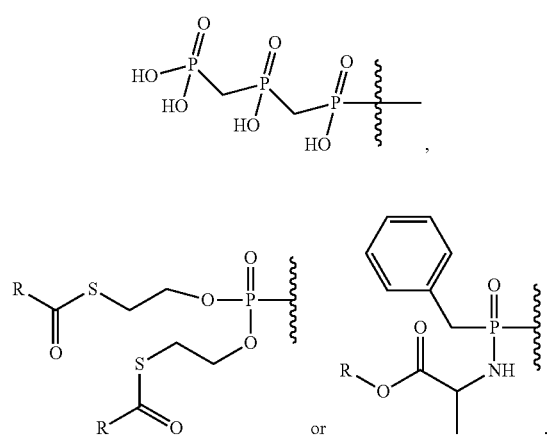

11. The method of claim 1 wherein $R^7$ is

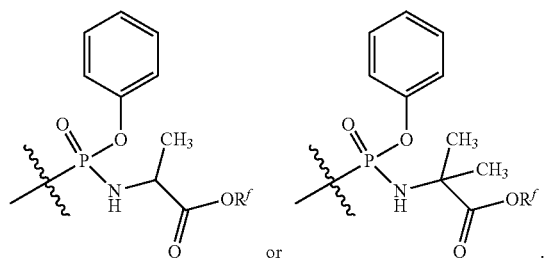

12. The method of claim 11 wherein $R^f$ is $C_1$-$C_8$ alkyl.

13. The method of claim 1 wherein $R^7$ is

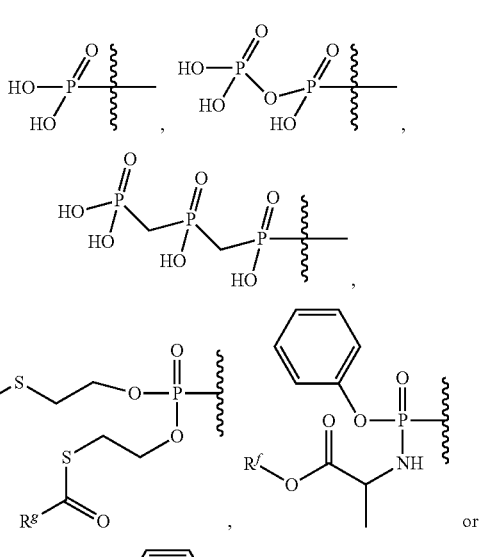

14. The method of claim 1 wherein $R^7$ is

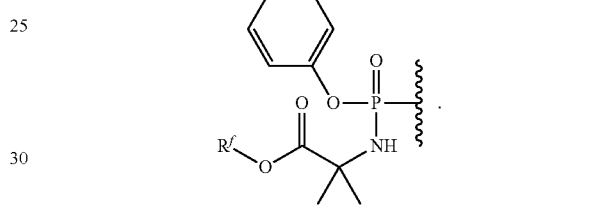

15. The method of claim 14 wherein $R^f$ is $C_1$-$C_8$ alkyl.
16. The method of claim 14 wherein $R^f$ is $C_1$-$C_6$ alkyl.
17. The method of claim 1 wherein $R^7$ is:

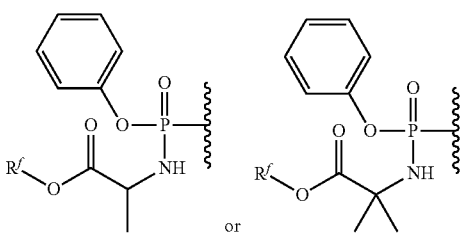

18. The method of claim 17 wherein $R^g$ is $C_1$-$C_8$ alkyl.
19. The method of claim 18 wherein $R^g$ is $C_1$-$C_6$ alkyl.
20. The method of claim 1 wherein $R^7$ is selected from the group consisting of:

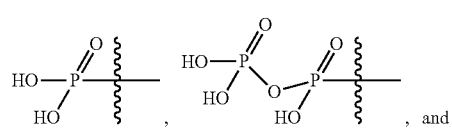, and
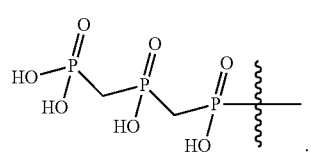
21. The method of claim 1 wherein $R^7$ is
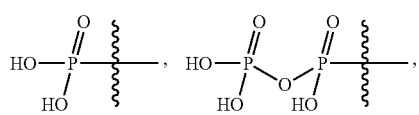
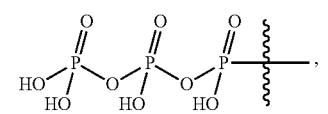
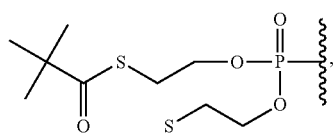
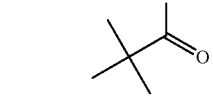
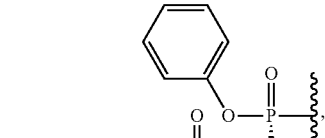
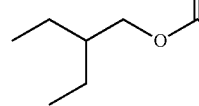
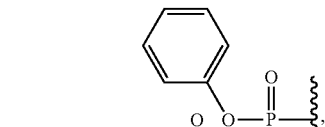
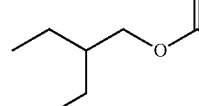 or 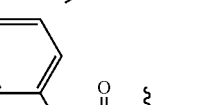
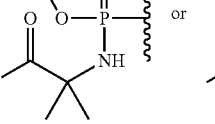
22. The method of claim 1 wherein the compound is:
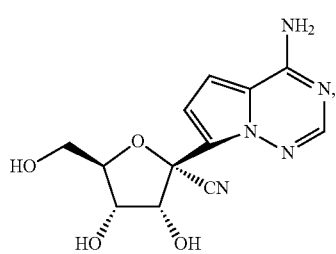
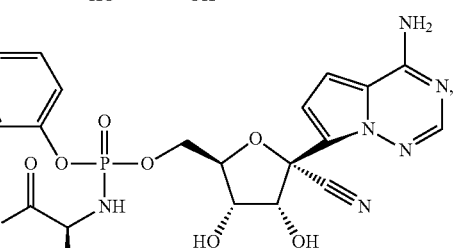
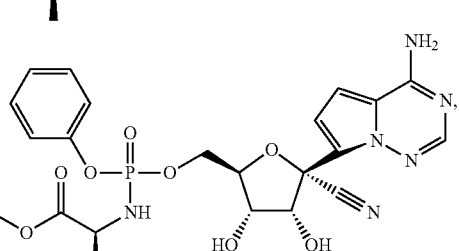
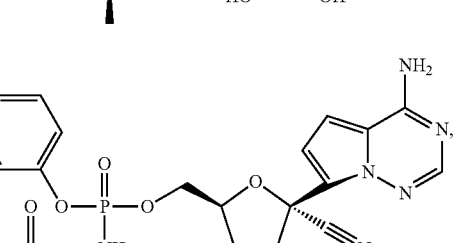
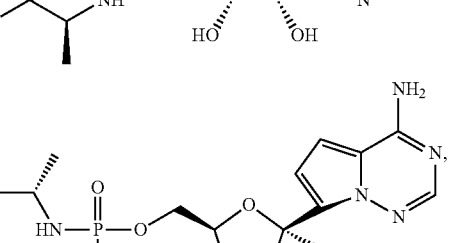
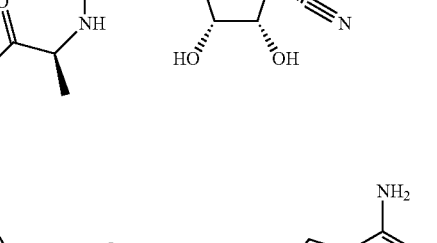, or
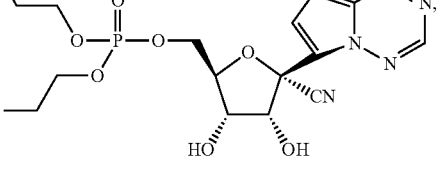

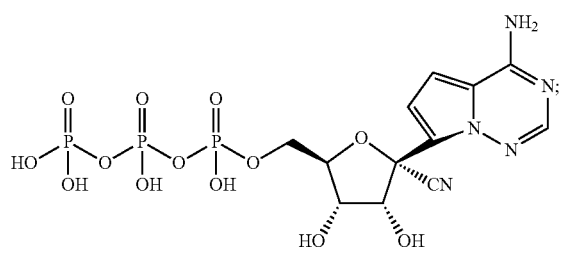 [SMILES: N#C[C@@]1(c2ccc3c(N)ncnn23)O[C@H](COP(=O)(O)OP(=O)(O)OP(=O)(O)O)[C@@H](O)[C@H]1O]
or a pharmaceutically acceptable salt or ester thereof.
23. The method of claim 1 wherein the compound is:
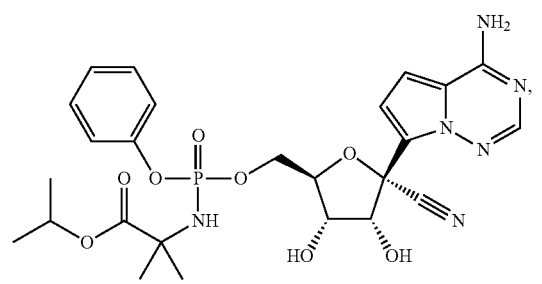
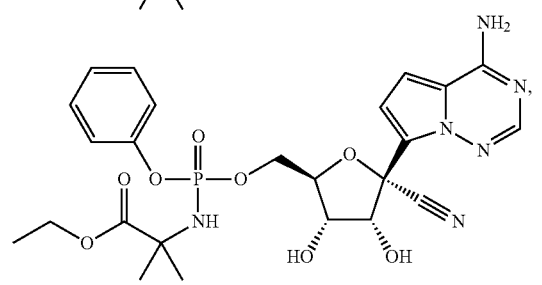
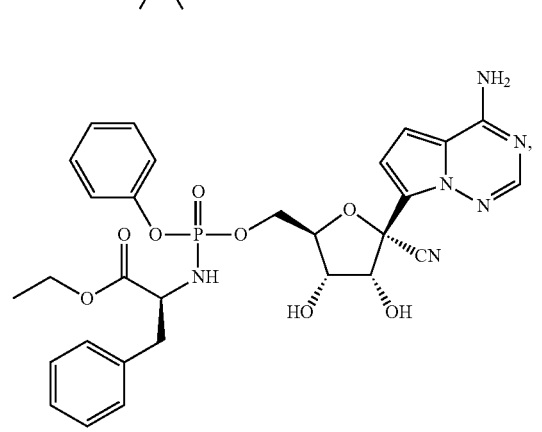
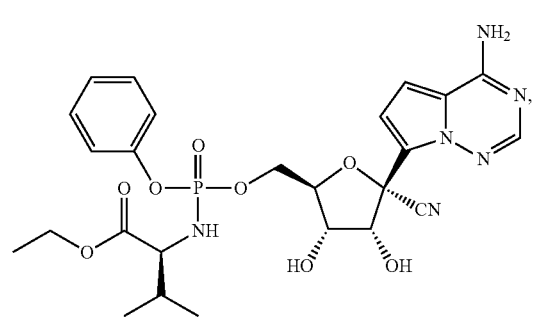
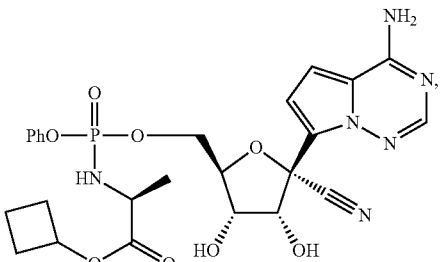
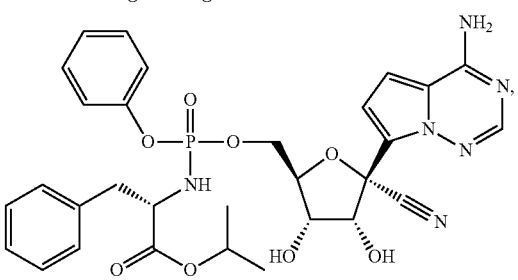
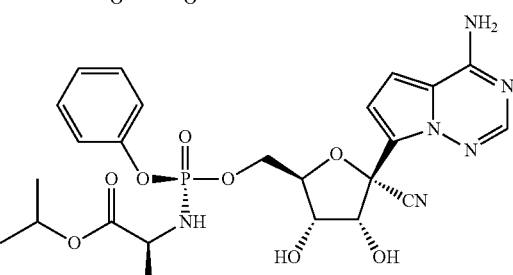
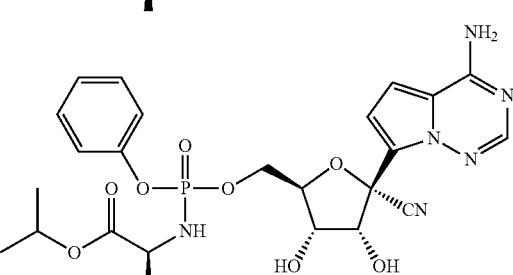
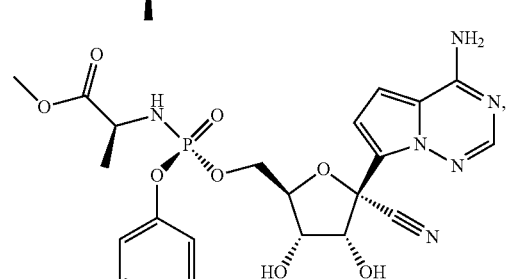
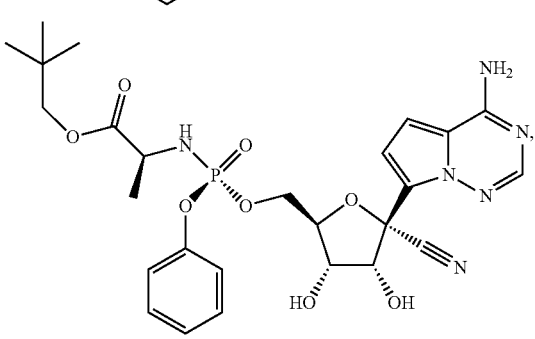

187
-continued
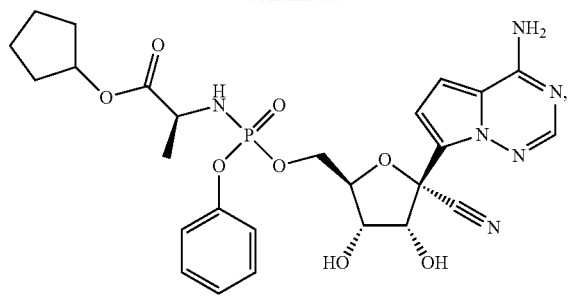
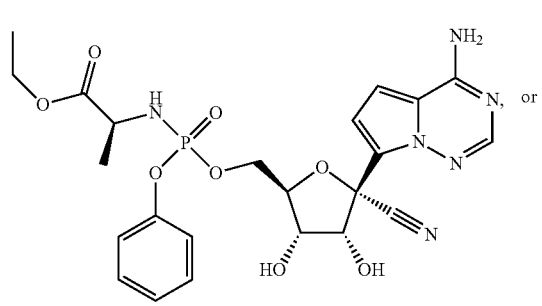
or
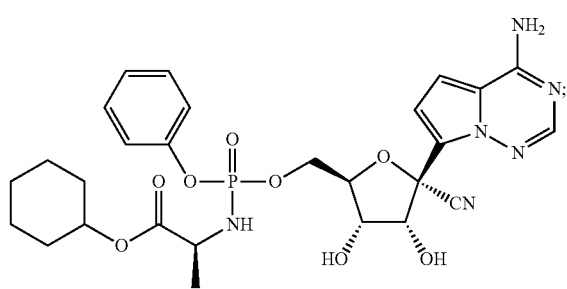
or a pharmaceutically acceptable salt or ester thereof.
24. The method of claim 1 wherein the compound is:
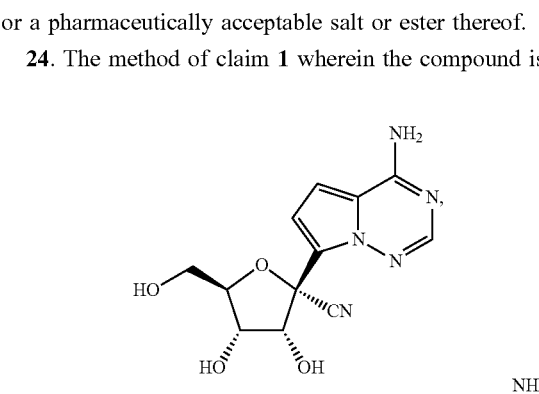
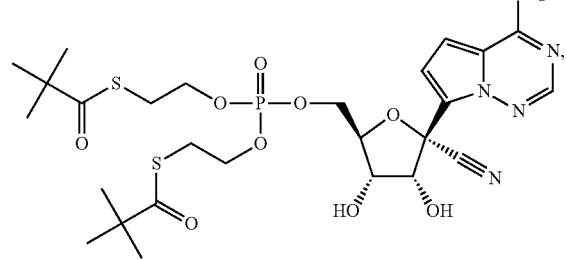
188
-continued
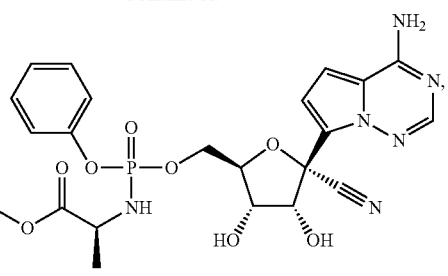
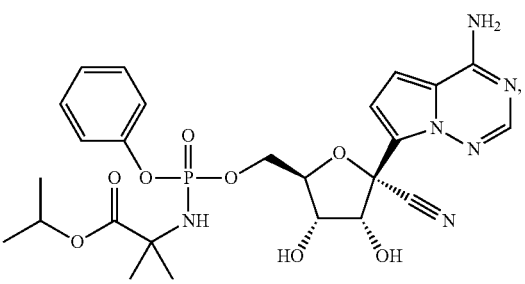
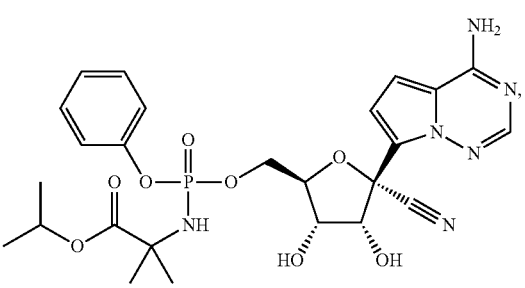
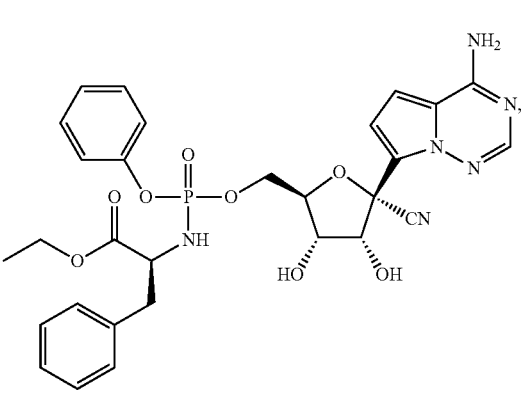
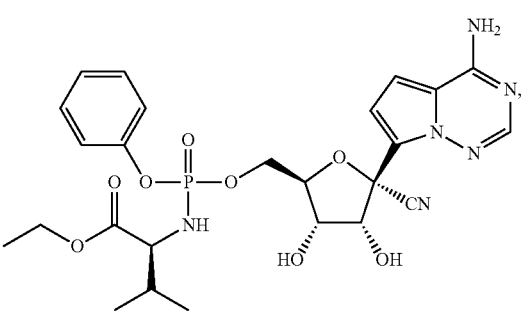

189
-continued
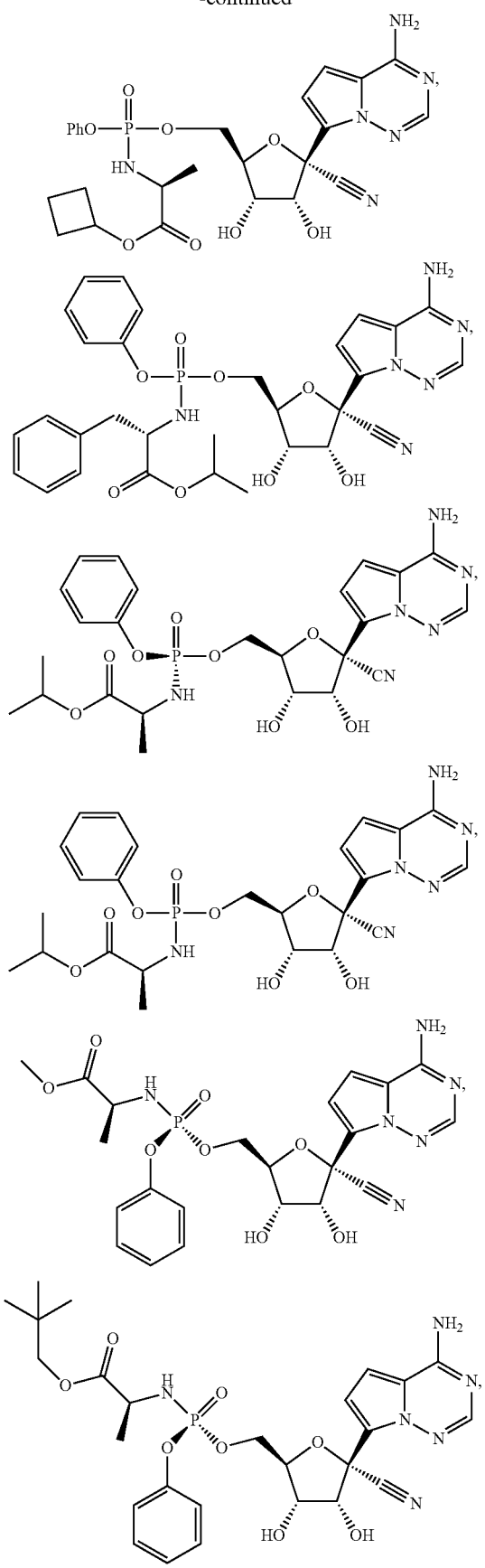
190
-continued
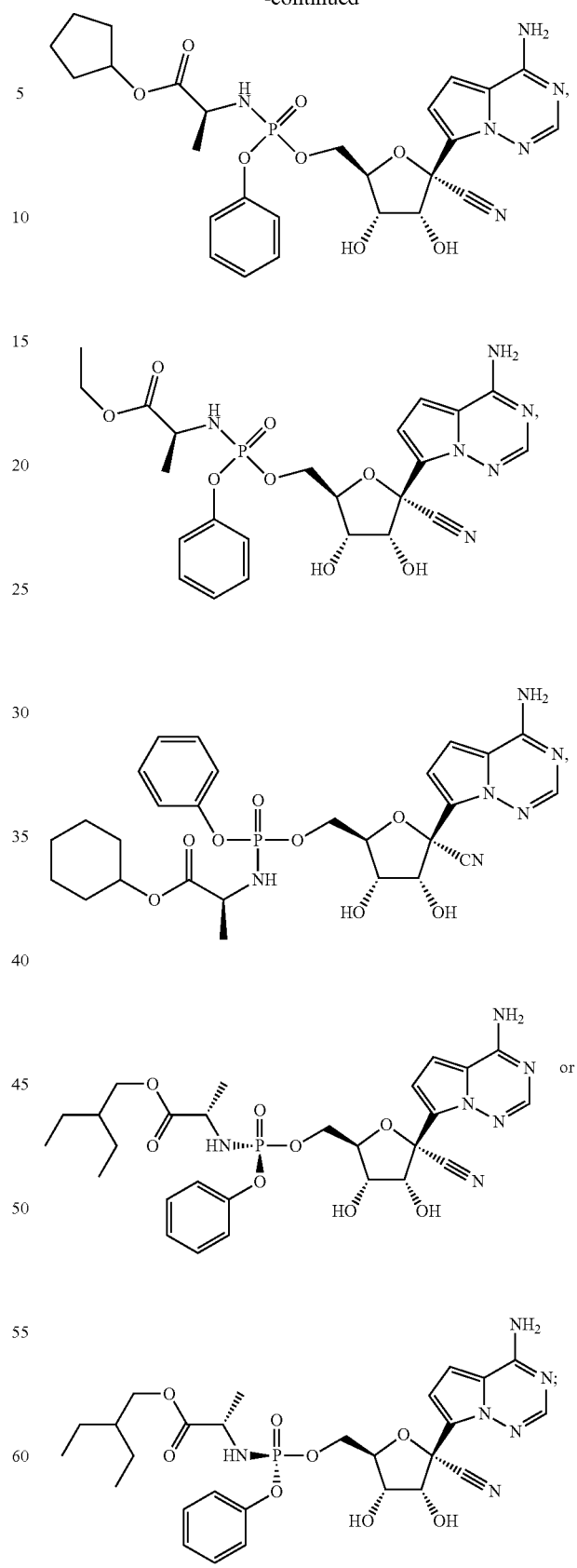
or a pharmaceutically acceptable salt or ester thereof.

25. The method of claim 1 wherein the compound is:

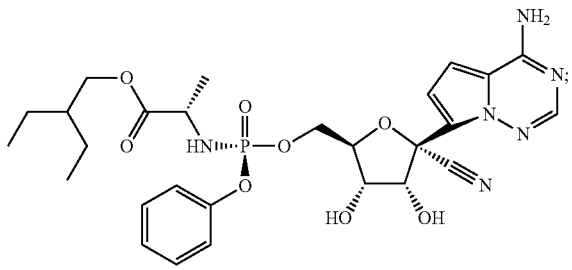 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

or a pharmaceutically acceptable salt or ester thereof.

26. The method of claim 1 further comprising administering a pharmaceutically acceptable carrier or excipient.

27. The method of claim 1 further comprising administering a therapeutically effective amount of at least one other therapeutic agent or composition thereof selected from the group consisting of a corticosteroid, an anti-inflammatory signal transduction modulator, a β2-adrenoreceptor agonist bronchodilator, an anticholinergic, a mucolytic agent, hypertonic saline and other drugs for treating Arenaviridae virus infections; or mixtures thereof.

28. The method of claim 27 wherein the at least one other therapeutic agent is selected from the group consisting of ribavirin, favipiravir (also known as T-705 or Avigan), T-705 monophosphate, T-705 diphosphate, T-705 triphosphate, ST-193, and mixtures thereof.

29. The method of claim 1 wherein the Arenaviridae infection is caused by an Arenaviridae virus.

30. The method of claim 1 wherein the Arenaviridae infection is caused by a Lassa virus.

31. The method of claim 1 wherein the Arenaviridae infection is caused by a Junin virus.

32. The method of claim 1 wherein the Arenaviridae infection is caused by a Lassa virus strain selected from the group consisting of Josiah, NL, z148, Macenta, AV, and CSF.

33. The method of claim 1 wherein an Arenaviridae polymerase is inhibited.

34. The method of claim 1 wherein the compound is:

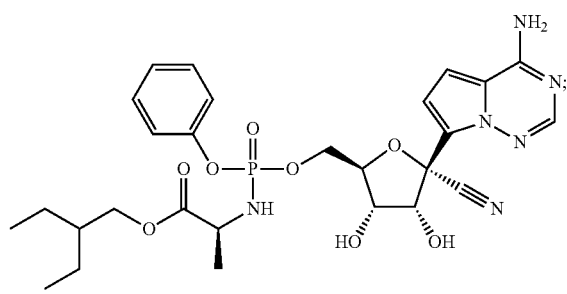 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccccc1]

or a pharmaceutically acceptable salt thereof.

35. The method of claim 1 wherein the compound is:

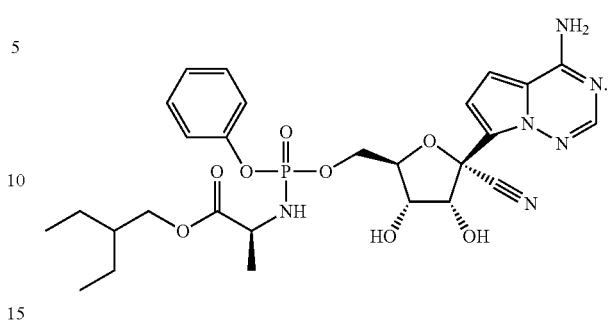

36. The method of claim 1 wherein the compound is:

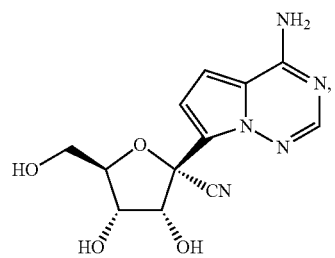 [SMILES: N#C[C@@]1(c2ccc3c(N)ncnn23)O[C@H](CO)[C@@H](O)[C@H]1O]

or a pharmaceutically acceptable salt thereof.

37. The method of claim 1 wherein the compound is:

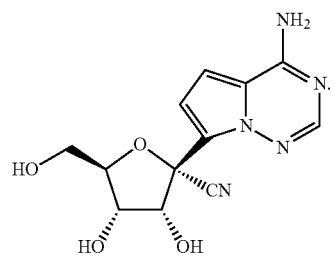 [SMILES: N#C[C@@]1(c2ccc3c(N)ncnn23)O[C@H](CO)[C@@H](O)[C@H]1O]

38. A method for treating an Arenaviridae infection in a human in need thereof comprising administering to the human a therapeutically effective amount of a compound of structure:

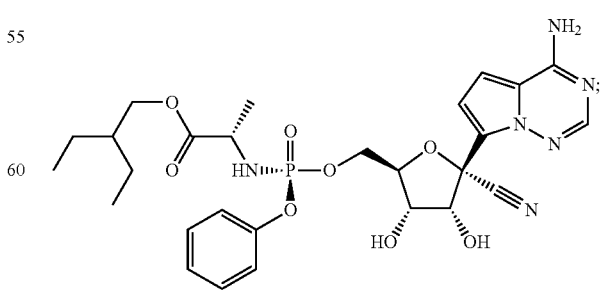

or a pharmaceutically acceptable salt thereof.

39. The method of claim 38 wherein the compound is:

[chemical structure]

40. The method of claim 38 wherein the Arenaviridae infection is caused by an Arenaviridae virus.

41. The method of claim 38 wherein the Arenaviridae infection is caused by a Lassa virus.

42. The method of claim 38 wherein the Arenaviridae infection is caused by a Junin virus.

43. The method of claim 38 wherein the Arenaviridae infection is caused by a Lassa virus strain selected from the group consisting of Josiah, NL, z148, Macenta, AV, and CSF.

* * * * *

UNITED STATES PATENT AND TRADEMARK OFFICE
CERTIFICATE OF CORRECTION

| | | |
|---|---|---|
| PATENT NO. | : 10,251,904 B2 | |
| APPLICATION NO. | : 15/267433 | |
| DATED | : April 9, 2019 | |
| INVENTOR(S) | : Michael O'Neil Hanrahan Clarke et al. | |

It is certified that error appears in the above-identified patent and that said Letters Patent is hereby corrected as shown below:

In the Specification

Column 26, Lines 31-33, delete "In another aspect of this embodiment, $R^8$ of Formula II is $N^{11}R^{12}$." and insert -- In another aspect of this embodiment, $R^8$ of Formula II is $NR^{11}R^{12}$. --

In the Claims

Column 177, Line 32, Claim 1, delete "$^+N(O)(R)$" and insert -- $^+N(O^-)(R)$ --

Column 177, Line 32, Claim 1, delete "$^+N(O)(OR)$" and insert -- $^+N(O^-)(OR)$ --

Column 177, Line 47, Claim 1, delete "-C N" and insert -- -CN --

Column 177, Line 51, Claim 1, delete "$^+N(O)(R)$" and insert -- $^+N(O^-)(R)$ --

Column 177, Line 52, Claim 1, delete "$^+N(O)(OR)$" and insert -- $^+N(O^-)(OR)$ --

Column 178, Line 3, Claim 1, delete "$^+N(O)(R)$" and insert -- $^+N(O^-)(R)$ --

Column 178, Line 3, Claim 1, delete "$^+N(O)(OR)$" and insert -- $^+N(O^-)(OR)$ --

Column 178, Line 26, Claim 1, delete "$NR^{11}N^{11}R^{12}$" and insert -- $NR^{11}NR^{11}R^{12}$ --

Column 179, Line 29, Claim 2, delete " $-S(O)_2(OR^{11})$," and insert -- $-S(O)_2(OR^{11})$, and --

Signed and Sealed this
Twentieth Day of June, 2023

*Katherine Kelly Vidal*

Katherine Kelly Vidal
*Director of the United States Patent and Trademark Office*

Column 181, Lines 11-24, Claim 9, delete " 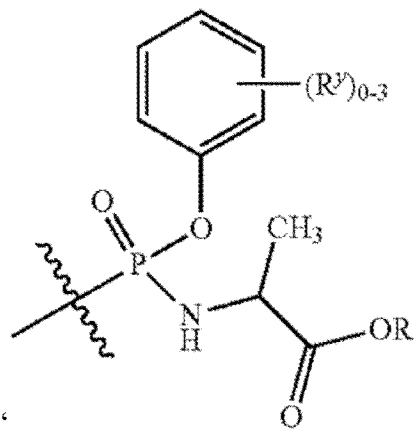 " and insert
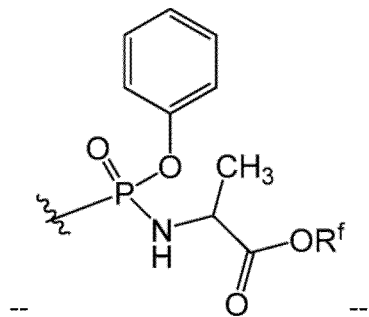 --
Column 181, Lines 34-39, Claim 10, delete
" 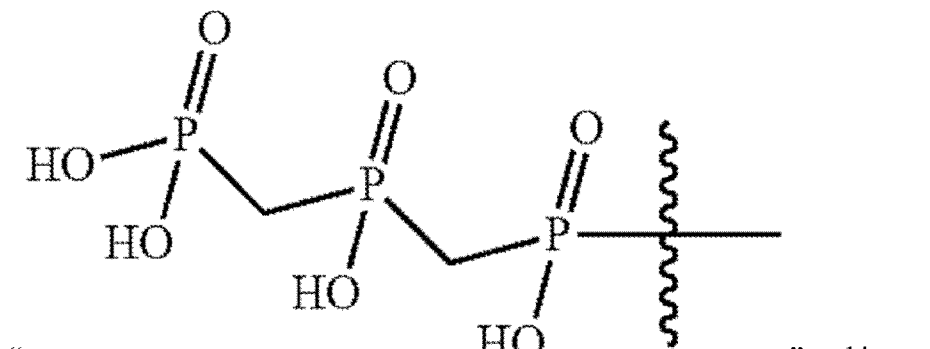 " and insert
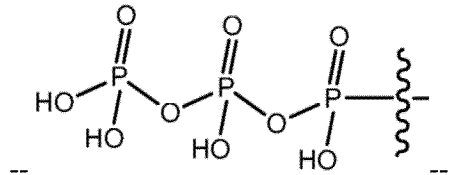 --

CERTIFICATE OF CORRECTION (continued)
U.S. Pat. No. 10,251,904 B2

Page 3 of 4

Column 181, Lines 40-50, Claim 10, delete " 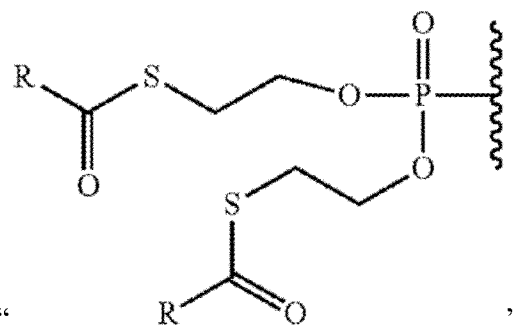 " and insert

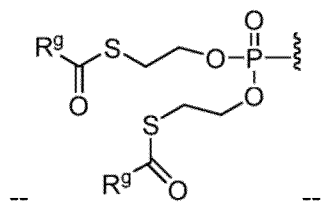

-- --

Column 181, Lines 40-50, Claim 10, delete " 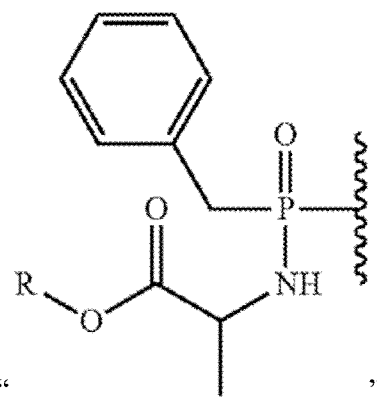 " and insert

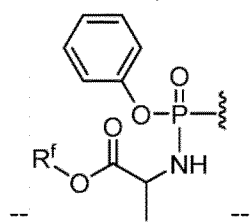

-- --

Column 182, Lines 9-14, Claim 13, delete

" 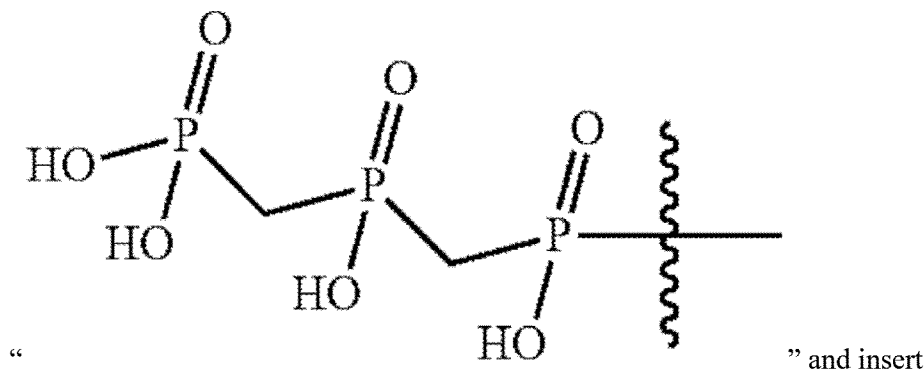 " and insert

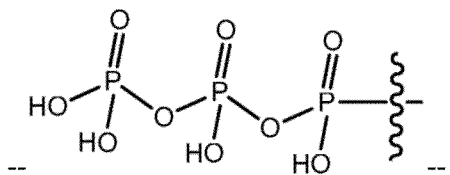
Column 183, Lines 10-15, Claim 20, delete
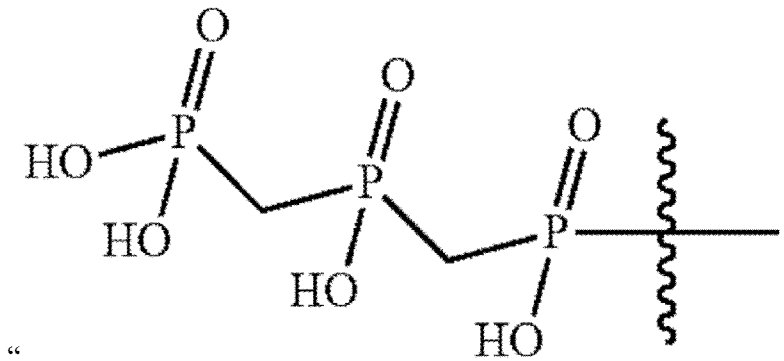
" and insert
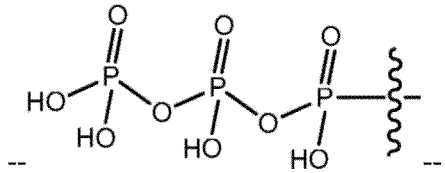
--
Column 188, Lines 26-36, Claim 24, delete
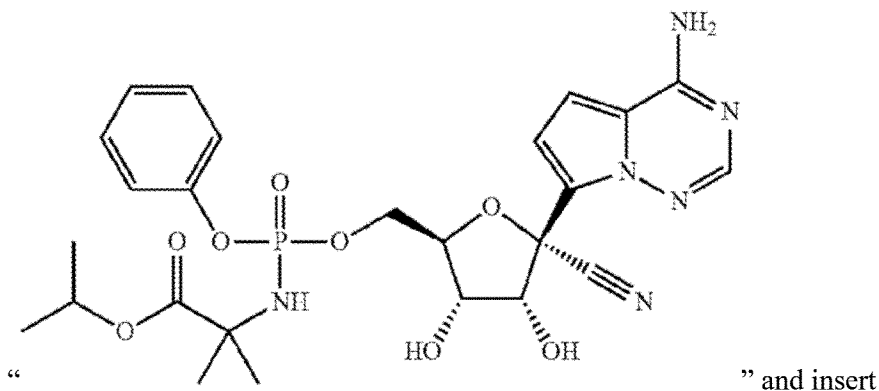
" and insert
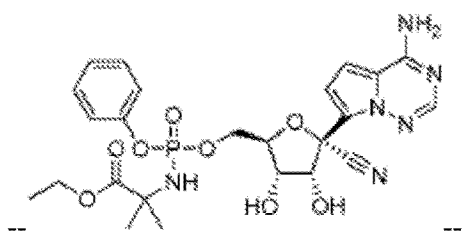
--

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic MERS-CoV Leader Forward Primer

<400> SEQUENCE: 1
gaatagcttg gctatctcac                                                   20

<210> SEQ ID NO 2
<211> LENGTH: 18
<212> TYPE: DNA
<213> ORGANISM: Artificial Sequence
<220> FEATURE:
<223> OTHER INFORMATION: Synthetic ORF1 Reverse Primer

<400> SEQUENCE: 2
cacaatccca ccagacaa                                                     18

<210> SEQ ID NO 3
<211> LENGTH: 20
<212> TYPE: DNA
<213> ORGANISM: Artificial Sequence
<220> FEATURE:
<223> OTHER INFORMATION: Synthetic ORF8 Reverse Primer

<400> SEQUENCE: 3
ttgttatcgg caaaggaaac                                                   20

<210> SEQ ID NO 4
<211> LENGTH: 24
<212> TYPE: DNA
<213> ORGANISM: Artificial Sequence
<220> FEATURE:
<223> OTHER INFORMATION: Synthetic SARS-CoV Leader Forward Primer

<400> SEQUENCE: 4
agccaaccaa cctcgatctc ttgt                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic ORF1 Reverse Primer

<400> SEQUENCE: 5
tgacaccaag aacaaggctc tcca                                              24

<210> SEQ ID NO 6
<211> LENGTH: 24
<212> TYPE: DNA
<213> ORGANISM: Artificial Sequence
<220> FEATURE:
```

```
<223> OTHER INFORMATION: Synthetic ORF9 Reverse Primer

<400> SEQUENCE: 6
attggtgttg attggaacgc cctg                                      24

<210> SEQ ID NO 7
<211> LENGTH: 20
<212> TYPE: DNA
<213> ORGANISM: Artificial Sequence
<220> FEATURE:
<223> OTHER INFORMATION: Synthetic GAPDH Forward Primer

<400> SEQUENCE: 7
tgcaccacca actgcttagc                                           20

<210> SEQ ID NO 8
<211> LENGTH: 21
<212> TYPE: DNA
<213> ORGANISM: Artificial Sequence
<220> FEATURE:
<223> OTHER INFORMATION: Synthetic GAPDH Reverse Primer

<400> SEQUENCE: 8
ggcatggact gtggtcatga g                                         21
```